(12) United States Patent
Castner et al.

(10) Patent No.: US 10,842,892 B2
(45) Date of Patent: *Nov. 24, 2020

(54) METHODS AND APPARATUS FOR SYNTHESIZING IMAGING AGENTS, AND INTERMEDIATES THEREOF

(71) Applicant: Lantheus Medical Imaging, Inc., North Billerica, MA (US)

(72) Inventors: James F. Castner, Groton, MA (US); Enrico Mongeau, Nashua, NH (US); Dianne D. Zdankiewicz, Londonderry, NH (US); Robert W. Siegler, Chelmsford, MA (US); Richard R. Cesati, Pepperell, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/901,286

(22) Filed: Feb. 21, 2018

(65) Prior Publication Data

US 2019/0290788 A1 Sep. 26, 2019

Related U.S. Application Data

(63) Continuation of application No. 15/433,387, filed on Feb. 15, 2017, now Pat. No. 10,022,462, which is a continuation of application No. 14/561,594, filed on Dec. 5, 2014, now Pat. No. 9,603,951, which is a continuation of application No. 13/577,674, filed as application No. PCT/US2011/024109 on Feb. 8, 2011, now Pat. No. 8,936,777.

(60) Provisional application No. 61/333,693, filed on May 11, 2010, provisional application No. 61/315,376, filed on Mar. 18, 2010, provisional application No. 61/302,477, filed on Feb. 8, 2010.

(51) Int. Cl.
*A61K 51/04* (2006.01)
*C07D 407/12* (2006.01)
*C07D 237/16* (2006.01)

(52) U.S. Cl.
CPC ........ *A61K 51/0459* (2013.01); *C07D 237/16* (2013.01); *C07D 407/12* (2013.01)

(58) Field of Classification Search
None
See application file for complete search history.

(56) References Cited

U.S. PATENT DOCUMENTS

| | | |
|---|---|---|
| 3,359,103 A | 12/1967 | Becker et al. |
| 4,783,462 A | 11/1988 | Mutsukado et al. |
| 4,874,861 A | 10/1989 | Ogura et al. |
| 4,910,201 A | 3/1990 | Kawamura et al. |
| 5,087,440 A | 2/1992 | Cacheris et al. |
| 5,088,499 A | 2/1992 | Unger |
| 5,093,105 A | 3/1992 | Flanagan et al. |
| 5,098,900 A | 3/1992 | Mutsukado et al. |
| 5,155,215 A | 10/1992 | Ranney |
| 5,169,848 A | 12/1992 | Bettarini et al. |
| 5,169,942 A | 12/1992 | Johnson |
| 5,228,446 A | 7/1993 | Unger et al. |
| 5,281,704 A | 1/1994 | Love et al. |
| 5,306,482 A | 4/1994 | Tartaglia et al. |
| 5,377,681 A | 1/1995 | Drane |
| 5,384,113 A | 1/1995 | Deutsch et al. |
| 5,393,512 A | 2/1995 | Vanderheyden et al. |
| 5,412,148 A | 5/1995 | Keana |
| 5,417,959 A | 5/1995 | Wallace |
| 5,436,325 A | 7/1995 | Johnson et al. |
| 5,520,904 A | 5/1996 | Nosco et al. |
| 5,547,656 A | 8/1996 | Unger |
| 5,567,411 A | 10/1996 | Keana et al. |

(Continued)

FOREIGN PATENT DOCUMENTS

| | | |
|---|---|---|
| CN | 101555232 A | 10/2009 |
| CN | 102336741 A | 2/2012 |

(Continued)

OTHER PUBLICATIONS

Office Action for CN201180016758.9, dated Jun. 26, 2014.
Extended European Search Report for EP11740546.4, dated Jun. 25, 2013.
Partial European Search Report for EP 17189439.7 dated Feb. 23, 2018.

(Continued)

*Primary Examiner* — Michael G. Hartley
*Assistant Examiner* — Jagadishwar R Samala
(74) *Attorney, Agent, or Firm* — Wolf, Greenfield & Sacks, P.C.

(57) ABSTRACT

The present invention generally relates to methods and system for the synthesis of imaging agents, and precursors thereof. The methods may exhibit improved yields and may allow for the large-scale synthesis of imaging agents, including imaging agents comprising a radioisotope (e.g., $^{18}$F). Various embodiments of the invention may be useful as sensors, diagnostic tools, and the like. In some cases, methods for evaluating perfusion, including myocardial perfusion, are provided. Synthetic methods of the invention have also been incorporated into an automated synthesis unit to prepare and purify imaging agents that comprise a radioisotope. In some embodiments, the present invention provides a novel methods and systems comprising imaging agent 1, including methods of imaging in a subject comprising administering a composition comprising imaging agent 1 to a subject by injection, infusion, or any other known method, and imaging the area of the subject wherein the event of interest is located.

8 Claims, 11 Drawing Sheets

(56) References Cited

U.S. PATENT DOCUMENTS

| | | |
|---|---|---|
| 5,585,112 A | 12/1996 | Unger et al. |
| 5,587,491 A | 12/1996 | Hoye et al. |
| 5,679,810 A | 10/1997 | Love et al. |
| 5,760,191 A | 6/1998 | Snow et al. |
| 5,801,228 A | 9/1998 | Hollister et al. |
| 5,804,161 A | 9/1998 | Long et al. |
| 5,811,073 A | 9/1998 | Kassis et al. |
| 5,827,073 A | 10/1998 | Leuscher et al. |
| 5,846,517 A | 12/1998 | Unger |
| 5,961,955 A | 10/1999 | Shochat et al. |
| 6,056,939 A | 5/2000 | Desreux et al. |
| 6,066,309 A | 5/2000 | Zamora et al. |
| 6,241,964 B1 | 6/2001 | Burns et al. |
| 6,565,889 B2 | 5/2003 | Zasadzinski et al. |
| 7,112,318 B2 | 9/2006 | Madar et al. |
| 7,344,702 B2 | 3/2008 | Casebier et al. |
| 7,410,998 B2 | 8/2008 | Nicolaou et al. |
| 7,485,283 B2 | 2/2009 | Radeke et al. |
| 7,824,659 B2 | 11/2010 | Casebier et al. |
| 7,847,092 B2 | 12/2010 | Moon et al. |
| 7,871,623 B2 | 1/2011 | Biswal et al. |
| 7,927,616 B2 | 4/2011 | Yamashita |
| 8,226,929 B2 | 7/2012 | Casebier et al. |
| 8,263,042 B2 | 9/2012 | Radeke et al. |
| 8,936,777 B2 | 1/2015 | Cesati et al. |
| 9,029,295 B2 | 5/2015 | Kuragano et al. |
| 9,161,997 B2 | 10/2015 | Casebier et al. |
| 9,408,927 B2 | 8/2016 | Robinson et al. |
| 9,550,000 B2 | 1/2017 | Robinson et al. |
| 9,603,951 B2 | 3/2017 | Lazewatsky et al. |
| 9,713,651 B2 | 7/2017 | Robinson et al. |
| 9,718,786 B2 | 8/2017 | Casebier et al. |
| 9,919,064 B2 | 3/2018 | Cesati et al. |
| 10,022,462 B2 | 7/2018 | Cesati et al. |
| 10,125,106 B2 | 11/2018 | Casebier et al. |
| 10,245,332 B2 | 4/2019 | Robinson et al. |
| 10,500,293 B2 | 12/2019 | Cesati et al. |
| 2003/0044354 A1 | 3/2003 | Carpenter et al. |
| 2003/0124054 A1 | 7/2003 | Toyohara et al. |
| 2004/0033197 A1 | 2/2004 | Madar et al. |
| 2004/0034239 A1 | 2/2004 | Nicolaou et al. |
| 2004/0142872 A1 | 7/2004 | Poduslo et al. |
| 2004/0142972 A1 | 7/2004 | Edgar et al. |
| 2005/0020594 A1 | 1/2005 | Hepperle et al. |
| 2005/0129612 A1 | 6/2005 | Zaczek et al. |
| 2005/0137213 A1 | 6/2005 | Cai et al. |
| 2005/0191238 A1 | 9/2005 | Casebier et al. |
| 2005/0244332 A1 | 11/2005 | Radeke et al. |
| 2006/0083681 A1 | 4/2006 | Purohit et al. |
| 2006/0127309 A1 | 6/2006 | Raffel et al. |
| 2007/0036716 A1 | 2/2007 | Casebier et al. |
| 2007/0082879 A1 | 4/2007 | Goodman |
| 2007/0258887 A1 | 11/2007 | Tamagnan et al. |
| 2009/0104118 A1 | 4/2009 | Radeke et al. |
| 2009/0297442 A1 | 12/2009 | Hemstad |
| 2010/0236958 A1 | 9/2010 | Veggeland et al. |
| 2010/0322855 A1 | 12/2010 | Chong et al. |
| 2011/0091374 A1 | 4/2011 | Robinson et al. |
| 2011/0160543 A1 | 6/2011 | Parsey et al. |
| 2012/0237445 A1 | 9/2012 | Castner et al. |
| 2012/0276006 A1 | 11/2012 | Casebier et al. |
| 2013/0028837 A1 | 1/2013 | Radeke et al. |
| 2013/0064769 A1 | 3/2013 | Cesati, III et al. |
| 2013/0101508 A9 | 4/2013 | Castner et al. |
| 2013/0144052 A1* | 6/2013 | Mueller ............... B01J 19/0093 536/122 |
| 2014/0328756 A1 | 11/2014 | Cesati, III et al. |
| 2015/0165074 A1 | 6/2015 | Lazewatsky et al. |
| 2015/0196672 A1 | 7/2015 | Cesati et al. |
| 2015/0230762 A1 | 8/2015 | Alpert et al. |
| 2015/0246143 A1 | 9/2015 | El Fakhri et al. |
| 2016/0130235 A1 | 5/2016 | Casebier et al. |
| 2016/0361448 A1 | 12/2016 | Robinson et al. |
| 2017/0202984 A1 | 7/2017 | Cesati et al. |
| 2017/0258947 A1 | 9/2017 | Cesati et al. |
| 2017/0266326 A1 | 9/2017 | Radeke et al. |
| 2018/0318456 A1 | 11/2018 | Cesati et al. |
| 2019/0127333 A1 | 5/2019 | Casebier et al. |

FOREIGN PATENT DOCUMENTS

| | | |
|---|---|---|
| EP | 0 169 375 A | 1/1986 |
| EP | 0 186 817 A | 7/1986 |
| EP | 0 111 415 B1 | 4/1990 |
| EP | 0 393 641 A2 | 10/1990 |
| EP | 0 627 424 A1 | 12/1994 |
| EP | 0 665 223 A1 | 8/1995 |
| EP | 0 727 225 A2 | 8/1996 |
| EP | 1 741 703 A1 | 1/2007 |
| JP | S60-004173 A | 1/1985 |
| JP | S61-017570 A | 1/1986 |
| JP | S61-130275 A | 6/1986 |
| JP | S61-260018 A | 11/1986 |
| JP | S61-267560 A | 11/1986 |
| JP | S62-005967 A | 1/1987 |
| JP | S62-123176 A | 6/1987 |
| JP | S63-159372 A | 7/1988 |
| JP | S63-159373 A | 7/1988 |
| JP | S63-159374 A | 7/1988 |
| JP | H02-088507 A | 3/1990 |
| JP | H02-279676 A | 11/1990 |
| JP | H03-220177 A | 9/1991 |
| JP | H04-235975 A | 8/1992 |
| JP | H07-252236 A | 10/1995 |
| JP | 2007-112725 A | 5/2007 |
| JP | 2011-507893 A | 3/2011 |
| JP | 2011-516592 A | 5/2011 |
| JP | 2012-149044 A1 | 8/2012 |
| WO | WO 91/14460 A1 | 10/1991 |
| WO | WO 92/17215 A1 | 10/1992 |
| WO | WO 94/12479 A1 | 6/1994 |
| WO | WO 94/22496 A1 | 10/1994 |
| WO | WO 95/11901 A1 | 5/1995 |
| WO | WO 95/33757 A1 | 12/1995 |
| WO | WO 00/09115 A1 | 2/2000 |
| WO | WO 00/078283 A1 | 12/2000 |
| WO | WO 2002/011715 A2 | 2/2002 |
| WO | WO 02/20008 A1 | 3/2002 |
| WO | WO 03/002157 A1 | 1/2003 |
| WO | WO 03/065882 A2 | 8/2003 |
| WO | WO 03/082350 A2 | 10/2003 |
| WO | WO 03/086476 A1 | 10/2003 |
| WO | WO 04/056400 A1 | 7/2004 |
| WO | WO 2005/009393 A2 | 2/2005 |
| WO | WO 2005/012319 A1 | 2/2005 |
| WO | WO 2005/079391 A2 | 9/2005 |
| WO | WO 2005/082425 A1 | 9/2005 |
| WO | WO 2005/103265 A1 | 11/2005 |
| WO | WO 2005/105159 A2 | 11/2005 |
| WO | WO 2007/021858 A2 | 2/2007 |
| WO | WO 2008/022979 A1 | 2/2008 |
| WO | WO 2008/075040 A2 | 6/2008 |
| WO | WO 2008/081852 A1 | 7/2008 |
| WO | WO 2008/083056 A2 | 7/2008 |
| WO | WO 2009/054653 A2 | 4/2009 |
| WO | WO 2009/086041 A1 | 7/2009 |
| WO | WO 2009/103478 A1 | 8/2009 |
| WO | WO 2009/108376 A2 | 9/2009 |
| WO | WO 2009/110984 A2 | 9/2009 |
| WO | WO 2009/127544 A1 | 10/2009 |
| WO | WO 2010/104818 A1 | 9/2010 |
| WO | WO 2010/120368 A2 | 10/2010 |
| WO | WO 2011/006610 A1 | 1/2011 |
| WO | WO 2011/097649 A2 | 8/2011 |
| WO | WO 2011/143360 A1 | 11/2011 |
| WO | WO 2013/058774 A2 | 4/2013 |
| WO | WO 2014/026079 A2 | 2/2014 |

OTHER PUBLICATIONS

Extended European Search Report for EP 17189439.7 dated Jun. 5, 2018.

International Search Report and Written Opinion for PCT/US2011/024109, dated Oct. 24, 2011.

(56) References Cited

OTHER PUBLICATIONS

International Preliminary Report on Patentability for PCT/US2011/024109, dated Aug. 23, 2012.
Alpert et al., Single-scan rest/stress imaging 18F-labeled flow tracers. Medical Physics. 2012;39(11):6609-20.
Anagnostopoulos et al., Assessment of myocardial perfusion and viability by Positron Emission Tomography. International Journal of Cardiology. 2013;167:1737-49.
Bateman et al., Diagnostic accuracy of rest/stress ECG-gated Rb-82 myocardial perfusion PET: comparison with ECG-gated Tc-99m sestamibi SPECT. J Nucl Cardiol. Jan.-Feb. 2006;13(1):24-33.
Beanlands et al., Diagnosis and prognosis of coronary artery disease: PET is superior to SPECT: Pro. Journal of Nuclear Cardiology. 2010;17: 683-95.
Beller, Quantification of myocardial blood flow with PET: Ready for clinical application. Journal of Nuclear Cardiology. 2012;19(5):877-878.
Bengel et al., Cardiac Positron Emission Tomography. Journal of the American College of Cardiology. 2009; 54: 1-15.
Bergmann et al., Noninvasive quantitation of myocardial blood flow in human subjects with oxygen-15-labeled water and positron emission tomography. J Am Coll Cardiol. Sep. 1989;14(3):639-52.
Berman D.S., Germano.G, Slomka, P.J., (2012). Improvement in PET myocardial perfusion image quality and quantification with Flurpiridaz F 18. Journal of Nuclear Cardiology 19(1): S38-45.
Berman et al., (2010) Comparison of 18F-BMS747158 and 82Rb PET vs SPECT for detection of myocardial ischemia. Journal of Nuclear Cardiology 17(4): 743. Abstract #31.17.
Berman et al., Flurpiridaz F-18 PET versus Tc-99m SPECT for myocardial perfusion imaging. Cardiology. 2013;125, Supplement 2:27.
Berman et al., Phase II Safety and Clinical Comparison with Single-Photon Emission Computed Tomography Myocardial Perfusion Imaging for Detection of Coronary Artery Disease. Journal of the American College of Cardiology. 2013;61(4):469-77.
Boogers et al., The role of nuclear imaging in the failing heart: Myocardial blood flow, sympathetic innervation, and future applications. Heart Failure Reviews. 2011. 16(4): 411-423.
Bousquet, J.-C. et al., "Gd-DOTA: Characterization of a New Paramagnetic Complex," Radiology, vol. 166, No. 3, pp. 693-698 (1988).
Brown, M. et al., "Delineation of myocardial oxygen utilization with carbon-11-labeled acetate," Circulation, vol. 76, No. 3, pp. 687-696 (1987).
Cao et al., Synthesis and antifeedant activity of new oxadiazolyl 3(2H)-pyridazinones. J Agric Food Chem. Jan. 1, 2003;51(1):152-5.
Case et al., Automatic registration of F-18 labeled BMS-747158 stress and rest myocardial perfusion images using 6D cross-correlation optimization. Journal of Nuclear Medicine. 2010; 51(Supplement 2): 1687.
Case et al., Imaging properties of F-18 labeled myocardial perfusion PET agent, BMS747158: dosage, acquisition time and scanner type. Journal of Nuclear Medicine. 2009;50 (Supplement 2): 418. 2 pages.
Case et al., Impact of image filtering, BMI, and gender on optimal dosage acquisition time product using a novel PET myocardial perfusion tracer: F-18 labeled Flurpiridaz. Journal of Nuclear Cardiology. 2011;18(4): 769-770. Abstract #14.32.
Case et al., Independence of myocardial functional parameters (LVEF, EDV, and ESV) across a large range of acquisition times and measured from a novel F-18 radiotracer, Flurpiridaz F-18. Journal of Nuclear Cardiology. 2010;17(4 Supplement 1): 725-726. Abstract #9.15.
Case et al., Iterative technique for optimizing injected tracer dosage and acquisition time for F-18 labeled myocardial perfusion tracer Flurpiridaz F-18. Journal of Nuclear Cardiology. 2010;17(4): 726. Abstract # 9.17.
Chary et al., Reductive cleavage of acetals/ketals. Synthetic Communications. 1999;29(8):1257-1261.

Cherednichenko et al., NADH oxidase activity of rat cardiac sarcoplasmic reticulum regulates calcium-induced calcium release. Biophys J. Jan. 2004;86(1-Part 2of 2, suppl):241a.
Clark et al., The present role of nuclear cardiology in clinical practice. Q J Nucl Med Mol Imaging. Mar. 2005;49(1):43-58.
Clark, Fluoride ion as a base in organic synthesis. Chem. Rev. 1980; 80(5):429-52.
Crane et al., Use of a tritiated (3H) analog of flurpiridaz F18 to characterize the pharmacokinetics, metabolism and excretion in normal human subjects. AAAPS. (2011) Abstract.
Di Carli et al., Cardiac PET/CT for the evaluation of known or suspected coronary artery disease. Radiographics. Sep.-Oct. 2011;31(5):1239-54. doi: 10.1148/rg.315115056.
Di Carli et al., Cardiac PET-CT. J Thorac Imaging. Feb. 2007;22(1):101-6.
Di Carli et al., Clinical myocardial perfusion PET/CT. J Nucl Med. May 2007;48(5):783-93.
Dilsizian et al., Journey in Evolution of Nuclear Cardiology: Will There Be Another Quantum Leap with the F-18-Labeled Myocardial Perfusion Tracers? Journal of the American College of Cardiology: Cardiovascular Imaging. 2012;5(12): 1269-84.
Emmett et al., Reversible regional wall motion abnormalities on exercise technetium-99m-gated cardiac single photon emission computed tomography predict high-grade angiographic stenoses. Journal of the American College of Cardiology. Mar. 20, 2002;39(6):991-8.
Esposti, Inhibitors of NADH—ubiquinone reductase: an overview. Biochimica et Biophysica Acta, vol. 1364, pp. 222-235 (1998).
Fleming et al., High-Dose Dipyridamole and Gated Sestamibi SPECT Imaging Provide Diagnostic Resting and Stress Ejection Fractions Useful for Predicting Extent of Coronary Artery Disease. Angiology. 2002;53(4):415-21.
Fukumoto et al., Detection of ischemic neuronal damage with [18F]BMS-747158-02, a mitochondrial complex-1 positron emission tomography ligand: Small animal PET study in rat brain. Synapse. 2012;66(10): 909-917.
Gaemperli et al., PET and PET/CT in cardiovascular disease. Annals of the New York Academy of Sciences. 2011;1228:109-36.
Garcia et al., What should we expect from cardiac PET? J Nucl Med. Jun. 1993;34(6):978-80.
Garcia, Quantitative Nuclear Cardiology: We are almost there! Journal of Nuclear Cardiology. 2012;19(3):424-437.
Garrison et al., Reaction mechanisms in the radiolysis of peptides, polypeptides, and proteins. Chem Rev. 1987;87:381-98.
Gewirtz, PET measurement of adenosine stimulated absolute myocardial blood flow for physiological assessment of the coronary circulation. Journal of Nuclear Cardiology. 2012;19(2):347-354.
Ghesani et al., Role of F-18 FDG positron emission tomography (PET) in the assessment of myocardial viability. Echocardiography. Feb. 2005;22(2):165-77.
Glover et al., Journey to find the ideal PET flow tracer for clinical use: are we there yet? J Nucl Cardiol. Nov.-Dec. 2007;14(6):765-8.
Glover et al., Comparison between 201Tl and 99mTc sestamibi uptake during adenosine-induced vasodilation as a function of coronary stenosis severity. Circulation. Feb. 1, 1995;91(3):813-20.
Glover et al., Myocardial 99mTc-tetrofosmin uptake during adenosine-induced vasodilatation with either a critical or mild coronary stenosis: comparison with 201Tl and regional myocardial blood flow. Circulation. Oct. 7, 1997;96(7):2332-8.
Glover et al., Myocardial kinetics of Tc-MIBI in canine myocardium after dipyridamole. Circulation. Feb. 1990;81(2):628-37.
Gout et al., Sulfasalazine, a potent suppressor of lymphoma growth by inhibition of the xc cystine transporter: a new action for an old drug. Leukemia, vol. 15, pp. 1633-1640 (2001).
Gropler, PET Radiotracers of the Cardiovascular System. PET Clinic 4. 2009: p. 69-87.
Han et al., Total Synthesis of 34-hydroxyasimicin and Its Photoactive Derivative for Affinity Labeling of the Mitochondrial Complex I. Chemistry—A European Journal, vol. 10, No. 9, pp. 2149-2158 (2004).
Heller, Practical issues regarding the incorporation of PET into a busy SPECT practice. Journal of Nuclear Cardiology. 2012;19, SUPPL.1:S12-S18.

(56) References Cited

OTHER PUBLICATIONS

Higgins et al., [3H]dihydrorotenone binding to NADH: ubiquinone reductase (complex I) of the electron transport chain: an autoradiographic study. J Neurosci. Jun. 15, 1996;16(12):3807-16.
Higuchi et al., A new 18F-labeled myocardial PET tracer: myocardial uptake after permanent and transient coronary occlusion in rats. J Nucl Med. Oct. 2008;49(10):1715-22. Epub Sep. 15, 2008.
Higuchi et al., A Novel [F-18] labeled PET Tracer for the Characterization of Coronary Artery Disease: Preliminary Evaluation in a Coronary Occlusion Rat Model Circulation. 2007;116:II_658 Abstract #2947.
Hsu et al., Cardiac phantom simulation of dose injection parameters for one-day rest/stress myocardial perfusion tracer. Journal of Nuclear Medicine. 2010;51(Supplement 2): 320.
Hsu et al., Remote camera qualification (RCQ) of PET and PET/CT scanners for BMS747158 F18 myocardial perfusion phase 3 clinical trial using a standardized phantom procedure. J Nucl Med. 2011;52 (Supplement 1):54.
Huang et al., Evaluation of absolute mbf at rest and stress with Flurpiridaz F-18 injection PET in normal subjects and patients with coronary artery disease (CAD) and in two types of scanners. Journal of Nuclear Cardiology. 2011;18(4): 783-784. Abstract #26.19.
Huang et al., Rabbit myocardial 82Rb kinetics and a compartmental model for blood flow estimation. Am J Physiol. Apr. 1989;256(4 Pt 2):H1156-64.
Huang et al., Streamlined quantification of absolute MBF at rest and stress with flurpiridaz F-18 injection PET in normal subjects and patients with coronary artery disease (CAD). J Nucl Med. 2011;52 (Supplement 1):1114.
Huisman et al., First Preclinical Study of a New F-18 Labeled PET Tracer for Myocardial Perfusion Imaging Circulation. 2007;116:II_718 Abstract # 3193.
Huisman et al., Initial characterization of an 18F-labeled myocardial perfusion tracer. J Nucl Med. Apr. 2008;49(4):630-6. Epub Mar. 14, 2008.
Igarashi et al., Summary of toxicology studies with Pyridaben. J Peticide Sci. 1994;19:Technical Information.
Jiang et al., Mimicry of annonaceous acetogenins: Enantioselective syntheiss of a (4R)-hydroxy analogue having potent antitumor activity. J. Org. Chem., vol. 67, No. 10, pp. 3404-3408 (2002).
Kadrmas et al., Single-scan dual-tracer FLT+FDG PET tumor characterization. Physics in Medicine and Biology. 2013;58:429-49.
Kagan et al., Comparison of flurpiridaz F 18 and FDG for assessment of left ventricular tissue mass following myocardial infarction in rats. Journal of Nuclear Medicine;2011:52(Supp.1):1097.
Kagan et al., LMI1195 and flurpiridaz F 18 PET imaging in evaluation of time-course changes in mismatch of cardiac denervated and perfusion defect areas following acute myocardial infarction. Journal of Nuclear Medicine. 2012;53, Supplement. 1:84.
Kann et al., Mitochondria and neuronal activity. Am J Physiol Cell Physiol. Feb. 2007;292(2):C641-57. Epub Nov. 8, 2006.
Knapp et al., Availability of rhenium-188 from the alumina-based tungsten-188/rhenium-188 generator for preparation of rhenium-188-labeled radiopharmaceuticals for cancer treatment. Anticancer Res. May-Jun. 1997;17(3B):1783-95.
Knuuti et al., Imaging highlights from the European Society of Cardiology, American Society of Nuclear Cardiology, and Heart Failure Society of America. Journal of the American College of Cardiology Imaging. 2008;1: 119-28.
Krivokapich et al., 13N Ammonia Myocardial Imaging at Rest and With Exercise in Normal Volunteers, Quantification of Absolute Myocardial Perfusion With Dynamic Positron Emission Tomography. Circulation, vol. 80, No. 5, pp. 1328-1337 (1989).
Kroemer, Mitochondria in cancer. Oncogene. Aug. 7, 2006;25(34):4630-2.
Lan et al., Non-invasive imaging modalities for the diagnosis of coronary artery disease: The present and the future. Tzu Chi Medical Journal. 2013, 7 pages.

Latli et al., Photoaffinity radioligand for NADH:ubiquinone oxidoreductase: [S-C3H2](trifluoromethyl)diazirinyl-pyridaben. J. Labelled Compounds Radiopharm. 1998;41(3):191-9.
Lazewatsky et al., Development of a method for the determination of dose ratio and minimum inter-injection interval for a one-day rest-stress protocol with BMS747158 PET myocardial perfusion agent. Journal of Nuclear Medicine. 2010;51(Supplement 2):600.
Lazewatsky et al., Dosimetry of BMS747158, a novel 18F labeled tracer for myocardial perfusion imaging, in nonhuman primates at rest. J Nucl Med. 2008;49(Supplement 1):15p.
Lazewatsky et al., Relative defect radioactivity and perceived defect severity are proportional with flurpiridaz F18 PET myocardial perfusion imaging. J Nucl Med. 2011;52 (Supplement 1):1115.
Le Guludec et al., Present and future of clinical cardiovascular PET imaging in Europe—a position statement by the European Council of Nuclear Cardiology (ECNC). European Journal of Nuclear Medicine and Molecular Imaging. 2008; 35: 1709-24.
Lee et al., Potential and practical adrenomedullary PET radiopharmaceuticals as an alternative to m-iodobenzylguanidine: m-(omega-[18F]fluoroalkyl)benzylguanidines. Bioconjug Chem. Jan.-Feb. 2004;15(1):104-11.
Lindell et al., The design and synthesis of novel inhibitors of NADH:ubiquinone oxidoreductase. Bioorganic & Medicinal Chemistry Letters, vol. 14, pp. 511-514 (2004).
Liu et al., Integrin avb3 directed radiopharmaceuticals for tumor imaging. Drugs of the Future, vol. 28, No. 6, pp. 551-564 (2003).
Maddahi et al., Comparison of F-18 labeled BMS747158 PET and TC-99m labeled spect myocardial perfusion imaging for detection and evaluation of coronary artery disease. Journal of the American College of Cardiology. 2010;55(10A): E616.
Maddahi et al., Comparison of flurpiridaz F 18 PET injection and Tc-99m labeled SPECT myocardial perfusion imaging for identifying severity and extent of stress induced myocardial ischemia in phase 2 clinical trials. J Nucl Med. 2011;52 (Supplement 1):444.
Maddahi et al., F-18 labeled BMS747158 PET myocardial perfusion imaging identifies more severe and extensive stress induced myocardial ischemia than Tc-99m Sestamibi SPECT. Journal of Nuclear Medicine. 2010;51(Supplement 2): 1739.
Maddahi et al., First human study of BMS747158, a novel F-18 labeled tracer for myocardial perfusion imaging. J Nucl Med. 2008;49:70P.
Maddahi et al., Human safety, dosimetry, biodistribution, and rest-stress myocardial imaging characteristics of the new F-18 labeled BMS747158 myocardial perfusion PET tracer. European Heart Journal. 2009;11(Supplement): S89. Abstract #432.
Maddahi et al., Phase 1 Human safety, dosimetry, Biodistribution and rest/stress myocardial imaging characteristics of F18 Labeled BMS 747158. (2009) Journal of the American College of Cardiology 53(10): A297. Abstract #1054-263.
Maddahi et al., Phase 2 clinical comparison of flurpiridaz F 18 injection PET and SPECT myocardial perfusion imaging for diagnosis of coronary artery disease. J Nucl Med. 2011;52 (Supplement 1):59.
Maddahi et al., Phase 2 safety and clinical comparison of flurpiridaz F18 injection PET and SPECT myocardial perfusion imaging for diagnosis of coronary artery disease. European Heart Journal Supplements. 2011;13( Supplement A ): A45. Abstract # 197.
Maddahi et al., Phase I, First-in-Human Study of BMS747158, a Novel 18F-Labeled Tracer for Myocardial Perfusion PET: Dosimetry, Biodistribution, Safety, and Imaging Characteristics After a Single Injection at Rest. J Nucl Med. 2011;52: 1490-9.
Maddahi et al., Preliminary results of absolute quantification of rest and stress myocardial blood flow with Flurpridaz F-18 PET in normal and coronary artery disease patients in a single-center study. Journal of Nuclear Cardiology. 2010;17(4): 743. Abstract # 31.18.
Maddahi et al., Protocols for same day rest-stress PET imaging with the new F-18 labeled BMS747158 myocardial perfusion tracer. European Heart Journal. 2009;11(Supp B): S89. Abstract #433.
Maddahi et al., Same day rest-stress protocols for PET imaging with the new F-18 labeled BMS747158 myocardial perfusion tracer. Journal of Nuclear Medicine. 2009;50(Supplement 2): 1173.

(56) References Cited

OTHER PUBLICATIONS

Maddahi, Properties of an ideal PET perfusion tracer: New PET tracer cases and data. Journal of Nuclear Cardiology. 2012;19(Supplement 1): S30-37.
Magerstadt et al., Gd(DOTA): An Alternative to Gd(DTPA) as a T1,2 Relaxation Agent for NMR Imaging of Spectroscopy. Magnetic Resonance in Medicine, vol. 3, pp. 808-812 (1986).
Marshall et al., Kinetic Analysis of a 125I-iodorotenone as a deposited myocardial flow tracer: Comparison with 99mTc-sestamibi. Journal of Nuclear Medicine, vol. 42, No. 2, pp. 272-281 (2001).
Marshall et al., Kinetic Analysis of a 18F-fluorodihydrorotenone as a deposited myocardial flow tracer: Comparison with 291T1. Journal of Nuclear Medicine, vol. 45, No. 11, pp. 1950-1959 (2004).
Martarello et al., Synthesis and evaluation of a new fluorine-18 labeled rotenoid as a potential pet probe of mitochondrial complex I activity. Journal of Labelled Compounds and Radiopharmaceuticals, vol. 42, No. 11, pp. 1039-1051 (1999).
Miller et al., Synthesis of 11C, 18F, 15O, and 13N radiolabels for positron emission tomography. Angew Chem Int Ed Engl. 2008;47(47):8998-9033.
Mistry et al., Toxicological evaluation of BMS-747158, a PET myocardial perfusion imaging agent. The Toxicologist. 2008;102:476.
Miyoshi et al., Essential structural factors of annonaceous acetogenenins as potent inhibitors of mitochondrial complex I. Biochimica et Biophysica Acta, vol. 1365, No. 3, pp. 443-452 (1998).
Miyoshi, Structure-activity relationships of some complex I inhibitors. Biochim Biophys Acta. May 6, 1998;1364(2):236-44.
Mou et al., Preparation and biodistribution of [18F]FP2OP as myocardial perfusion imaging agent for positron emission tomography. Bioorg Med Chem. Feb. 2010;18(3):1312-20. Epub Dec. 26, 2009.
Mou et al., Synthesis and preliminary evaluation of 18F-labeled pyridazine analogues for myocardial perfusion imaging with PET. J Nucl Med. Mar. 2012;53(3):472-9. doi: 10.2967/jnumed.111.088096. Epub Feb. 2, 2012.
Mukherjee, Fluorinated benzamide neuroleptics--2. Synthesis and radiosynthesis of (S)-N-[(1-ethyl-2-pyrrolidinyl) methyl]-5-(3-[18F]fluoropropyl)-3-substituted-2-methoxybenzamides. Int J Rad Appl Instrum A. 1991;42(8):713-21.
Murthy et al., Non-invasive quantification of coronary vascular dysfunction for diagnosis and management of coronary artery disease. Journal of Nuclear Cardiology. 2012;19(5):1060-1072.
Nakanishi et al., Acetogenins as selective inhibitors of the human ovarian 1A9 tumor cell line. Journal of Medicinal Chemistry, vol. 46, No. 15, pp. 3185-3188 (2003).
Nakazato et al., CFR and FFR assessment with PET and CTA: Strengths and limitations. Current Cardiology Reports. 2014;16(5):484-94.
Nakazato et al., Myocardial perfusion imaging with PET. Imaging in Medicine. 2013;5(1):35-46.
Nekolla et al., Assessment of imaging properties of a new F-18 labelled flow tracer in a pig model. J Am Coll Cardiol. 2008;51:A170.
Nekolla et al., Evaluation of a new myocardial PET tracer 18F-BMS-747158-02 (18F-BMS): Comparison to 13N ammonia and validation with microspheres. J Nucl Med. 2008; 49 (Supplement 1):29P.
Nekolla et al., Evaluation of the novel myocardial perfusion positron-emission tomography tracer 18F-BMS-747158-02: comparison to 13N-ammonia and validation with microspheres in a pig model. Circulation. May 5, 2009;119(17):2333-42. Epub Apr. 20, 2009.
Nekolla et al., Model free quantification of myocardial flow reserve with flurpiridaz F 18: Validation with microspheres in a pig model. European Heart Journal. 2011;13, SUPPL.A:A94. No. 420.
Nekolla et al., Novel F-18 Labeled PET Myocardial Perfusion Tracers: Bench to Bedside. Current Cardiology Reports. 2011;13:145-150.
Nicolaou et al., Combinatorial synthesis of novel and potent inhibitors of NADH: ubiquinone oxidoreductase. Chem Biol. Dec. 2000;7(12):979-92.

Ohira et al., Current and Future Clinical Applications of Cardiac Positron Emission Tomography. Circulation Journal. 2013;77(4):836-48.
Okun et al., Three classes of inhibitors share a common binding domain in mitochondrial complex I (NADH:ubiquinone oxidoreductase). J Biol Chem. Jan. 29, 1999;274(5):2625-30.
Paterson et al., Imaging Heart Failure; Current and Future Applications. Canadian Journal of Cardiology. 2013;29:317-28.
Paterson et al., Radionuclide ventriculography assessment of synchrony and entropy: Comparison of SPECT and planar techniques. European Heart Journal. 2011;13(Supplement A):A93-94. No. 419.
Pauwels et al., Fluorine-18-radiolabeled pharmaceuticals for imaging with positron emission tomography, excluding [18F]-fluorodeoxyglucose. Drugs of the Future. 2002;27:655-67.
Pike, PET radiotracers: crossing the blood-brain barrier and surviving metabolism. Trends Pharmacol Sci. Aug. 2009;30(8):431-40. doi: 10.1016/j.tips.2009.05.005. Epub Jul. 16, 2009.
Purohit et al., Quinazoline derivatives as MC-I inhibitors: evaluation of myocardial uptake using Positron Emission Tomography in rat and non-human primate. Bioorg Med Chem Lett. Sep. 1, 2007;17(17):4882-5. Epub Jun. 14, 2007.
Purohit et al., Synthesis and biological evaluation of pyridazinone analogues as potential cardiac positron emission tomography tracers. J Med Chem. May 22, 2008;51(10):2954-70. Epub Apr. 19, 2008.
Radeke et al., Synthesis and biological evaluation of the mitochondrial complex 1 inhibitor 2[4-(4-fluorobutyl)benzylsulfanyl]-3-methylchromene-4-one as a potential cardiac positron emission tomography tracer. J Med Chem. Sep. 6, 2007;50(18):4304-15. Epub Aug. 15, 2007.
Rahmim et al., Towards quantitative myocardial perfusion PET in the clinic. Journal of the American College of Radiology. 2014;11(4):429-32.
Ramsay et al., Interaction of 1-methyl-4-phenylpyridinium ion (MPP+) and its analogs with the rotenone/piericidin binding site of NADH dehydrogenase. J Neurochem. Apr. 1991;56(4):1184-90.
Ravert et al., Radiosynthesis of 3-[18F]fluoropropyl and 4-[18F]fluorobenzyl triarylphosphonium ions. J Lab Comp Radiopharm. 2004;47(8):469-76.
Rimoldi, Assessing the activity of cardiac sympathetic innervations with a novel PET tracer. European Journal of Nuclear Medicine and Molecular Imaging. 2012;39(12):1901-3.
Rischpler et al., Advances in PET myocardial perfusion imaging: F-18 labeled tracers. Annals of Nuclear Medicine. 2012;26(1):1-6.
Ritchie et al., Guidelines for clinical use of cardiac radionuclide imaging. Report of the American College of Cardiology/American Heart Association Task Force on Assessment of Diagnostic and Therapeutic Cardiovascular Procedures (Committee on Radionuclide Imaging), developed in collaboration with the American Society of Nuclear Cardiology. J Am Coll Cardiol. Feb. 1995;25(2):521-47.
Rubin et al., The cell biology of the blood-brain barrier. Annu Rev Neurosci. 1999;22:11-28.
Runge et al., MR Imaging of Rat Brain Glioma: Gd-DTPA versus Gd-DOTA. Radiology, vol. 166, No. 3, pp. 835-838 (1988).
Santi et al., Toxicology of rotenone. Farmaco Sci. Apr. 1965;20:270-9.
Saraste et al., PET: Is myocardial flow quantification a clinical reality? Journal of Nuclear Cardiology. 2012;19(5):1044-1059.
Schelbert et al., N-13 ammonia as an indicator of myocardial blood flow. Circulation. Jun. 1981;63(6):1259-72.
Schuler et al., Functional coupling of PSST and ND1 subunits in NADH: ubiquinone oxidoreductase established by photoaffinity labeling. Biochimica et Biophysica Acta, vol. 1506, pp. 79-87 (2001).
Schuler et al., The insecticide target in the PSST subunit of complex I. Pest Manag Sci. Oct. 2001;57(10):932-40.
Schyler, PET tracers and radiochemistry. Ann Acad Med Singapore. Mar. 2004;33(2):146-54.
Shaw et al., From adequate evidence to optimal evidence. JACC: Cardiovascular Imaging. 2012;5(12):1292-1293.

(56) References Cited

OTHER PUBLICATIONS

Sherif et al., Evaluation of a novel (18)F-labeled positron-emission tomography perfusion tracer for the assessment of myocardial infarct size in rats. Circulation: Cardiovascular Imaging. Mar. 2009;2(2):77-84.

Sherif et al., Evaluation of the novel PET perfusion tracer 18F BMS747158-02 for measurement of myocardial infarct size in a rat model. J Nucl Med. 2008; 49 (Supplement 1):186P.

Sherif et al., Reply: Simplified Quantification of Myocardial Flow Reserve with 18F-Flurpiridaz: Validation with Microspheres in a Pig Model. Journal of Nuclear Medicine. 2011;52(11): 1835-1836.

Sherif et al., Simplified quantification of myocardial flow reserve with flurpiridaz F-18: Validation with Microspheres in a pig model. Journal of Nuclear Medicine. 2011;52: 617-624.

Singh et al., A versatile route to 2-alkyl-/aryl-amino-3-formyl and heter-annelated-chromosones, through a facile nucleophilic substitution at C2 in 2-(N-methylanilino)-3-formylchromones. Tetrahedron. 2002;58(12):2471-80.

Sirion et al., An efficient F-18 labeling method for PET study: Huisgen 1,3-dipolar cycloaddition of bioactive substances and F-18-labeled compounds. Tetrahedron Letters. Jun. 4, 2007;48(23):3953-7.

Slomka et al., Multicenter development of normal perfusion and function limits for stress and rest flurpiridaz F-18 Cardiac PET. Journal of Nuclear Cardiology. 2010;17(4): 725. Abstract #9.14.

Soderquist et al., Reductive cleavage of acetals and ketals with 9-borabicyclo[3.3.1]nonane. Org Process Res Dev. 2006;10(5):1076-9.

Strauss et al., Society of Nuclear Medicine Procedure Guideline for Myocardial Perfusion Imaging. Soc. Nucl Med Pro Guide Man. Jun. 2002:9-17.

Strauss, Editorial Viewpoint: Myocardial Imaging for Mitochondrial Membrane Potential. Journal of the American College of Cardiology: Cardiovascular Imaging. 2012;5(3):293-96.

Suratkal et al., Treadmill ECG Test Combined with Myocardial Perfusion Imaging for Evaluation of Coronary Artery Disease : Analysis of 340 Cases. Journal of the Association of Physicians of India. Jun. 2003;51:561-4.

Takalkar et al., Cardiac assessment with PET. PET Clinics. 2011; 6(3): 313-326.

Talpade et al., In vivo labeling of mitochondrial complex I (NADH:ubiquinone oxidoreductase) in rat brain using [(3)H]dihydrorotenone. J Neurochem. Dec. 2000;75(6):2611-21.

Tamarappoo et al., Comparison of myocardial stress perfusion defect assessment using 99mTc Sestamibi SPECT vs 18F-BMS747158 PET. Journal of Nuclear Cardiology. 2010;17(4): 742. Abstract #31.14.

Tang et al., Automated commercial synthesis system for preparation of O-(2-[18F]fluoroethyl)-L-tyrosine by direct nucleophilic displacement on a resin column. J. Label Compd Radiopharm 2003; 46:661-668.

Tsukada et al., Novel PET Probes 18F-BCPP-EF and 18F-BCPP-BF for Mitochondrial Complex I: A PET Study in Comparison with 18F-BMS-747158-02 in Rat Brain. Journal of Nuclear Medicine. 2014;55:473-80.

Udelson, Advances in myocardial perfusion imaging. Journal of Nuclear Cardiology. 2012;19, SUPPL. 1:S1-S2.

Ueno et al., Comparison of the inhibitory action of natural rotenone and its stereoisomers with various NADH-ubiquinone reductases. Eur J Biochem. Oct. 1, 1994;225(1):411-7.

Ueno et al., Structural factors of rotenone required for inhibition of various NADH-ubiquinone oxidoreductases. Biochim Biophys Acta. Sep. 30, 1996;1276(3):195-202.

Unger, Pesticide synthesis handbook. Technology and Engineering. 1996:523-4. Google books result.

Vallabhajosula, Guest Editorial: New PET Radiopharmaceuticals as Molecular Imaging Probes. Seminars in Nuclear Medicine. 2011:244-5.

Vanbrocklin et al., (F-18)fluorodihydrorotenone: Synthesis and evaluation of a mitochondrial electron transport chain (ETC) complex I probe for PET. Journal of Nuclear Medicine, vol. 35, No. 5 Suppl., p. 73P (1994).

Vanbrocklin et al., Fluorine-18 labeled dihydrorotenone analogs: preparation and evaluation of PET mitochondrial probes. Journal of Labelled Compounds and Radiopharmaceuticals, Symposium abstracts (continue in part IV). 1994; 35:217-19.

Vanbrocklin et al., Mitochondrial avid radioprobes. Preparation and evaluation of 7'(Z)-[125I]iodorotenone and 7'(Z)-[125I]iodorotenol. Nucl Med Biol. Jan. 2007;34(1):109-16. Epub Nov. 28, 2006.

Volkov et al., Interaction of Acetals and Ortho-Ethers With Triisobutylaluminum. Zhurnal Organicheskoi KHIMII. Dec. 31, 1986; 22(8):1787-1788.

Von Schulthess et al., Clinical positron emission tomography/magnetic resonance imaging applications. Seminars in Nuclear Medicine. 2013;43(1):3-10.

Walker, The NADH: ubiquinone oxidoreductase (complex I) of respiratory chains. Quarterly Review of Biophysics, vol. 25, No. 3, pp. 253-324 (1992).

Wallace, A mitochondrial paradigm of metabolic and degenerative diseases, aging, and cancer: a dawn for evolutionary medicine. Annu Rev Genet. 2005;39:359-407.

Wang et al., Insights into amyloid-beta-induced mitochondrial dysfunction in Alzheimer disease. Free Radic Biol Med. Dec. 15, 2007;43(12):1569-73. Epub Sep. 21, 2007.

Wells et al., Comparison of attenuation, dual-energy window, and model-based scatter correction of low-count SPECT to 82Rb PET/CT quantified myocardial perfusion scores. Journal of Nuclear Cardiology. Published online: Jun. 5, 2013. 12 pages.

Woo et al., Automatic 3D registration of dynamic stress and rest (82)Rb and flurpiridaz F 18 myocardial perfusion PET data for patient motion detection and correction. Medical Physics. 2011;38(11): 6313-26.

Wood et al., Fenazaquin Acaricide Specific Binding Sites in NADH: Ubiquinone Oxidoreductase and Apparently the ATP Synthase Stalk. Pest Biochem Phys. Feb. 1996;54(2):135-45.

Yalamanchili et al., Mechanism of uptake and retention of F-18 BMS-747158-02 in cardiomyocytes: a novel PET myocardial imaging agent. J Nucl Cardiol. Nov.-Dec. 2007;14(6):782-8. Epub Oct. 22, 2007.

Yu et al., [18F]-RP1012: A Novel Myocardial Perfusion Imaging Agent for use with positron emission tomography (PET). Circulation Supplement 2, 112(17), 11-761, Abstract #3546, 2005.

Yu et al., A novel cardiac PET imaging agent. International Hospital Equipment and Solutions. 2009; 35(4):14-5.

Yu et al., Assessment of 18F-labeled mitochondrial complex I inhibitors as PET myocardial perfusion imaging agents in rats, rabbits, and primates. Eur J Nucl Med Mol Imaging. Jan. 2009;36(1):63-72. Epub Aug. 21, 2008.

Yu et al., BMS-747158-02: a novel PET myocardial perfusion imaging agent. Journal of Nuclear Cardiology, vol. 14. No. 6, pp. 789-798 (2007).

Yu et al., Cardiac imaging and safety evaluation of BMS747158, a novel PET myocardial perfusion imaging agent, in chronic myocardial compromised rabbits. J Nuclear Cardiology. 2010;17(4):631-6.

Yu et al., Cardiac imaging and uptake of BMS747158-02 under various experimental conditions. J Nucl Med. 2008; 49 (Supplement 1):187P.

Yu et al., Effects of Food Intake and Anesthetic on Cardiac Imaging and Uptake of BMS-747158-02 in Comparison with FDG. Journal Nuclear Cardiology. Sep.-Oct. 2009;16(5):763-8.

Yu et al., Evaluation of LMI1195, a Novel 18F-Labeled Cardiac Neuronal PET Imaging Agent, in Cells and Animal Models. Circulation: Cardiovascular Imaging 2011 4: 435-443.

Yu et al., In-vivo Assessment of Mitochondrial Complex-1 Inhibitors as Myocardial Perfusion Imaging Agents (MPIA). Circulation Supplement 2, 112 (17), II-474, Abstract #2283, 2005.

Yu et al., LMI119 PET imaging in evaluation of regional cardiac sympathetic denervation and its potential role in antiarrhythmic drug treatment. European Journal of Nuclear Medicine and Molecular Imaging. 2012;39(12):1910-1919.

(56) References Cited

OTHER PUBLICATIONS

Yu et al., Myocardial Perfusion Imaging with 18F-Chromone Based MC-1 Inhibitors. Molecular Imaging. 2006;5(3):372-3. Abstract ID: 642 Poster board space:105.

Yu et al., The next generation of cardiac positron emission tomography imaging agents: discovery of flurpiridaz f-18 for detection of coronary disease. Seminars Nucl Med. Jul. 2011;41(4):305-13.

Yu et al., Value of flurpiridaz F 18 myocardial SUV analysis in clinical assessment of intermediate to severe coronary stenosis. Journal of Nuclear Cardiology. 2013;20,Supplement 1: S44-S45.

Ziadi et al., The clinical utility of assessing myocardial blood flow using positron emission tomography. Journal of Nuclear Cardiology. 2010; 17:571-581.

Bax et al., $^{123}$I-mIBG scintigraphy to predict inducibility of ventricular arrhythmias on cardiac electrophysiology testing: a prospective multicenter pilot study. Circ Cardiovasc Imaging. Sep. 2008;1(2):131-40. Epub Jul. 30, 2008.

Laruelle et al., Relationships between radiotracer properties and image quality in molecular imaging of the brain with positron emission tomography. Mol. Imaging Biol. 2003;5(6):363-75.

Raffel et al., Radiolabeled phenethylguanidines: novel imaging agents for cardiac sympathetic neurons and adrenergic tumors. J Med Chem. May 3, 2007;50(9):2078-88. Epub Apr. 10, 2007.

Wieland et al., Adrenal medulla 1,2,7,11 imaging agents: a structure-distribution relationship study of radiolabeled aralkylguanidines. J Medic Chem. Feb. 1, 1984;27(2):149-55.

U.S. Appl. No. 16/828,119, filed Mar. 24, 2020, Radeke et al.

U.S. Appl. No. 16/663,425, filed Oct. 25, 2019, Cesati et al.

\* cited by examiner

METHODS AND APPARATUS FOR SYNTHESIZING IMAGING AGENTS, AND INTERMEDIATES THEREOF

RELATED APPLICATIONS

The present application is a continuation of U.S. patent application Ser. No. 15/433,387 filed on Feb. 15, 2017, entitled "Methods and Apparatus for Synthesizing Imaging Agents, and Intermediates Thereof", which is a continuation of U.S. patent application Ser. No. 14/561,594 filed on Dec. 5, 2014, entitled "Methods and Apparatus for Synthesizing Imaging Agents, and Intermediates Thereof", which is a continuation of U.S. patent application Ser. No. 13/577,674 filed on Nov. 26, 2012, entitled "Methods and Apparatus for Synthesizing Imaging Agents, and Intermediates Thereof", which is a national stage filing under 35 U.S.C. § 371 of International Application No. PCT/US2011/024109, filed on Feb. 8, 2011, entitled "Methods and Apparatus for Synthesizing Imaging Agents, and Intermediates Thereof", each of which is incorporated herein by reference. International Application No. PCT/US2011/024109 claims priority under 35 U.S.C. § 119(e) to U.S. provisional application, U.S. Ser. No. 61/302,477, filed Feb. 8, 2010, entitled "Methods and Apparatus for Synthesizing Contrast Agents, Including Radiolabeled Contrast Agents;" U.S. provisional application, U.S. Ser. No. 61/315,376, filed Mar. 18, 2010, entitled "Methods for Synthesizing Contrast Agents and Precursors Thereof;" and U.S. provisional application, U.S. Ser. No. 61/333,693, filed May 11, 2010, entitled "Compositions, Methods, and Systems for Imaging," each of which is incorporated herein by reference.

FIELD OF THE INVENTION

The present invention relates to systems, compositions, methods, and apparatuses for synthesizing imaging agents, and precursors thereof.

BACKGROUND OF THE INVENTION

Mitochondria are membrane-enclosed organelles distributed through the cytosol of most eukaryotic cells. Mitochondria are especially concentrated in myocardial tissue.

Complex 1 ("MC-1") is a membrane-bound protein complex of 46 dissimilar subunits. This enzyme complex is one of three energy-transducing complexes that constitute the respiratory chain in mammalian mitochondria. This NADH-ubiquinone oxidoreductase is the point of entry for the majority of electrons that traverse the respiratory chain, eventually resulting in the reduction of oxygen to water (*Q. Rev. Biophys.* 1992, 25, 253-324). Examples of inhibitors of MC-1 include deguelin, piericidin A, ubicidin-3, rolliniastatin-1, rolliniastatin-2 (bullatacin), capsaicin, pyridaben, fenpyroximate, amytal, MPP+, quinolines, and quinolones (BBA 1998, 1364, 222-235). Studies have shown that interrupting the normal function of mitochondria could advantageously concentrate certain compounds in the mitochondria, and hence in the mitochondria-rich myocardial tissue. Compounds that include an imaging moiety (e.g., $^{18}$F) can be useful in determining such a build-up of compounds, thereby providing valuable diagnostic markers for myocardial perfusion imaging. In addition, such compounds may find application for the diagnosis of coronary artery disease (CAD).

CAD is a major cause of death in modern industrialized countries and it has been found previously that assessments of regional myocardial perfusion at rest and during stress (exercise or pharmacologic coronary vasodilation) are valuable for noninvasive diagnosis of CAD. While myocardial perfusion imaging (MPI) with Positron Emission Tomography (PET) has been shown to be superior in some embodiments as compared to single photon emission computed tomography (SPECT), widespread clinical use of PET MPI has been limited by the previously available PET myocardial perfusion tracers.

Several PET blood flow tracers, such as rubidium-82 ($^{82}$Rb) chloride, nitrogen-13 ($^{13}$N) ammonia, and oxygen-15 ($^{15}$O) water, have been developed and validated for assessment of myocardial perfusion. $^{13}$N and $^{15}$O are cyclotron-produced isotopes with short half-lives. Therefore, their use is limited to facilities with an on-site cyclotron. Although $^{82}$Rb is a generator-produced tracer, its short half-life, the high cost of the generator, and the inability to perform studies in conjunction with treadmill exercise have made this tracer impractical for widespread use. Tracers that comprise $^{18}$F have, however, found potential application as imaging agents.

While current methods for preparing compounds comprising an imaging moiety include [$^{18}$F]-fluorination chemistry, many methods focus on nucleophilic [$^{18}$F]-fluorination chemistry using potassium fluoride (KF). Characteristically, these methods generate the elemental fluoride source through anion exchange between, for example, potassium carbonate ($K_2CO_3$) and a cyclotron-produced [$^{18}$F]-containing species, and often require addition of the aza-crown ether Kryptofix® 222 (4,7,13,16,21,24-hexaoxa-1,10-diazabicyclo[8.8.8]-hexacosane) to enhance reactivity. While suitable for production of clinical quantities, the moderate efficiency, demanding purification and complex implementation of such method may not be suitable for widespread commercial application.

Accordingly, improved methods, systems, and apparatuses are needed for the synthesis of imaging agents.

SUMMARY OF THE INVENTION

The invention provides, in a broad sense, methods for synthesizing imaging agents and their precursors, compounds that are imaging agents precursors, and methods of use thereof.

In one aspect, in invention provides a method of synthesizing an imaging agent comprising formula:

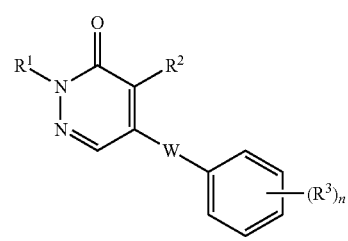

wherein W is alkyl or heteroalkyl, optionally substituted; $R^1$ is alkyl, optionally substituted; $R^2$ is hydrogen or halide; each $R^3$ can be the same or different and is alkyl optionally substituted with an imaging moiety or heteroalkyl optionally substituted with an imaging moiety; and n is 1, 2, 3, 4, or 5; the method comprising steps of: etherification of precursor compounds comprising formulae:

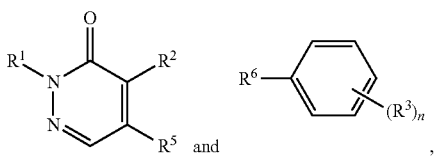 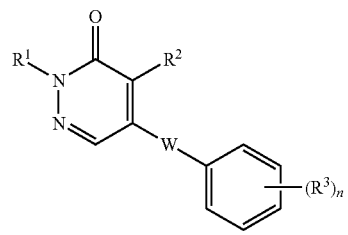

wherein n is 1, 2, 3, 4, or 5; $R^1$ is alkyl, optionally substituted; $R^2$ is hydrogen or halide; $R^3$ can be the same or different and are alkyl, heteroalkyl, or a carbonyl-containing group, each optionally substituted, $R^5$ is hydroxyl or halide; and $R^6$ is alkyl, heteroalkyl, or a carbonyl-containing group, each optionally substituted, wherein, when $R^5$ is hydroxyl, at least one of $R^6$ and $R^3$ comprises a leaving group; or wherein $R^5$ is halide, at least one of $R^6$ or $R^3$ comprises a hydroxyl, to produce a compound comprising formula:

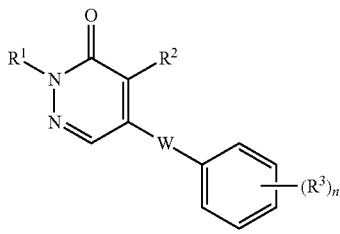

wherein W is alkyl or heteroalkyl, optionally substituted; $R^1$ is alkyl, optionally substituted; $R^2$ is hydrogen or halide; each $R^3$ can be the same or different and is alkyl optionally substituted with hydroxyl or heteroalkyl optionally substituted with hydroxyl; wherein at least one $R^3$ comprises hydroxyl; and n is 1, 2, 3, 4, or 5; $R^1$ is alkyl, optionally substituted; $R^2$ is hydrogen or halide; $R^3$ can be the same or different and are alkyl, heteroalkyl, or a carbonyl-containing group, each optionally substituted; reacting a compound comprising formula:

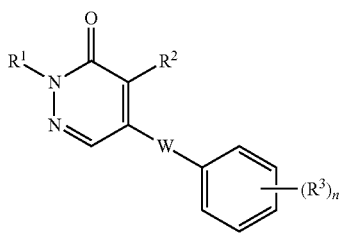

wherein W is alkyl or heteroalkyl, optionally substituted; $R^1$ is alkyl, optionally substituted; $R^2$ is hydrogen or halide; each $R^3$ can be the same or different and is alkyl optionally substituted with hydroxyl or heteroalkyl optionally substituted with hydroxyl; wherein at least one $R^3$ comprises hydroxyl; and n is 1, 2, 3, 4, or 5; with a sulfonate-containing species to produce a sulfonate-containing compound comprising formula:

wherein W is alkyl or heteroalkyl, optionally substituted; $R^1$ is alkyl, optionally substituted; $R^2$ is hydrogen or halide; each $R^3$ can be the same or different and is alkyl optionally substituted with a sulfonate-containing group or heteroalkyl optionally substituted with a sulfonate-containing group; wherein at least one $R^3$ comprises a sulfonate-containing group; and n is 1, 2, 3, 4, or 5; replacing the sulfonate-containing group of the sulfonate-containing compound with an imaging moiety to yield a compound comprising formula:

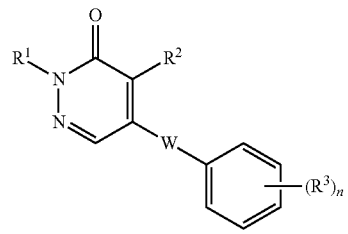

wherein W is alkyl or heteroalkyl, optionally substituted; $R^1$ is alkyl, optionally substituted; $R^2$ is hydrogen or halide; each $R^3$ can be the same or different and is alkyl optionally substituted with an imaging moiety or heteroalkyl optionally substituted with an imaging moiety; and n is 1, 2, 3, 4, or 5; provided that at least one fluorine species is present in the compound.

In one aspect, the invention provides a method for $^{18}F$-labeling a compound comprising formula:

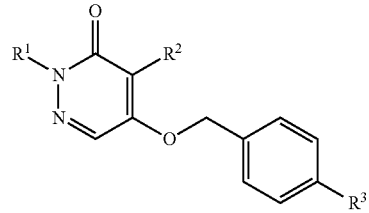

wherein $R^1$ is alkyl; $R^2$ is hydrogen or halogen; and $R^3$ is alkyl substituted with a sulfonate-containing group, alkoxy substituted with a sulfonate-containing group, or alkoxyalkyl substituted with a sulfonate-containing group. The method comprises reacting the compound with an $^{18}F$ species in the presence of an ammonium salt or a bicarbonate salt to form a product comprising the $^{18}F$ species.

In some embodiments, $R^3$ is alkoxyalkyl substituted with a sulfonate-containing group. In some embodiments, the sulfonate-containing group is mesylate, tosylate, triflate, or 1,2-cyclic sulfate. In some embodiments, $R^2$ is a halogen. In one embodiment, $R^2$ is chloride. In some embodiments, $R^1$ is a methyl, ethyl, propyl, n-butyl, s-butyl, or t-butyl. In some embodiments, $R^1$ is t-butyl. In some embodiments, the product comprises formula:

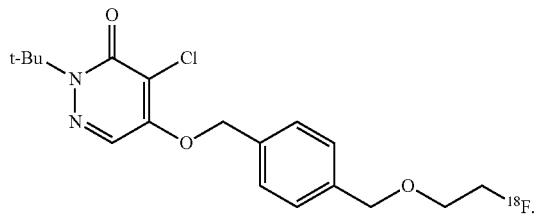

In another aspect, the invention provides a method for synthesizing a precursor to (or of) an imaging agent, comprising reacting a compound comprising formula (III) with a nucleophile, wherein formula (III) comprises the structure:

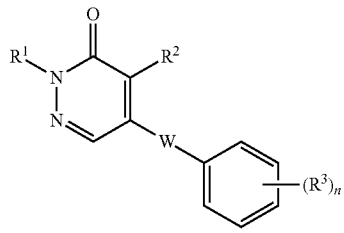

(III)

wherein W is alkyl or heteroalkyl, optionally substituted; $R^1$ is alkyl, optionally substituted; $R^2$ is hydrogen or halide; each $R^3$ can be the same or different and is an alkyl optionally substituted with a leaving group or heteroalkyl optionally substituted with a leaving group, provided $R^3$ comprises at least one leaving group; and n is 1, 2, 3, 4, or 5, provided at least one $R^3$ is substituted with a leaving group; with a nucleophile wherein the nucleophile replaces the at least one leaving group to produce a product (or precursor).

In some embodiments, the nucleophile is ethylene glycol. In some embodiments, reacting the compound with the nucleophile occurs in the presence of a base. The base may be but is not limited to a metal or a metal salt. The base may be sodium metal, sodium hydride, potassium t-butoxide, potassium carbonate, or potassium hydroxide. In some embodiments, the base is potassium t-butoxide or potassium hydroxide. In some embodiments, the base is potassium t-butoxide.

In some embodiments, reacting the compound with the nucleophile occurs in the presence of a catalyst. The catalyst may be a tetraalkylammonium iodide including but not limited to a tetraethylammonium iodide.

In some embodiments, the leaving group is a halide including but not limited to bromide.

In some embodiments, W is —O(CH$_2$)—; $R^1$ is t-butyl; $R^2$ is chloride; and $R^3$ is alkyl substituted with a leaving group.

In some embodiments, the compound comprising formula (III) comprises the structure:

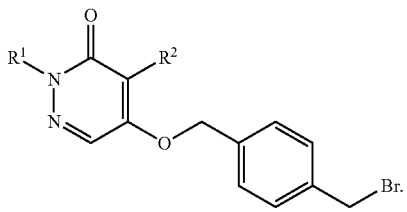

In some embodiments, the compound comprising formula (III) comprises the structure:

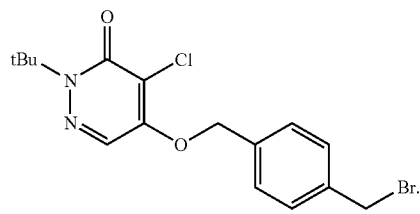 [SMILES: CC(C)(C)n1ncc(OCc2ccc(CBr)cc2)c(Cl)c1=O]

In some embodiments, the product (or precursor) comprises formula:

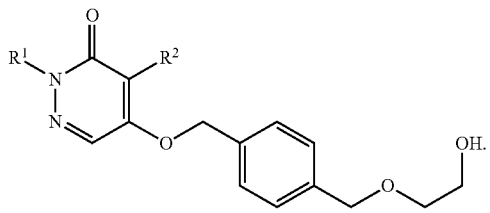

In some embodiments, the product (or precursor) comprises formula:

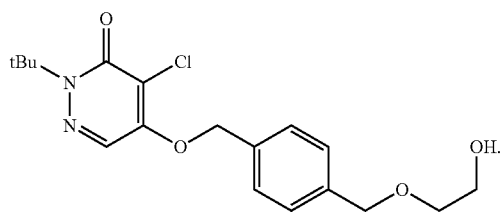 [SMILES: CC(C)(C)n1ncc(OCc2ccc(COCCO)cc2)c(Cl)c1=O]

In some embodiments, the method further comprises reacting a compound comprising formula (IV) with a reactant comprising a leaving group to produce the compound comprising formula (III), wherein formula (IV) comprises the structure:

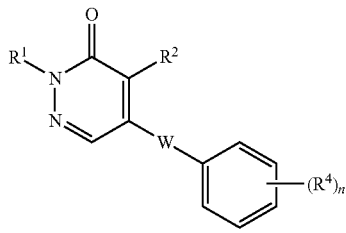

(IV)

wherein W is alkyl or heteroalkyl, optionally substituted; $R^1$ is alkyl, optionally substituted; $R^2$ is hydrogen or halide; each $R^4$ can be the same or different and is an alkyl optionally substituted with hydroxyl or heteroalkyl optionally substituted with hydroxyl; provided $R^4$ comprises at least one hydroxyl group; and n is 1, 2, 3, 4, or 5; and wherein the at least one hydroxyl is replaced with the leaving group.

In some embodiments, reacting the compound comprising formula (IV) is performed in the presence of a halogenation reagent. In some embodiments, the halogenation reagent is a brominating reagent. The brominating reagent may be phosphorus tribromide, pyridinium dibromide, or a combination of carbon tetrabromide and triphenylphospine, although it is not so limited.

In some embodiments, W is —O(CH$_2$)—; $R^1$ is t-butyl; $R^2$ is chloride; and $R^4$ is alkyl substituted with hydroxyl.

In some embodiments, the compound comprising formula (IV) comprises the structure:

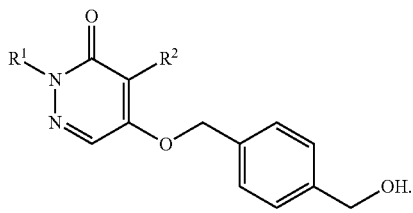

In some embodiments, the compound comprising formula (IV) comprises the structure:

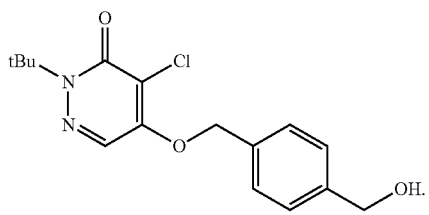 [SMILES: CC(C)(C)n1ncc(OCc2ccc(CO)cc2)c(Cl)c1=O]

In some embodiments, the product comprises formula:

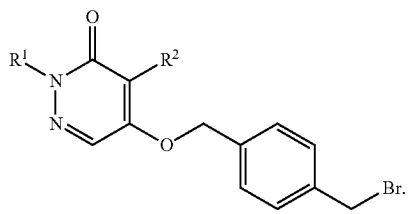

In some embodiments, the product comprises formula:

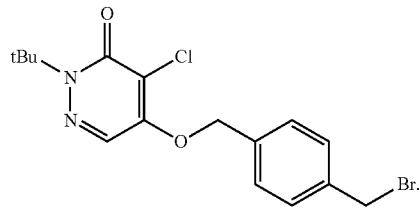 [SMILES: CC(C)(C)n1ncc(OCc2ccc(CBr)cc2)c(Cl)c1=O]

In some embodiments, the compound comprising formula (IV) is formed by etherification of precursor compounds comprising formulae (IVa) and (IVb):

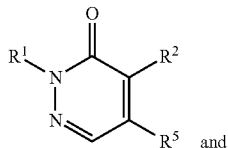

(IVa)

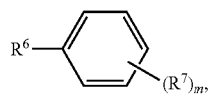

(IVb)

wherein m is 1, 2, 3, 4, or 5 or greater; $R^1$ is alkyl, optionally substituted; $R^2$ is hydrogen or halide; $R^5$ is hydroxyl or halide; and $R^6$ and $R^7$ can be the same or different and each is alkyl, heteroalkyl, or a carbonyl-containing group, each of which may be optionally and independently substituted, wherein when $R^5$ is hydroxyl at least one of $R^6$ and $R^7$ comprises a leaving group or a group that can be replaced by a leaving group, or when $R^5$ is halide, at least one of $R^6$ and $R^7$ comprise a hydroxyl.

In some embodiments, the compound comprising formula (IV) is formed by etherification of the compounds comprising formulae:

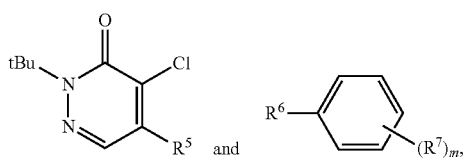

wherein m is 1 or greater; $R^1$ is alkyl, optionally substituted; $R^2$ is hydrogen or halide; $R^5$ is hydroxyl or halide; and $R^6$ and $R^7$ can be the same or different and each is alkyl, heteroalkyl, or a carbonyl-containing group, any of which may be substituted, wherein when $R^5$ is hydroxyl at least one of $R^6$ and $R^7$ comprises a leaving group or a group that can be replaced by a leaving group, or when $R^5$ is halide, at least one of $R^6$ and $R^7$ comprises a hydroxyl.

In some embodiment, the compound comprising formula (IV) is formed by etherification of precursor compounds comprising formulae (IVa) and (IVd):

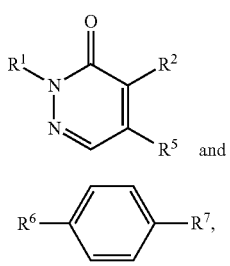

(IVa)

and (IVd)

wherein $R^1$ is alkyl, optionally substituted; $R^2$ is hydrogen or halide; $R^5$ is hydroxyl or halide; and $R^6$ and $R^7$ can be the same or different and each is alkyl, heteroalkyl, or a carbonyl-containing group, each of which may be optionally and independently substituted, wherein when $R^5$ is hydroxyl at least one of $R^6$ and $R^7$ comprises a leaving group, or when $R^5$ is halide, at least one of $R^6$ and $R^7$ comprises a hydroxyl.

In some embodiments, the compound comprising formula (IV) is formed by etherification of compounds comprising formulae:

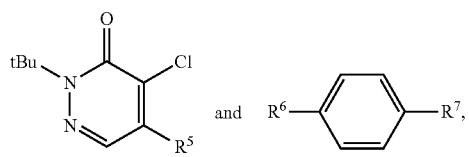

wherein $R^1$ is alkyl, optionally substituted; $R^2$ is hydrogen or halide; $R^5$ is hydroxyl or halide; and $R^6$ and $R^7$ can be the same or different and each is alkyl, heteroalkyl, or a carbonyl-containing group, any of which may be substituted, wherein when $R^5$ is hydroxyl at least one of $R^6$ and $R^7$ comprises a leaving group, or when $R^5$ is halide, at least one of $R^6$ and $R^7$ comprises a hydroxyl, or when $R^5$ is halide, at least one of $R^6$ and $R^7$ comprises a hydroxyl.

In some embodiments, the etherification comprises reacting the precursor compounds in the presence of a base. In some embodiments, the base comprises a carbonate ion.

In some embodiments, $R^5$ is halide; and $R^6$ and $R^7$ is each substituted alkyl.

In some embodiments, $R^5$ is chloride; and $R^6$ and $R^7$ is each alkyl substituted with a hydroxyl.

In some embodiments, the compound comprising formula (IV) is synthesized by etherification of precursor compounds comprising formulae:

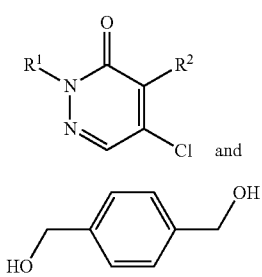

(IVe)

(IVf)

wherein $R^1$ is alkyl, optionally substituted; $R^2$ is hydrogen or halide; to form a product comprising formula:

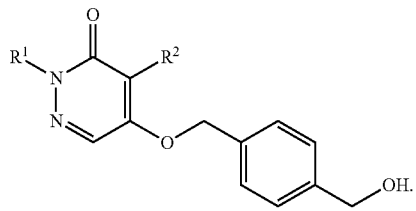

In some embodiments, the compound comprising formula (IV) is synthesized by etherification of compounds comprising formulae:

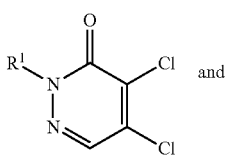

to form a product comprising formula:

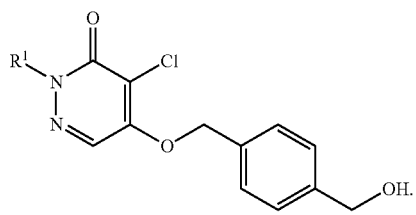

In some embodiments, $R^5$ is hydroxyl; and $R^6$ is a carbonyl-containing group and $R^7$ is a substituted alkyl. In some embodiments, $R^5$ is hydroxyl; and $R^6$ is an ester and $R^7$ is alkyl substituted with a leaving group.

In some embodiments, the compound comprising formula (IV) is synthesized by etherification of the compounds comprising formulae:

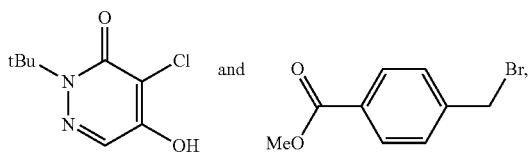 [SMILES: CC(C)(C)n1ncc(O)c(Cl)c1=O ; COC(=O)c1ccc(CBr)cc1]

to form a product comprising formula:

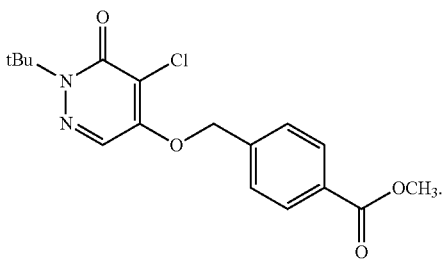 [SMILES: COC(=O)c1ccc(COc2cnn(C(C)(C)C)c(=O)c2Cl)cc1]

In some embodiments, the method further comprises exposing the product to a reducing agent to convert the ester group to an alcohol. The reducing agent may be lithium aluminum hydride, lithium borohydride, or diisobutylaluminum hydride (DIBAL-H), although it is not so limited.

In another aspect, the invention provides a method for synthesizing an imaging agent comprising contacting an imaging agent precursor with a fluoride species and an ammonium salt under conditions that result in the fluoride species replacing the leaving group to produce an imaging agent comprising the fluoride species wherein the molar ratio of ammonium salt to imaging agent precursor is less than 1.5:1, including about 1:1 or less.

In some embodiments, the molar ratio of ammonium salt to imaging agent precursor is about 1:1 or less, or about 0.75:1 or less, or about 0.5:1 or less, or about 0.25:1 or less, or about 0.05:1 or less. In some embodiments, the molar ratio of ammonium salt to imaging agent precursor is from about 1:1 to about 0.5:1. In some embodiments, the molar ratio of ammonium salt to imaging agent precursor ranges from about 1.4:1 to about 0.05:1.

In some embodiments, the ammonium salt is ammonium bicarbonate, ammonium hydroxide, ammonium acetate, ammonium lactate, ammonium trifluoroacetate, ammonium methanesulfonate, ammonium p-toluenesulfonate, ammonium nitrate, ammonium iodide, or ammonium bisulfate. In some embodiments, the ammonium salt is a tetraalkylammonium salt. The ammonium salt may be $R_4NHCO_3$, wherein R is alkyl. The ammonium salt may be $Et_4NHCO_3$.

In another aspect, the invention provides a method for synthesizing an imaging agent, comprising contacting an imaging agent precursor with a fluoride species and a bicarbonate salt under conditions that result in the fluoride species replacing the leaving group to produce an imaging agent comprising the fluoride species, wherein the molar ratio of bicarbonate salt to imaging agent precursor is less than 1.5:1, including about 1:1 or less.
In some embodiments, the molar ratio of bicarbonate salt to imaging agent precursor is about 1:1 or less, or about 0.75:1 or less, or about 0.5:1 or less, or about 0.25:1 or less, or about 0.05:1. In some embodiments, the molar ratio of bicarbonate salt to imaging agent precursor is from about 1:1 to about 0.5:1. In some embodiments, the molar ratio of bicarbonate salt to imaging agent precursor ranges from about 1.4:1 to about 0.05:1. In some embodiments, wherein the molar ratio of bicarbonate salt to imaging agent precursor is from about 0.5:1 to about 1:1.

In some embodiments, the bicarbonate salt is a metal bicarbonate. The bicarbonate salt may be sodium bicarbonate, calcium bicarbonate, potassium bicarbonate, or magnesium bicarbonate, although it is not so limited.

In some embodiments, the bicarbonate salt is ammonium bicarbonate. In some embodiments, the bicarbonate salt is an tetraalkylammonium bicarbonate. The bicarbonate salt comprises the formula $R_4NHCO_3$, wherein R is alkyl. The bicarbonate salt may be $Et_4NHCO_3$.

In some embodiments, the imaging agent precursor is further exposed to a cryptand, such as but not limited to 4,7,13,16,21,24-Hexaoxa-1,10-diazabicyclo[8.8.8]-hexacosane.

In some embodiments, contacting is performed in the absence of a carbonate salt such as but not limited to potassium carbonate.

In some embodiments, the contacting is performed in the absence of a cryptand, such as but not limited to 4,7,13,16,21,24-Hexaoxa-1,10-diazabicyclo[8.8.8]-hexacosane.

In another aspect, the invention provides a method for synthesizing an imaging agent, comprising contacting an imaging agent precursor with a fluoride species under conditions that result in the fluoride species replacing the leaving group to produce an imaging agent comprising the fluoride species, wherein the contacting is performed at a pH below 7. In some embodiments, the contacting is performed at a pH below 6, or at a pH below 5, or at a pH between 5 and 6.

In some embodiments, the leaving group is a sulfonate-containing group. The leaving group may be a mesylate, tosylate, triflate, or 1,2,-cyclic sulfate group. In some embodiments, the leaving group is a tosylate group. In some embodiments, the fluoride species is an $^{18}F$ ion.

In some embodiments, the imaging agent precursor comprises formula (I):

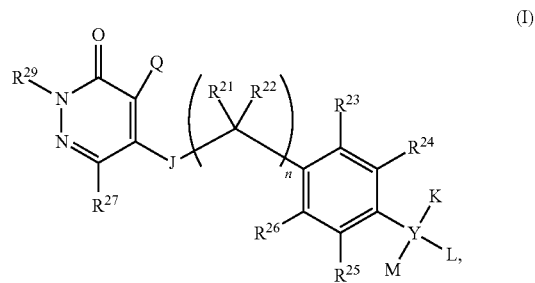

wherein J is selected from the group consisting of $N(R^{28})$, S, O, C(=O), C(=O)O, $NHCH_2CH_2O$, a bond, and C(=O)$N(R^{27})$; when present, K is selected from the group consisting of hydrogen, alkoxyalkyl optionally substituted with a leaving group, alkyloxy optionally substituted with a leaving group, aryl optionally substituted with a leaving group, $C_1$-$C_6$ alkyl optionally substituted with a leaving group, heteroaryl optionally substituted with a leaving group, and a leaving group; when present, L is selected from the group consisting of hydrogen, alkoxyalkyl optionally substituted with a leaving group, alkyloxy optionally substituted with a leaving group, aryl optionally substituted with a leaving group, $C_1$-$C_6$ alkyl optionally substituted with a leaving group, heteroaryl optionally substituted with a leaving group, and a leaving group; M is selected from the group consisting of hydrogen, alkoxyalkyl optionally substituted with a leaving group, alkyloxy optionally substituted with a leaving group, aryl optionally substituted with a leaving group, $C_1$-$C_6$ alkyl optionally substituted with a leaving group, heteroaryl optionally substituted with a leaving group, and a leaving group; or L and M, together with the atom to which they are attached, may form a three-, four-, five-, or six-membered carbocyclic ring; Q is halo or haloalkyl; n is 0, 1, 2, or 3; $R^{21}$, $R^{22}$, $R^{27}$, and $R^{28}$ are independently selected from hydrogen, $C_1$-$C_6$ alkyl optionally substituted with a leaving group, and a leaving group; $R^{23}$, $R^{24}$, $R^{25}$, and $R^{26}$ are independently selected from hydrogen, halogen, hydroxyl, alkyloxy, $C_1$-$C_6$ alkyl optionally substituted with a leaving group, and a leaving group; $R^{29}$ is $C_1$-$C_6$ alkyl optionally substituted with a leaving group; and Y is selected from the group consisting of a bond, carbon, and oxygen; provided that when Y is a bond, K and L are absent, and M is selected from the group consisting of aryl optionally substituted with a leaving group and heteroaryl optionally substituted with a leaving group; and provided that when Y is oxygen, K and L are absent, and M is selected from hydrogen, alkoxyalkyl optionally substituted with a leaving group, aryl optionally substituted with a leaving group, $C_1$-$C_6$ alkyl optionally substituted with a leaving group, and heteroaryl optionally substituted with a leaving group; provided that at least one leaving group is present in formula (I).

In some embodiments, the imaging agent comprises formula (II):

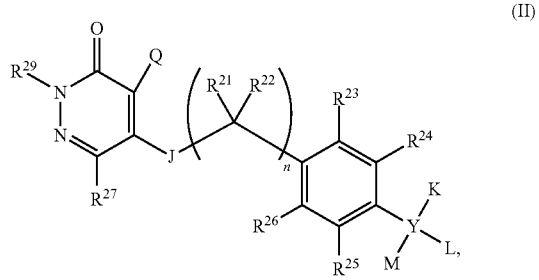

(II)

wherein J is selected from the group consisting of $N(R^{28})$, S, O, C(=O), C(=O)O, $NHCH_2CH_2O$, a bond, and C(=O)$N(R^{27})$; when present, K is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety; when present, L is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety; M is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety; or L and M, together with the atom to which they are attached, may form a three- or four-membered carbocyclic ring; Q is halo or haloalkyl; n is 0, 1, 2, or 3; $R^{21}$, $R^{22}$, $R^{27}$, and $R^{28}$ are independently selected from hydrogen, $C_1$-$C_6$ alkyl optionally substituted with an imaging moiety, and an imaging moiety; $R^{23}$, $R^{24}$, $R^{25}$, and $R^{26}$ are independently selected from hydrogen, halogen, hydroxyl, alkyloxy, $C_1$-$C_6$ alkyl optionally substituted with an imaging moiety, and an imaging moiety; $R^{29}$ is $C_1$-$C_6$ alkyl optionally substituted with an imaging moiety; and Y is selected from the group consisting of a bond, carbon, and oxygen; provided that when Y is a bond, K and L are absent, and M is selected from the group consisting of aryl optionally substituted with an imaging moiety and heteroaryl optionally substituted with an imaging moiety; and provided that when Y is oxygen, K and L are absent, and M is selected from hydrogen, alkoxyalkyl optionally substituted with an imaging moiety, aryl optionally substituted with an imaging moiety, $C_1$-$C_6$ alkyl optionally substituted with an imaging moiety, and heteroaryl optionally substituted with an imaging moiety; provided that at least one imaging moiety is present in formula (II), wherein the imaging moiety is $^{18}F$.

In some embodiments, J is O. In some embodiments, $R^{29}$ is methyl, ethyl, n-propyl, i-propyl, n-butyl, i-butyl, or t-butyl, each optionally substituted with a leaving group. In some embodiments, $R^{29}$ is t-butyl. In some embodiments, Q is chloro. In some embodiments, each of $R^{21}$, $R^{22}$, $R^{23}$, $R^{24}$, $R^{25}$, $R^{26}$, and $R^{27}$ is hydrogen.

In some embodiments, Y is carbon, K and L are hydrogen, and M is selected from the group consisting of alkoxyalkyl optionally substituted with a leaving group, alkyloxy optionally substituted with a leaving group, aryl optionally substituted with a leaving group, $C_1$-$C_6$ alkyl optionally substituted with a leaving group, heteroaryl optionally substituted with a leaving group, and a leaving group.

In some embodiments, Y is carbon, K and L is each hydrogen, and M is alkyloxy optionally substituted with a leaving group.

In some embodiments, the imaging agent precursor comprises formula:

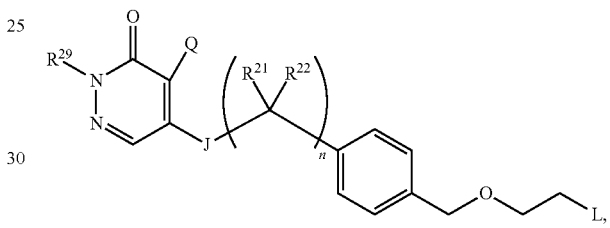

wherein L is a leaving group.

In some embodiments, the imaging agent comprises formula:

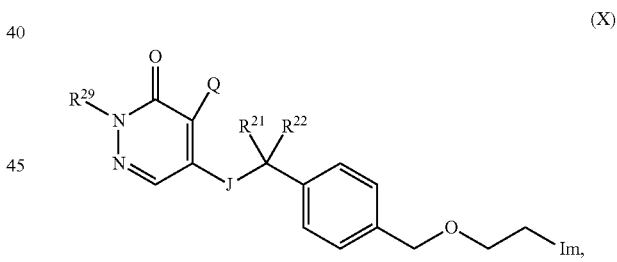

(X)

wherein Im is an imaging moiety.

In some embodiments, the imaging agent precursor comprises:

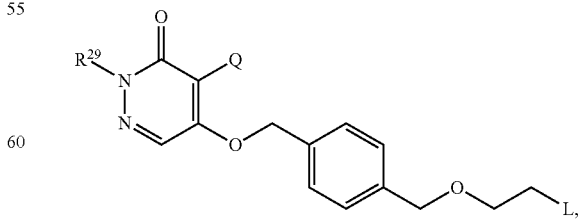

wherein L is a leaving group.

In some embodiments, the imaging agent comprises formula:

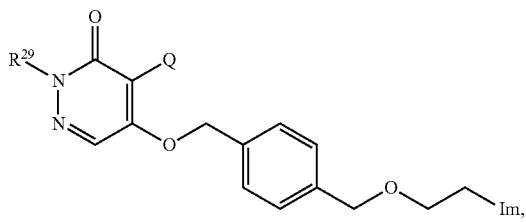

wherein Im is an imaging moiety.

In some embodiments, the imaging agent precursor comprises formula:

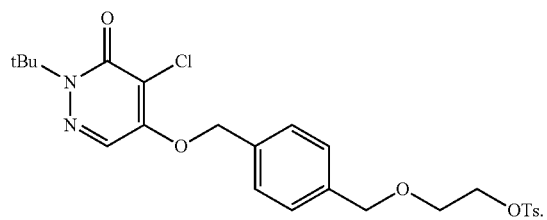 [SMILES: Cc1ccc(S(=O)(=O)OCCOCc2ccc(COc3cnn(C(C)(C)C)c(=O)c3Cl)cc2)cc1]

In some embodiments, the imaging agent comprising the fluoride species comprises formula:

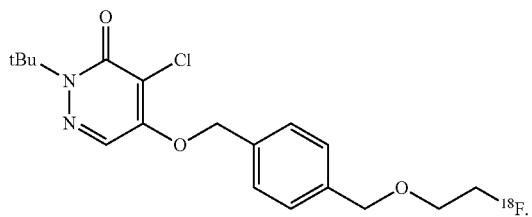

In some embodiments, the method further comprises purifying the imaging agent using at least one purification technique. In some embodiments, the purification technique is chromatography such as but not limited to HPLC. In some embodiments, the purification technique is filtration such as but not limited to filtration through a C-18 resin.

In some embodiments, the method further comprises combining the imaging agent with a stabilizing agent. In some embodiments, the stabilizing agent is ascorbic acid, or a salt thereof In another aspect, the invention provides a method for manufacturing an imaging agent comprising formula:

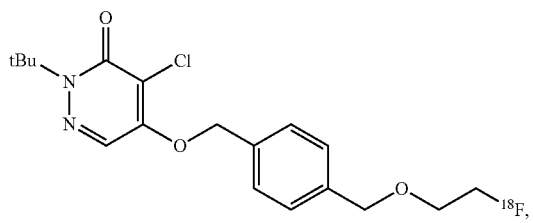

the method comprising, (a) contacting a tosylate precursor comprising formula:

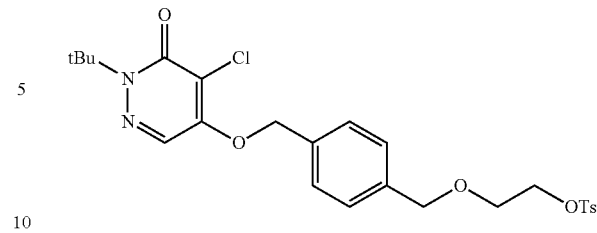

with an anhydrous fluoride species associated with an ammonium salt; (b) heating the mixture of (a); (c) cooling the heated mixture; (d) adding H$_2$O to the cooled mixture; (e) purifying the mixture from the hydrated mixture of (d) using HPLC with an H$_2$O/MeCN eluent; and (f) diluting the eluent with a solution of ascorbic acid or a salt thereof.

In some embodiments, step (b) comprises heating the mixture to a temperature between 50° C. and 250° C. In some embodiments, step (b) comprises heating the mixture for less than 5 minutes, less than 10 minutes, less than 20, minutes, or less than 30 minutes.

In some embodiments, the method further comprises (g) contacting the diluted eluent of (f) with a C18 resin; (h) washing the contacted C18 resin with a solution of ascorbic acid or a salt thereof; (i) eluting

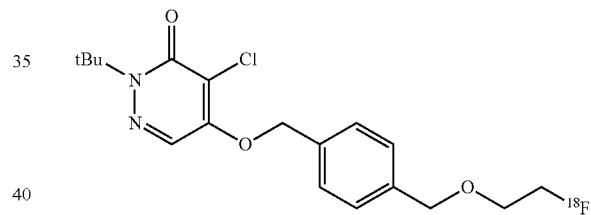

from the C18 resin with absolute ETOH; and (j) diluting the eluent of (i) with a solution or ascorbic acid or a salt thereof.

In some embodiments, the method further comprises (k) aseptically filtering the diluted eluent of (j), and (l) optionally, determining the presence of

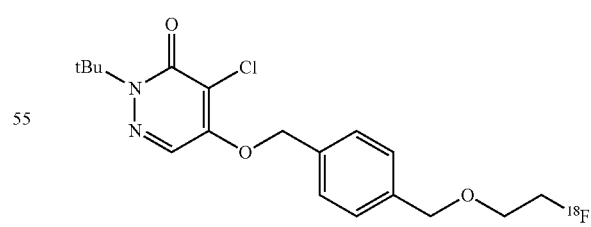

in a sample of the aseptic filtrate of (k).

In other aspects, the invention provides imaging agents made by any of the preceding methods.

Thus, in one aspect, the invention provides an imaging agent comprising formula:

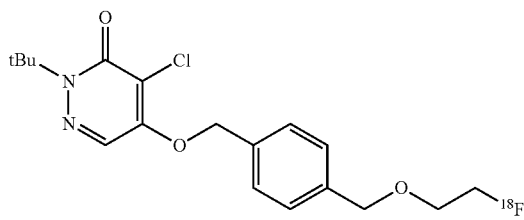 [SMILES: CC(C)(C)n1ncc(OCc2ccc(COCC[18F])cc2)c(Cl)c1=O]

wherein the imaging agent is manufactured by (a) contacting a tosylate precursor comprising formula:

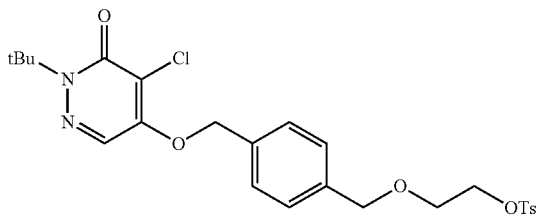 [SMILES: Cc1ccc(S(=O)(=O)OCCOCc2ccc(COc3cnn(C(C)(C)C)c(=O)c3Cl)cc2)cc1]

with an anhydrous fluoride species associated with an ammonium salt; (b) heating the mixture of (a); (c) cooling the heated mixture; (d) adding H₂O to the cooled mixture; (e) purifying the mixture from the hydrated mixture of (d) using HPLC with an H₂O/MeCN eluent; and (f) diluting the eluent with a solution of ascorbic acid or a salt thereof.

In some embodiments, step (b) comprises heating the mixture to a temperature between 50° C. and 250° C. In some embodiments, step (b) comprises heating the mixture less than 5 minutes, less than 10 minutes, less than 20, minutes, or less than 30 minutes.

In some embodiments, the manufacturing further comprises (g) contacting the diluted eluent of (f) with a C18 resin; (h) washing the contacted C18 resin with a solution of ascorbic acid or a salt thereof; (i) eluting

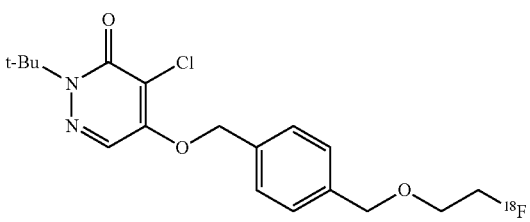 [SMILES: CC(C)(C)n1ncc(OCc2ccc(COCC[18F])cc2)c(Cl)c1=O]

from the C18 resin with absolute ETOH; and (j) diluting the eluent of (i) with a solution of ascorbic acid or a salt thereof.

In some embodiments, the manufacturing further comprises: (k) aseptically filtering the diluted eluent of (j), and (l) optionally, determining the presence of

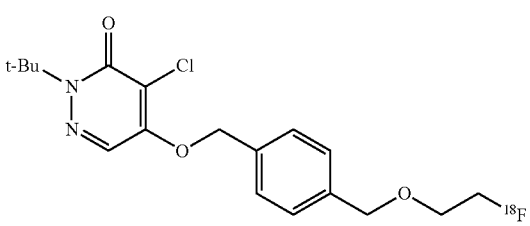 [SMILES: CC(C)(C)n1ncc(OCc2ccc(COCC[18F])cc2)c(Cl)c1=O]

in a sample of the aseptic filtrate of (k).

In another aspect, the invention provides a method for synthesizing a fluorinated compound, comprising reacting, in the presence of a carbonate or bicarbonate, (i) a precursor of the fluorinated compound comprising an alkoxyalkyl group substituted with a halide or a sulfonate-containing group, with (ii) a salt comprising a fluoride species and weakly coordinating cation.

In some embodiments, the alkoxyalkyl group is substituted with a sulfonate-containing group. In some embodiments, the sulfonate-containing group is mesylate, tosylate, triflate or 1,2-cyclic sulfate. In some embodiments, the sulfonate-containing group is tosylate. In some embodiments, the weakly coordinating cation is a tetraalkylammonium cation. In some embodiments, the fluoride species is enriched for $^{18}F$ isotope.

In another aspect, the invention provides a method for synthesizing a fluorinated compound comprising reacting, in the presence of a carbonate or bicarbonate, (i) a precursor of the fluorinated compound comprising an alkoxyalkyl substituted with a halide or a sulfonate-containing group, with (ii) an $^{18}F$ isotope.

In another aspect, the invention provides a method for synthesizing a fluorinated compound, comprising reacting (i) a precursor of the fluorinated compound comprising an alkoxyalkyl substituted with a halide or a sulfonate-containing group, with (ii) an $^{18}F$ isotope, in the presence of a tetraalkylammonium bicarbonate or tetraalkylammonium carbonate. In some embodiments, the reaction is carried out in the presence of a tetraalkylammonium bicarbonate.

In some embodiments, the tetraalkylammonium bicarbonate is tetraethylammonium bicarbonate, tetrabutylammonium bicarbonate, or tetrahexylammonium bicarbonate.

In another aspect, the invention provides a method for $^{18}F$-labeling comprising formula:

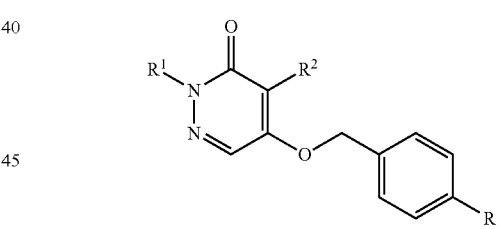

wherein R is -lower alkyl-sulfonate, $R^1$ is an $C_1$-$C_{10}$ alkyl, and $R^2$ is H or a halogen, comprising reacting the compound with $^{18}F$ in the presence of a tetraalkylammonium bicarbonate or tetraalkylammonium carbonate. In some embodiments, R is —(CH₂)O(CH₂)ₙ-sulfonate-containing group, wherein n is an integer from 1 to 5. In some embodiments, the sulfonate-containing group is mesylate, tosylate, triflate, or 1,2-cyclic sulfate. In some embodiments, $R^2$ is a halogen. In some embodiments, $R^2$ is chloride. In some embodiments, $R^1$ is methyl, ethyl, propyl or butyl. In some embodiments, $R^1$ is t-butyl. In some embodiments, R is —CH₂—O—CH₂—CH₂-tosylate, $R^1$ is t-butyl and $R^2$ is chloride.

In another aspect, the invention provides a method for synthesizing a precursor to an imaging agent, comprising reacting a compound comprising formula (V):

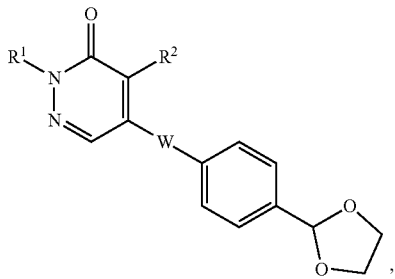

wherein W is alkyl or heteroalkyl, optionally substituted; $R^1$ is alkyl, optionally substituted; and $R^2$ is hydrogen or halide; with a nucleophile or a radical species to produce a compound comprising formula (VI):

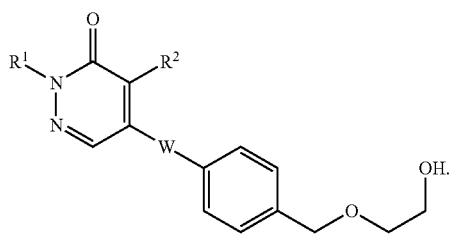

In some embodiments, the nucleophile is a hydride ion. In some embodiments, the hydride ion is generated from diisobutylaluminum hydride (DIBAL-H). In some embodiments, the radical species is H•.

In some embodiments, the compound comprising formula (V) wherein W is —OCH$_2$— is synthesized by etherification of precursor compounds comprising formulae (Va) and (Vb):

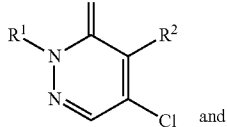

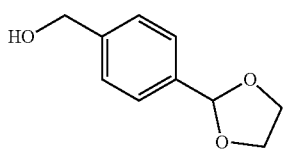

to form a product comprising formula:

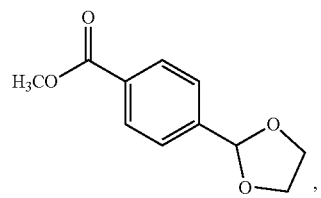 [SMILES: COC(=O)c1ccc(C2OCCO2)cc1]

In some embodiments, $R^1$ is t-butyl and $R^2$ is Cl.

In some embodiments, etherification comprises reacting the precursor compounds in the presence of a base. In some embodiments, the base comprises a carbonate ion. In some embodiments, the base comprises a hydroxide ion. In some embodiments, the base is sodium hydroxide or tetramethyl ammonium hydroxide. In some embodiments, the etherification reaction comprises exposure to sodium hydroxide and benzyl triethylammonium chloride.

In some embodiments, the compound comprising formula (Vb) is produced by exposing the compound comprising formula:

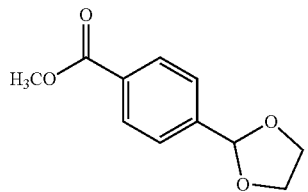 [SMILES: COC(=O)c1ccc(C2OCCO2)cc1]

to a reducing agent. In some embodiments, the reducing agent is lithium aluminum hydride or lithium borohydride. In some embodiments, the reducing agent is lithium aluminum hydride.

In some embodiments, the compound comprising formula:

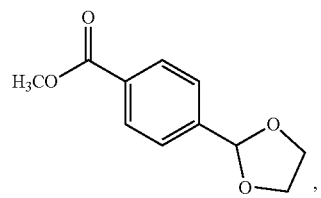 [SMILES: COC(=O)c1ccc(C2OCCO2)cc1]

is produced by reacting methyl 4-formyl benzoate with ethylene glycol in the presence of an acid.

In another aspect, the invention provides a method for forming a sulfonate-containing precursor of an imaging agent, comprising reacting a compound comprising formula:

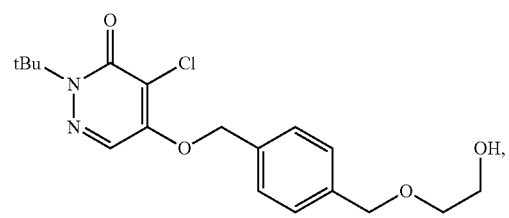 [SMILES: CC(C)(C)n1ncc(OCc2ccc(COCCO)cc2)c(Cl)c1=O]

with a sulfonate-containing species to form a product comprising a sulfonate-containing precursor of an imaging agent.

In some embodiments, the sulfonate-containing group is mesylate, tosylate, or triflate. In some embodiments, the sulfonate-containing group is tosylate. In some embodiments, the sulfonate-containing precursor of an imaging agent comprising the formula:

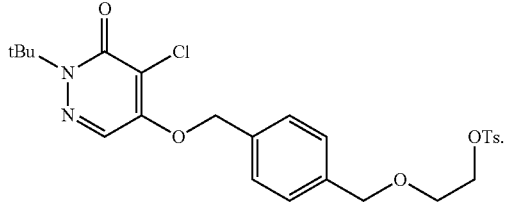 [SMILES: Cc1ccc(S(=O)(=O)OCCOCc2ccc(COc3cnn(C(C)(C)C)c(=O)c3Cl)cc2)cc1]

In some cases, the sulfonate-containing precursor is reacted with an imaging moiety to form an imaging agent.

In some embodiments, the imaging moiety is a radioisotope. In some embodiments, the imaging moiety is $^{11}$C, $^{13}$N, $^{18}$F, $^{123}$I, $^{125}$I, $^{99m}$Tc, $^{95}$Tc, $^{111}$In, $^{62}$Cu, $^{64}$Cu, $^{67}$Ga, or $^{68}$Ga. In some embodiments, the imaging moiety is $^{18}$F.

In some embodiments, the imaging agent has the structure:

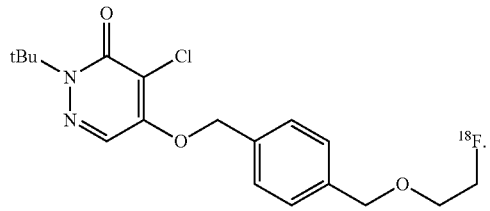

In another aspect, the invention provides a method for synthesizing an imaging agent, comprising reacting precursor compounds comprising formulae:

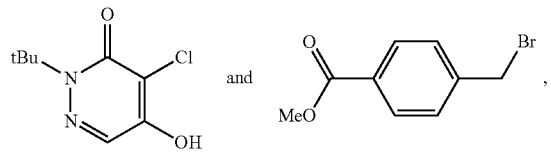 [SMILES: CC(C)(C)n1ncc(O)c(Cl)c1=O ; COC(=O)c1ccc(CBr)cc1]

via an etherification reaction to form a first compound comprising the formula:

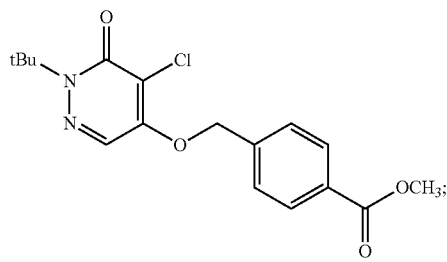 [SMILES: COC(=O)c1ccc(COc2cnn(C(C)(C)C)c(=O)c2Cl)cc1]

exposing the first compound to a reducing agent to form a second compound comprising a benzylic alcohol; treating the second compound with phosphorus tribromide to form a third compound comprising a benzylic bromide; reacting the third compound with ethylene glycol to produce a fourth compound comprising the formula:

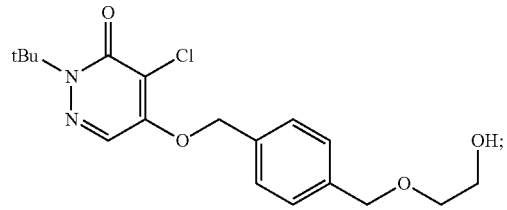 [SMILES: CC(C)(C)n1ncc(OCc2ccc(COCCO)cc2)c(Cl)c1=O]

and reacting the fourth compound with a sulfonate-containing species to form a product comprising a sulfonate-containing precursor of an imaging agent. In some cases, the method further comprises reacting the sulfonate-containing precursor of an imaging agent with an imaging moiety to form the imaging agent.

In another aspect, the invention provides a compound having the structure:

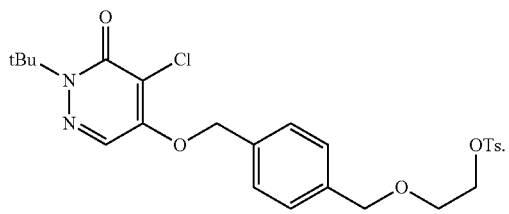 [SMILES: Cc1ccc(S(=O)(=O)OCCOCc2ccc(COc3cnn(C(C)(C)C)c(=O)c3Cl)cc2)cc1]

wherein the compound is synthesized using any of the preceding methods.

In another aspect, the invention provides a compound comprising formula:

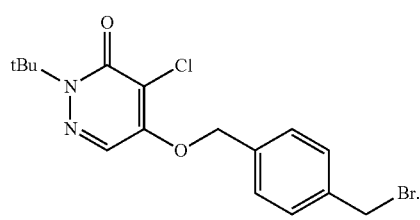 [SMILES: CC(C)(C)n1ncc(OCc2ccc(CBr)cc2)c(Cl)c1=O]

In another aspect, the invention provides a compound comprising formula:

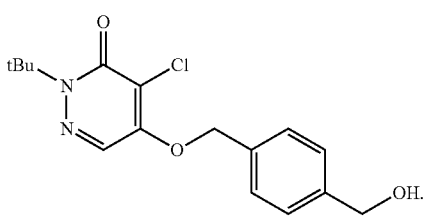 [SMILES: CC(C)(C)n1ncc(OCc2ccc(CO)cc2)c(Cl)c1=O]

In another aspect, the invention provides a compound comprising formula:

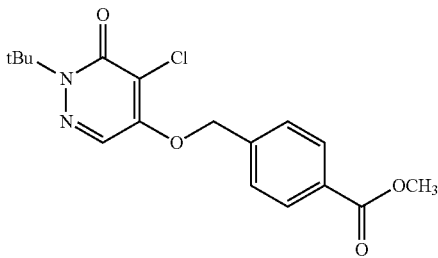 [SMILES: COC(=O)c1ccc(COc2cnn(C(C)(C)C)c(=O)c2Cl)cc1]

In another aspect, the invention provides a compound comprising formula:

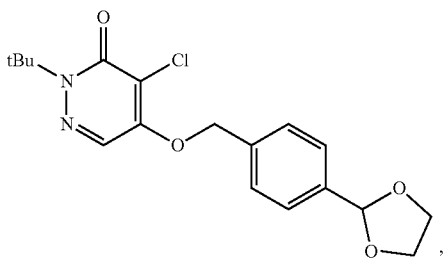 [SMILES: CC(C)(C)n1ncc(OCc2ccc(C3OCCO3)cc2)c(Cl)c1=O]

In another aspect, the invention provides a method of imaging a subject, comprising administering to a subject a first dose of imaging agent comprising the formula:

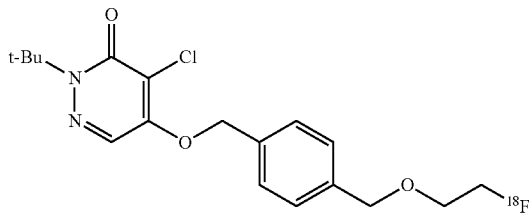 [SMILES: CC(C)(C)n1ncc(OCc2ccc(COCC[18F])cc2)c(Cl)c1=O]

in an amount between about 1 mCi and about 4 mCi; acquiring at least one first image of a portion of the subject; subjecting the subject to stress; administering to the subject undergoing stress a second dose of the imaging agent in an amount greater than the first dose of the imaging agent by at least about 1.5 times the first dose of the imaging agent; and acquiring at least one second image of the portion of the subject.

In some embodiments, the second dose of the imaging agent is administered within less than about 48 hours, 24 hours, 18 hours, 12 hours, 6 hours, 5 hours, 4 hours, 3 hours, 2 hours, 1 hour, 30 minutes, or 15 minutes after acquiring the at least one first image. In some embodiments, the second dose of the imaging agent is at least 2.0 times greater than the first dose of the imaging agent. In some embodiments, the first image is obtained during an image acquisition period between 1 and 20 minutes. In some embodiments, the second image is obtained during an image acquisition period between 1 and 20 minutes. In some embodiments, the portion of the subject is at least a portion of the cardiovascular system. In some embodiments, the portion of the cardiovascular system is at least a portion of the heart. In some embodiments, the acquiring employs positron emission tomography.

In some embodiments, the method further comprises determining the presence or absence of a cardiovascular disease or condition in the subject. In some embodiments, the cardiovascular disease is coronary artery disease or myocardial ischemia.

In some embodiments, the imaging agent is administered as a formulation comprising water, less than about 5% ethanol, and less than about 50 mg/mL sodium ascorbate. In some embodiments, the formulation comprising the imaging agent is administered via an intravenous bolus injection. In some embodiments, the stress is induced by exercising the subject. In some embodiments, the second dose of the imaging agent is administered during the exercise.

In some embodiments, the first dose of the imaging agent is between about 1.0 mCi to about 2.5 mCi. In some embodiments, the first dose of the imaging agent is between about 1.7 mCi to about 2.0 mCi. In some embodiments, the first dose of the imaging agent is between about 2.5 to about 3.0 mCi.

In some embodiments, the wait time between acquiring at least one first image of a portion of the subject and administering to the subject a second dose of the imaging agent is 60 minutes. In some embodiments, the second dose of the imaging agent is administered in an amount that is at least 2.5, or at least 3.0 times greater than the first dose of the imaging agent. In some embodiments, the second dose of the imaging agent is administered in an amount between 2.5 and about 5.0, or 2.5 and 4.0, or 3.0 and 4.0 time greater, or between 3.0 and 5.0 times greater than the first dose of the imaging agent. In some embodiments, the second dose of the imaging agent is between about 8.6 mCi and about 9.0 mCi, or between about 8.6 mCi and about 9.5 mCi, or between about 9.0 to about 9.5 mCi.

In some embodiments, the stress is pharmacological stress. In some embodiments, the pharmacological stress is induced by administering a pharmacological stress agent to the subject. In some embodiments, the pharmacological stress agent is a vasodilator. In some embodiments, the vasodilator is adenosine. In some embodiments, the second dose of the imaging agent is administered after the subject has been administered the pharmacological stress agent. In some embodiments, the second dose of the imaging agent is administered when the subject is at peak vasodilation from the pharmacological stress agent.

In some embodiments, the first dose of the imaging agent is between about 2.0 mCi to about 3.5 mCi. In some embodiments, the first dose of the imaging agent is between about 2.4 mCi to about 3.0 mCi or between about 2.4 mCi to about 2.9 mCi. In some embodiments, the first dose of the imaging agent is between about 2.5 mCi to about 3.0 mCi or between about 2.5 mCi and about 3.5 mCi.

In some embodiments, the wait time between acquiring at least one first image of a portion of the subject and administering to the subject a second dose of the imaging agent is 30 minutes. In some embodiments, the second dose of the imaging agent is administered in an amount at least 2.0 times greater than the first dose of the imaging agent. In some embodiments, the second dose of the imaging agent is administered in an amount that is between 2 to 3 times greater than the first dose of the imaging agent, including 2.1, 2.2, 2.3, 2.4, 2.5, 2.6, 2.7, 2.8, or 2.9 times greater.

In some embodiments, the second dose of the imaging agent is between about 5.7 mCi and about 6.2 mCi. In some embodiments, the second dose of the imaging agent is between about 6.0 mCi and about 6.5 mCi or between about 5.7 mCi and about 6.5 mCi. In some embodiments, the total of the first and second dose of the imaging agent does not exceed about 14 mCi.

In another aspect, the invention provides a syringe comprising a composition comprising the imaging agent comprises the formula:

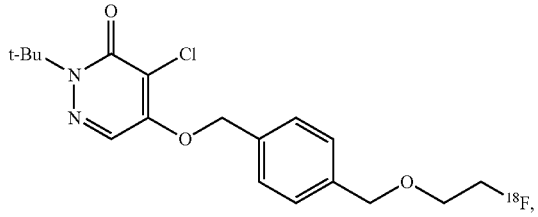

wherein the syringe adsorbs less than 20%, 19%, 18%, 17%, 16%, 15%, 14%, 13,% 12%, 11%, 10%, 9%, 8%, 7%, 6%, 5%, 4%, 3%, 2%, 1%, or 0.5% of the imaging agent. In some cases, the syringe adsorbs between about 1% and about 20%, or between about 5% and about 15%, or between about 1% and about 15%, or between 2% and about 10%, or between about 5% and about 20%.

In some embodiments, the syringe comprises a plunger that adsorbs less than 20%, 19%, 18%, 17%, 16%, 15%, 14%, 13,% 12%, 11%, 10%, 9%, 8%, 7%, 6%, 5%, 4%, 3%, 2%, 1%, or 0.5% of the imaging agent. In some embodiments, the syringe comprises a plunger that is not rubber-tipped. In some embodiments, the syringe is a latex-free syringe. In some embodiments, the syringe comprises no rubber, and no silicon lubricants. In some embodiments, the syringe is a non-reactive syringe. In some cases, the syringe adsorbs between about 1% and about 20%, or between about 5% and about 15%, or between about 1% and about 15%, or between 2% and about 10%, or between about 5% and about 20%.

In some embodiments, the syringe further comprises sodium ascorbate, ethanol, and water. In some embodiments, the imaging agent is in a solution comprising less than 4% ethanol and less than 50 mg/mL sodium ascorbate in water.

In some embodiments, the imaging agent is present in the syringe in a dose between about 1.5 and about 14 mCi.

In another aspect, the invention provides a method of imaging a subject, comprising subjecting a subject to stress; administering to the subject a first dose of an imaging agent comprising the formula:

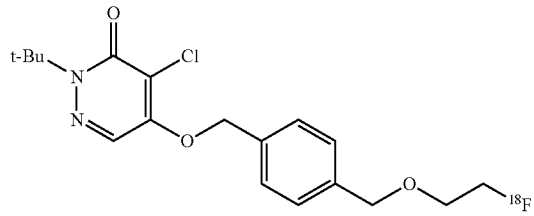 [SMILES: CC(C)(C)n1ncc(OCc2ccc(COCC[18F])cc2)c(Cl)c1=O]

in an amount between about 1 mCi and about 4 mCi; acquiring at least one first image of a portion of the subject; administering to the subject a second dose of the imaging agent in an amount greater than the first dose of the imaging agent; and acquiring at least one second image of the portion of the subject.

In some embodiments, the amount of the second dose is more than 1.5 times the amount of the first dose.

In another aspect, the invention provides a method of imaging a subject, comprising subjecting a subject to stress; administering to the subject a dose of an imaging agent comprising formula:

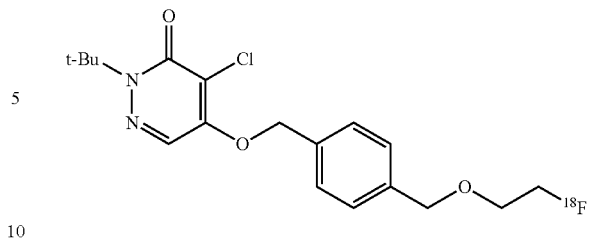

in an amount less 20 mCi; and acquiring at least one first image of a portion of the subject.

In some embodiments, the amount of the dose is less than 14 mCi. In some embodiments, the amount of the dose is between 1 mCi and 4 mCi.

In another aspect, the invention provides a cassette for the preparation of an imaging agent comprising formula:

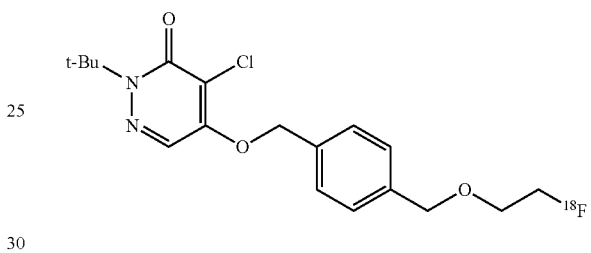

comprising: (i) a vessel containing an imaging agent precursor comprising formula:

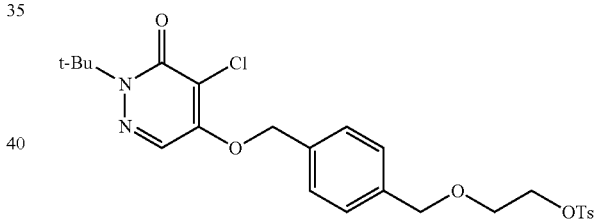

and (ii) a conduit for adding a source of $^{18}$F.

In another aspect, the invention provides an automated reaction system, comprising:

the foregoing cassette. In another aspect, the invention provides an apparatus for synthesizing an imaging agent comprising a linear arrangement of a plurality of stopcock manifolds connected one or more of the components selected from the group consisting of a [$^{18}$O]H$_2$O recovery system, gas inlet, reservoir with solution of imaging agent precursor, vial, anion exchange cartridge, C-18 cartridge, syringe, solvent reservoir, reaction vessel, HPLC system, collection vessel, reservoir for solution of ascorbic acid or salt thereof, and exhaust outlet.

In some embodiments, the apparatus further comprising tubing. In some embodiment, the apparatus further comprising an imaging agent synthesis module, wherein the apparatus is fluidically connected to the apparatus. In some embodiments, the apparatus is capable of carrying out the method as described herein. In some embodiments, the apparatus is capable of preparing an imaging agent comprising formula:

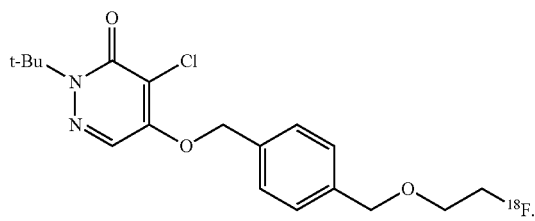

In some embodiments, the invention provides an apparatus comprising the components arranged as shown in FIG. 8. In some cases, the components are arranged in the order: (1) gas inlet; (2) [$^{18}$O]H$_2$O recovery system; (3) anion exchange cartridge; (4) MeCN reservoir; (5) syringe; (6) reservoir with solution of imaging agent precursor; (7) reaction vessel; (8) HPLC system; (9) reservoir with solution of ascorbic acid or a salt thereof; (10) collection vessel; (11) ethanol reservoir; (12) vial with final product; (13) Sep-pack cartridge; (14) reservoir with solution of ascorbic acid or a salt thereof; (15) reaction vessel; and (16) exhaust outlet.

Figure 1:
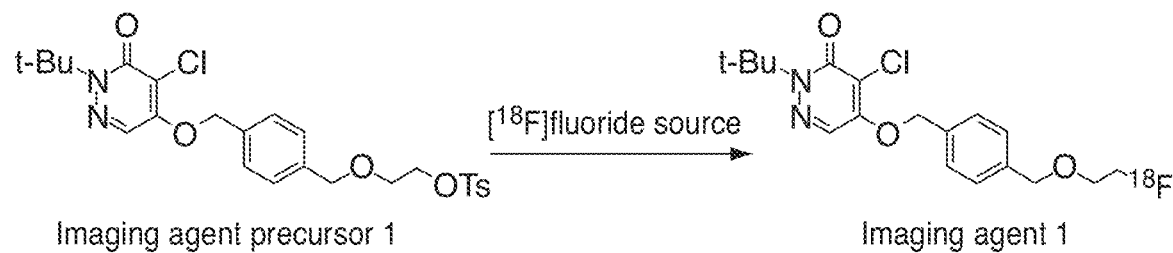
FIG. 1 shows an example of a nucleophilic [$^{18}$F]-fluorination reaction using an imaging agent precursor and a fluoride source to form an imaging agent.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION OF CERTAIN EMBODIMENTS OF THE INVENTION

The present invention generally relates to systems, compositions, cassettes, methods, and apparatuses for the synthesis of imaging agents and precursors thereof. In some aspects the invention relates to imaging agents synthesized using methods described herein.

In some embodiments, the present invention relates to methods for synthesizing an imaging agent, for example, by reacting an imaging agent precursor with a source of an imaging moiety. As described herein, in some cases, the method involves the use of one or more additives (e.g., salts) that may facilitate a chemical reaction. The methods may exhibit improved yields and may allow for the widespread synthesis of imaging agents, including imaging agents comprising a radioisotope (e.g., $^{18}$F). The imaging agents may be useful as sensors, diagnostic tools, and the like. Synthetic methods for preparing an imaging agent have also been designed to use an automated synthesis system to prepare and purify imaging agents that comprise a radioisotope. In some aspects, the invention allows radiolabeled imaging agents to be made using a nucleophilic reaction system, including, but not limited to, the Explora GN or RN synthesis system (Siemens Medical Solutions USA, Inc.), GE-Tracerlab-MX synthesis system (GE Healthcare), Eckert & Zeigler Modular-Lab Synthesis system, etc., which are commonly available at PET manufacturing facilities (PMF).

In some embodiments, the present invention provides methods for synthesizing an imaging agent precursor, wherein the imaging agent precursor is reacted with a source of an imaging moiety to form the imaging agent. As will be understood by those of ordinary skill in the art, it is advantageous to utilize methods which involve high-yielding reactions and a relatively low number of synthetic and/or purification steps. Accordingly, many of the methods provided herein for synthesizing an imaging agent precursor provide the imaging agent precursor in fewer steps than previously reported, with greater ease of synthesis and/or at a higher yield.

In some embodiments, the present invention provides methods of imaging, including methods of imaging in a subject that includes administering a composition or formulation (e.g., that comprises imaging agent 1, as described herein) to the subject by injection, infusion, or any method of administration, and imaging a region of the subject that is of interest. Regions of interest may include, but are not limited to, the heart, cardiovascular system, cardiac vessels, blood vessels (e.g., arteries, veins), brain, and other organs. A parameter of interest, such as blood flow, cardiac wall motion, or perfusion, can be imaged and detected using methods and/or systems of the invention. In some cases, methods for evaluating perfusion, including myocardial perfusion, are provided.

As used herein, the term "imaging agent" refers to any species that includes at least one atom, or group of atoms, that may generate a detectable signal itself, or upon exposure to an external source of energy (e.g., electromagnetic radiation, ultrasound, etc.). Typically, the imaging agent may be administered to a subject in order to provide information relating to at least a portion of the subject (e.g., human). In some cases, an imaging agent may be used to highlight a specific area of a subject, rendering organs, blood vessels, tissues, and/or other portions more detectable and more clearly imaged. By increasing the detectability and/or image quality of the object being studied, the presence and extent of disease and/or injury can be determined. The imaging agent may include a radioisotope for nuclear medicine imaging. A non-liming example of an imaging agent, also referred herein as imaging agent 1, comprises the formula:

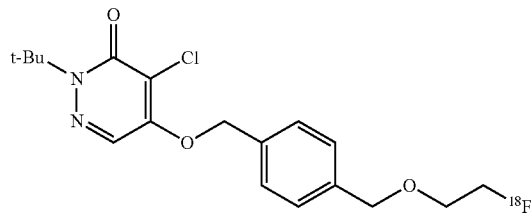 [SMILES: CC(C)(C)n1ncc(OCc2ccc(COCC[18F])cc2)c(Cl)c1=O]

As used herein, an "imaging moiety" refers to an atom or group of atoms that is capable of producing a detectable signal itself or upon exposure to an external source of energy (e.g., imaging agents comprising imaging moieties may allow for the detection, imaging, and/or monitoring of the presence and/or progression of a condition), pathological disorder, and/or disease. Nuclear medicine imaging agents can include $^{11}$C, $^{13}$N, $^{18}$F, $^{123}$I, $^{125}$I, $^{99m}$Tc, $^{95}$Tc, $^{111}$In, $^{62}$Cu, $^{64}$Cu, $^{67}$Ga, and $^{68}$Ga as the imaging moiety. In some embodiments, the imaging moiety is $^{18}$F. Imaging agents based on $^{18}$F have been used for imaging hypoxia and cancer (*Drugs of the Future* 2002, 27, 655-667).

In some embodiments, a compound (e.g., an imaging agent, a fluoride species) may be isotopically-enriched with fluorine-18. "Isotopically-enriched" refers to a composition containing isotopes of an element such that the resultant isotopic composition is other than the natural isotopic composition of that element. With regard to the compounds provided herein, when a particular atomic position is designated as $^{18}$F, it is to be understood that the abundance of $^{18}$F at that position is substantially greater than the natural abundance of $^{18}$F, which is essentially zero. In some embodiments, a fluorine designated as $^{18}$F may have a minimum isotopic enrichment factor of about 0.01%, about 0.05%, about 0.1%, about 0.2%, about 0.3%, about 0.4%, about 0.5%, about 0.75%, about 1%, about 2%, about 3%, about 4%, about 5%, about 10%, about 15%, about 20%, about 30%, about 40%, about 50%, about 60%, about 70%, about 80%, about 90%, about 95%, or greater. The isotopic enrichment of the compounds provided herein can be determined using conventional analytical methods known to one of ordinary skill in the art, including mass spectrometry and HPLC.

Exemplary Methods for Synthesizing Imaging Agents

The present invention provides methods for synthesizing imaging agents. In some cases, the imaging agent is formed by reacting an imaging agent precursor with an imaging moiety. In certain embodiments, a method involves reacting between an imaging agent precursor comprising a leaving group with a source of an imaging moiety (e.g., a fluoride species).

For example, the imaging moiety replaces the leaving group via a substitution reaction, such as an $S_N2$ or $S_N1$ reaction. That is, during the reaction an imaging moiety replaces the leaving group, thereby producing the imaging agent.

The methods described herein may be used for the synthesis of a wide variety of imaging agents from an imaging agent precursor. Generally, the imaging agent precursor may include at least one leaving group that may be displaced by an imaging moiety, such as an $^{18}$F species. Imaging agent precursors may be synthesized using methods known to those of ordinary skill in the art and as described below.

In some embodiments, the imaging agent precursor comprises formula (I):

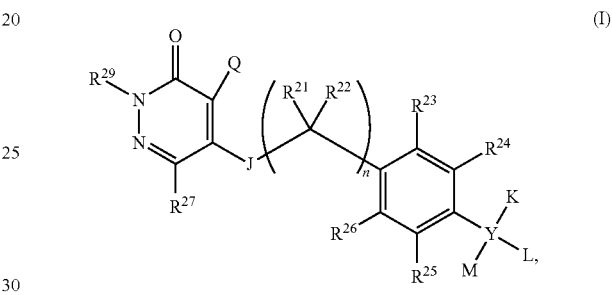

wherein:

J is selected from the group consisting of $N(R^{28})$, S, O, $C(=O)$, $C(=O)O$, $NHCH_2CH_2O$, a bond, and $C(=O)N(R^{27})$;

when present, K is selected from the group consisting of hydrogen, alkoxyalkyl optionally substituted with a leaving group, alkyloxy optionally substituted with a leaving group, aryl optionally substituted with a leaving group, $C_1$-$C_6$ alkyl optionally substituted with a leaving group, heteroaryl optionally substituted with a leaving group, and a leaving group;

when present, L is selected from the group consisting of hydrogen, alkoxyalkyl optionally substituted with a leaving group, alkyloxy optionally substituted with a leaving group, aryl optionally substituted with a leaving group, $C_1$-$C_6$ alkyl optionally substituted with a leaving group, heteroaryl optionally substituted with a leaving group, and a leaving group;

M is selected from the group consisting of hydrogen, alkoxyalkyl optionally substituted with a leaving group, alkyloxy optionally substituted with a leaving group, aryl optionally substituted with a leaving group, $C_1$-$C_6$ alkyl optionally substituted with a leaving group, heteroaryl optionally substituted with a leaving group, and a leaving group; or L and M, together with the atom to which they are attached, may form a three-, four-, five-, or six-membered carbocyclic ring;

Q is halo or haloalkyl;

n is 0, 1, 2, or 3;

$R^{21}$, $R^{22}$, $R^{27}$, and $R^{28}$ are independently selected from hydrogen, $C_1$-$C_6$ alkyl optionally substituted with a leaving group, and a leaving group;

$R^{23}$, $R^{24}$, $R^{25}$, and $R^{26}$ are independently selected from hydrogen, halogen, hydroxyl, alkyloxy, $C_1$-$C_6$ alkyl optionally substituted with a leaving group, and a leaving group;

$R^{29}$ is $C_1$-$C_6$ alkyl optionally substituted with a leaving group; and

Y is selected from the group consisting of a bond, carbon, and oxygen; provided that when Y is a bond, K and L are absent, and M is selected from the group consisting of aryl optionally substituted with a leaving group and heteroaryl optionally substituted with a leaving group; and provided that when Y is oxygen, K and L are absent, and M is selected from hydrogen, alkoxyalkyl optionally substituted with a leaving group, aryl optionally substituted with a leaving group, $C_1$-$C_6$ alkyl optionally substituted with a leaving group, and heteroaryl optionally substituted with a leaving group;

provided that at least one leaving group is present in formula (I).

In some embodiments, a method of the present invention comprises preparing an imaging agent comprising formula (II):

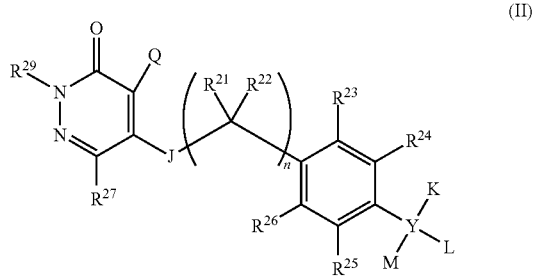

(II)

wherein:

J is selected from the group consisting of $N(R^{28})$, S, O, C(=O), C(=O)O, $NHCH_2CH_2O$, a bond, and C(=O)N($R^{27}$);

when present, K is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety;

when present, L is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety;

M is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety; or L and M, together with the atom to which they are attached, may form a three-, four-, five-, or six-membered carbocyclic ring;

Q is halo or haloalkyl;

n is 0, 1, 2, or 3;

$R^{21}$, $R^{22}$, $R^{27}$, and $R^{28}$ are independently selected from hydrogen, $C_1$-$C_6$ alkyl optionally substituted with an imaging moiety, and an imaging moiety;

$R^{23}$, $R^{24}$, $R^{25}$, and $R^{26}$ are independently selected from hydrogen, halogen, hydroxyl, alkyloxy, $C_1$-$C_6$ alkyl optionally substituted with an imaging moiety, and an imaging moiety;

$R^{29}$ is $C_1$-$C_6$ alkyl optionally substituted with an imaging moiety; and Y is selected from the group consisting of a bond, carbon, and oxygen; provided that when Y is a bond, K and L are absent, and M is selected from the group consisting of aryl optionally substituted with an imaging moiety and heteroaryl optionally substituted with an imaging moiety; and provided that when Y is oxygen, K and L are absent, and M is selected from hydrogen, alkoxyalkyl optionally substituted with an imaging moiety, aryl optionally substituted with an imaging moiety, $C_1$-$C_6$ alkyl optionally substituted with an imaging moiety, and heteroaryl optionally substituted with an imaging moiety;

provided that at least one imaging moiety is present in formula (II). That is, the imaging agent comprising formula (II) is formed from an imaging agent precursor comprising formula (I), wherein a leaving group of the imaging agent precursor comprising formula (I) is replaced by an imaging moiety. In some embodiments, the imaging moiety is $^{18}F$.

In some cases, J is selected from $N(R^{27})$, S, O, C(=O), C(=O)O, $NHCH_2CH_2O$, a bond, or C(=O)N($R^{27}$). In some cases when present, K is selected from hydrogen, alkoxyalkyl optionally substituted with a leaving group, alkyloxy, aryl, $C_1$-$C_6$ alkyl optionally substituted with a leaving group, heteroaryl, and a leaving group. In some cases, when present, L is selected from hydrogen, alkoxyalkyl optionally substituted with a leaving group, alkyloxy, aryl, $C_1$-$C_6$ alkyl optionally substituted with a leaving group, heteroaryl, and a leaving group. In some case, M is selected from hydrogen, alkoxyalkyl optionally substituted with a leaving group, alkyloxy, aryl, $C_1$-$C_6$ alkyl optionally substituted with a leaving group, heteroaryl, and a leaving group. In some cases, L and M, together with the atom to which they are attached, form a three- or four-membered carbocyclic ring. In some cases Q is halo or haloalkyl. In some cases, n is 0, 1, 2, or 3. In some cases, $R^{21}$, $R^{22}$, $R^{23}$, $R^{24}$, $R^{25}$, $R^{26}$, and $R^{27}$ are independently selected from hydrogen, $C_1$-$C_6$ alkyl optionally substituted with a leaving group, and a leaving group. In some cases $R^{29}$ is $C_1$-$C_6$ alkyl optionally substituted with a leaving group. In some cases, Y is selected from a bond, carbon, and oxygen; provided that when Y is a bond, K and L are absent and M is selected from aryl and heteroaryl; and provided that when Y is oxygen, K and L are absent and M is selected from hydrogen, alkoxyalkyl optionally substituted with a leaving group, aryl, $C_1$-$C_6$ alkyl optionally substituted with a leaving group, and heteroaryl.

In some cases, J is O. In some cases $R^{29}$ is methyl, ethyl, n-propyl, i-propyl, n-butyl, i-butyl, or t-butyl, each may be optionally substituted with a leaving group. In certain embodiment, $R^{29}$ is t-butyl. In some cases, Q is chloro. In some cases, all of $R^{21}$, $R^{22}$, $R^{23}$, $R^{24}$, $R^{25}$, $R^{26}$, and $R^{27}$ are hydrogen. In some cases, Y is carbon, K and L are hydrogen, and M is alkoxyalkyl optionally substituted with a leaving group, alkyloxy optionally substituted with a leaving group, aryl optionally substituted with a leaving group, $C_1$-$C_6$ alkyl optionally substituted with a leaving group, heteroaryl optionally substituted with a leaving group, or a leaving group. In some cases, Y is carbon, K and L are hydrogen, and M is alkyloxy optionally substituted with a leaving group.

In some embodiments, the imaging agent precursor comprises the formula:

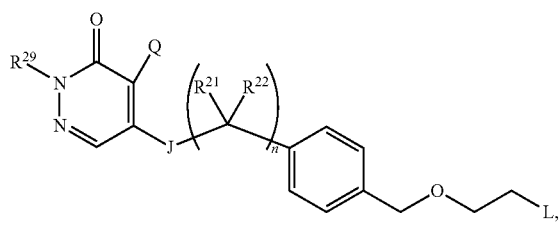

wherein $R^{21}$, $R^{22}$, $R^{29}$, Q, J, and n are as described herein, and L is a leaving group.

In some embodiments, the imaging agent comprises the formula:

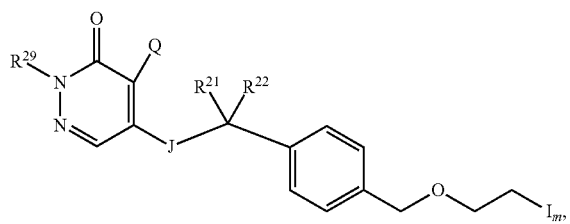

wherein $R^{21}$, $R^{22}$, $R^{29}$, Q, J, and n are as described herein, and $I_m$ is an imaging moiety.

In some embodiments, the imaging agent precursor comprises the formula:

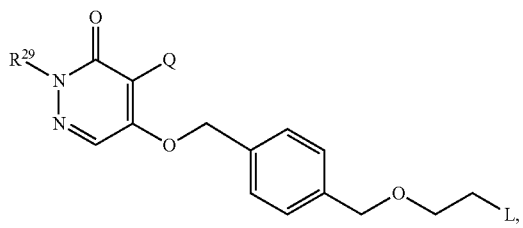

wherein $R^{29}$ and Q are as described herein, and L is a leaving group.

In some embodiments, the imaging agent comprises the formula:

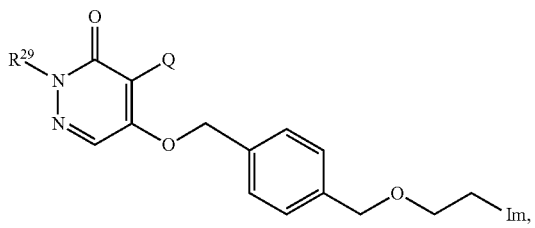

wherein $R^{29}$ and Q are as described herein, and Im is an imaging moiety.

In one set of embodiments, the imaging agent precursor comprises the formula:

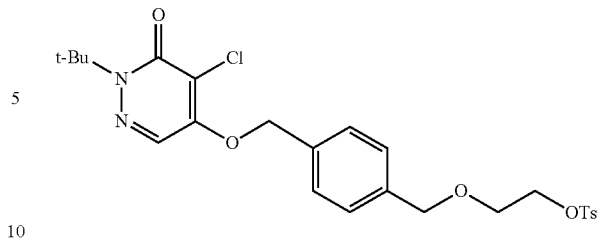

herein referred to as imaging agent precursor 1 (see FIG. 1).

In some cases, the imaging agent comprises the formula:

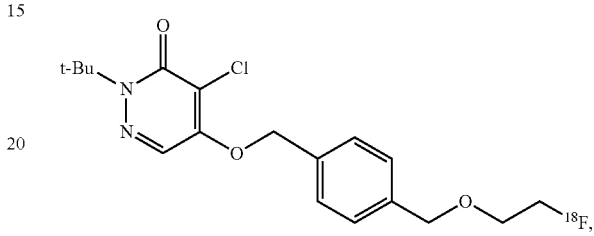

herein referred to as imaging agent 1 (see FIG. 1).

Figure 10:
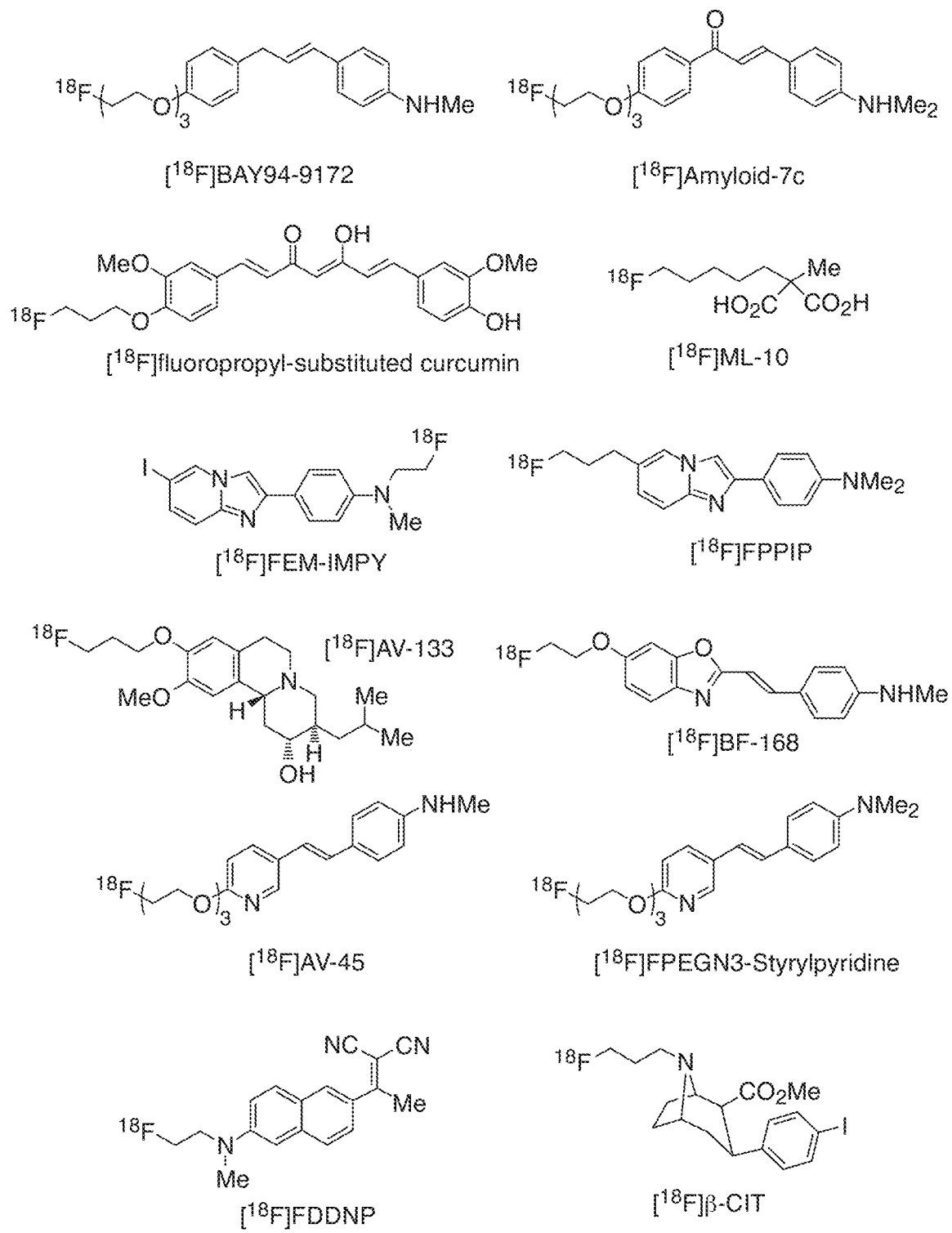
FIG. 10 illustrates non-limiting examples of imaging agents which may be prepared using the fluorination methods as described herein, in some embodiments.

Other non-limiting examples of imaging agents that may be prepared using a fluorination methods of the present invention are shown in FIG. 10. In some cases, the imaging agent precursor is not a salt.

Various methods may be used to synthesize an imaging agent precursor of the formula (I), including an etherification reaction (e.g., Mitsonobu reaction) between two alcohols, or between a phenol and an alcohol. In some cases, a leaving group may be installed by conversion of a hydroxyl group into a tosylate group or other leaving group, for example, by reaction with p-toluenesulfonate chloride in the presence of a base (e.g., DMAP). Additional methods for the synthesis of an imaging agent having the structure comprising formula (II) or an imaging agent precursor having the structure comprising formula (I) are described in International Publication No. WO2005/079391, the contents of which are incorporated herein by reference.

In some embodiments, a method for synthesizing an imaging agent comprises contacting an imaging agent precursor (e.g., a compound comprising formula (I)) with a fluoride species and an ammonium salt under conditions that result in the fluoride species replacing the leaving group to produce an imaging agent (e.g., a compound comprising formula (II)) comprising the fluorine species wherein the molar ratio of ammonium salt to imaging agent precursor is less than about 1.5:1, or about 1:1 or less (or any ratio described herein).

In some embodiments, a method for synthesizing an imaging agent comprises contacting an imaging agent precursor (e.g., a compound comprising formula (I)) with a fluoride species and a bicarbonate salt under conditions that result in the fluoride species replacing the leaving group to produce an imaging agent (e.g., a compound comprising formula (II)) comprising the fluorine species, wherein the molar ratio of bicarbonate salt to imaging agent precursor is less than about 1.5:1, or is about 1:1 or less (or any ratio described herein).

In some embodiments, a method for synthesizing an imaging agent comprises contacting an imaging agent precursor (e.g., a compound comprising formula (I)) with a fluoride species under conditions that result in the fluoride species replacing the leaving group to produce an imaging agent (e.g., a compound comprising formula (II)) comprising the fluorine species, wherein the contacting is performed at a pH below 7.

In some embodiments, a method for $^{18}$F-labeling a compound comprising the formula:

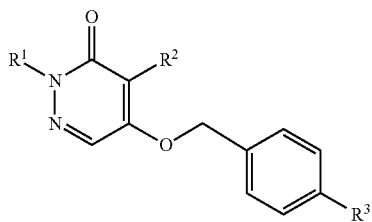

wherein:
R$^1$ is alkyl, optionally substituted;
R$^2$ is hydrogen or halogen; and
R$^3$ is alkyl substituted with a sulfonate-containing group, alkoxy substituted with a sulfonate-containing group, or alkoxyalkyl substituted with a sulfonate-containing group, comprises reacting the compound with an $^{18}$F species in the presence of an ammonium salt or a bicarbonate salt to form a product comprising the $^{18}$F species.

In some embodiments, a method for manufacturing an imaging agent comprising the formula:

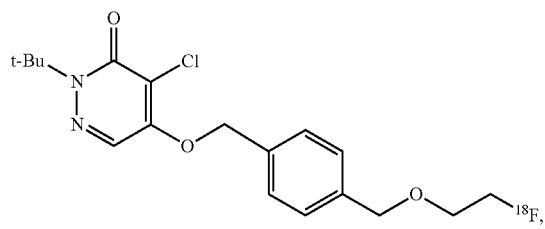

comprises
(a) contacting a tosylate precursor comprising the formula:

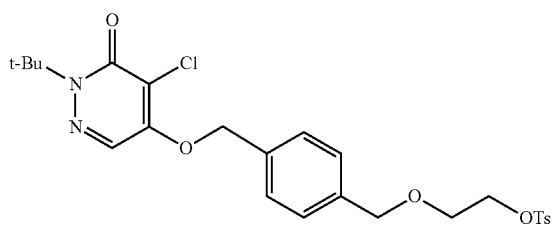 [SMILES: Cc1ccc(S(=O)(=O)OCCOCc2ccc(COc3cnn(C(C)(C)C)c(=O)c3Cl)cc2)cc1]

with a fluoride species associated with an ammonium salt;
(b) heating the mixture of (a);
(c) cooling the heated mixture;
(d) adding H$_2$O to the cooled mixture;
(e) purifying the mixture from the hydrated mixture of (d) using HPLC with an H$_2$O/MeCN eluent; and
(f) diluting the eluent with a solution of ascorbic acid or a salt thereof.

In some cases, step (b) comprises heating the mixture to a temperature between 50° C. and 250° C. In some cases, the heating step (b) comprises heating the mixture for less than 5 minutes, less than 10 minutes, less than 20, minutes, or less than 30 minutes. In some cases, the method further comprises:
(g) contacting the diluted eluent of (f) with a C18 resin;
(h) washing the contacted C18 resin with a solution of ascorbic acid or a salt thereof;
(i) eluting

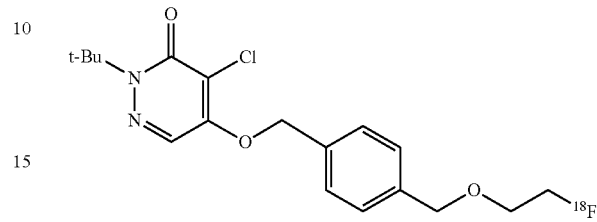

from the C18 resin with absolute ethanol; and
(j) diluting the eluent of (i) with a solution of ascorbic acid or a salt thereof (e.g., sodium salt).

In some cases, the method further comprises
(k) aseptically filtering the diluted eluent of (j), and
(l) optionally, determining the presence of

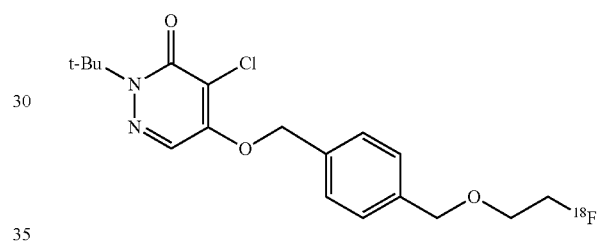

in a sample of the aseptic filtrate of (k).

In some embodiments, an imaging agent comprising the formula:

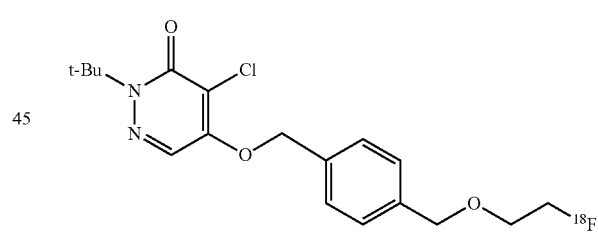

is manufactured by:
(a) contacting a tosylate precursor comprising the formula:

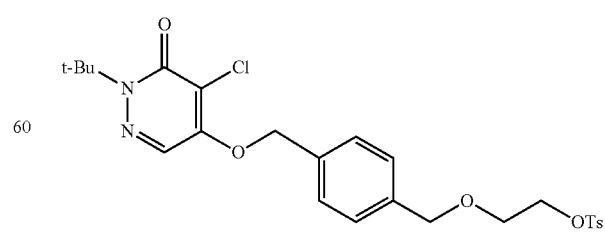

with an anhydrous fluoride species associated with an ammonium salt;

(b) heating the mixture of (a);
(c) cooling the heated mixture;
(d) adding H₂O to the cooled mixture;
(e) purifying the mixture from the hydrated mixture of (d) using HPLC with an H₂O/MeCN eluent; and
(f) diluting the eluent with a solution of ascorbic acid or a salt thereof.

In some cases, step (b) comprises heating the mixture to a temperature between 50° C. and 250° C. In some cases, the heating step (b) comprises heating the mixture less than 5 minutes, less than 10 minutes, less than 20, minutes, or less than 30 minutes. In some cases, the manufacturing further comprises:

(g) contacting the diluted eluent of (f) with a C18 resin;
(h) washing the contacted C18 resin with a solution of ascorbic acid or a salt thereof;
(i) eluting

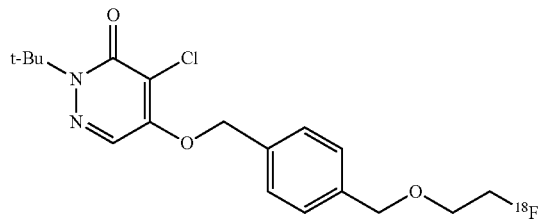 [SMILES: CC(C)(C)n1ncc(OCc2ccc(COCC[18F])cc2)c(Cl)c1=O]

from the C18 resin with absolute ethanol; and
(j) diluting the eluent of (i) with a solution of ascorbic acid or a salt thereof.

In some cases, the manufacturing further comprises:
(k) aseptically filtering the diluted eluent of (j), and
(l) optionally, determining the presence of

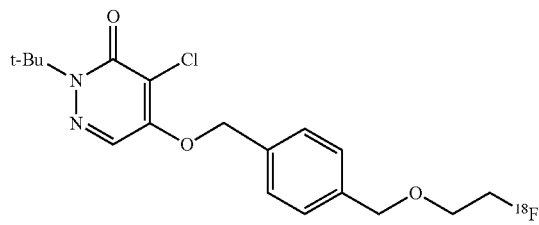 [SMILES: CC(C)(C)n1ncc(OCc2ccc(COCC[18F])cc2)c(Cl)c1=O]

in a sample of the aseptic filtrate of (k).

In some embodiments, a method for synthesizing a fluorinated compound comprises reacting, in the presences of a carbonate or bicarbonate ion, (i) a precursor of the fluorinated compound comprising an alkoxyalkyl group substituted with a halide or a sulfonate-containing group, with (ii) a salt comprising a fluoride species and weakly coordinating cation.

As used herein, the term "leaving group" is given its ordinary meaning in the art of synthetic organic chemistry and refers to an atom or a group capable of being displaced by a nucleophile. Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, haloformates, and the like. In some cases, the leaving group is a sulfonic acid ester, such as toluenesulfonate (tosylate, TsO), methanesulfonate (mesylate, MsO), or trifluoromethanesulfonate (triflate, TfO). In some cases, the leaving group may be a brosylate, such as p-bromobenzenesulfonyl. In some cases, the leaving group may be a nosylate, such as 2-nitrobenzenesulfonyl. The leaving group may also be a phosphineoxide (e.g., formed during a Mitsunobu reaction) or an internal leaving group such as an epoxide or cyclic sulfate. In some embodiments, the leaving group is a sulfonate-containing group. In some embodiments, the leaving group is a tosylate group.

In certain embodiments, the invention provides methods of synthesizing an imaging agent comprising a halogen. For example, the method may involve a halogenation reaction. In some embodiments, methods for synthesizing an imaging agent comprising a fluoride (e.g., enriched with $^{18}$F) are provided. The method comprises contacting an imaging agent precursor with a source of a fluoride under conditions that result in the fluoride replacing a leaving group of the precursor to produce an imaging agent comprising a fluoride species. In certain embodiments, the method involves a nucleophilic fluorination reaction. That is, an imaging agent precursor comprising a leaving group is reacted in the presence of a fluoride species, whereby $S_N2$ or $S_N1$ displacement of the leaving group by the fluoride species produces the imaging agent. In some embodiments, the fluoride species is enriched with $^{18}$F. FIG. 1 shows an illustrative example, where imaging agent precursor 1 is treated with an $^{18}$F species to produce imaging agent 1 via a substitution reaction.

In some embodiments, one or more additives may be incorporated into the reaction mixture of the imaging agent precursor and the fluoride species. The additive may, in some cases, facilitate reaction between the imaging agent precursor and the fluoride species and/or may aid in stabilizing the imaging agent. For example, the fluoride species may have relatively low reactivity (e.g., nucleophilicity), and addition of an additive may enhance the reactivity of the fluoride species. As an illustrative embodiment, a fluorine species may be a negatively charged fluoride ion (e.g., an isotopically-enriched $^{18}$F ion), and an additive may be used to bind to any positively charged counterions present within the reaction mixture, thereby enhancing the reactivity of the fluoride ion. In some embodiments, the additives may decrease the rate of undesired side reactions, as described below.

In some cases, the additive may be combined with the fluoride species prior to contact with the imaging agent precursor. For example, in certain embodiments a solution comprising the fluoride species and the additive is prepared, and the solution is added to the imaging agent precursor. In other embodiments, a solid comprising the fluoride species and the additive is prepared, and the solid is contacted with the imaging agent precursor. In certain embodiments, the fluoride species is adsorbed onto a solid support (e.g., an anion exchange column), and a solution comprising the additive is used to elute the fluoride species from the solid support. The eluted solution is then contacted with the imaging agent precursor, or is concentrated to produce a solid, which is then contacted with the imaging agent precursor.

In some embodiments, the additive is a bicarbonate salt. In certain embodiments, it has been discovered that substitution of a carbonate salt with a bicarbonate salt (such as KHCO₃) results in considerable improvement of both fluorination efficiency and starting material integrity. As used herein, the term "bicarbonate salt" refers to a salt comprising a bicarbonate or hydrogen carbonate ion ($HCO_3^-$ ion). The bicarbonate salt may be a metal bicarbonate, such as sodium bicarbonate, calcium bicarbonate, potassium bicarbonate, magnesium bicarbonate, and the like. In certain embodiments, the bicarbonate salt is potassium bicarbonate ($KHCO_3$). In some embodiments, the bicarbonate salt comprises a non-metal counterion, such as ammonium bicarbonate. For example, the bicarbonate salt may be a tetraalkylammonium bicarbonate salt having the formula, $R_4NHCO_3$, wherein R is alkyl. In some embodiments, R may be a lower alkyl, such as methyl, ethyl, propyl, butyl, pentyl, hexyl, or the like. In certain embodiments, the ammonium salt is $Et_4NHCO_3$. In other embodiments, the salt is $Me_4NHCO_3$, $i\text{-}Pr_4NHCO_3$, $n\text{-}Pr_4NHCO_3$, $n\text{-}Bu_4NHCO_3$, $i\text{-}Bu_4NHCO_3$, or $t\text{-}Bu_4NHCO_3$.

As described further in Example 14, it is thought that reaction conditions which activate larger differential rates of fluorination would result in a more efficient and chemoselective process; that is, a decreased rate of hydrolysis or increased rate of fluorination would result. The studies outlined herein revealed that although required for anion exchange, $K_2CO_3$ did little to enhance fluorination over baseline levels and served primarily a detrimental role in the fluorination reaction. However, in contrast, addition of $KHCO_3$ produced a marked increase in fluorination over the same concentration range, while decomposition pathways remained poorly differentiated. These facts, coupled with the observation that [$^{18}$F]NaF exchange with tetraalkylammonium cations can directly produce a highly active nucleophilic fluoride source, led to investigation of a series of salts in an effort to identify related counterion affects that increase the rate of fluorination.

A comprehensive screen of ammonium salts identified a dramatic enhancement of fluorination efficiency in the presence of bicarbonate anion (e.g., see Table 1); only modest dependency on size of the alkyl substituent was observed within the series methyl→ethyl→butyl (e.g., Example 14).

Subsequent optimization of salt stoichiometry revealed that at levels as low as 25 mol % of the tetraalkylammonium bicarbonate to an imaging agent precursor (e.g., 0.25:1) resulted in near complete conversion of the imaging agent precursor to the imaging agent; once again, unproductive consumption of starting material occurred with increasing base concentration revealing an optimum stoichiometry range for the modified reaction conditions. Related studies directed toward determination of the optimal precursor concentration revealed a concentration threshold.

This reagent combination also demonstrated rapid conversion and significantly improved chemoselectivity toward fluorination over the $K_2CO_3$/Kryptofix® 222 method. In fact, a more detailed evaluation of crude reaction mixtures revealed a dramatic reduction in overall decomposition rates as evidenced by the absence of hydrolytic impurities (e.g., as described in Example 14); a result which may be attributed to a lower solution pH in the absence of Kryptofix® 222 (5-6 vs. 9-10).

In some embodiments, the additive is a salt comprising a cation that forms a weakly coordinating salt with a fluoride species. As used herein, a "cation that forms a weakly coordinating salt with a fluoride species" refers to a cation that renders a fluoride species reactive within a fluorination reaction. For example, the cation may not strongly bind to the fluoride species, allowing the fluoride species to act as a nucleophile during a nucleophilic fluorination reaction, Those of ordinary skill the art would be able to select an appropriate cation that would be suitable as a weakly coordinating counterion for a fluoride species. For example, the cation may be have a relatively large atomic radius and/or may be a weak Lewis base. In some cases, the cation may be selected to be lipophilic. In some cases, the cation may comprise one or more alkyl groups. Examples of weakly coordinating cations include cesium ions, ammonium ions, and the like. Examples of weakly coordinating cations include weakly coordinating salts of hexamethylpiperidindium, $S(NMe_2)_3$, $P(NMe_2)_4$, tetraaalkylphosphonium salts, tetraarylphosphonium salts, (e.g. tetraphenylphosphonium), hexakis(dimethylamino)diphosphazenium, tris(dimethylamino)sulfonium, etc.

In some embodiments, the additive is an ammonium salt, i.e., a salt comprising a substituted or unsubstituted ammonium ion. In some cases, the ammonium ion is a weakly coordinating cation. In some cases, the ammonium salt has the formula, $R_4NX$, where each R can be the same or different and is alkyl, heteroalkyl, aryl, heteroaryl, or heterocyclic, each optionally substituted, and X is a negatively charged counterion. In some cases, R is alkyl, heteroalkyl, aryl, heteroaryl, or heterocyclic, each optionally substituted. The ammonium salt may include a wide range of negatively charged counterions, including halides, carbonates, bicarbonates, and the like. Examples of ammonium salts include, but are not limited to, ammonium bicarbonate salts, ammonium hydroxide salts, ammonium acetate salts, ammonium lactate salts, ammonium trifluoroacetate salts, ammonium methanesulfonate salts, ammonium p-toluenesulfonate salts, ammonium nitrate salts, ammonium halide salts (e.g., ammonium iodide salts), ammonium bisulfate salts, and the like.

In one set of embodiments, the ammonium salt is a tetraalkylammonium salt, such as a tetraalkylammonium bicarbonate salt. For example, the ammonium salt may have the formula, $R_4NHCO_3$, wherein each R is independently alkyl. In some cases, R is optionally substituted. In some embodiments, the alkyl group is a lower $C_1$-$C_6$ alkyl group. In some embodiments, the tetraalkylammonium salt is a basic tetraalkylammonium salt.

The salt additive (e.g., bicarbonate salt and/or ammonium salt) may be utilized in the reaction such that the molar ratio of the salt additive to the imaging agent precursor is less than about 1.5:1. In some cases, the molar ratio is about 1.5:1 or less, about 1.4:1 or less, about 1.3:1 or less, about 1.25:1 or less, about 1.2:1 or less, about 1.1:1 or less, about 1:1 or less, about 0.75:1 or less, about 0.5:1 or less, about 0.25:1 or less, about 0.1:1 or less, or about 0.05:1 or less. In some cases, the ratio is greater than about 0.05:1, greater than about 0.01:1, or greater than about 0.25:1. In some embodiments, the molar ratio of salt additive to imaging agent precursor is about 0.5:1 to about 1:1, or about 0.25:1 to about 1:1, or about 0.25:1 to about 0.75:1, about 1.49:1 to about 0.05:1, or between about 1.4:1 to about 0.25:1, or between about 0.25:1 and about 1.4:1, or between about 0.25:1 and about 1.25:1.

Without wishing to be bound by theory, the use of bicarbonate and ammonium salts may aid in decreasing the rate of competing reactions such as hydrolysis during nucleophilic fluorination of an imaging agent precursor.

In some embodiments, the additive may be used in combination with a species capable of enhancing the reactivity of the fluoride species or otherwise facilitating conversion of the imaging agent precursor to the imaging agent. For example, the species may be a compound capable of chelating one or more ions (e.g., metal ions) that may be present within the reaction mixture. Without wishing to be bound by theory, the species may be used to chelate a counterion to a fluoride species, such as a potassium ion, thereby increasing the reactivity (e.g., nucleophilicity) of the fluoride species. In certain embodiments, the additive is used in combination with a multidentate ligand, such as a crown ether or a cryptand that is capable of chelating a metal ion. The multidentate ligand (e.g., cryptand) may be selected based on the metal ion to be chelated. The multidentate ligand may be, for example, 4,7,13,16,21,24-hexaoxa-1,10-diazabicyclo[8.8.8]-hexacosane (e.g., Kryptofix® 222). Other cryptands will be known to those of ordinary skill in the art.

Some embodiments may involve the use of a bicarbonate salt in combination with 4,7,13,16,21,24-hexaoxa-1,10-diazabicyclo[8.8.8]-hexacosane. In a specific embodiment, potassium bicarbonate may be used in combination with 4,7,13,16,21,24-hexaoxa-1,10-diazabicyclo[8.8.8]-hexacosane.

In another set of embodiments, it may be advantageous to utilize the methods described herein in the absence of a cryptand. The term "cryptand" is given its ordinary meaning in the art and refers to a bi- or a polycyclic multidentate ligand for a cation. For example, the method may be carried out using an ammonium salt, in the absence of a cryptand (e.g., such as 4,7,13,16,21,24-hexaoxa-1,10-diazabicyclo[8.8.8]-hexacosane).

In another set of embodiments, the method is performed in the absence of a carbonate salt.

In some embodiments, the use of a salt additive in the reaction increases the yield by about 10%, about 20%, about 30%, about 40%, about 50%, about 60%, about 70%, about 80%, about 90%, about 100%, about 200%, about 300%, about 400%, about 500%, or greater, relative to conducting the reaction under essentially the same conditions but in the absence of a salt additive.

Those of ordinary skill in the art will be able to select and/or determine the appropriate set of reaction conditions (e.g., concentration, temperature, pressure, reaction time, solvents, etc.) suitable for use in a particular application. The imaging agent may be further processed using one or more purification techniques, and may optionally be combined with additional components, such as a stabilizing agent.

Those of ordinary skill in the art would be able to select a source of a fluoride species suitable for use in the methods described herein. The term "fluoride species" as used herein refers to a fluoride atom or group of atoms comprising at least one fluoride atom, wherein the fluoride atom is capable of reacting with another compound (e.g., an imaging agent precursor). In some embodiments, an isotopically-enriched $^{18}$F species may be produced by the nuclear reaction $^{18}$O (p,n)$^{18}$F from proton bombardment of [$^{18}$O]H$_2$O in a cyclotron. The method may involve treating a solution of the $^{18}$F species to remove any impurities, such as unreacted [$^{18}$O]H$_2$O. For example, a solution of the $^{18}$F species may be filtered through an anion exchange column, where the $^{18}$F species is retained on the cationic resin matrix while the [$^{18}$O]H$_2$O is eluted. The $^{18}$F species is then removed by washing the anion exchange column with various mixtures of solvents and optional additives (e.g., salt additives), forming an $^{18}$F-containing solution. In some cases, the anion exchange column is washed with an aqueous solution of a salt, such as KHCO$_3$ or Et$_4$NHCO$_3$.

In some cases, the $^{18}$F-containing solution is combined with additional components prior to reaction with an imaging agent precursor. For example, one or more solvents may be added to dilute the $^{18}$F-containing solution to a selected concentration. In one set of embodiments, the $^{18}$F-containing solution is diluted with acetonitrile.

In some cases, the $^{18}$F-containing solution may be concentrated to dryness by exposure to elevated temperature and/or reduced pressure to form an anhydrous $^{18}$F-containing solid. In some embodiments, the $^{18}$F-containing solid may further comprise one or more additives (e.g., salt additives). The chemical composition of the $^{18}$F-containing solid may depend on the number and kind of additives used in preparation of the $^{18}$F-containing solution. For example, a solution of potassium bicarbonate may be used to elute the $^{18}$F species from the anion exchange column, thereby resulting in an $^{18}$F-containing solid comprising [$^{18}$F]KF. In another example, a solution of ammonium bicarbonate is used to elute the $^{18}$F species from the anion exchange column, thereby resulting in an $^{18}$F-containing solid comprising [$^{18}$F]Et$_4$NF.

In some cases, the solution comprising the $^{18}$F species is heated to a temperature ranging from room temperature to about 200° C. In some embodiments, the solution is heated to a temperature ranging from 90-120° C. In some cases, the solution is heated to about 75° C., about 85° C., about 95° C., about 105° C., about 115° C., about 125° C., or greater. In some cases, the solution is placed under a reduced pressure of about 100 mm Hg, about 125 mm Hg, about 150 mm Hg, about 175 mm Hg, about 200 mm Hg, about 225 mm Hg, about 250 mm Hg, about 275 mm Hg, about 300 mm Hg, about 325 mm Hg, about 350 mm Hg, about 375 mm Hg, about 400 mm Hg, or greater. In some cases, the solution is placed under a reduced pressure of about 100 mbar, about 125 mbar, about 150 mbar, about 175 mbar, about 200 mbar, about 225 mbar, about 250 mbar, about 275 mbar, about 280 mbar, about 300 mbar, about 325 mbar, about 350 mbar, about 375 mbar, about 400 mbar, about 450 mbar, about 500 mbar, or greater. Those of ordinary skill in the art would be able to select and/or determine conditions suitable for a particular reaction. In some embodiments, the solution is concentrated to dryness at about 150 mm Hg and about 115° C. In some embodiments, the solution is concentrated to dryness at about 375 mm Hg and about 115° C. In some embodiments, the solution is concentrated to dryness at about 400 mbar and about 110-150° C. In some embodiments, the solution is concentrated to dryness at about 280 mbar and about 95-115° C.

The fluoride species and/or the additive, if present, is then contacted with the imaging agent precursor under conditions that result in conversion of the imaging agent precursor to the imaging agent product via nucleophilic fluorination. Those of ordinary skill in the art would be able to select conditions suitable for use in a particular reaction. For example, the ratio of fluoride species to imaging agent precursor may be selected to be about 1:10,000 or more, about 1:5000 or more, about 1:3000 or more, about 1:2000 or more, 1:1000 or more, 1:500 or more, 1:100 or more, 1:50 or more, 1:10 or more, 1:5 or more, or, in some cases, 1:1 or more. In some embodiments, the fluoride species may be present at about 10 mol %, or about 5 mol %, or about 3 mol %, or about 2 mol %, or about 1 mol % or about 0.5 mol %, or about 0.1 mol %, or about 0.05 mol %, or about 0.01 mol % relative to the amount of imaging agent precursor. In some embodiments, at least of the fluoride species provided is enriched in $^{18}$F. For example, the ratio of $^{18}$F species to imaging agent precursor may be selected to be about 1:1,000,000 or more, or about 1:500,000 or more, or about 1:250,000 or more, or about 1:100,000 or more, or about 1:50,000 or more, or about 1:25,000 or more, or about 1:10,000 or more, about 1:5000 or more, about 1:3000 or more, about 1:2000 or more, 1:1000 or more, 1:500 or more, 1:100 or more, 1:50 or more, 1:10 or more, 1:5 or more, or, in some cases, 1:1 or more.

In some embodiments, the nucleophilic fluorination reaction is carried out in the presence of one or more solvents, for example, an organic solvents, a non-organic solvent (e.g., an aqueous solvent), or a combination thereof. In some cases, the solvent is a polar solvent or a non-polar solvent. In some embodiments, the solvent is an aqueous solution, such as water. The solvent comprises at least about 0.001% water, at least about 0.01% water, at least about 0.1% water, at least about 1% water, at least about 5%, at least about 10%, at least about 20% water, at least about 30% water, at least about 40% water, at least about 50% water, or greater. In some cases, the solvent may comprise between about 0.1% and 100% water, about 1% to about 90%, about 1% to about 70%, about 1% to about 50%, or about 10% to about 50%. In some cases, the solvent comprises no more than 10% water, 5% water, 4% water, 3% water, 2% water, 1% water, or 0.5% water. In some cases, the solvent comprises between about 0.01% water and about 5% water, or between about 0.01% water and about 2% water, or between about 0.1% water and about 0.2% water.

Other non-limiting examples of solvents useful in the inventive methods include, but are not limited to, non-halogenated hydrocarbon solvents (e.g., pentane, hexane, heptane, cyclohexane, etc.), halogenated hydrocarbon solvents (e.g., dichloromethane, chloroform, fluorobenzene, trifluoromethylbenzene, etc.), aromatic hydrocarbon solvents (e.g., toluene, benzene, xylene, etc.), ester solvents (e.g., ethyl acetate, etc.), ether solvents (e.g., tetrahydrofuran, dioxane, diethyl ether, dimethoxyethane, etc.), and alcohol solvents (e.g., ethanol, methanol, propanol, isopropanol, etc.). Other non-limiting examples of solvents include acetone, acetic acid, formic acid, dimethyl sulfoxide, dimethyl formamide, acetonitrile, and pyridine. In some embodiments, the reaction is carried out in a polar solvent, such as acetonitrile.

In one set of embodiments, an anhydrous $^{18}$F-containing solid, optionally comprising an additive, may be contacted with a solution of an imaging agent precursor (e.g., a tosylate precursor), and the resulting solution is heated to an elevated temperature for a select period of time. The solution may be, for example, an acetonitrile solution. In other embodiments, a solution of the $^{18}$F species and additive, if present, is contacted with a solid imaging agent precursor or a solution of the imaging agent precursor.

Some embodiments involve contacting the imaging agent precursor with the fluoride species in a solution having a pH below about 7, below about 6, or, below about 5. In some cases, the solution has a pH between about 5 and about 6, or between about 5 and, about 7 or between about 4 and about 7.

In some cases, the solution comprising the $^{18}$F species, imaging agent precursor, and, optionally, additive, is heated at an elevated temperature for a period of time. For example, the solution may be heated to about 50° C., about 60° C., about 70° C., about 80° C., about 90° C., about 100° C., about 110° C., about 120° C., 150° C., about 170° C., about 200° C., about 225° C., about 250° C. or greater, for a period of 5 minutes or less, 10 minutes or less, 20 minutes or less, 30 minutes or less. It should be understood that other temperatures and reaction times may be used. Upon completion of the reaction, the reaction mixture is then cooled (e.g., to room temperature) and optionally diluted with a solvent, such as water.

Upon completion of the fluorination reaction, the resulting imaging agent is optionally subjected to one or more purification steps. In some cases, the synthesis, purification, and/or formulation of an imaging agent (e.g., a compound comprising formula (II)) may be prepared using an automated reaction system comprising a cassette, wherein the cassette may comprise a synthesis module, a purification module, and/or a formulation module. Automated reaction systems and cassettes are described herein.

Purification and isolation may be performed using methods known to those skilled in the art, including separation techniques like chromatography, or combinations of various separation techniques known in the art, for example, extractions, distillation, and crystallization. In one embodiment, high performance liquid chromatography (HPLC) is used with a solvent, or mixture of solvents, as the eluent, to recover the product. In some cases, the eluent includes a mixture of water and acetonitrile, such as a 45:55 water:acetonitrile mixture. The content of water in the eluent may vary from, for example, about 1% to about 50%. In some cases, HPLC may be performed using a C18 column.

The product may be further processed using additional purification techniques, such as filtration. In some cases, the imaging agent may be purified using HPLC, to produce a solution of HPLC mobile phase and the imaging agent. The HPLC mobile phase may be subsequently exchanged for a solution of ascorbic acid or a salt thereof, and ethanol solution, by filtration through a C-18 resin (e.g., C18 Sep-Pak® cartridge). In some embodiments, the solution of the HPLC mobile phase and the imaging agent is filtered through a C-18 resin, where the imaging agent remains on the resin and the other components, such as acetonitrile and/or other solvents or components, are removed via elution. The C-18 resin may be further washed with a solution of ascorbic acid or a salt thereof, and the filtrate discarded. To recover the purified imaging agent, the C-18 resin is washed with a solvent, such as ethanol, and the resulting solution is optionally further diluted with an ascorbic acid solution or a salt thereof, as described herein.

Optionally, the recovered product is combined with one or more stabilizing agents, such as ascorbic acid or a salt thereof. For example, a solution comprising the purified imaging agent may be further diluted with a solution of ascorbic acid or a salt thereof. As described herein, a formulation may be prepared via an automated reaction system comprising a cassette.

In some cases, a solution comprising the imaging agent product may be sterile filtered (e.g., using a 13 mm diameter, Millipore, Millex PVDF 0.22 μm sterilizing filter) into a sterile product vial. The sterile product vial may be a commercially available, pre-sterilized unit that is not opened during the production process, as any imaging agents (or other components) may be aseptically inserted through the septum prior to use. Those of ordinary skill in the art would be able to select suitable vials and production components, including commercially available, pre-sterilized units comprising a 0.22 μm pore size membrane venting filter and quality control sampling syringes.

Following aseptic filtration, individual doses may be filled in syringes, labeled, and shipped to a clinical site. Dosing administration techniques, kits, cassettes, method and systems (e.g., automated reaction systems) for synthesis of the imaging agent, and testing procedures are described herein. In some embodiments, the product is dispensed into a 3 or 5 mL syringe and labeled for distribution. Labels may be prepared at a radiopharmacy and applied to a syringe shield and shipping container. Additional labels may be provided in the shipping container for inclusion in clinical site records.

The imaging agents may be used in a method of imaging, including methods of imaging a patient comprising administering the imaging agent to the patient by injection, infusion, or any other method, and imaging an area of the patient, as described herein. In some embodiments, a portion of a heart of the patient is imaged.

Exemplary Methods for the Synthesis of Imaging Agent Precursors

Methods are also provided for synthesizing imaging agent precursors, and intermediates thereof. In some cases, the methods for synthesizing an imaging agent precursor (e.g., a compound comprising formula (I)) exhibits improved yields and/or may allow for the large-scale synthesis of the imaging agent precursors and/or intermediates thereof. Some embodiments provide the ability to synthesize a desired product without need for purification, such as chromatography, which can be time-consuming and/or expensive with the loss of product. As noted above, FIG. 1 shows an illustrative example of an imaging agent precursor which has been utilized in the synthesis of an imaging agent for imaging myocardial perfusion. The leaving group (i.e., tosylate group) is replaced with an imaging moiety, for example, $^{18}F$, as described herein, thereby forming an imaging agent.

In some embodiments, an imaging agent precursor is formed via a reaction in which a bond between a heteroatom and an alkyl, heteroalkyl, aryl, or heteroaryl group is formed. For example, the reaction may be an alkylation reaction, such as an etherification reaction. In some embodiments, the reaction involves a hydroxyl-containing nucleophilic species reacting with an electrophilic species to form an ether linkage. As used herein, the term "ether" or "ether linkage" is given its ordinary meaning in the art and refers to the group, $R^a$—O—$R^b$, where $R^a$ and $R^b$ can be the same or different and are alkyl, heteroalkyl, aryl, or heteroaryl, any of which may be substituted. For example, the reaction may involve nucleophilic addition of the oxygen atom of the hydroxyl-containing species to an electrophilic species. In some embodiments, the reaction may involve coupling between two alcohols via, for example, a Mitsunobu reaction.

Figure 3:
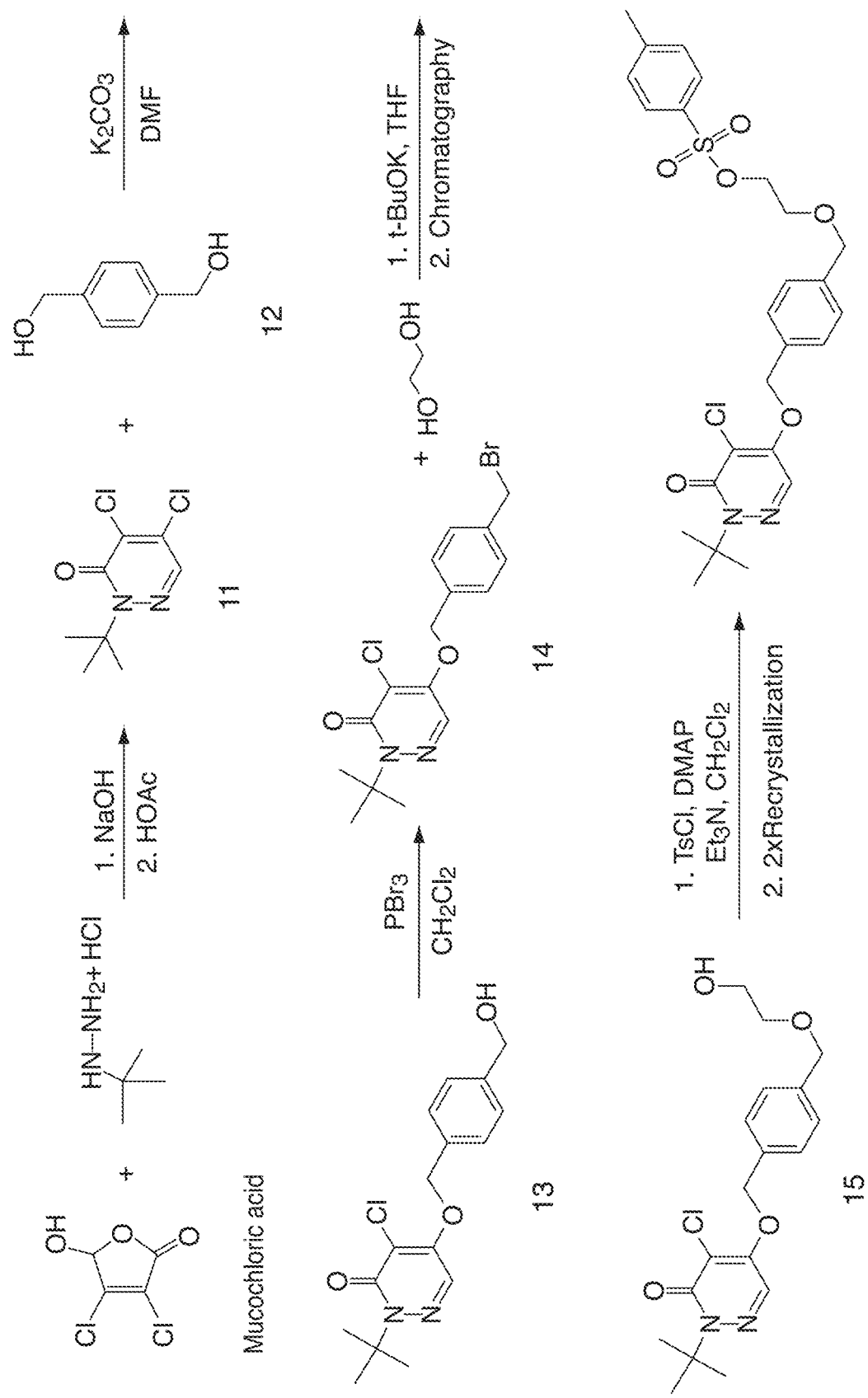
FIG. 3 shows an exemplary synthesis of an intermediate compound.
Figure 4:
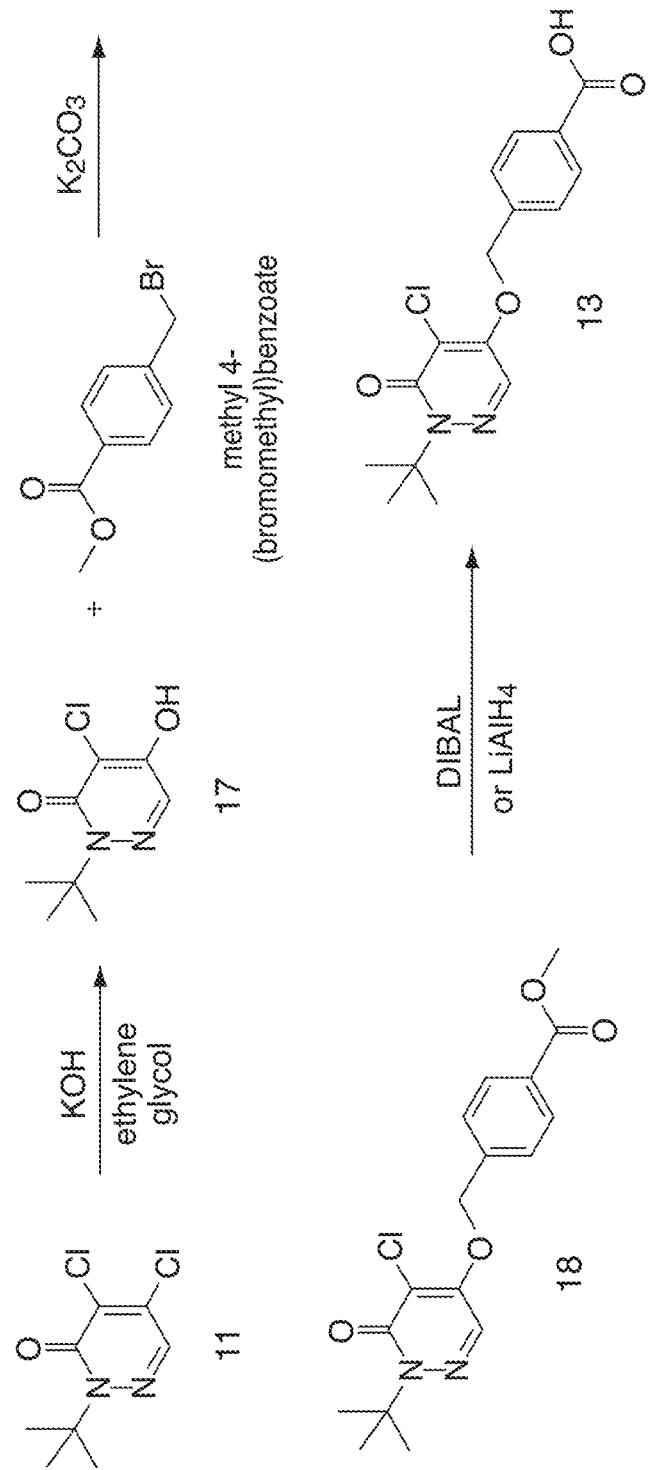
FIG. 4 shows an alternative synthesis of an intermediate compound.

In some cases, the etherification reaction includes formation of a bond between an oxygen atom and an alkyl, aryl, heteroalkyl, heteroaryl, carbocyclic, or heterocyclic group. FIG. 3 shows an illustrative embodiment of an etherification reaction between benzenedimethanol 12 and dichloropyridazinone 11 to form the benzyl alcohol 13. In another embodiment, FIG. 4 shows an etherification reaction between hydroxychloropyridazinone 17 and methyl 4-bromomethylbenzoate to afford pyridazinone ester 18.

In some embodiments, the inventive method involves reacting a compound comprising formula (III):

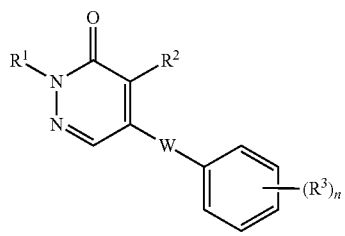
(III)

wherein:
W is alkyl or heteroalkyl, optionally substituted;
$R^1$ is alkyl, optionally substituted;
$R^2$ is hydrogen or halide;
each $R^3$ can be the same or different and is alkyl optionally substituted with a leaving group, or heteroalkyl optionally substituted with a leaving group; and
n is 1, 2, 3, 4, or 5;

with a nucleophile, wherein the nucleophile replaces the leaving group to produce a product. For example, the nucleophile may be ethylene glycol, and an etherification reaction may be carried out as described herein. In some embodiments, the reaction is performed in the presence of a base, such as potassium t-butoxide or potassium hydroxide. In some cases, $R^3$ is alkyl substituted with a leaving group and/or n is 1. In some embodiments, the compound comprising formula (III) comprises the structure:

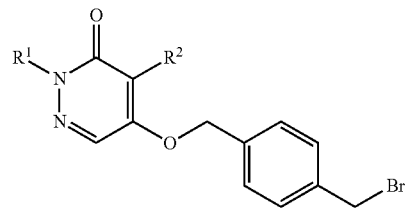

wherein the leaving group is Br, and the product of the reaction comprises formula:

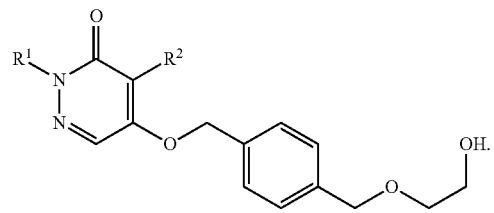

wherein $R^1$ and $R^2$ are as defined herein.

In some cases, a compound comprising formula (III) comprises the structure:

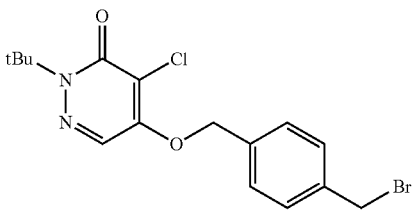 [SMILES: CC(C)(C)n1ncc(OCc2ccc(CBr)cc2)c(Cl)c1=O]

and the product of the etherification reaction comprises the formula:

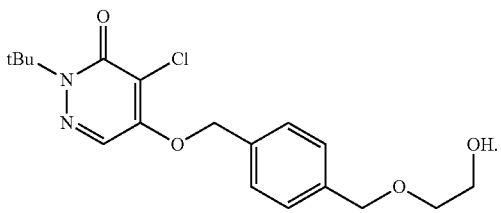 [SMILES: CC(C)(C)n1ncc(OCc2ccc(COCCO)cc2)c(Cl)c1=O]

In some cases, the compound comprising formula (III) may act as a nucleophile and may be reacted with an electrophile, to produce a product. For example, $R^3$ may be —CH$_2$OH, and the electrophile may be ethylene oxide.

In some embodiments, the method comprises reacting a compound comprising formula (IV):

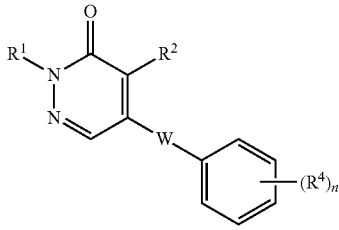

(IV)

wherein:

R¹ is alkyl, optionally substituted;

R² is hydrogen or halide;

W is alkyl or heteroalkyl, optionally substituted;

each R⁴ can be the same or different and is alkyl optionally substituted with hydroxyl or heteroalkyl optionally substituted with hydroxyl; and n is 1, 2, 3, 4, or 5;

with a reactant, wherein the hydroxyl group is replaced with a portion of the reactant to form a leaving group associated with the compound. In some cases, R⁴ is alkyl substituted with hydroxyl and/or n is 1. In some embodiments, reacting the compound comprising formula IV involves exposure to a halogenation reagent, such as phosphorus tribromide, pyridinium dibromide, or a combination of carbon tetrabromide and triphenylphospine. In some embodiments, the halogenation reagent is phosphorus tribromide.

In some embodiments, W is —O(CH₂)—; R¹ is t-butyl; R² is chloride; and R⁴ is alkyl substituted with hydroxyl. In some cases, n is 1.

In some embodiments, the compound comprising formula (IV) comprises the structure:

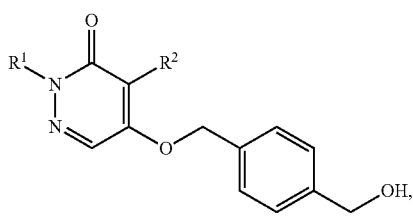

and the product comprises the structure:

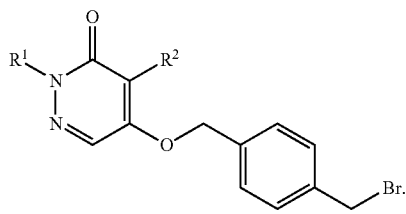

In some embodiments, the compound comprising formula (IV) comprises the structure:

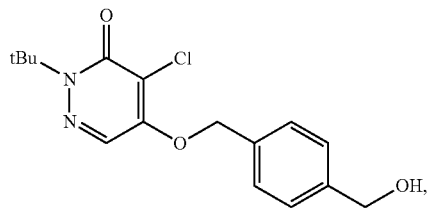 [SMILES: CC(C)(C)n1ncc(OCc2ccc(CO)cc2)c(Cl)c1=O]

and the product comprises the structure:

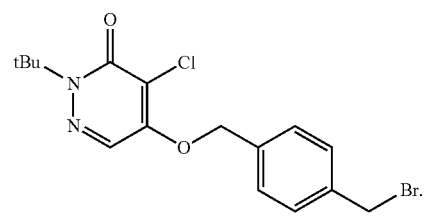 [SMILES: CC(C)(C)n1ncc(OCc2ccc(CBr)cc2)c(Cl)c1=O]

In some cases, a method is provided for synthesizing a compound comprising formula (IV). In some cases, the method comprises synthesizing the compound comprising formula (IV) via an etherification reaction between compounds comprising formulae (IVa) and (IVb):

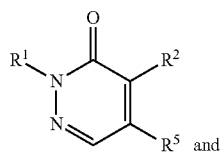

(IVa)

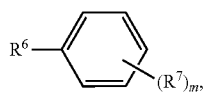

(IVb)

wherein:

R¹ is alkyl, optionally substituted;

R² is hydrogen or halide;

m is 1, 2, 3, 4, or 5 or greater;

R⁵ is hydroxyl or halide; and each R⁶ and R⁷ can be the same or different and are alkyl, heteroalkyl, or a acyl group, each optionally substituted, wherein, when R⁵ is hydroxyl, at least one of R⁶ and R⁷ comprises a leaving group or a moiety that can be replace by a leaving group (e.g., hydroxyl), or when R⁵ is halide, at least one of R⁶ and R⁷ comprises a hydroxyl.

In some cases, a compound comprising formula (IVa) comprises the structure:

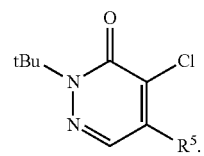

wherein R⁵ is as described herein.

In one set of embodiments, the compound comprising formula II is synthesized by an etherification reaction between compounds comprising formulae (IVa) and (IVd):

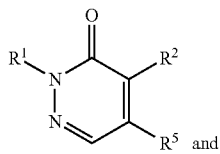
(IVa)

(IVd)

wherein:

R¹ is alkyl, optionally substituted;

R² is hydrogen or halide;

R⁵ is hydroxyl or halide; and

R⁶ and R⁷ can be the same or different and are alkyl, heteroalkyl, or a carbonyl group, each optionally substituted, wherein, when R⁵ is hydroxyl, at least one of R⁶ and R⁷ comprises a leaving group, or when R⁵ is halide, at least one of R⁶ and R⁷ comprises a hydroxyl. In one set of embodiments, R⁵ is hydroxyl, R⁶ is a carbonyl group, and R⁷ is a substituted alkyl. In some cases, R⁵ is hydroxyl, R⁶ is an ester, and R⁷ is alkyl substituted with a leaving group.

In some cases, a compound comprising formula (IVa) comprises the structure:

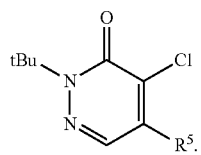

wherein R⁵ is as defined herein.

The etherification reaction may be carried out as described herein, and may comprise exposure of the precursor compounds to a base, such as potassium carbonate.

In some embodiments, R⁵ is halide; and R⁶ and R⁷ are each alkyl, optionally substituted. In some embodiments, R⁵ is chloride; and R⁶ and R⁷ are each alkyl substituted with hydroxyl. In one embodiment, an etherification reaction between compounds comprising formulae (IVe) and (IVf):

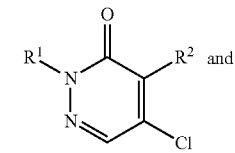
(IVe)

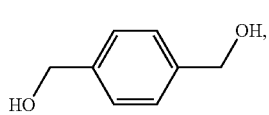
(IVf)

forms a product comprising the formula:

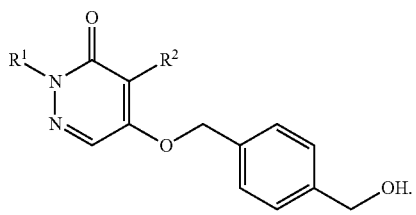

In one embodiment, an etherification reaction between compounds comprising formulae:

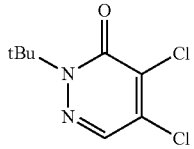 and 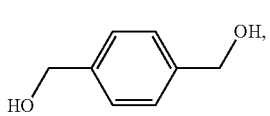

forms a product comprising formula:

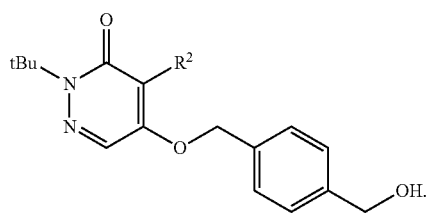

In one embodiment, an etherification reaction between compounds comprising formulae:

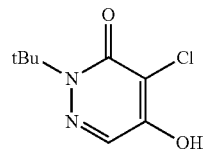 and 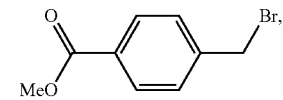

forms a product comprising formula:

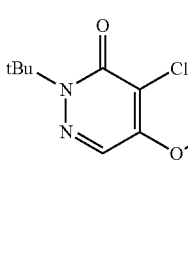

The product may be reduced with a reducing agent, such as lithium aluminum hydride, lithium borohydride, or diisobutylaluminum hydride (DIBAL-H), thereby converting the ester group into an alcohol.

As shown by the illustrative embodiment in FIG. 3, benzenedimethanol 12 and dichloropyridazinone 11 may be reacted via an etherification reaction in the presence of potassium carbonate in DMF to form benzyl alcohol 13. In some embodiments, a disubstituted impurity is also formed wherein benzenedimethanol 12 becomes alkylated at both hydroxyl groups, which may later be removed via chromatographic purification. Conversion of benzyl alcohol 13 to benzyl bromide 14 may be carried out with a variety of brominating agents, such as phosphorous tribromide in dichloromethane. Subsequent conversion of benzyl bromide 14 to alcohol 15 may be completed by reaction with ethylene glycol in the presence of potassium t-butoxide in tetrahydrofuran, in some cases at elevated temperature. Alcohol 15 may then be purified by column chromatography to remove any impurities, including disubstituted impurities formed during the synthesis of benzyl alcohol 13. Alcohol 15 may then be further reacted with p-toluenesulfonyl chloride in the presence of DMAP, triethylamine, and dichloromethane to form imaging agent precursor 1, which may be purified via recrystallization. Using the method shown in FIG. 5, the overall yield for synthesizing alcohol 15 starting from compound 11 (e.g., 2-(t-butyl)-4,5-dichloropyridazin-3 (2H)-one) and compound 12 (e.g., 1,4-benzenedimethanol) may be at least 10%, at least 20%, at least 30%, or at least 40%, using chromatography as the purification method. In some cases, the overall yield for synthesizing alcohol 15 starting from compound 11 and compound 12 is approximately 43%, using chromatography as the purification method.

FIG. 4 shows an alternate approach to the synthesis of alcohol 13 involving reaction of dichloropyridazinone 11 with potassium hydroxide in ethylene glycol to afford chlorohydroxypyridazinone 17, which may then be reacted with methyl 4-bromomethylbenzoate in the presence of potassium carbonate in DMF to afford pyridazinone ester 18. Next, reduction of pyridazinone ester 18, for example, using either DIBAL-H or lithium aluminum hydride, may produce benzyl alcohol 13, which may then be converted to alcohol 15 and imaging agent precursor 1, as described herein. One advantageous feature of the synthetic scheme shown in FIG. 4 is the reduction or elimination of disubstituted impurities that may be formed in the synthetic scheme shown in FIG. 3. This provides the ability to purify benzyl alcohol 13 without the use of chromatography. In some cases, recrystallization methods alone may be used to afford an intermediate compound of very high purity. For example, benzyl alcohol 13 may be purified by recrystallization from isopropyl acetate. Additionally, the synthetic scheme shown in FIG. 4 may provide a more simplified process, which may be performed with high-yield reactions and without the need for additional protection/deprotection steps. Using the method shown in FIG. 4, the overall yield for synthesizing alcohol 15 starting from compound 17 (e.g., 2-(t-butyl)-4-chloro-5-hydroxypyridazin-3(2H)-one) and methyl 4-bromomethylbenzoate may be at least 10%, at least 20%, at least 30%, or at least 40%, without the use of chromatography for purification. In some cases, the overall yield for synthesizing alcohol 15 starting from compound 17 and methyl 4-bromomethylbenzoate is 48%, without the use of chromatography as a purification method.

In some embodiments, an etherification reaction (e.g., see FIG. 3, etherification reaction to form benzyl alcohol 13) is performed in the presence of a base. The base may be, for example, a metal or a metal salt, such as a carbonate, a metal alkoxide, or the like. In some embodiments, the base may be an organic moiety, such as an amine. Examples of bases include, but are not limited to, metals (e.g., sodium metal), alkoxides such as sodium t-butoxide or potassium t-butoxide, an alkali metal amide such as sodium amide, lithium diisopropylamide or an alkali metal bis(trialkylsilyl)amides such as lithium bis(trimethylsilyl)amide or sodium bis(trimethylsilyl) amide, amines (e.g., triethylamine, trimethylamine, Et(i-Pr)$_2$N, Cy$_2$MeN, 4-(dimethylamino)pyridine (DMAP), 2,6-lutadine, N-methylpyrrolidine (NMP), quinuclidine), 1,5-diazabicycl[4.3.0]non-5-ene (DBN), 1,5-diazabicyclo[5.4.0]undec-5-ene (DBU), ammonium salts (e.g., ammonium hydroxide, tetramethyl ammonium hydroxide), alkali and alkaline earth carbonates, alkali and alkaline earth bicarbonates, alkali and alkaline earth hydroxides (e.g., sodium hydroxide, potassium hydroxide), and alkali and alkaline earth hydrides, (e.g., NaH, LiH, KH, K$_2$CO$_3$, Na$_2$CO$_3$, Tl$_2$CO$_3$, Cs$_2$CO$_3$, K(Ot-Bu), Li(Ot-Bu), Na(Ot-Bu) K(OPh), Na(OPh)). In some embodiments, the base is sodium metal, sodium hydride, potassium t-butoxide, sodium methoxide, potassium carbonate, sodium carbonate, cesium carbonate, or potassium hydroxide. In some embodiments, the base is cesium carbonate. In some embodiments, the base is potassium hydroxide. In some embodiments, the base is sodium hydroxide. In some embodiments, the base is potassium t-butoxide. In some embodiments, the base is tetramethyl ammonium hydroxide. It should be understood that an etherification reaction may also be conducted in the absence of a base.

One or more additives may be incorporated into the etherification reaction mixture to facilitate the reaction. In some cases, the etherification reaction may be performed in the presence of a catalyst. For example, the catalyst may be a salt, such as an ammonium salt. In some embodiments, the catalyst may be a tetraalkylammonium halide, such as, but not limited to, tetraethylammonium iodide. In some embodiments, the catalyst may be a phase transfer catalyst. As used herein, the term "phase transfer catalyst" refers to any species capable of facilitating the migration of a compound from a first phase into a second, different phase, for example, during the course of a chemical reaction. In some embodiments, the phase transfer catalyst enhances migration of a compound from one phase into a different phase, wherein a chemical reaction takes place. Some examples of phase transfer catalysts include, but are not limited to, benzyl triethylammonium chloride, tetrabutylammonium chloride, tetraethyl ammonium chloride, tetrabutylammonium sulfate, tetraoctylammonium sulfate, and tetramethyl ammonium hydroxide. The phase transfer catalyst may be used in combination with, for example, a base or other chemical reagent. In some embodiments, the reaction involves exposure to sodium hydroxide and a phase transfer catalyst, such as benzyl triethylammonium chloride.

An etherification reaction may optionally be carried out in the presence of one or more solvents. The solvent may be, for example, an organic solvent (e.g., toluene), an aqueous solvent, or a combination thereof. In some cases, the solvent may be a polar solvent (e.g., polar protic solvents, polar aprotic solvents). Examples of polar solvents include, but are not limited to, acetone, ethyl acetate, dimethylformamide (DMF), dimethyl sulfoxide (DMSO), acetonitrile, alcohols, or combinations thereof. In one set of embodiments, the etherification reaction is performed in the presence of DMF. In one set of embodiments, the etherification reaction is performed in the presence of THF. In some cases, the etherification reaction may be performed in the presence of an ionic liquid. In some embodiments, the etherification reaction is performed in the absence of solvent. For example, the compound may be reacted in neat ethylene glycol.

In some cases, the components of an etherification reaction is heated or cooled to any temperature from about 0° C. to about 200° C., for a period of time. In some embodiments, the solution is heated to a temperature from about 20° C. to about 100° C., or from about 40° C. to about 70° C. In some cases, the solution may be heated to about 20° C., about 30° C., about 40° C., about 50° C., about 60° C., about 70° C., about 80° C., or greater. In some embodiments, the etherification reaction mixture is maintained at about 20° C. In some embodiments, the etherification reaction mixture is maintained at room temperature. In some embodiments, the etherification reaction mixture is heated to about 60° C. In some embodiments, the etherification reaction mixture is heated to about 65° C. The reaction may be heated/cooled/maintained at a particular temperature for a period of time, such as up to about 1 hour, about 2 hours, about 3 hours, about 4 hours, about 5 hours, about 10 hours, about 15 hours, about 20 hours, about 25 hours, about 30 hours, or more. In one set of embodiments, the reaction mixture is heated at about 65° C. for about 4 hours. In another set of embodiments, the reaction mixture is maintained at about 20° C. for about 18 hours. It should be understood that other temperatures and reaction times may also be used.

In some embodiments, the method involves a reduction reaction (e.g., see FIG. 4, reduction of pyridazinone ester 18). The term "reduction reaction" is given its ordinary meaning in the art and refers to a chemical reaction in which the oxidation state of at least one atom is reduced. For example, the reduction reaction may involve reduction of an ester or a ketone to an alcohol. The reduction reaction may be carried out using reducing reagents known to those of ordinary skill in the art, including lithium aluminum hydride, lithium borohydride (with or without methanol additive), and diisobutylaluminum hydride (DIBAL-H) in a variety of solvents including tetrahydrofuran, methyltetrahydrofuran, and dichloromethane. In one set of embodiments, the reduction reagent may be a 25% w/w solution of DIBAL-H in toluene, using 2-methyltetrahydrofuran as a cosolvent.

In some embodiments, the invention provides methods for the synthesis of a compound (e.g., intermediate compound) comprising a leaving group. Leaving groups are described herein. In some embodiments, the leaving group is a halide, such as a bromide.

In some cases, the compound includes a moiety (e.g., hydroxyl) which may be readily converted into a leaving group. For example, the compound may include a hydroxyl group which is converted into a tosylate group upon reaction with p-toluenesulfonyl chloride. In other embodiments, a compound may include a hydroxyl group which may be treated with a phosphine (e.g., triphenylphosphine, TPP) and diethylazodicarboxylate (DEAD) using Mitsunobu chemistry to form a leaving group.

In one set of embodiments, the method involves converting a hydroxyl group to a leaving group. For example, the method may involve replacing the hydroxyl group with a leaving group such as a halide (e.g., bromide). In some embodiments, the compound substituted with a hydroxyl group is exposed to a halogenation reagent. In some cases, the halogenation reagent is a brominating reagent, such as phosphorus tribromide, pyridinium dibromide, or a combination of carbon tetrabromide and triphenylphospine. In one set of embodiments, the brominating reagent is phosphorus tribromide.

A halogenation reaction may be performed in the presence of one or more solvents. In some embodiments, the solvent is an organic solvent, such as dichloromethane, chloroform, benzene, or toluene. In one set of embodiments, the solvent used is dichloromethane.

In some cases, the halogenation reaction mixture is heated or cooled to any temperature ranging from 0° C. to about 200° C., for a period of time. In some embodiments, the solution is heated to a temperature ranging from about 20° C. to about 100° C. In some cases, the solution is heated to about 20° C., about 30° C., about 40° C., about 50° C., or greater, including temperatures in between. In some embodiments, the halogenation reaction mixture is maintained at 20° C. The reaction may be heated/cooled/maintained at a particular temperature for a period of time, such as up to 10 minutes, 30 minutes, 1 hour, 2 hours, 3 hours, 4 hours, 5 hours, 10 hours, or more. In another set of embodiments, the reaction mixture is maintained at 20° C. for 30 minutes. It should be understood that other temperatures and reaction times may also be used.

The synthesis of an imaging agent precursor may include other reactions, including ring-opening reactions, reduction reactions, protection/deprotection reactions, and the like.

After any reaction, the compounds (e.g., intermediates, products) described herein may be subjected to one or more purification steps. Purification and isolation may be performed using methods known to those skilled in the art, including separation techniques like chromatography, or combinations of various separation techniques as are known the art. In some embodiments, column chromatography is used with silica or alumina as the stationary phase and a solvent, or mixture of solvents, as the eluent, to recover the product. In some cases, the eluent may include a mixture of a non-polar solvent and a polar solvent. For example, the eluent may include a mixture of heptane and ethyl acetate.

In some cases, the synthesis or a particular reaction may be conducted without need for purification. In some embodiments, a compound or intermediate may be purified using recrystallization, a process which may be repeated until the desired level of purity of the product is obtained. In one embodiment, the compound or intermediate is recrystallized at least once, two times, three times, or four or more times to achieve the desired level of purity. For example, the compound or intermediate may be obtained at a purity of greater than or equal to 50%, 80%, 85%, 90%, 95%, 97%, 98%, 98.5%, or 99.8%. Recrystallization may be achieved using a single solvent, or a combination of solvents. In some cases, recrystallization is achieved by dissolving the compound or intermediate in a solvent such as hexane at elevated temperatures, and then cooling the solution to produce a precipitate. In certain embodiments the compound is recrystallized from hexane.

Some embodiments may involve a ring-opening reaction. For example, a ring-opening reaction may be performed upon exposure of a compound comprising a ring to a nucleophile, optionally in the presence of a catalyst. In some embodiments, the nucleophile may be a hydride (e.g., $H^-$). In some embodiments, the ring-opening reaction may be performed in the presence of a metal-containing catalyst, such as zirconium chloride.

In some embodiments, the method involves reacting a compound comprising formula (V):

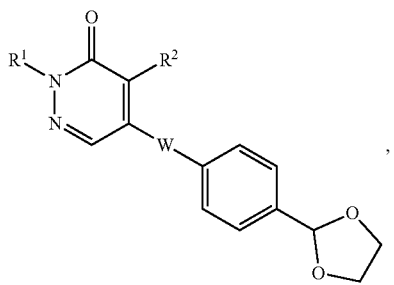

wherein:

W is alkyl or heteroalkyl, optionally substituted;

R¹ is alkyl, optionally substituted; and

R² is hydrogen or halide, with a nucleophile or a radical species to produce a compound comprising formula (VI),

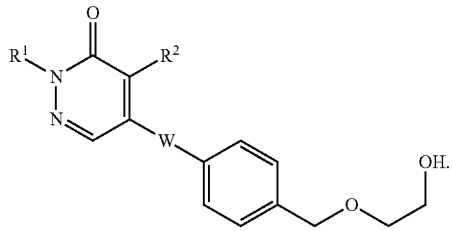

Some embodiments involve exposure of the compound comprising formula (V) to a nucleophile. In some embodiments, the nucleophile is a hydride ion (e.g., H⁻). In some cases, reacting the compound involves contacting the compound with diisobutylaluminum hydride (DIBAL-H).

The ring-opening reaction may also occur via a radical reaction. For example, the compound comprising formula (V) may be exposed to a radical species, such as a hydrogen radical (e.g., H•), in order to produce the compound comprising formula (VI). In some embodiments, the radical species may be generated by a catalyst, such as SmI₂.

In some embodiments, methods are provided for synthesizing a compound comprising formula (VI). For example, an etherification reaction is performed between compounds comprising formulae (Va) and (Vb):

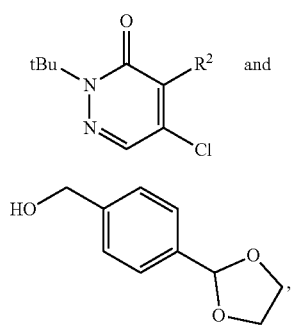

to form a product comprising the formula:

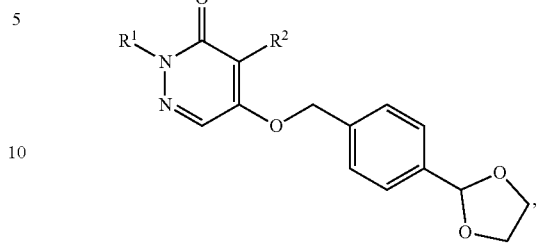

wherein:

R¹ is alkyl, optionally substituted; and

R² is hydrogen or halide.

For example, an etherification reaction between compounds comprising the formulae:

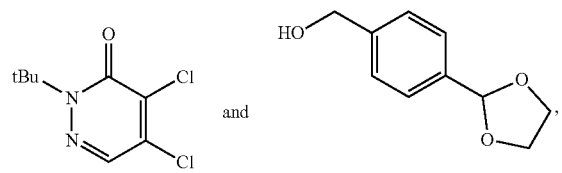 [SMILES: CC(C)(C)n1ncc(Cl)c(Cl)c1=O ; "and" ; OCc1ccc(C2OCCO2)cc1]

forms a product comprising the formula:

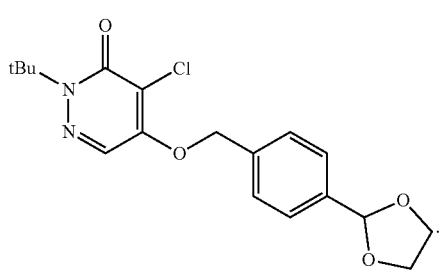 [SMILES: CC(C)(C)n1ncc(OCc2ccc(C3OCCO3)cc2)c(Cl)c1=O]

This etherification reaction may be performed as described herein and may involve exposure to a base (e.g., cesium carbonate, sodium hydroxide, tetramethyl ammonium hydroxide), optionally in the presence of a phase transfer catalyst. In some embodiments, the etherification reaction involves exposure to sodium hydroxide and benzyl triethylammonium chloride. In some cases, the etherification reaction is performed in the presence of a phase transfer catalyst and an ionic liquid.

In one set of embodiments, an etherification reaction between compounds comprising formulae (Vc) and (Vb):

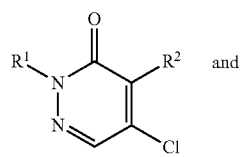

-continued (Vb)

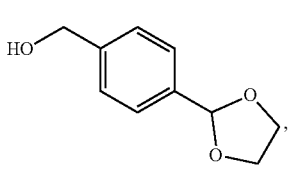

under Mitsunobu conditions (e.g., PPh$_3$ and DEAD) forms a product comprising the formula:

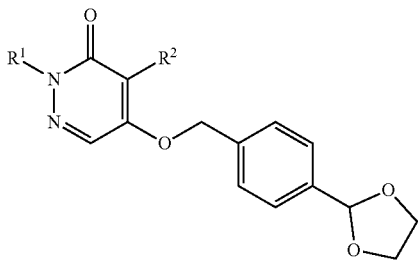

wherein R$^1$ is alkyl, optionally substituted; and
R$^2$ is hydrogen or halide.

For example, an etherification reaction between compounds comprising formulae:

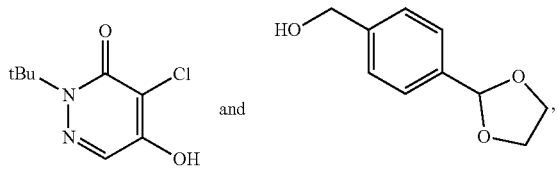 [SMILES: CC(C)(C)n1ncc(O)c(Cl)c1=O ; "and" ; OCc1ccc(C2OCCO2)cc1]

under Mitsunobu conditions (e.g., PPh$_3$ and DEAD) forms a product comprising the formula:

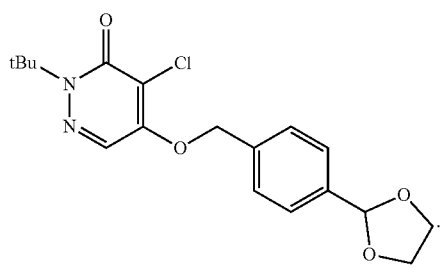 [SMILES: CC(C)(C)n1ncc(OCc2ccc(C3OCCO3)cc2)c(Cl)c1=O]

Some embodiments may further involve the synthesis of a compound comprising formula (VII):

(VII)

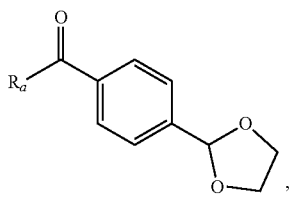

wherein R$^a$ may be hydrogen, hydroxyl, halide (e.g., chloride), O-alkyl, O-heteroalkyl, O-aryl, O-heteroaryl, S-alkyl, S-heteroalkyl, S-aryl, S-heteroaryl, alkyl, heteroalkyl, aryl, or heteroaryl, any of which may be optionally substituted. In some cases, R$^a$ is O-alkyl such as O-methyl, O-ethyl, O-propyl, and the like. In some embodiments, R$^a$ is O-methyl. For example, the method may involve the reaction of methyl 4-formyl benzoate with ethylene glycol in the presence of an acid to produce a compound comprising formula (VII). The compound comprising formula (VII) may be further reacted, for example, to install a leaving group on the compound. In some cases, the leaving group is a hydroxyl group. In one set of embodiments, R$^a$ is methyl, and the carboxy group is treated with a reducing agent such as lithium aluminum hydride, sodium bis(2-methoxyethoxy)aluminum hydride or lithium borohydride to produce a benzylic alcohol.

Figure 5:
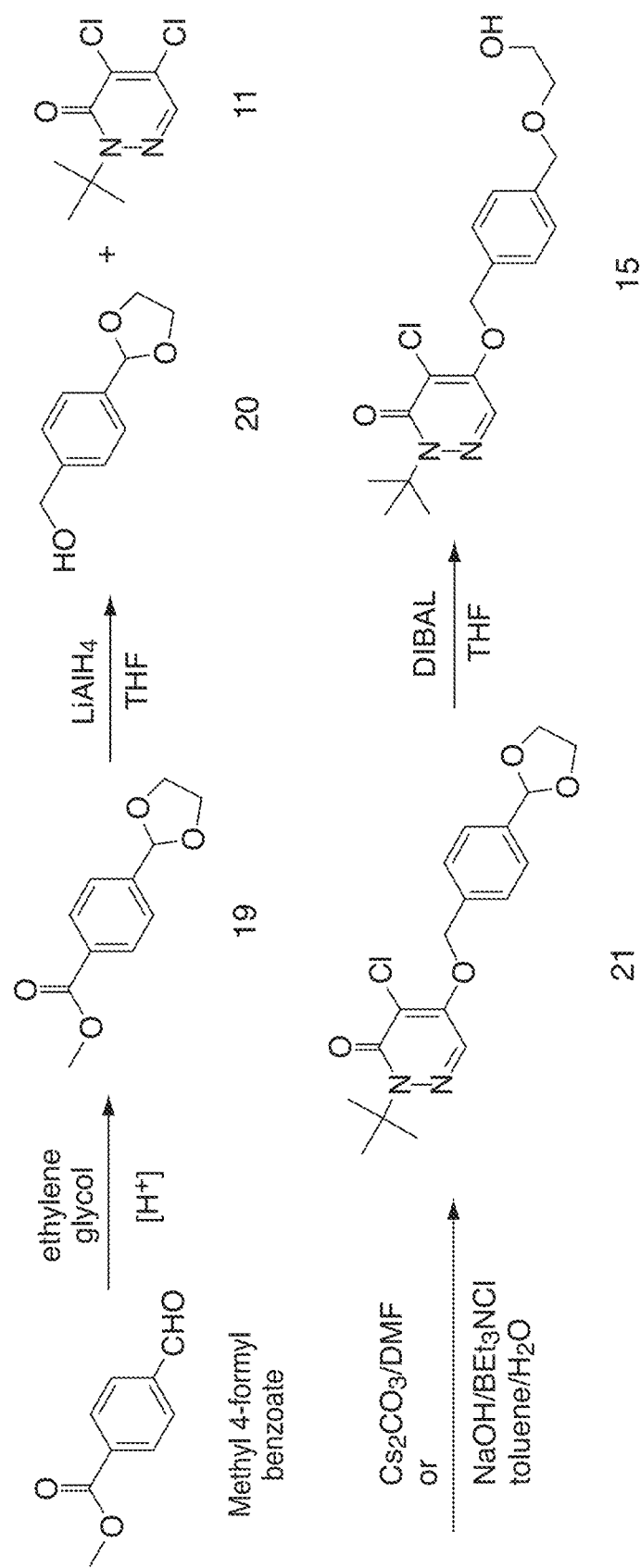
FIG. 5 shows another alternative synthesis of an intermediate compound.

FIG. 5 shows an illustrative embodiment for synthesizing alcohol 15 using a ring-opening reaction. The first step involves the conversion of ether methyl 4-formyl benzoate or 4-formylbenzoic acid to the corresponding acetal through the reaction with ethylene glycol in the presence of an acid. In some embodiments, methyl 4-formyl benzoate and ethylene glycol are reacted in the presence of toluenesulfonic acid and toluene. The solvent may be heated at reflux, using azeotropic distillation to remove any water that is produced in order to drive the reaction to completion. The derived acid or ester 19 may then be reduced to benzyl alcohol 20 with lithium aluminum hydride, sodium bis(2-methoxyethoxy) aluminum hydride, lithium borohydride (e.g., for an ester), or borane (e.g., for an acid). In some cases, lithium aluminum hydride or sodium bis(2-methoxyethoxy)aluminum hydride may be used as the reducing agent. Benzyl alcohol 20 may then be reacted with dichloropyridazinone 11 via an etherification reaction as described herein to afford compound 21. For example, the etherification reaction may be carried out with cesium carbonate, potassium carbonate, or sodium hydroxide in the presence of a variety of phase transfer catalysis reagents, such as, but not limited to, benzyl triethylammonium chloride. In one set of embodiments, the etherification reaction involves the use of cesium carbonate in dimethylformamide. In another set of embodiments, the etherification reaction involves the use of sodium hydroxide with 1-10% benzyl triethylammonium chloride in toluene.

The acetal ring of compound 21 may then be opened to the corresponding alcohol 15 using diisobutylaluminum hydride (DIBAL-H). In some cases, the ring-opening reaction may be carried out in the presence of a catalyst, such as a metal-containing catalyst (e.g., zirconium chloride) or an organic catalyst (e.g., 9-borabicyclononane (9-BBN) dimer).

In some cases, the components of the ring-opening reaction is heated or cooled to any temperature from about −78° C. to about 200° C., for a period of time. In some embodiments, the reaction mixture may be maintained at any temperature from about −78° C. to about room temperature. In some cases, the reaction mixture may be maintained at about −60° C., about −50° C., about −40° C., about −30° C., about −20° C., about −10° C., about 0° C., including all temperatures in between, or greater. In some embodiments, the ring-opening reaction mixture may be maintained at −40° C. In some embodiments, the ring-opening reaction mixture may be maintained at room temperature. The reaction may be heated/cooled/maintained at a particular temperature for a period of time, such as about 10 minutes, about 30 minutes, about 1 hour, about 2 hours, about 3 hours, about 4 hours, about 5 hours, about 10 hours, or any amount of time in between, or more. In another set of embodiments, the reaction mixture may be maintained at about −40° C. for about 1 hour. It should be understood that other temperatures and reaction times may also be used.

Purification of compound 16 may be performed by successive recrystallizations from cumene and/or isobutyl acetate. For example, see Example 37E.

Figure 6:
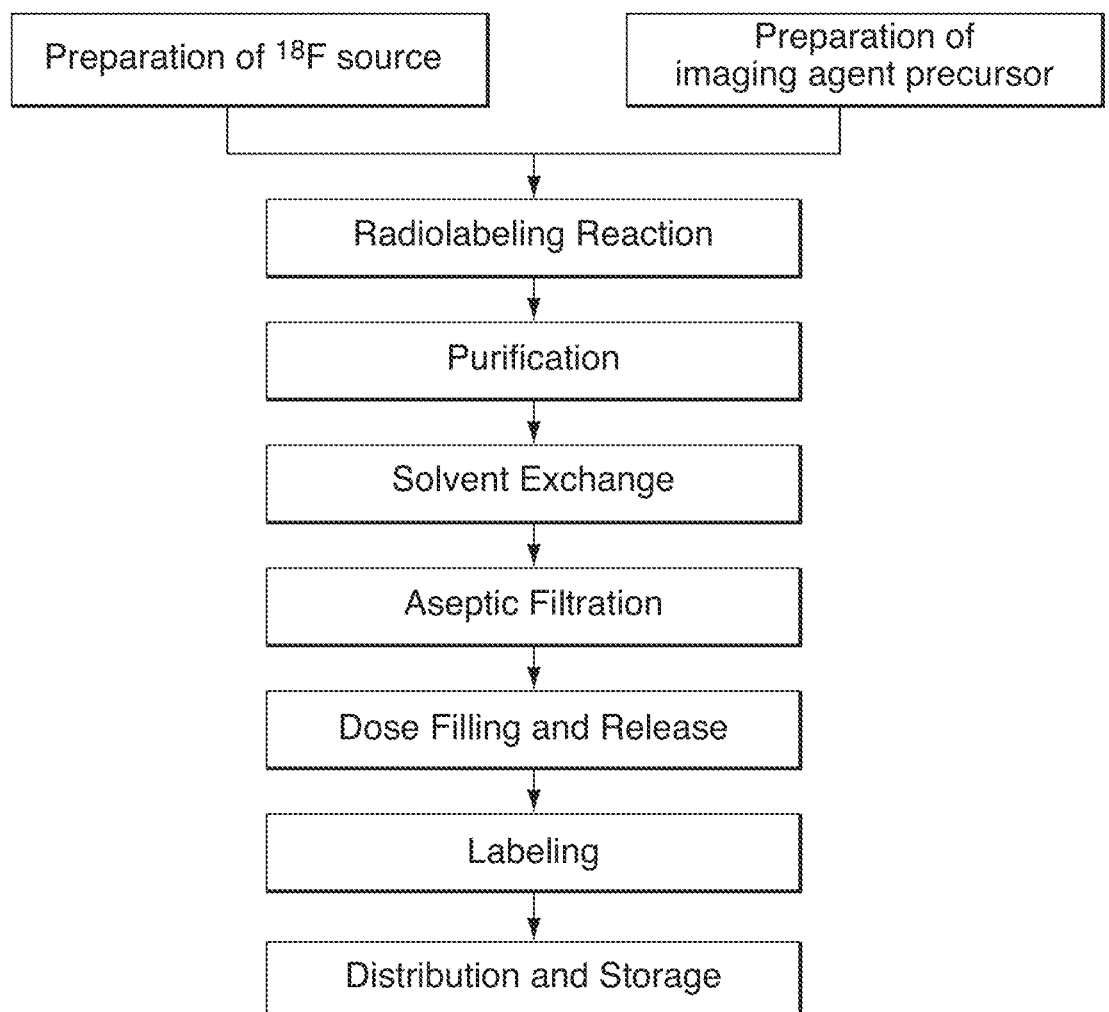
FIG. 6 shows a flow chart describing a method for synthesizing an imaging agent.

Using the method shown in FIG. 6, the overall yield for synthesizing alcohol 15 starting from methyl 4-formylbenzoate may be at least 10%, at least 20%, at least 30%, at least 40%, or at least 50%, without or with the use of chromatography for purification. In some cases, the overall yield for synthesizing alcohol 15 starting from methyl 4-formylbenzoate is approximately 50%, without the use of chromatography for purification.

Any of the methods for synthesizing an imaging agent precursor described herein may further comprise the act of exposing the compound comprising formula (VIII):

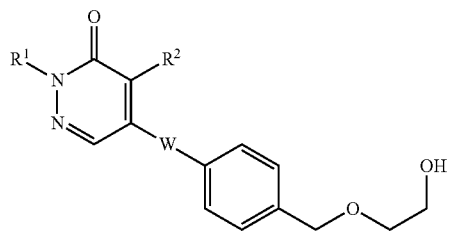

(VIII)

with a reagent comprising a leaving group to form a compound comprising formula (IX):

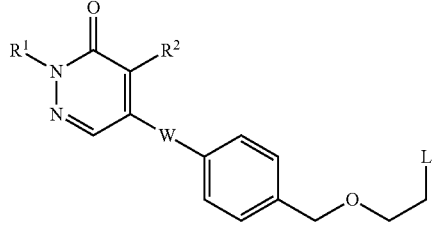

(IX)

wherein W is alkyl or heteroalkyl, optionally substituted;

$R^1$ is alkyl, optionally substituted;

$R^2$ is hydrogen or halide; and

L is a leaving group.

In some cases, the reagent is a sulfonate-containing species and the leaving group is a sulfonate-containing group (e.g., a sulfonate-containing precursor of an imaging agent). In some embodiments, the sulfonate-containing group is mesylate, tosylate, or triflate. In one set of embodiments, the sulfonate-containing group is tosylate. Additional examples of leaving groups are described herein.

For example, the act of exposing the compound comprising the formula:

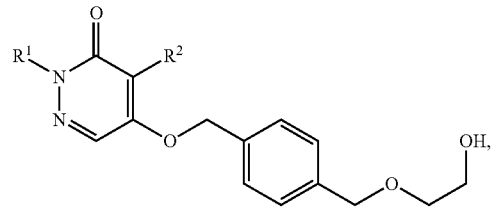

to a reactant comprising a leaving group forms a product comprising the formula:

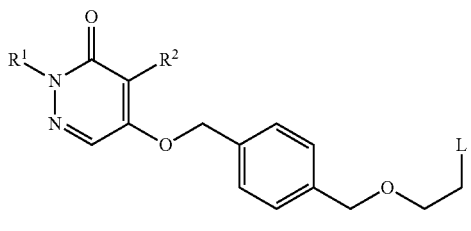

wherein $R^1$, $R^2$, and L are as described herein.

In one embodiment, exposure of a compound comprising the formula:

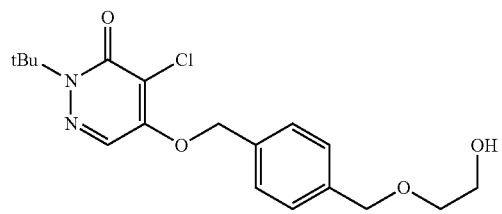 [SMILES: CC(C)(C)n1ncc(OCc2ccc(COCCO)cc2)c(Cl)c1=O]

to a reactant comprising a tosylate group forms the product comprising the formula:

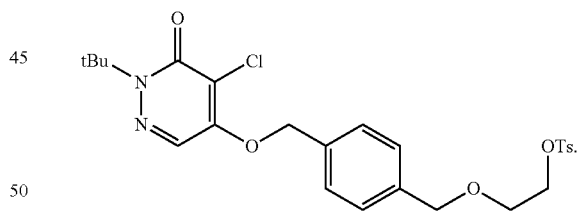

Some embodiments for synthesizing an imaging agent precursor described herein provide novel compounds (e.g., intermediates). In some embodiments, the compound comprises the structure:

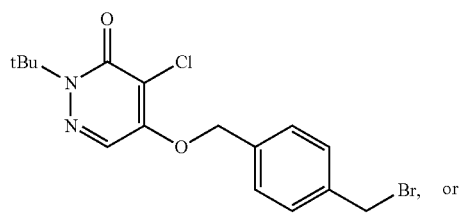

-continued

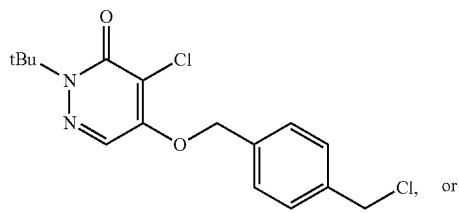, or

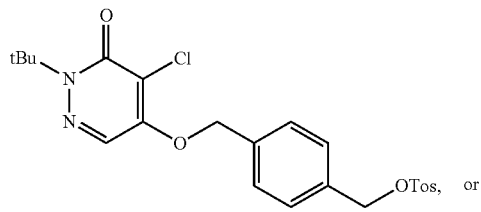, or

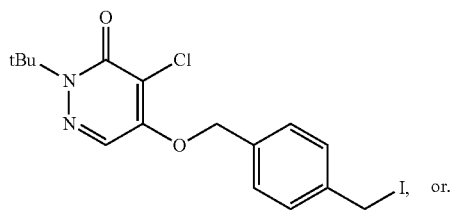, or.

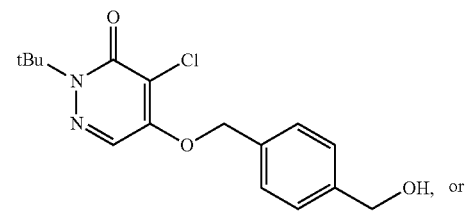, or

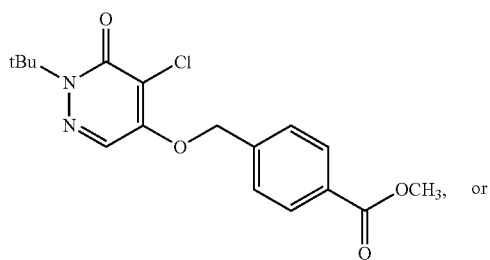, or

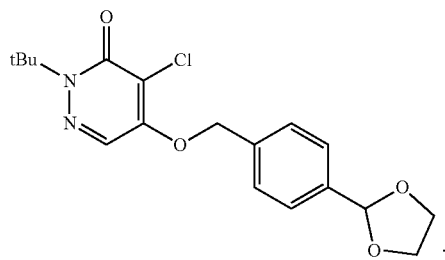.

Exemplary Methods and Applications of Imaging Agents

In some embodiments, the present invention relates to methods of imaging, including methods of imaging in a subject that includes administering a composition or formulation that includes imaging agent 1 to the subject by injection, infusion, or any other known method, and imaging a region of the subject that is of interest. As described herein, (2-t-butyl-4-chloro-5-[4-(2-($^{18}$F)fluoroethoxymethyl)-benzyloxy]-2H-pyridazin-3-1, or imaging agent 1, comprises the formula:

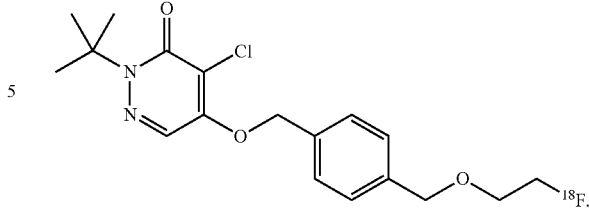

Imaging agent 1 binds to the mitochondrial complex I of the electron transport chain with high affinity. Imaging agent 1 shows selective uptake to the heart due to the high density of mitochondria in the myocardium. Regions of interest may include, but are not limited to, the heart, cardiovascular system, cardiac vessels, blood vessels (e.g., arteries, veins) brain, and other organs. A parameter of interest, such as blood flow, cardiac wall motion, etc., can be imaged and detected using methods and/or systems of the invention. In some aspects of the invention, methods for evaluating perfusion, including myocardial perfusion, are provided.

In some embodiments, methods of the present invention include (a) administering to a subject a composition that includes imaging agent 1, and (b) acquiring at least one image of at least a portion of the subject. In some cases, acquiring employs positron emission tomography (PET) for visualizing the distribution of imaging agent 1 within at least a portion of the subject. As will be understood by those of ordinary skill in the art, imaging using methods of the invention may include full body imaging of a subject, or imaging of a specific body region or tissue of the subject that is of interest. For example, if a subject is known to have, or is suspected of having myocardial ischemia, methods of the invention may be used to image the heart of the subject. In some embodiments, imaging may be limited to the heart, or may include the heart and its associated vascular system.

In some embodiments of the invention, methods of diagnosing or assisting in diagnosing a disease or condition, assessing efficacy of treatment of a disease or condition, or imaging in a subject with a known or suspected cardiovascular disease or condition are provided. A cardiovascular disease can be any disease of the heart or other organ or tissue nourished by the vascular system. The vascular system includes coronary arteries, and all peripheral arteries supplying nourishment to the peripheral vascular system and the brain, as well as veins, arterioles, venules, and capillaries. Examples of cardiovascular diseases include diseases of the heart, such as coronary artery disease, myocardial infarction, myocardial ischemia, angina pectoris, congestive heart failure, cardiomyopathy (congenital or acquired), arrhythmia, or valvular heart disease. In some embodiments, the methods disclosed herein are useful for monitoring and measuring coronary artery disease and/or myocardial perfusion. For example, a method described herein can determine the presence or absence of coronary artery disease and/or the presence or absence of myocardial infarct. Conditions of the heart may include damage, not brought on by disease but resulting from injury—e.g., traumatic injury, surgical injury. In some cases, methods of the invention may include determining a parameter of, or the presence or absence of, myocardial ischemia, rest (R) and/or stress (S) myocardial blood flows (MBFs), coronary flow reserve (CFR), coronary artery disease (CAD), left ventricular ejection fraction (LVEF), end-systolic volume (ESV), end-diastolic volume (EDV), and the like.

In some cases, a subject to whom a method of the invention is applied, may have signs or symptoms suggestive of myocardial ischemia or myocardial infarction. In some cases methods of the invention can be used to identify early or pre-disease conditions that indicate that a subject is at increased risk of a disease. In some instances, methods of the invention can be used to determine a subject's risk of future cardiac events such as myocardial infarction or cardiac death. Imaging methods of the invention can be used to detect myocardial ischemia in subjects already diagnosed as having a myocardial ischemia disorder or condition, or in subjects that have no history or diagnosis of such a condition. In other instances, methods of the invention can be used to obtain measurements that provide a diagnosis or aid in providing a diagnosis of a myocardial ischemia disorder or condition. In some instances, a subject may be already be undergoing drug therapy for a myocardial ischemia disorder or condition, while in other instances a subject may not be undergoing therapy for myocardial ischemia. In some embodiments, methods of the invention can be used to assess efficacy of a treatment for a disease or condition. For example, the heart can be visualized using imaging agents of the invention before, during, and/or after treatment of a condition affecting the heart of a subject. Such visualization may be used to assess a disease or condition, and aid in selection of a treatment regimen, e.g. therapy, surgery, medications, for the subject.

A PET imaging agent may have a high first-pass extraction fraction and can track regional myocardial blood flow over a wide range. These features may permit detection of milder decreases in coronary flow reserve and accurate estimation of absolute myocardial blood flow (MBF). PET imaging agents of the invention provide these and other features and are also available as a unit dose from regional PET radiopharmacies, obviating the need for on-site cyclotrons or costly Rb-82 generators.

In some embodiments of the invention, imaging agent 1 is used as an imaging agent in combination with positron emission tomography (PET) or with other imaging methods including, but not limited to SPECT imaging. In some embodiments of the invention, imaging agent 1 is administered to a subject and imaged in the subject using PET. As will be known to those of ordinary skill in the art, PET is a non-invasive technique that allows serial images and measurements to be obtained in a single subject over a time period. PET imaging used in methods of the invention may be carried out using known systems, methods, and/or devices. In some embodiments of the invention, PET imaging is conducted using a cardiac imaging system. A cardiac imaging system may include PET imaging functionality and a control unit configured to drive the imaging functionality to perform a PET imaging procedure on a portion of the subject before, during, and/or after administration of imaging agent 1 to the subject. In some cases, the control unit is configured to drive the imaging functionality to perform a PET imaging procedure. The control unit may comprise a computer system and/or software. In such a case, the computer system may be programmed or configured to execute the required methods for acquiring and/or analyzing the images. Further, the system may include a data storage device that is readable by a machine, embodying a set of instructions executable by the machine to perform the required methods of acquiring and/or analyzing the images.

The useful dosage of the imaging agent to be administered and the particular mode of administration will vary depending upon such factors as age, weight, and particular region to be imaged, as well as the particular imaging agent used, the diagnostic use contemplated, and the form of the formulation, for example, suspension, emulsion, microsphere, liposome, or the like, as described herein, and as will be readily apparent to those skilled in the art.

In some embodiments, an imaging agent is administered at a low dosage and the dosage increased until the desirable diagnostic effect is achieved. In one embodiment, the above-described imaging agents may be administered by intravenous injection, usually in saline solution, at a dose of about 0.1 to about 100 mCi per 70 kg body weight (and all combinations and subcombinations of dosage ranges and specific dosages therein), or between about 0.5 and about 50 mCi, or between about 0.1 mCi and about 30 mCi, or between 0.5 mCi and about 20 mCi. For use as nuclear medicine imaging agents, the imaging agents, dosages, administered by intravenous injection, may range from about 0.1 pmol/kg to about 1000 pmol/kg (and all combinations and subcombinations of dosage ranges and specific dosages therein), and in some embodiments, less than 150 pmol/kg.

Imaging systems and components thereof will be known to those of ordinary skill in the art. Many imaging systems and components (e.g., cameras, software for analyzing the images, etc.) are known and commercially available, for example, a Siemens Biograph-64 scanner. Any technique, software, or equipment that reduces or eliminates motion in static perfusion images may be used in methods of the invention, because spatial blurring and artifacts can be caused by patient motion during image acquisition. In some embodiments of the invention, images may be acquired in list mode, and may be static, dynamic, or gated images. An appropriate period of time for acquiring images can be determined by one of ordinary skill in the art, and may vary depending on the cardiac imaging system, the imaging agent (e.g., amount administered, composition of the imaging agent, subject parameters, area of interest). As used herein a "period of acquiring images" or an "image acquisition period" may be a period of obtaining a single continuous image, or may be a period during which one or more individual discrete images are obtained. Thus, a period of image acquisition can be a period during which one or more images of one or more regions of a subject are acquired.

In some embodiments of the invention, a period of image acquisition after administration of an imaging agent of the invention to a subject may be between about 30 seconds and about 60 minutes, between about 1 minute and about 30 minutes, between about 5 minutes and about 20 minutes, or at least about 1 minute, about 3 minutes, about 5 minutes, about 6 minutes, about 7 minutes, about 8 minutes, about 9 minutes, about 10 minutes, about 15 minutes, about 20 minutes, about 30 minutes, 4 about 5 minutes, about 60 minutes, or greater. For example, in a rest/stress imaging protocol there would be at least two periods of image acquisition with at least one corresponding to the rest segment and least one corresponding to the stress segment. In some embodiments, imaging may be continuous over the imaging period of time, or images may be acquired at intervals such as in periodic or gated imaging.

In some aspects of the invention, gated acquisition is used to acquire images from a subject to whom an imaging agent prepared by methods of such as imaging agent 1 has been administered. Gated imaging can be used in various aspects of the invention, and for example, may provide images of a beating heart of a subject and may be used to attain a functional evaluation of how well a heart is beating. Gated imaging can be performed by acquiring separate images from the subject at specific intervals during a period of image acquisition. A non-limiting example of gated imaging is a case when a period of image acquisition is about 10 minutes long, and images are acquired at repeated intervals during the 10 minute period. The frequency of acquisition of images during the period can be set by the operator, for example, the frequency can be at least every about 1 msec, about 5 msec, about 10 msec, about 20 msec, about 50 msec, about 100 msec, about 125 msec, about 250 msec, or more. The length of the interval is set by the operator to be triggered by an event, such as a cardiac R wave, with the length of the interval is defined by the number of time bins desired per R wave to R wave interval. Those of skill in the art will be familiar with the concept and methods of gated image acquisition and can use known methods to obtain gated images using imaging agent 1 as an imaging agent.

Image acquisition in gated imaging can be triggered at specific intervals, for example, image acquisition can be triggered using an EKG of the heart. In a non-limiting example, an R wave-gated scanner may trigger acquisition of an image and the mean length of time between one R wave of a heart and the next can be stored. The number of images to collect can then be determined. For example, a first image can be acquired at 125 msec, a second image can be acquired at 250 msec, a third image can be acquired at 375 msec, etc.—thus images in that R interval may be acquired at 125 msec intervals. When the next R interval begins, the collection of images resets and image data is then acquired into the "first" image at 125 msec from that R interval start time, and then into the "second" image collected 250 msec from that R interval start time, etc. Thus, within each R interval image acquisition is added into the initial image of the series and incremented into successive images in the series so that a sequence of images can be collected at a desired frequency with the zero time being reset at the start of each R interval. Acquired gated images can be used to provide an image of heart motion and can provide information on heart wall thickness, whether or not one or more sections of the heart are not moving or beating (e.g. a wall motion defect). Use of gated imaging may provide data with which to judge perfusion of the heart, such as ejection fraction, and to visualize and identify reduced, absent, paradoxical or asynchronous wall motion. Use of gated imaging may also provide data with which to improve assessment of myocardial perfusion, judge cardiac function and to visualize and identify asynchronous wall motion.

In some cases, PET imaging may be used to assess myocardial viability via the ability of this technique to demonstrate metabolic consequences of myocardial ischemia. Using PET imaging, myocardial segments that are likely to improve after revascularization can be identified. In some cases, PET imaging may be used in the detection of coronary artery disease and can also serve as an alternative test for subjects who cannot undergo treadmill exercise stress testing. In some embodiments, a stress test method (e.g., pharmacological stress, exercise stress) may be employed with PET using methods of the invention to qualitatively or quantitatively assess one or more parameters of cardiac function during infusion of the imaging agent. Agents for, and methods of, inducing stress, for example, using exercise or pharmacological stress are well known in the art. Suitable induction of stress can be carried out using established, known agents and methods. Functions usefully measured using methods of the invention include, but are not limited to, in various embodiments, imaging of myocardial perfusion, imaging, or measurement of ventricular function, and measuring coronary blood flow velocity.

In some cases, methods for imaging the heart of a subject may include administering a first dose of imaging agent 1 to the subject while the subject is at rest, acquiring at least one first image of the heart, followed by subjecting the subject to stress (e.g., exercise stress or pharmacological stress) and administering a second dose of imaging agent 1 to the subject during the period of stress, and acquiring at least one other image of the heart.

In some embodiments, the dose of imaging agent 1 to be used during exercise-induced stress in a rest/stress protocol is greater than that necessary for pharmacologically-induced stress with the ratio of exercise-induced stress dose to pharmacologically-induced stress dose being greater then or equal to about 1.2, about 1.3, about 1.4, about 1.5, about 1.6, about 1.7, about 1.8, about 1.9, or greater. With respect to pharmacological stress, in some embodiments of the invention that involve rest/stress imaging methods, the dose of imaging agent 1 administered for imaging during the pharmacological stress is a minimum of two times the dose of imaging agent 1 administered for imaging at rest. With respect to exercise stress, in some embodiments of the invention that involve rest/stress imaging methods, the dose of imaging agent 1 administered for imaging during the exercise-induced stress is a minimum of three times the dose of imaging agent 1 administered for imaging at rest. In some embodiments of the invention, for imaging first at rest followed by imaging with stress, the dose of imaging agent 1 administered at rest will be lower than the dose of imaging agent 1 administered at stress.

In some cases, imaging methods of the invention may be completed in a single day (e.g., less than about 24 hours, less than about 12 hours, less than about 6 hours, less than about 4 hours, less than about 2 hours, less than about 1 hour), as described herein. In other cases, methods may be completed in longer periods of time, e.g. over more than about 24 hours, about 36 hours, or about 48 hours.

Imaging agent 1 may be provided in any suitable form, for example, in a pharmaceutically acceptable form. In some cases, imaging agent 1 is included in a pharmaceutically acceptable composition. In some embodiments, imaging agent 1 is provided as a composition comprising ethanol, sodium ascorbate, and water. In some cases, the composition comprises less than 20 weight % ethanol, less than 15 weight % ethanol, less than 10 weight % ethanol, less than 8 weight % ethanol, less than 6 weight % ethanol, less than 5 weight % ethanol, less than 4 weight % ethanol, less than 3 weight % ethanol, or less ethanol. In some cases, the composition comprises less than 100 mg/mL, less than 75 mg/mL, less than 60 mg/mL, less than 50 mg/mL, less than 40 mg/mL, less than 30 mg/mL, or less sodium ascorbate in water. In a particular non-limiting embodiment, imaging agent 1 is provided as a solution in water comprising less than 4% ethanol and less than 50 mg/mL sodium ascorbate in water.

An imaging agent 1 composition for injection may be prepared in an injection syringe. Imaging agent 1 may be prepared by a radiopharmacy (e.g., using the methods described herein) and/or a PET manufacturing center and provided to a health-care professional for administration. In some aspects of the invention, imaging agent 1 is provided, for example, in a syringe or other container, with ≤50 mg/mL sodium ascorbate in water, ≤4 wt % ethanol, and about 1 to 14 mCi of imaging agent 1. The amount of imaging agent 1 may vary depending on whether a rest or stress dose is being administered. For example, a higher amount of imaging agent 1 may be provided in a syringe or container for use in a stress dose administration than provided in a syringe for use in a rest administration. A dose of imaging agent 1 may be diluted with saline (e.g., as described herein), if needed to obtain a practical dose volume. For example, if the activity concentration of imaging agent 1 is so high that only 0.1 mL is need for an appropriate dose for a subject, the solution can be diluted, e.g., with sterile saline, so the syringe contains 0.5 ml to 4 or more ml of an imaging agent 1 solution for administration. In some embodiments of the invention, an injection volume for imaging agent 1 is between 0.5 and 5 ml, 1 and 4 ml, 2 and 3 ml, at least 0.5 ml, 1 ml, 2 ml, 3 ml, 4 ml, 5 ml, 6 ml, 7 ml, 8 ml, 9 ml, 10 ml, or more. Those of skill in the art will recognize how to dilute imaging agent 1 to produce a sufficient dose volume for administration. In some aspects of the invention, imaging agent 1 is provided in a container such as a vial, bottle, or syringe, and may be transferred, as necessary, into a suitable container, such as a syringe for administration.

Syringes that include an adsorbent plunger tip may result in 10 to 25% of imaging agent 1 activity remaining in the syringe after injection. Syringes lacking an adsorbent plunger tip may be used, such as a 3 or 5 mL NORM-JECT (Henke Sass Wolf, Dudley, Mass.) or other equivalent syringe lacking an adsorbent plunger tip. Reduction of adsorption in the syringe can increase the amount of imaging agent 1 that is transferred from the syringe and administered to the subject in methods of the invention. A syringe used in methods of the invention may comprise imaging agent 1, and be a non-adsorbing, or reduced adsorbent syringe. In some embodiments a non-adsorbent or reduced-adsorbent syringe is a syringe that has been coated or treated to reduce imaging agent 1 adsorption. In some embodiments, a non-adsorbent or reduced-adsorbent syringe is a syringe that lacks an adsorbent plunger tip. In some embodiments, a syringe used in conjunction with the invention adsorbs less than 20%, 19%, 18%, 17%, 16%, 15%, 14%, 13%, 12%, 11%, 10%, 9%, 8%, 7%, 6%, 5%, 4%, 3%, 2%, 1%, or 0.5% of imaging agent 1 it contains. In certain aspects of the invention, a syringe that contains imaging agent 1 does not include a rubber or latex tip on the plunger. In some cases a syringe used in methods of the invention, includes a plunger that adsorbs less than 20%, 19%, 18%, 17%, 16%, 15%, 14%, 13%, 12%, 11%, 10%, 9%, 8%, 7%, 6%, 5%, 4%, 3%, 2%, 1%, or 0.5% of imaging agent 1 that the syringe contains. A syringe of the invention may also comprise sodium ascorbate, ethanol, and water, and certain embodiments of the invention include a syringe containing imaging agent 1 in a solution comprising less than 4% ethanol and less than 50 mg/mL sodium ascorbate in water. A syringe of the invention may be a syringe that is latex free, rubber free, and/or lubricant free. A syringe of the invention may contain imaging agent 1 in an amount between about 1.5 and about 14 mCi. A syringe of the invention may contain about 20 mCi or less of imaging agent 1.

Components of a composition comprising imaging agent 1 may be selected depending on the mode of administration to the subject. Various modes of administration that effectively deliver imaging agents of the invention to a desired tissue, cell, organ, or bodily fluid will be known to one of ordinary skill in the art. In some embodiments, the imaging agent is administered intravenously (e.g., intravenous bolus injection) using methods known to those of ordinary skill in the art. As used herein, a dose that is "administered to a subject" means an amount of the imaging agent, e.g. imaging agent 1, that enters the body of the subject. In some embodiments, due to factors such as partial retention of imaging agent such as imaging agent 1 in a syringe, tubing, needles, catheter, or other equipment used to administer the imaging agent to a subject, the amount of an imaging agent such as imaging agent 1 that is measured or determined to be in the a syringe or other equipment prepared for administration may be more than the amount in the dose that is administered to the subject. In some embodiments, an injection of an imaging agent is followed by a flushing injection of normal saline, into the subject, using the same tubing, needle, port, etc., used for administration of imaging agent 1. Flushing may be performed immediately following administration of imaging agent 1, or up to 1 min, 2 min, 3 min, 5 min, or more, after the administration. The volume of saline or other agent for flushing may be up to 5 ml, 6 ml, 7 ml, 8 ml, 9 ml, 10 ml, 15 ml, 20 ml, or more. As will be understood by those of ordinary skill in the art, in embodiments where imaging agent 1 is administered using a syringe or other container, the true amount of imaging agent 1 administered to the subject may be corrected for any imaging agent 1 that remains in the container. For example, the amount of radioactivity remaining in the container, and tubing and needle or delivery instrument that carried the imaging agent from the container and into the subject can be determined after the imaging agent has been administered to the subject and the difference between the starting amount of radioactivity and the amount remaining after administration indicates the amount that was delivered into the subject. In some cases, the container or injection device (e.g., catheter, syringe) may be rinsed with a solution (e.g., saline solution) following administration of imaging agent 1.

In some embodiments of the invention, the total amount of imaging agent 1 administered to a subject over a given period of time, e.g., in one session, is less than or equal to about 50 mCi, less than or equal to 40 mCi, less than or equal to 30 mCi, less than or equal to 20 mCi, less than or equal to 18 mCi, less than or equal to 16 mCi, less than or equal to 15 mCi, less than or equal to 14 mCi, less than or equal to 13 mCi, less than or equal to 12 mCi, less than or equal to 10 mCi, less than or equal to 8 mCi, less than or equal to 6 mCi, less than or equal to 4 mCi, less than or equal to 2 mCi, less than or equal to 1 mCi, less than or equal to 0.5 mCi. The total amount administered may be determined based on a single dose or multiple doses administered to a subject within a given time period of up to 1 minute, 10 minutes, 30 minutes, 1 hour, 2 hours, 6 hours, 12 hours, 24 hours, 48 hours, or more.

Based on radiation dose studies, the desirable maximum dose administered to a subject may be based on determining the amount of imaging agent 1 which limits the radiation dose to about 5 rem to the critical organ and/or about 1 rem effective dose (ED) or lower, as will be understood by those of ordinary skill in the art. In a particular embodiment, the desirable maximum dose or total amount of imaging agent 1 administered is less than or equal to about 25 mCi, or less than or equal to about 14 mCi over a period of time of up to 30 min, 1 hour, 2 hours, 6 hours, 12 hours, 24 hours, 48 hours, or more. In some embodiments, the maximum dose of imaging agent 1 administered to a subject may be less than 3.5 µg per 50 kg of body weight per day. That is, in some embodiments of the invention, the maximum dose of imaging agent 1 administered to a subject may be less than about 0.07 µg of imaging agent 1 per kg of body weight per day.

In some embodiments, methods of the invention include administering to a subject a first dose (e.g., rest dose) of imaging agent 1 while the subject is at rest, and performing a first PET imaging procedure (e.g., a PET rest imaging procedure) and acquiring at least a first image of a portion of a subject. In some cases, after administering an imaging agent such as imaging agent 1 while the subject is at rest, the subject may be subjected to stress and during the stress a second dose (e.g., stress dose) of an imaging agent such as imaging agent 1 is administered to the subject, and a second PET imaging procedure (e.g., a PET stress imaging procedure) is performed on the subject and at least one other image of a portion of the subject may be acquired. The above is an example of a method that may be referred to as a rest-stress test. The time between the completion of the first PET imaging procedure and administration of the second imaging agent dose is referred to as the wait time. In some cases, a rest-stress test may be completed in a period of time of less than 48 hours, less than 36 hours, less than 24 hours, less than 12 hours, less than 6 hours, less than 5 hours, less than 4 hours, less than 3 hours, less than 2 hours, less than 1 hour, less than 30 minutes, or less.

In some embodiments, the amount of imaging agent 1 administered in a first dose to a subject at rest (e.g., rest dose in a rest-stress test) is between about 1 mCi and about 5 mCi, between about 2 mCi and about 4 mCi, between about 2.5 mCi and about 3.5 mCi, or about 3 mCi. Following administration of the first dose of imaging agent 1, a PET imaging procedure may be performed and at least one first image may be acquired of at least a portion of the subject.

In some cases, the amount of imaging agent 1 administered to a subject during stress may be based on the amount of imaging agent 1 administered to the subject at rest. That is, the dosing during stress may be based, at least in part, on a dosing ratio (DR) (e.g., ratio of stress-dose to rest-dose). The DR may depend on numerous factors as will be known to those of ordinary skill in the art, and in some cases, may depend on the method of inducing stress in the subject. In some cases, the DR is between 1 and 5, between 1 and 4, between 1 and 3, between 2 and 5, or between 2 and 4. In some cases, the DR is at least 1, at least 1.5, at least 2, at least 3, at least 4, or at least 5. In some cases, the DR is between 2.5 and 5.0, or 2.5 and 4.0, or 3.0 and 4.0, or 3.0 and 5.0 times greater than the first dose of the imaging agent. In some cases, the DR required for a subject subjected to exercise stress is more than the DR and/or time interval used for a subject subjected to pharmacological stress. This may be due, in part, to a lower net myocardial uptake of radioactivity with exercise. In some cases, the DR employed for a subject subjected to exercise stress is between 2 and 4, between 2.5 and 3.5, or at least 3.0, at least 3.5, at least 4.0, or more, in embodiments wherein the wait time is at least 15 minutes 30 minutes, 1 hour, 1.5 hours, 2 hours, or the like. In some cases, the DR employed for a subject subjected to pharmacological stress is between 1 and 3, or between 1.5 and 2.5, or at least 2.0, at least 2.2, or at least 2.5, or more, in embodiments wherein the wait time is at least 15 minutes, 30 minutes, 1 hour, 1.5 hours, 2 hours, or the like. In a particular embodiment, for a subject subjected to pharmacological stress, a DR of at least 2.2 for a wait time of at least 15 minutes or at least 30 minutes is employed, and/or for a subject subjected to exercise stress, a DR of at least 3.0 for a wait time of at least 30 minutes or at least 1 hour is employed.

In some cases, the imaging agent is between about 2.0 mCi and about 3.5 mCi, or 2.4 mCi to about 2.9 mCi, or between about 2.5 mCi to about 3.0 mCi, or between about 2.5 mCi and about 3.5 mCi.

In a particular embodiment, for pharmacological stress (e.g., vasodilator stress induced by administration of adenosine or regadenoson), a dose of about 2.9 mCi to about 3.4 mCi rest is provided during rest, and a dose of about 2.0 to about 2.4 times the rest dose is provided during stress, with a wait time of at least about 15 minutes or at least about 30 minutes.

In some cases, the second dose of the imaging agent is between about 5.7 mCi and about 6.2 mCi, or between about 6.0 mCi and about 6.5 mCi, and about 5.7 mCi and about 6.5 mCi.

In another embodiment, for exercise stress, a dose of about 1.7 mCi to about 2.0 mCi is provided during rest, and a dose of about 3.0 to about 3.6 times the rest dose is provided during stress, with a wait time of at least about 30 minute or at least about 60 minutes. In some cases, the second dose of the imaging agent is between about 8.6 mCi and about 9.0 mCi, or between about 9.0 and about 9.5 mCi, or between about 8.6 mCi and about 9.5 mCi.

In another embodiment, for pharmacological stress, a dose of between about 2.4 mCi and about 2.9 mCi is administered during rest, and a dose between about 5.7 mCi and about 6.2 mCi is administered during stress (e.g., DR of at least about 2), wherein the wait time is at least about 15 minutes or at least about 30 minutes. In another embodiment, for exercise stress, a dose of between about 1.7 mCi and about 2.0 mCi is administered during rest, and a dose of between about 8.6 mCi and about 9.0 mCi is administered during stress (e.g., DR at least about 3), wherein the wait time is at least 30 minutes or at least 60 minutes.

In a particular embodiment, for pharmacological stress, a dose of about 2.9 mCi to about 3.3 mCi rest is provided during rest, and a dose of 2.0 to 2.4 times the rest dose is provided during stress, with a wait time of at least 15 minutes or at least 30 minutes. In another embodiment, for exercise stress, a dose of about 2.9 mCi to about 3.3 mCi is provided during rest, and a dose of 3.0 to 3.6 times the rest dose is provided during stress, with a wait time of at least 30 minute or at least 60 minutes.

In yet another embodiment, for pharmacological stress, a dose of about 2.5 mCi to about 3.0 mCi rest is provided during rest and a dose about 6 mCi to about 6.5 mCi is provided during stress. In still yet another embodiment, for exercise stress, a dose of about 2.5 mCi to about 3.0 mCi rest is provided during rest and a dose about 9 mCi to about 9.5 mCi is provided during stress.

In some embodiments, administering during the stress includes beginning administering the second dose within a period of time after completing the rest imaging procedure (e.g., the wait period). In some cases, the second dose may be administered at a period of time of at least 5 minutes, 10 minutes, 15 minutes, 20 minutes, 30 minutes, 40 minutes, 45 minutes, 50 minutes, 60 minutes, 70 minutes, 80 minutes, 90 minutes, 2 hours, 4 hours, 6 hours, 12 hours, 24 hours, or greater, after completing the rest imaging procedure. In some cases, the second dose is administered at a time period of between 5 minutes and 30 days, between 5 minutes and 20 days, between 5 minutes and 10 days, between 5 minutes and 5 days, between 5 minutes and 4 days, between 5 minutes and 3 days, between 5 minutes and 48 hours, between 5 minutes and 24 hours, between 5 minutes and 12 hours, between 5 minutes and 2 hours, between 5 minutes and 90 minutes, between 10 minutes and 60 minutes after completing the rest imaging procedure.

For stress testing in methods of the invention, a subject may be subjected to stress using procedures known to those of ordinary skill in the art. In some cases, the subject may be subjected to stress using procedures including exercise stress and/or pharmacological stress. Pharmacological stress may be induced by administering to the subject a pharmacological agent such as a vasodilator. Examples of useful pharmacological stress agents, include, but are not limited to adenosine, dobutamine, dipyridamole, regadenoson, binodeneson, apadeneson, and other adenosine A2a receptor agonists. Dosing and administration of pharmacological stress inducing agents, such as vasodilators, are well known in the art and can be determined for use in conjunction with methods and systems of the invention. Exercise stress may be induced using a treadmill, exercise bicycle, hand crank, or other equipment suitable to increase a subject's heart rate through increased exertion.

In some embodiments of the invention a rest/stress method is followed. In a rest/stress method a period of rest and imaging is followed by a period of stress and imaging, with the order being rest first, followed by stress. In certain embodiments of the invention, a stress/rest method may be used. In a stress/rest method, a period of stress and imaging is followed by a period of rest and imaging, with the order being stress first, followed by rest. In some aspects of the invention, imaging agent 1 can be used in a "stress only" method, in which stress is induced in a subject for imaging with imaging agent 1 with no rest imaging during the subject session. In some embodiments of the invention, imaging agent 1 can be used in a "rest only" method, in which a subject does not undergo stress induction, but is only imaged with imaging agent 1 at rest in that session.

Exemplary Cassettes and Reaction Systems

In some embodiments, systems, methods, kits, and cassettes are provided for the synthesis of an imaging agent (e.g., imaging agent 1). In some embodiments, an imaging agent may be prepared using an automated reaction system comprising a disposable or single use cassette. The cassette may comprise all the non-radioactive reagents, solvents, tubing, valves, reaction vessels, and other apparatus and/or components necessary to carry out the preparation of a given batch of imaging agent. The cassette allows the reaction system to have the flexibility to make a variety of different imaging agents with minimal risk of cross-contamination, by simply changing the cassette. By the term "cassette" is meant a piece of apparatus designed to fit removably and interchangeably onto automated reaction systems, in such a way that mechanical movement of moving parts of the automated reaction system controls the operation of the cassette from outside the cassette, ie., externally. In certain embodiments, a cassette comprises a linear arrangement of valves, each linked to a port where various reagents, cartridges, syringes, and/or vials can be attached, by either needle puncture of a septum-sealed vial, or by gas-tight, marrying joints. Each valve may have a male-female joint which interfaces with a corresponding moving arm of the automated synthesizer. External rotation of the arm can control the opening or closing of the valve when the cassette is attached to the automated reaction system. Additional moving parts of the automated reaction system are designed to clip onto syringe plunger tips, and thus raise or depress syringe barrels. An automated reaction system may further include a controller and one or more controllable valves in electrical communication with the controller. An automated reaction system may also include additional vessels, valves, sensors, heaters, pressurizing elements, etc., in electrical communication with the controller. An automated reaction system may be operated by a controller using suitable software for control of valve openings and closings, heating, cooling, pressure levels, fluid movement, flow rate, etc. The automated reaction system may optionally include a computer operating system, software, controls, etc., or other component. In addition, the automated reaction system may comprise a mount for the cassette.

Examples of automated reaction systems (e.g., a nucleophilic reaction system), include, but are not limited to, the Explora GN or RN synthesis system (Siemens Medical Solutions USA, Inc.), GE-Tracerlab-MX synthesis system (GE Healthcare), Eckert & Zeigler Modular-Lab Synthesis system, etc., which are commonly available at PET manufacturing facilities.

The automated reaction systems may carry-out numerous steps, as outlined in FIG. 6, including, but not limited to, preparation of the $^{18}$F fluoride species, providing an imaging agent precursor, optionally in a solution (e.g., as described herein, for example, imaging agent precursor 1 in acetonitrile), a radiolabeling reaction (e.g., reaction of the $^{18}$F species and the imaging agent precursor to form the imaging agent) optionally in a synthesis module, purification (e.g., by preparative HPLC), solvent exchange (e.g., by SepPak), aseptic filtration, and release into a container. For example, see Examples 9, 10, and 11.

Figure 7:
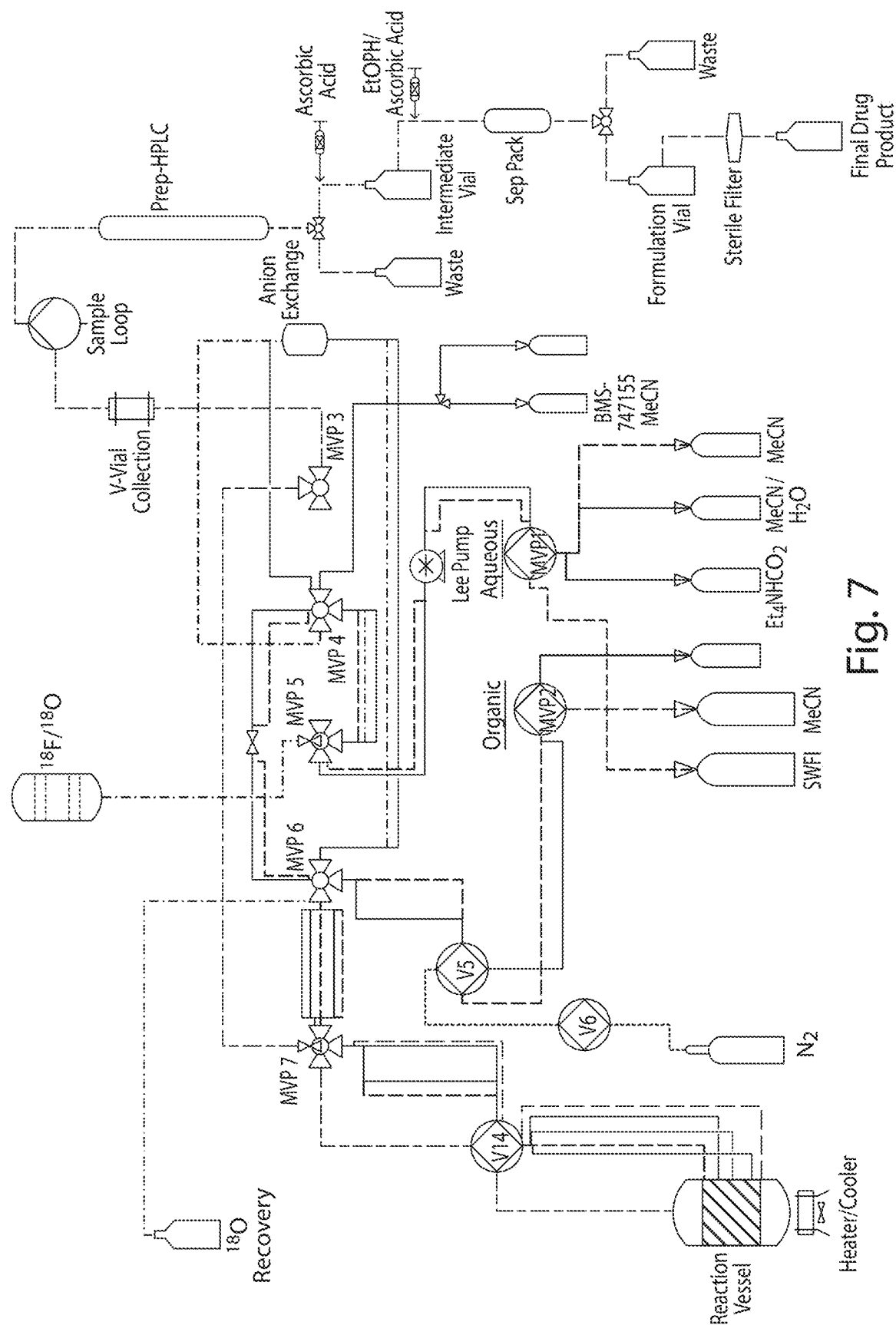
FIG. 7 is a schematic representation of a system for synthesizing an imaging agent using a modified Explora GN synthesis module.
Figure 8:
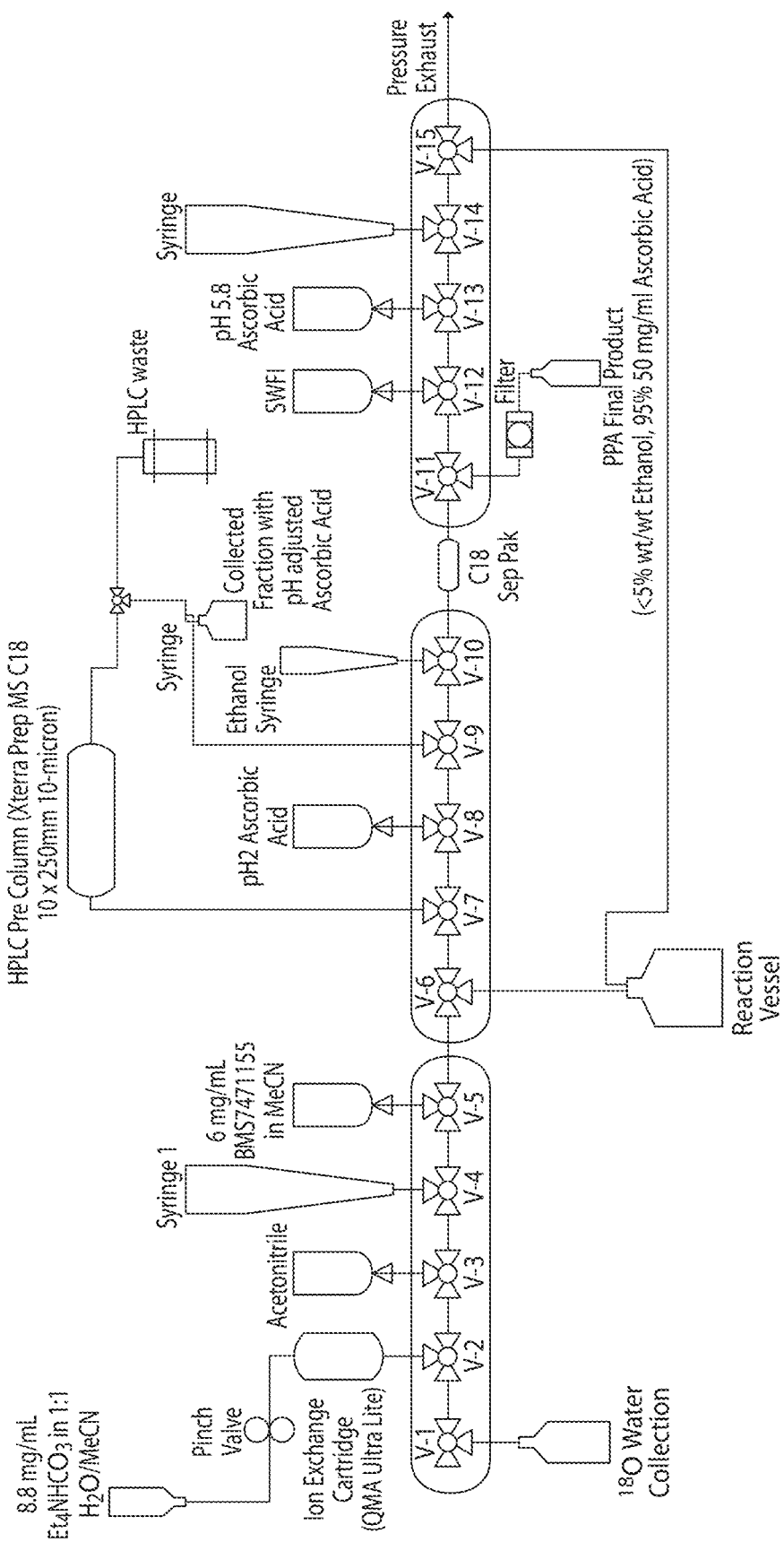
FIG. 8 is a schematic representation of a cassette, with associated columns and reagents for synthesizing an imaging agent using a modified GE-Tracerlab-MX synthesis module.

In some embodiments, the automated reaction system may make use of a cassette comprising a reaction module in fluid connection with a purification module and/or a formulation module. FIGS. 7 and 8 show schematic representations of cassettes in connection with exemplary reaction systems for synthesizing an imaging agent comprising a reaction module, a purification module, and/or a formulation module.

For example, the reaction module may include a reaction chamber in which conversion of the imaging agent precursor to the imaging agent is performed. The reaction module may include a source of a fluoride species (e.g., $^{18}$F), a source of the imaging agent precursor, a source of an additive (e.g., salt additive), and other sources of additional components such as solvents, each of which may optionally be fluidly connected to the reaction chamber. The reaction module may also comprise an anion exchange column for purification of the fluoride species, prior to introduction into the reaction chamber.

Upon reaction, the resulting imaging agent product is transferred from the reaction module to the purification module for further processing, treatment, and/or purification. The purification module may include, for example, a column (e.g., an HPLC column) fluidly connected to one or more sources of solvents to be used as eluents. The purification module may further comprise a source of a stabilizing agent (e.g., ascorbic acid or a salt thereof), which may be added to the imaging agent upon purification (e.g., by HPLC). The purified imaging agent is then transferred to the formulation module, where further purification and formulation may be performed. The formulation module may include a filter for aseptic filtration and/or a C-18 column for solvent exchange.

In another embodiment, a cassette comprises a reaction module and a formulation module. A reaction module of the invention may include a source of $^{18}$F, a filter to remove unreacted [$^{18}$O]H$_2$O, a source of an ammonium salt, a source for a diluent for the $^{18}$F, a source for an imaging agent precursor, (e.g., imaging agent precursor 1 shown in FIG. 1, or other imaging agent precursor), a source for an H$_2$O diluent for the imaging agent precursor, a reaction vessel for reacting the $^{18}$F and the imaging agent precursor, a solid phase extraction column (e.g., a C18 column, or other suitable column) in fluid communication with the reaction vessel. The solid phase extraction column includes a solid sorbent to adsorb the radiolabeled imaging agent product on the sorbent. At least a portion of the residual reaction impurities pass through solid phase extraction column without adsorbing on the sorbent. The reaction module also includes a source of wash solutions in fluid communication with the solid phase extraction column for providing wash solutions to elute the remaining impurities on the sorbent, and includes a source of an eluent (e.g., as H$_2$O/MeCN, or other suitable eluent) in fluid communication with the solid phase extraction column for eluting the radiolabeled imaging agent product off the sorbent. The reaction module may also include a source of a diluent for the eluted radiolabeled imaging agent.

A formulation module of an apparatus of the invention may be in fluid communication with a reaction module and may include a solid phase extraction cartridge that includes a solid sorbent (e.g., C-18, or other suitable sorbent) to adsorb the diluted radiolabeled imaging agent, a source of wash solutions (e.g., comprising ascorbic acid, a salt thereof, or other suitable wash solution) in fluid communication with the solid phase extraction cartridge for providing wash solutions to wash off any remaining impurities on the sorbent, and a source of eluting fluid (e.g., ethanol, or other suitable eluting fluid) in fluid communication with the solid phase extraction cartridge for eluting the radiolabeled imaging agent product off the sorbent. The formulation module may also include a source of a diluent (e.g., comprising ascorbic acid, a salt thereof, or other suitable diluent), for diluting the eluted radiolabeled imaging agent. The formulation module may also be in fluid communication with a sterilizing filter (e.g., a Millipore Millex GV PVDF sterilizing filter, or other suitable sterilizing filter).

In a particular embodiment, a cassette is provided for use with an automated synthesis module, for example, a GE TRACERlab MX synthesis module. In one embodiment, a cassette comprises a disposable sterilized assembly of molded stopcock manifolds specifically designed for use with the automated synthesis module (e.g., GE TRACERlab MX synthesis module). Individual manifolds are connected in a linear or non-linear fashion to form a directional array that dictates the flow path of reagents used in the preparation of an imaging agent (e.g., imaging agent 1) injection. In some embodiments, the main body of the cassette contains at least one manifold comprising a plurality of manifold positions (e.g., stockcocks). For example, the main body may comprise at least one, two, three, four or more, manifolds. The cassette may comprise between 1 to 20 manifold positions, between 1 to 15 manifold positions, between 5 and 20 manifold positions, between 5 and 15 manifold positions. Each of the manifolds may or may not be symmetrical. In one embodiment, the main body of the cassette contains three plastic manifolds each fitted with five standard molded stopcocks, thereby having a total of 15 total manifold positions. Individual stopcocks are adapted with luer fittings to accommodate solvents, reagents, syringes, tubing required for gas and liquid handling, etc. The stopcocks are adapted for solvents and reagents and may be fitted with plastic spikes upon which inverted punch vials are located, while those featuring tubing and syringes are fitted with male luer connections according to function. In some embodiments, the cassette comprises a linear arrangement of a plurality of stopcock manifolds connected one or more of the components selected from the group consisting of a gas inlet, anion exchange cartridge, C-18 cartridge, syringe, solvent reservoir, reaction vessel, HPLC system, collection vessel, reservoir for solution of ascorbic acid or salt thereof, and exhaust outlet. In some cases, the cassette further comprises tubing. In some cases, the cassette further comprising an imaging agent synthesis module, wherein the apparatus is fluidically connected to the cassette. In some cases, the apparatus is capable carrying out the method of synthesizing an imaging agent as described herein (e.g., a method of synthesizing imaging agent 1).

The cassette configuration required for the preparation of imaging 1 injection is depicted in FIG. 8. The following provides a description of the attachments to each of the 15 manifold positions: 1) luer connection (2)—gas inlet and [$^{18}$O]H$_2$O recovery; 2) anion exchange cartridge—QMA Light; 3) spike connection—MeCN; 4) syringe—empty; 5) spike connection—imaging agent precursor 1; 6) luer connection—reaction vessel; 7) HPLC inlet; 8) spike connection—ascorbic acid; 9) luer connection—collection vessel; 10) syringe—EtOH; 11) luer connection—final product vial; 12) spike connection—SWFI; 13) spike connection—ascorbic acid; 14) syringe—empty; 15) luer connection (2)—reaction vessel and exhaust. Manifold one (stopcocks 1-5) is joined to manifold two (stopcocks 6-10) using two male luer connections fitted with a short length of silicon tubing. Manifold two is connected to manifold three (stopcocks 11-15) using a C-18 Sep-Pak® and the appropriate luer adapters. Individual manifold connections, luer fittings and all silicon tubing are readily available from commercial suppliers.

In some embodiments, the present invention provides a cassette for the preparation of an imaging agent comprising the formula:

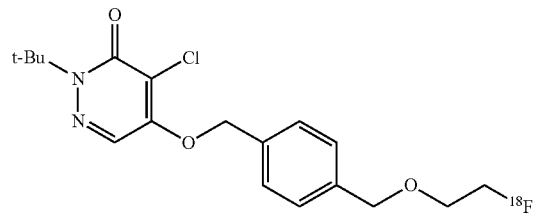 [SMILES: CC(C)(C)n1ncc(OCc2ccc(COCC[18F])cc2)c(Cl)c1=O]

comprising: (i) a vessel containing an imaging agent precursor comprising the formula:

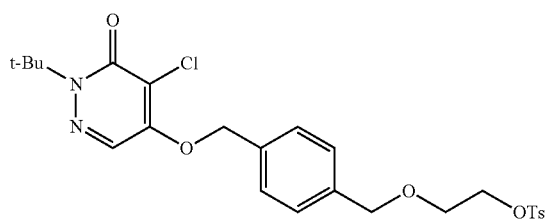 [SMILES: Cc1ccc(S(=O)(=O)OCCOCc2ccc(COc3cnn(C(C)(C)C)c(=O)c3Cl)cc2)cc1]

and (ii) a conduit for adding a source of $^{18}$F.

Pharmaceutical Compositions

Once an imaging agent or an imaging agent precursor has been prepared or obtained, it may be combined with one or more pharmaceutically acceptable excipients to form a pharmaceutical composition that is suitable for administering to a subject, including a human. As would be appreciated by one of skill in this art, the excipients may be chosen, for example, based on the route of administration as described below, the agent being delivered, time course of delivery of the agent, and/or the health/condition of the subject.

Pharmaceutical compositions of the present invention and for use in accordance with the present invention may include a pharmaceutically acceptable excipient or carrier. As used herein, the term "pharmaceutically acceptable excipient" or "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be administered to humans and/or to animals, parenterally, intranasally, intraperitoneally, or via a nasal spray. The mode of administration will vary depending on the intended use, as is well known in the art. Alternatively, formulations of the present invention may be administered parenterally as injections (intravenous, intramuscular, or subcutaneous). These formulations may be prepared by conventional means, and, if desired, the subject compositions may be mixed with any conventional additive.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Exemplary Kits

In some embodiments, systems, methods, kits, and cassettes kits for the preparation of an imaging agent (e.g., imaging agent 1) are provided for detecting, imaging, and/or monitoring myocardial perfusion. In some embodiments, kits for the administration of an imaging agent (e.g., imaging agent 1) are provided. Kits of the invention may include, for example, a container comprising an imaging agent, or an imaging agent precursor, and instructions for use. Kits may include a sterile, non-pyrogenic, formulation comprising a predetermined amount of an imaging agent (e.g., imaging agent 1), and optionally other components. In some aspects of the invention, a kit may include one or more syringes that contain an imaging agent (e.g., imaging agent 1) to be prepared for administration to a subject. A container that may be used in conjunction with an imaging agent (e.g., imaging agent 1) (e.g. to deliver and/or administer an imaging agent (e.g., imaging agent 1) to a subject) may be a syringe, bottle, vial, tubes, etc. Exemplary syringes that may be included in a kit of the invention are syringes lacking an adsorbent plunger tip, such as a 3 or 5 mL NORM-JECT (Henke Sass Wolf, Dudley, Mass.), or other equivalent syringe lacking an adsorbent plunger tip. An imaging agent (e.g., imaging agent 1) may be provided in a kit and additional preparations before use may optionally include diluting the imaging agent to a usable concentration. Instructions in a kit of the invention may relate to methods for, methods of diluting the imaging agent, methods of administering the imaging agent to a subject for diagnostic imaging, or other instructions for use.

In some cases, a kit can also include one or more vials containing a diluent for preparing an imaging agent (e.g., imaging agent 1) composition for administration to a subject (e.g., human). A diluent vial may contain a diluent such as physiological saline, water, buffered solution, etc. for diluting an imaging agent (e.g., imaging agent 1). For example, the imaging agent (e.g., imaging agent 1) may be packaged in a kit in a ready-to-inject formulation, or may require some reconstitution or dilution whereby a final composition/formulation for injection or infusion is prepared.

Instructions in a kit of the invention may also include instructions for administering the imaging agent (e.g., imaging agent 1) to a subject and may include information on dosing, timing, stress induction, etc. For example, a kit may include an imaging agent described herein, along with instructions describing the intended application and the proper administration of the agent. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration. In some cases, the instructions can include instructions for mixing a particular amount of the diluent with a particular amount of a concentrated solution of the imaging agent or a solid preparation of the imaging agent, whereby a final formulation for injection or infusion is prepared for example, such that the resulting solution is at a suitable concentration for administration to a subject (e.g., at a concentration as described herein). A kit may include a whole treatment regimen of the inventive compound (e.g., a rest dose and a stress dose).

The kit may contain any one or more of the components described herein in one or more containers. As an example, in one embodiment, the kit may include instructions for mixing one or more components of the kit and/or isolating and mixing a sample and applying to a subject. The kit may include a container housing an agent described herein. The agent may be in the form of a liquid, gel or solid (powder). The agent may be prepared sterilely, packaged in syringe and shipped refrigerated. Alternatively it may be housed in a vial or other container for storage. A second container may have other agents prepared sterilely. Alternatively the kit may include an active agent premixed and shipped in a syringe, vial, tube, or other container. The kit may have one or more or all of the components required to administer the agents to a patient, such as a syringe, topical application devices, or iv needle tubing and bag.

It also will be understood that containers containing the components of a kit of the invention, whether the container is a bottle, a vial (e.g., with a septum), an ampoule, an infusion bag, or the like, can include additional indicia such as conventional markings that change color when the preparation has been autoclaved or otherwise sterilized. A kit of the invention may further include other components, such as syringes, labels, vials, tubing, catheters, needles, ports, and the like. In some aspect of the invention, a kit may include a single syringe containing the imaging agent (e.g., imaging agent 1) sufficient for administration and in some aspects of the invention a kit may include two separate syringes, one comprising imaging agent 1 to be administered to a subject for rest imaging, and a second syringe comprising imaging agent 1 for administration to a subject for stress imaging.

Buffers useful in the preparation of imaging agents and kits include, for example, phosphate, citrate, sulfosalicylate, and acetate buffers. A more complete list can be found in the United States Pharmacopoeia. Lyophilization aids useful in the preparation of imaging agents and kits include, for example, mannitol, lactose, sorbitol, dextran, FICOLL® polymer, and polyvinylpyrrolidine (PVP). Stabilization aids useful in the preparation of imaging agents and kits include, for example, ascorbic acid, cysteine, monothioglycerol, sodium bisulfite, sodium metabisulfite, gentisic acid, and inositol. Solubilization aids useful in the preparation of imaging agents and kits include, for example, ethanol, glycerin, polyethylene glycol, propylene glycol, polyoxyethylene sorbitan monooleate, sorbitan monoloeate, polysorbates, poly(oxyethylene)-poly(oxypropylene)-poly(oxyethylene) block copolymers ("Pluronics") and lecithin. In certain embodiments, the solubilizing aids are polyethylene glycol, cyclodextrins, and Pluronics. Bacteriostats useful in the preparation of imaging agents and kits include, for example, benzyl alcohol, benzalkonium chloride, chlorbutanol, and methyl, propyl, or butyl paraben.

Definitions

For convenience, certain terms employed in the specification, examples, and appended claims are listed here.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl, etc.). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, cyclochexyl, and the like.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, poly(ethylene glycol), alkyl-substituted amino, tetrahydrofuranyl, piperidinyl, morpholinyl, etc.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moieties having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl) heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary ($-NH_2$), secondary ($-NHR_x$), tertiary ($-NR_xR_y$), or quaternary ($-N^+R_xR_yR_z$) amine, where $R_x$, $R_y$ and $R^z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "aryloxy" refers to the group, —O-aryl. The term "acyloxy" refers to the group, —O-acyl.

The term "alkoxyalkyl" refers to an alkyl group substituted with at least one alkoxy group (e.g., one, two, three, or more, alkoxy groups). For example, an alkoxyalkyl group may be —($C_{1-6}$-alkyl)-O—($C_{1-6}$-alkyl), optionally substituted. In some cases, the alkoxyalkyl group may be optionally substituted with another alkyoxyalkyl group (e.g., —($C_{1-6}$-alkyl)-O—($C_{1-6}$-alkyl)-O—($C_{1-6}$-alkyl), optionally substituted.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction.

As used herein the term "acquiring" an image means obtaining an image.

The term "diagnostic imaging," as used herein, refers to a procedure used to detect an imaging agent.

A "diagnostic kit" or "kit" comprises a collection of components, termed the formulation, in one or more vials, which are used in a clinical or pharmacy setting to synthesize diagnostic radiopharmaceuticals. For example, the kit may be used by the practicing end user in a clinical or pharmacy setting to synthesize and/or use diagnostic radiopharmaceuticals. In some embodiments, the kit may provide all the requisite components to synthesize and/or use the diagnostic pharmaceutical except those that are commonly available to the practicing end user, such as water or saline for injection, a solution of the radionuclide, equipment for processing the kit during the synthesis and manipulation of the radiopharmaceutical, if required, equipment necessary for administering the radiopharmaceutical to the subject such as syringes, shielding, imaging equipment, and the like. In some embodiments, imaging agents may be provided to the end user in their final form in a formulation contained typically in one vial or syringe, as either a lyophilized solid or an aqueous solution.

As used herein, a "portion of a subject" refers to a particular region of a subject, location of the subject. For example, a portion of a subject may be the brain, heart, vasculature, cardiac vessels, of a subject.

As used herein a "session" of testing may be a single testing protocol that a subject undergoes. In some cases a session may include rest/stress imaging protocol; stress/rest imaging protocol; rest only imaging protocol; or a stress only imaging protocol. A session of testing can take place in less than 24 hours or less than 48 hour.

As used herein, the term "subject" refers to a human or non-human mammal or animal. Non-human mammals include livestock animals, companion animals, laboratory animals, and non-human primates. Non-human subjects also specifically include, without limitation, horses, cows, pigs, goats, dogs, cats, mice, rats, guinea pigs, gerbils, hamsters, mink, and rabbits. In some embodiments of the invention, a subject is referred to as a "patient." In some embodiments, a patient or subject may be under the care of a physician or other health care worker, including, but not limited to, someone who has consulted with, received advice from or received a prescription or other recommendation from a physician or other health care worker.

Any of the compounds described herein may be in a variety of forms, such as, but not limited to, salts, solvates, hydrates, tautomers, and isomers.

In certain embodiments, the imaging agent is a pharmaceutically acceptable salt of the imaging agent. The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In certain embodiments, the compound is in the form of a hydrate or solvate. The term "hydrate" as used herein refers to a compound non-covalently associated with one or more molecules of water. Likewise, the term "solvate" refers to a compound non-covalently associated with one or more molecules of an organic solvent.

In certain embodiments, the compound described herein may exist in various tautomeric forms. The term "tautomer" as used herein includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

In certain embodiments, the compounds described herein may exist in various isomeric forms. The term "isomer" as used herein includes any and all geometric isomers and stereoisomers (e.g., enantiomers, diasteromers, etc.). For example, "isomer" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

These and other aspects of the present invention will be further appreciated upon consideration of the following Examples, which are intended to illustrate certain particular embodiments of the invention but are not intended to limit its scope, as defined by the claims.

EXAMPLES

Example 1

Synthesis of 4-(2-hydroxyethoxymethyl)benzoic acid methyl ester

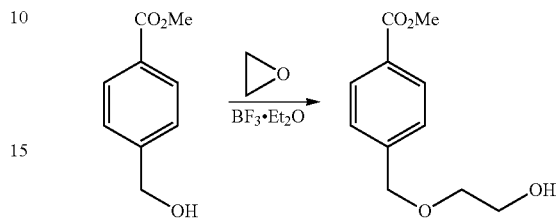

To a two-neck round bottom flask, which was equipped with a Dewar condenser, a solution of 4-hydroxymethylbenzoic acid methyl ester (2.50 g, 0.015 mol) in anhydrous dichloromethane (30 mL) was cooled to −10° C. in a salt/ice bath. Ethylene oxide (1.10 mL) was added to the cooled stirring solution dropwise followed by the addition of boron trifluoride etherate (0.51 ml). The reaction mixture was stirred for 45 minutes and then warmed to room temperature for 30 minutes to boil off any excess of ethylene oxide from the reaction mixture. The reaction mixture was then diluted with brine. The aqueous layer was extracted with dichloromethane (3 times). All of the organic layers were combined, dried over $Na_2SO_4$, filtered, and concentrated to provide an oil. The crude material was purified using silica gel chromatography (4:1 pentane:ethyl acetate) to provide the desired product (537 mg, 2.56 mmol) in 17% yield. $^1H$ ($CDCl_3$ 8.36, 600 MHz): δ (2H, d, J=8.4 Hz), 7.41 (2H, d, J=8.5 Hz), 4.62 (3H, s), 3.92 (2H, s), 3.78 (m, 2H), 3.63 (2H, m); $^{13}C$ ($CDCl_3$ 167.1, 143.5, 130.0, 129.8, 127.5, 72.9, 72.0, 150 MHz): δ 62.1, 52.3.

Example 2

Synthesis of 4-[2-(t-butyldimethylsilanyloxy)ethoxymethyl]benzoic acid methyl ester To a solution of the product of Example 1 (544.5 mg, 2.59 mmol) in anhydrous DMF (26 mL) was added imidazole (264 mg, 3.89 mmol) and TBDMS-Cl (586 mg, 3.89 mmol).

The reaction mixture stirred at room temperature overnight and was quenched with water. The aqueous layer was extracted with ethyl acetate (3×). All combined organic layers were dried over Na₂SO₄, filtered, and concentrated. The crude material was purified using silica gel chromatography (4:1 pentane:ethyl acetate) to provide the desired product (677.5 mg, 2.19 mmol) in 84% yield. ¹H (CDCl₃ 8.01, 600 MHz): δ (2H, d, J=8.3 Hz), 7.42 (2H, d, J=8.4 Hz), 4.63 (2H, s), 3.91 (2H, s), 3.82 (2H, t, J=5.0), 3.58 (2H, t, J=5.1 Hz), 0.91 (9H, s), 0.07 (6H, s); ¹³C (CDCl₃ 166.5, 143.5, 129.2, 128.8, 126.5, 72.1, 71.6, 150 MHz): δ 62.3, 51.5, 25.4, 17.9, −5.8.

Example 3

Synthesis of {4-[2-(t-butyldimethylsilanyloxy)ethoxymethyl]phenyl}methanol

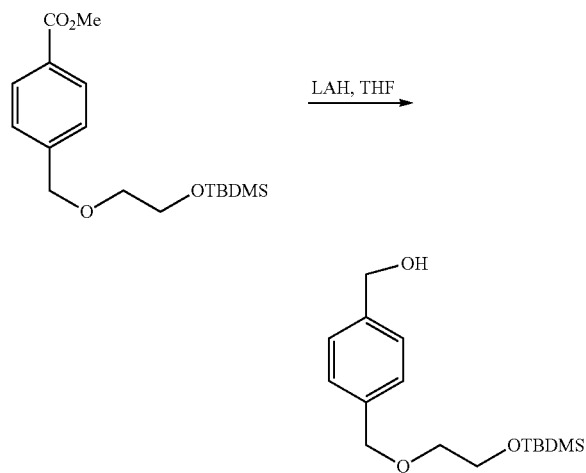

To a solution of the product of Example 2 (670 mg, 2.18 mmol) dissolved in anhydrous THF (22 mL) was added a solution of LAH (1.0 M solution in THF, 2.18 mL, 2.18 mmol) dropwise. After completion of addition the reaction mixture was stirred at room temperature for 3 hours. The reaction mixture was diluted with water. The aqueous layer was extracted with ethyl acetate (3×). All combined organic layers were dried over Na₂SO₄, filtered, and concentrated to provide an oil (587 mg, 1.98 mmol), which was used in the next step without any further purification (91% yield). ¹H (CDCl₃ 7.34 (4H, s), 4.68 (2H, s), 4.57 (2H, s), 3.80, 600 MHz): δ (2H, t, J=5.2 Hz), 3.56 (2H, t, J=5.3 Hz), 1.69 (1H, br s), 0.90 (9H, s), 0.07 (6H, s); ¹³C (CDCl₃ 140.4, 138.3, 128.0, 127.2, 73.2, 71.9, 65.4, 150 MHz): δ 63.0, 26.2, 18.6, −5.0.

Example 4

Synthesis of 2-t-butyl-5-{4-[2-(t-butyldimethylsilanyloxy)ethoxymethyl]benzyloxy}-4-chloro-2H-pyridazin-3-one

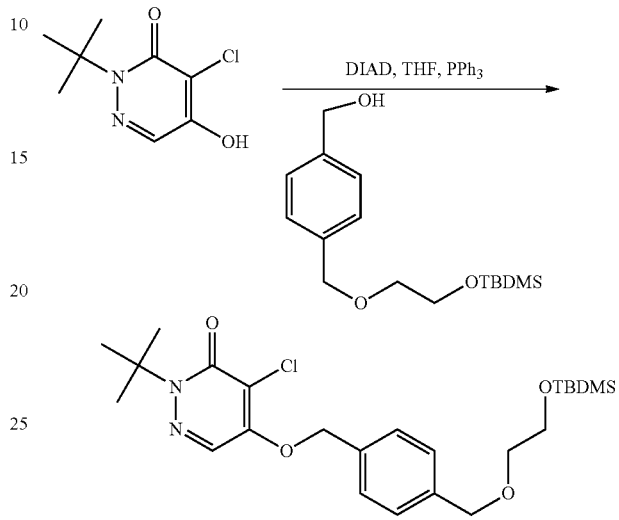

To solution of the product of Example 3 (437 mg, 1.48 mmol) and 2-t-butyl-4-chloro-5-hydroxy-2H-pyridazin-3-one (250 mg, 1.23 mmol) dissolved in anhydrous THF (12 mL) was added solid PPh₃ (485 mg, 1.85 mmol) and diisopropyl azodicarboxylate (DIAD, 0.358 mL, 1.85 mmol). After completion of addition the reaction mixture continued to stir at room temperature. After 20 hours, the reaction mixture was diluted with water. The aqueous layer was separated and extracted with ethyl acetate (3×). All combined organic layers were dried over Na₂SO₄, filtered, and concentrated to provide an oil. The crude material was purified using silica gel chromatography (4:1 pentane:ethyl acetate) to provide the desired product 528 mg, 1.10 mmol) in 89% yield. ¹H (CDCl₃ 7.70 (1H, s), 7.38 (4H, m), 5.30 (2H, s), 4.58, 600 MHz): δ (2H, s), 3.80 (2H, t, J=5.4 Hz), 3.57 (2H, t, J=5.4 Hz), 1.63 (9H, br s), 0.90 (9H, s), 0.07 (6H, s); ¹³C (CDCl₃ 159.0, 153.7, 138.8, 134.4, 128.3, 127.3, 150 MHz): δ 125.1, 118.5, 72.8, 71.7, 71.6, 66.4, 61.9, 29.7, 27.9, 25.6, −5.1.; HRMS calcd for C₂₄H₃₇ClN₂O₄Si: 481.228389, found 481.2282.

Example 5

Synthesis of 2-t-butyl-4-chloro-5-[4-(2-hydroxyethoxymethyl)benzyloxy]-2H-pyridazin-3-one

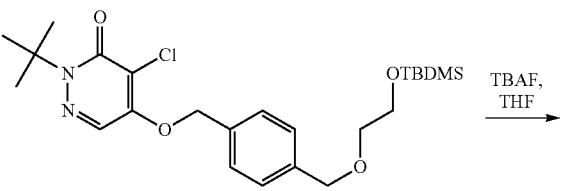

-continued

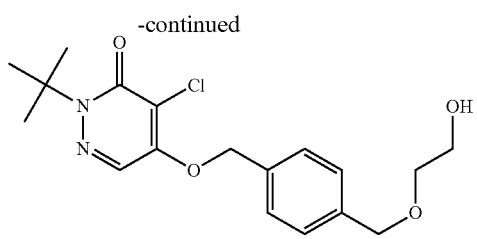

To a solution of the product of Example 4 (528 mg, 1.09 mmol) dissolved in anhydrous THF (11 mL) was added a solution of TBAF (1.0 M solution in THF, 1.65 mL, 1.65 mmol) dropwise. After completion of addition the reaction was stirred at room temperature for 1 hour and then quenched with water. The aqueous layer was separated and extracted with ethyl acetate (3×). All combined organic layers were dried over $Na_2SO_4$, filtered, and concentrated to provide an oil. The crude material was purified using silica gel chromatography (4:1 hexanes:ethyl acetate) to provide the desired product (311 mg, 0.850 mmol) in 78% yield. $^1$H (CDCl$_3$, 600 MHz): δ 7.70 (1H, s), 7.38 (4H, m), 5.30 (2H, s), 4.56 (2H, s), 3.76 (2H, t, J=4.9 Hz), 3.60 (2H, t, J=4.8 Hz), 2.00 (1H, br s), 1.61 (9H, br s); $^{13}$C (CDCl$_3$ 159.0, 153.6, 150 MHz): δ 138.8, 134.4, 128.2, 127.2, 125.1, 118.3, 72.8, 71.6, 71.6, 66.4, 61.9, 27.8; HRMS calcd for $C_{18}H_{23}ClN_2O_4$: 367.141911, found 367.1419.

Example 6

Synthesis of toluene-4-sulfonic acid 2-[4-(1-t-butyl-5-chloro-6-oxo-1,6-dihydro-pyridazin-4-yloxymethyl)-benzyloxyl]-ethyl ester

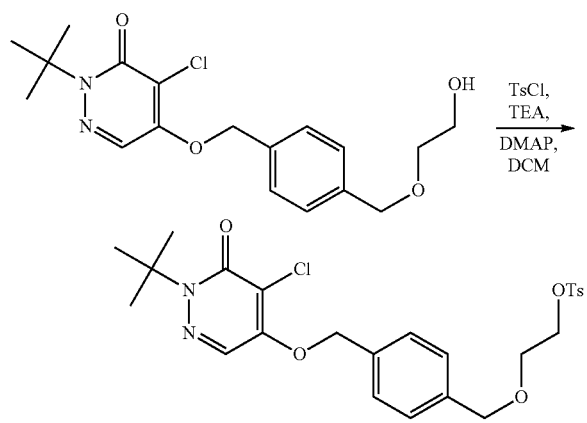

To a solution of the product of Example 5 (200 mg, 0.546 mmol) dissolved in anhydrous dichloromethane (5.50 mL) was added TsCl (125 mg, 0.656 mmol), DMAP (100 mg, 0.819 mmol) and triethylamine (0.091 mL, 0.656 mmol). The reaction mixture continued stirring at room temperature. After 22 hours the reaction mixture was diluted with water. The aqueous layer was separated and extracted with ethyl acetate (3×). All combined organic layers were dried over $Na_2SO_4$, filtered, and concentrated to provide an oil. The crude material was purified using silica gel chromatography (3:2 pentane:ethyl acetate) to provide the desired product (232 mg, 0.447 mmol) in 82% yield. $^1$H (CDCl$_3$ 7.79, 600 MHz): δ (2H, d, J=8.3 Hz), 7.71 (1H, s), 7.38 (2H, d, J=8.2 Hz), 7.32 (4H, m), 5.30 (2H, s), 4.50 (2H, s), 4.21 (2H, m), 3.69 (2H, m), 2.43 (3H, s), 1.63 (9H, br s); $^{13}$C (CDCl$_3$ 159.0, 153.7, 144.8, 138.8, 150 MHz): δ 134.4, 133.1, 129.8, 128.1, 128.0, 127.2, 125.1, 118.4, 72.8, 71.7, 69.2, 67.8, 66.4, 27.9, 21.6; HRMS calcd for $C_{25}H_{29}ClN_2O_6$: 521.150762, found 521.1503.

Example 7

Preparation of [$^{18}$F]Fluoride

[$^{18}$F]Fluoride was produced by proton bombardment of [$^{18}$O]H$_2$O in a cyclotron; the nuclear chemical transformation is shown below and may be summarized as $^{18}$O (p,n) $^{18}$F. For purposes of the bombardment, the chemical form of the $^{18}$O is H$_2$$^{18}$O. The chemical form of the resulting $^{18}$F is fluoride ion.

$^{18}$O+proton→$^{18}$F+neutron

According to established industry procedures, [$^{18}$O]H$_2$O (2-3 mL) housed within a tantalum target body using Havar® foil, was bombarded with 11 MeV protons (nominal energy); where the proton threshold energy for the reaction is 2.57 MeV and the energy of maximum cross section is 5 MeV. Target volume, bombardment time and proton energy each may be adjusted to manage the quantity of [$^{18}$F]fluoride produced.

Example 8

Preparation of Imaging Agent Precursor 1 Acetontrile Concentrate

Imaging agent precursor 1 (20.4 g, 39.2 mmol), as shown in FIG. 1, was dissolved in anhydrous MeCN (3400 mL) then transferred through an Opticap XL2 Durapore filter (0.2 μm) into 5 mL glass vials; 2.0 mL fill volume. The vials were then fitted with rubber septa, sealed with an aluminum crimp and stored at ambient temperature prior to use.

Example 9

General Preparation of Imaging Agent 1

The following example describes a general procedure for synthesizing imaging agent 1, as shown in FIG. 1. Aqueous [$^{18}$F]fluoride, as prepared in Example 7, was transferred from the cyclotron to a synthesis module, then filtered through an anion exchange column to remove unreacted [$^{18}$O]H$_2$O; [$^{18}$F]fluoride was retained within the cationic resin matrix. The column was then washed with aqueous Et$_4$NHCO$_3$ with transfer to the reaction vessel. The resulting solution was diluted with MeCN then concentrated to dryness using elevated temperature and reduced pressure. The mixture of anhydrous [$^{18}$F]Et$_4$NF and and Et$_4$NHCO$_3$ thus obtained was treated with the acetonitrile solution of imaging agent precursor 1, as prepared in Example 8, then warmed to 90-100° C. and maintained 10-20 min. After cooling, the solution was diluted with H$_2$O then directly purified by HPLC on a Waters Xterra MS C18 column using a H$_2$O/MeCN eluent. The main product peak was collected, diluted with ascorbic acid then transferred to the formulation module. In another case, similar steps and conditions were employed as above except the solution was warmed to 85-120° C. and maintained 5-20 min, followed by cooling and diluting with 1:1 H$_2$O/MeCN.

Example 10

Preparation of Imaging Agent 1 Using the Explora RN Synthesis Module

The product of Example 7 was transferred from cyclotron to the synthesis module then filtered through an anion exchange column to remove unreacted [$^{18}$O]H$_2$O; [$^{18}$F] fluoride was retained within the cationic resin matrix. The column was then washed with Et$_4$NHCO$_3$ (5.75 μmol; 0.500 mL of a 11.5 mM solution in H$_2$O) with transfer to the reaction vessel. The resulting solution was diluted with MeCN (0.500 mL) then concentrated to dryness; 150 mm Hg at 115° C. for 4 min. The mixture of anhydrous [$^{18}$F] Et$_4$NF and Et$_4$NHCO$_3$ thus obtained was treated with the product of Example 8 (11.5 μmol; 1.00 mL of a 11.5 mM solution in MeCN) then warmed to 90° C. and maintained 20 min. After cooling to 35° C., the solution was diluted with H$_2$O (1.00 mL) then directly purified by HPLC on a Waters Xterra MS C18 column (10 μm; 10×250 mm) using a 45:55 H$_2$O/MeCN eluent at a flow rate of 5 mL/min. The main product peak eluting at 11 min was collected, diluted with ascorbic acid (10 mL of a 0.28 M solution in H$_2$O; pH 2) then transferred to the formulation module; 58% decay corrected radiochemical yield.

In another case, similar steps and conditions were employed as above except the Et$_4$NHCO$_3$ was 11.5 μmol (0.500 mL of a 23.0 mM solution in H$_2$O); the solution was concentrated to dryness at 280 mbar, 95-115° C., 4 min; the mixture of anhydrous [$^{18}$F]Et$_4$NF and Et$_4$NHCO$_3$ treated with the product of Example 8 was warmed to 90° C. and maintained 10 min; and the product had 61% decay corrected radiochemical yield.

Example 11a

Preparation of Imaging Agent 1 Using the Eckhert & Ziegler Modular-Lab Synthesis Module The product of Example 7 was transferred from cyclotron to the synthesis module then filtered through an anion exchange column to remove unreacted [$^{18}$O]H$_2$O; [$^{18}$F] fluoride was retained within the cationic resin matrix. The column was then washed with Et$_4$NHCO$_3$ (11.5 μmol; 0.500 mL of a 23.0 mM solution in H$_2$O) with transfer to the reaction vessel. The resulting solution was diluted with MeCN (0.500 mL) then concentrated to dryness; 375 mm Hg at 115° C. for 10 min. The mixture of anhydrous [$^{18}$F]Et$_4$NF and Et$_4$NHCO$_3$ thus obtained was treated with the product of Example 8 (11.5 μmol; 1.00 mL of a 11.5 mM solution in MeCN) then warmed to 110° C. and maintained 10 min. After cooling to 20° C., the solution was diluted with H$_2$O (1.00 mL) then directly purified by HPLC on a Waters Xterra MS C18 column (10 μm; 10×250 mm) using a 45:55 H$_2$O/MeCN eluent at a flow rate of 5 mL/min. The main product peak eluting at 11 min was collected, diluted with ascorbic acid (10 mL of a 0.28 M solution in H$_2$O; pH 2) then transferred to the formulation module; 68% decay corrected radiochemical yield.

In another case, similar steps and conditions were employed as above except the ersulting solution was concentrated to dryness a 400 mbar, 110-150° C., 10 min; the mixture of anhydrous [$^{18}$F]Et$_4$NF and Et$_4$NHCO$_3$ treated with the product of Example 8 was warmed to 120° C. and maintained 10 min; and the cooling was conducted at 35° C.

Example 11b

Preparation of Imaging Agent 1 Using the Explora GN Synthesis Module

The product of Example 7 was transferred from cyclotron to the synthesis module then filtered through an anion exchange column to remove unreacted [$^{18}$O]H$_2$O; [$^{18}$F] fluoride was retained within the cationic resin matrix. The column was then washed with Et$_4$NHCO$_3$ (11.5 μmol; 1.00 mL of a 11.5 mM solution in H$_2$O) with transfer to the reaction vessel. The resulting solution was diluted with MeCN (1.00 mL) then concentrated to dryness; 110-115° C. Additional MeCN (1.50 mL) was then added and the solution concentrated to dryness once again. The mixture of anhydrous [$^{18}$F]Et$_4$NF and Et$_4$NHCO$_3$ thus obtained was treated with the product of Example 8 (11.5 μmol; 1.00 mL of a 11.5 mM solution in MeCN) then warmed to 120° C. and maintained 10 min. After cooling to 60° C., the solution was diluted with H$_2$O/MeCN (3.00 mL; 2:1 v/v) then directly purified by HPLC on a Waters Xterra MS C18 column (10 μm; 10×250 mm) using a 45:55 H$_2$O/MeCN eluent at a flow rate of 5 mL/min. The main product peak eluting at 11 min was collected, diluted with ascorbic acid (10 mL of a 0.28 M solution in H$_2$O; pH 2) then transferred to the formulation module; 68% decay corrected radiochemical yield.

Example 11c

Preparation of Imaging Agent 1 Using the GE TRACERLab MX Synthesis Module

The product of Example 7 was transferred from cyclotron to the synthesis module then filtered through an anion exchange column to remove unreacted [$^{18}$O]H$_2$O; [$^{18}$F] fluoride was retained within the cationic resin matrix. The column was then washed with Et$_4$NHCO$_3$ (23.0 μmol; 0.500 mL of a 46.0 mM solution in 1:1 H$_2$O/MeCN) with transfer to the reaction vessel. The resulting solution was diluted with MeCN then concentrated to dryness; 150 mbar, 105° C., 8 min. Additional MeCN was then added and the drying process repeated; the process of MeCN addition followed by evaporation was repeated three times. The mixture of anhydrous [$^{18}$F]Et$_4$NF and Et$_4$NHCO$_3$ thus obtained was treated with the product of Example 8 (23.0 μmol; 2.00 mL of a 11.5 mM solution in MeCN) then warmed to 85° C. and maintained 10 min. The resulting solution was then diluted with H$_2$O (2.00 mL) and directly purified by HPLC on a Waters Xterra MS C18 column (10 μm; 10×250 mm) using a 45:55 H$_2$O/MeCN eluent at a flow rate of 5 mL/min. The main product peak eluting at 11 min was collected, diluted with ascorbic acid (10 mL of a 0.28 M solution in H$_2$O; pH 2) then transferred to the formulation module; 63% decay corrected radiochemical yield.

Example 12

Solvent Exchange Process

The product of Example 10 or 11 was transferred from purification to the formulation module then filtered through a C18 Sep-Pak® cartridge to remove MeCN; Imaging agent 1 was retained within the C18 resin matrix and the filtrate discarded. The cartridge was successively washed with ascorbic acid (10 mL of a 0.28 M solution in $H_2O$; pH 2), the filtrate discarded, then absolute EtOH (0.50 mL), and the filtrate collected. The ethanol concentrate of imaging agent 1 thus obtained was further diluted with ascorbic acid (10.0 mL of a 0.28 M solution in $H_2O$) in preparation for final aseptic filtration.

Example 13

Aseptic Filtration Process

The final product vial assembly was constructed from the following pre-sterilized components: one 30 mL product vial, one Millipore Millex GV4 venting filter (0.22 μm×4 mm), one tuberculin syringe (1 mL) and one insulin syringe (0.5 mL). The product of Example 12 was then transferred from formulation to the final product vial assembly through a Millipore Millex GV PVDF sterilizing filter (0.22 μm×13 mm). Quality control samples are then removed, using the syringe assemblies, to complete all product release requirements.

Example 14

Upon evaluation of several experimental parameters in the nucleophilic fluorination of imaging agent precursor 1 (FIG. 1) using $K_2CO_3$/Kryptofix® 222 overall reaction complexity was shown to increase with added $K_2CO_3$; comparable fluorination efficiency was observed regardless of reagent stoichiometry. Elevated base (e.g., carbonate) levels were simply correlated to unproductive consumption of starting material (e.g., imaging agent precursor). Substitution of $K_2CO_3$ with $KHCO_3$ resulted in considerable improvement of both fluorination efficiency and starting material integrity. The solution pH remained uniform regardless of base identity and reagent stoichiometry; the presence or absence of Kryptofix® 222 determines global solution pH. The fluorination efficiency remained stable regardless of reagent stoichiometry, indicating a more complex role of added base within the reaction coordinate.

Figure 2:
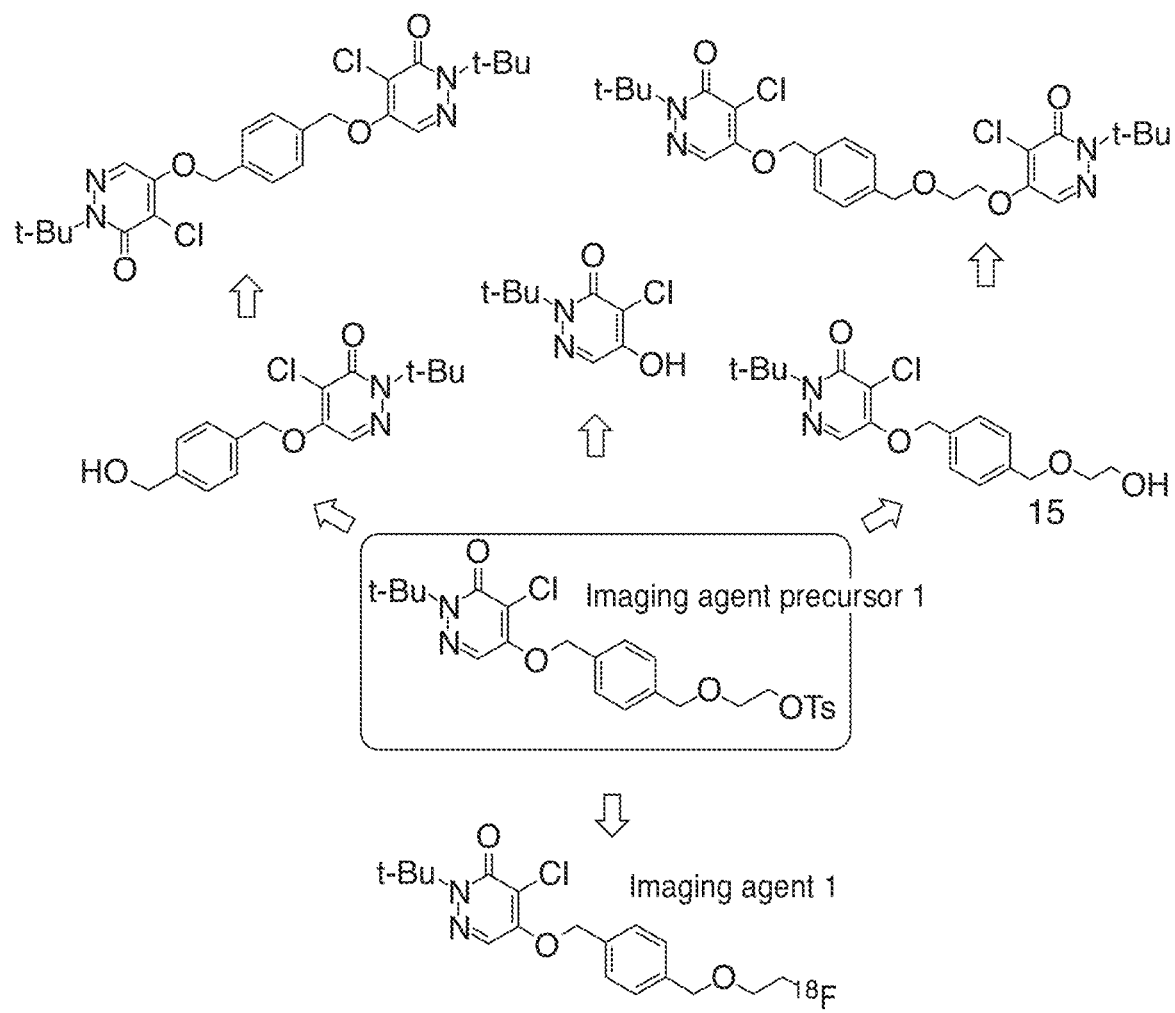
FIG. 2 shows various reaction pathways of an imaging agent precursor during a nucleophilic fluorination reaction.

FIG. 2 shows various possible reaction pathways, which traces unproductive consumption of starting material to a series of base-mediated hydrolysis reactions and dimerization events. Variable time and temperature experiments confirmed the comparable rates of hydrolysis and fluorination in the nucleophilic fluorination reaction shown in FIG. 1, using the $K_2CO_3$/Kryptofix® 222 in the presence of $K_2CO_3$. Thus, reaction conditions which activate larger differential rates of fluorination are desired in order to advance a more efficient and chemoselective process; that is, a decreased rate of hydrolysis and/or increased rate of fluorination.

As noted above, $K_2CO_3$ did little to enhance fluorination over baseline levels and served primarily a detrimental role in the reaction. In contrast, added $KHCO_3$ produced a marked increase in fluorination over the same dynamic range, while decomposition pathways remained poorly differentiated. These facts, coupled with the knowledge that [$^{18}$F]NaF exchange with tetraalkylammonium cations is known to directly produce a highly active nucleophilic fluoride source, led to the investigation of a series of commercially available salts in an effort to identify related counterion affects that amplify the rate of fluorination (e.g., see FIG. 1).

A series of different bases was used in the nucleophilic fluorination of a tosylate precursor using TBAF as a source of fluoride (shown above), according to the following procedure. A 2 mL glass vial was charged with both $Bu_4NF$ (1.15 μmol; 13.4 μL of a 85.9 mM solution in $H_2O$) and $Bu_4NHCO_3$ (10.4 μmol; 138 μL of a 75.0 mM solution in $H_2O$), then warmed to 95° C. and maintained 10 min under a stream of dry nitrogen. The resulting solid mixture was treated with the product of Example 8 (11.5 μmol; 1.00 mL of a 11.5 mM solution in MeCN) then warmed to 90° C. and maintained 10 min. After cooling to 22° C., the resulting solution was diluted with $H_2O$ then directly analyzed by HPLC on a Zorbax SB-C18 column (4.6×50 mm) using a $H_2O$/MeCN gradient containing 0.1% $HCO_2H$ with a flow rate of 1.00 mL/min. The reaction yield was then calculated through comparison of the integrated peak area for the product in the crude reaction mixture to that of the authentic standard product (Table 1); results obtained through substitution of several alternate salt forms are also provided for comparison.

An enhancement of fluorination efficiency was observed in the presence of bicarbonate anion. Additionally, a modest dependence on size of the alkyl substituent was observed when R=methyl→ethyl→butyl (data not shown).

A ~1.5-fold improvement in yield was observed using the KF-Kryptofix® 222 method when changing from no added salt, to one equivalent potassium carbonate, to one equivalent potassium bicarbonate.

TABLE 1

Comparison of salt form identity and fluorination yield.

| salt form | % yield |
|---|---|
| bicarbonate | 81.4 |
| hydroxide | 35.5 |
| acetate | 2.8 |
| lactate | 38.7 |
| trifluoroacetate | 3.7 |
| methanesulfonate | 39.6 |
| p-toluenesulfonate | 15.0 |
| nitrate | 45.1 |
| iodide | 44.6 |
| bisulfate | <2% |
| none | 44.1 |

Figure 9A:
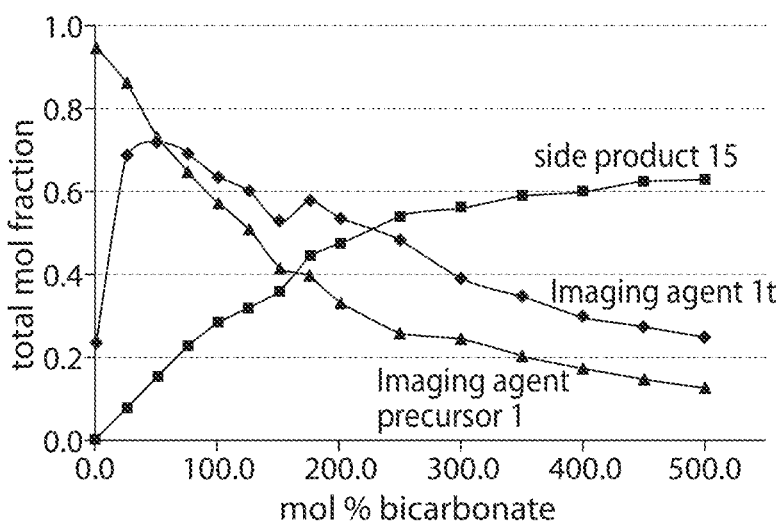
FIGS. 9A to 9C include a graph illustrating the changes in product distribution as a function of molar concentration of bicarbonate salt (FIG. 9A), a graph illustrating the product distribution as a function of reaction time (FIG. 9B), and a graph illustrating the changes in product distribution as a function of molar concentration of imaging agent precursor (FIG. 9C).
Figure 9B:
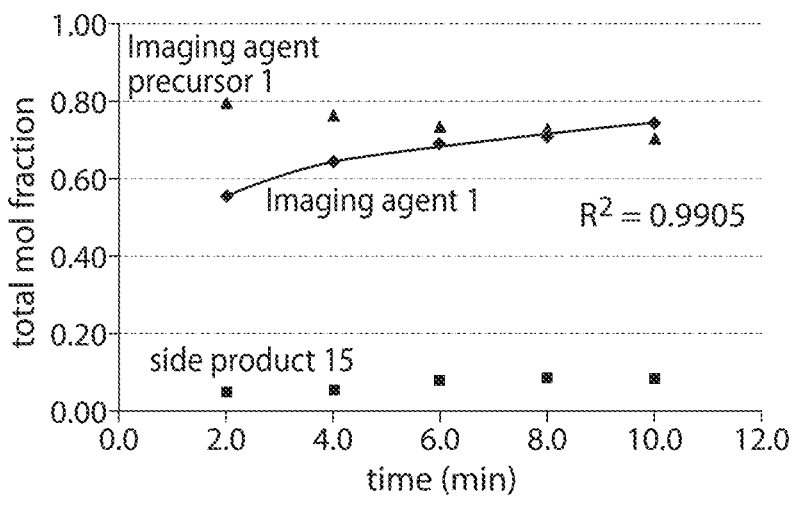
Figure 9C:
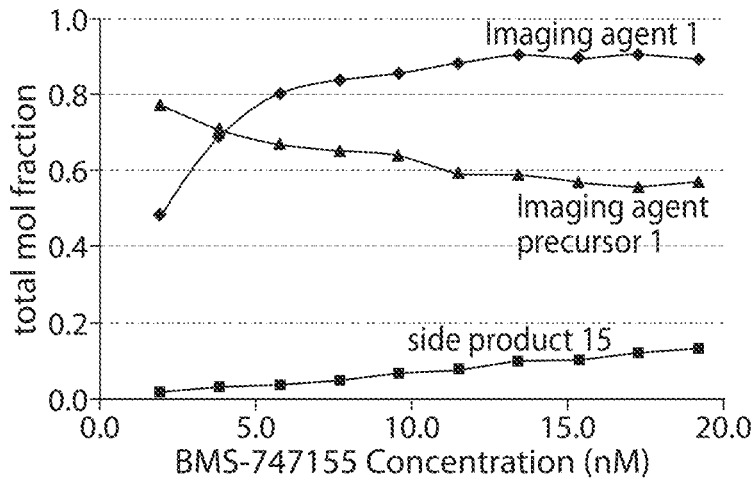

Additionally, the amount of salt additive was varied, relative to the amount of starting material (e.g., imaging agent precursor), in order to investigate the effect of salt additive concentration on the reaction. FIG. 9A shows a graph illustrating the changes in product distribution as a function of molar concentration of bicarbonate salt and FIG. 9B shows a graph illustrating the product distribution as a function of reaction time. Investigation of the salt stoichiometry revealed that 25 mol % (or 0.25 equivalents, relative to the imaging agent precursor) of tetraalkylammonium bicarbonate was needed for complete conversion and unproductive consumption of starting material occurred with increasing base concentration revealing an optimum stoichiometry range for the modified reaction conditions. Related studies directed toward determination of the optimal precursor concentration revealed a rather distinct concentration threshold. FIG. 9C illustrates a threshold of >3 mg/ml.

The use of tetraalkylammonium bicarbonate as an additive in the absence of Kryptofix® 222 during nucleophilic fluorination resulted in rapid conversion to the desired product and significantly improved chemoselectivity toward fluorination, relative to the use of $K_2CO_3$/Kryptofix® 222 method. A detailed evaluation of crude reaction mixtures revealed a dramatic reduction in overall decomposition rates when tetraalkylammonium bicarbonate was used, as evidenced by the absence of four hydrolytic impurities present when K₂CO₃/Kryptofix® 222 was used. Without wishing to be bound by theory, this may be attributed to the fact that the use of a tetraalkylammonium bicarbonate allows the reaction to be conducted at a lower absolute pH (e.g., a pH of about 5-6).

Example 15

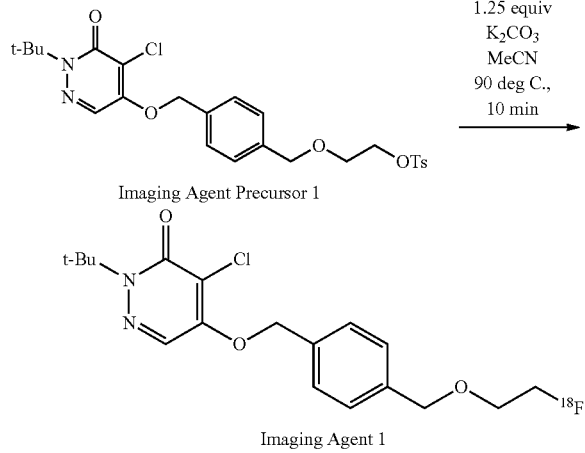

The following example investigates the effect of the presence of potassium carbonate in a nucleophilic fluorination reaction. A yield of 36% is obtained in the presence of potassium carbonate, while a yield of 35% is obtained in the absence of potassium carbonate.

Example 16

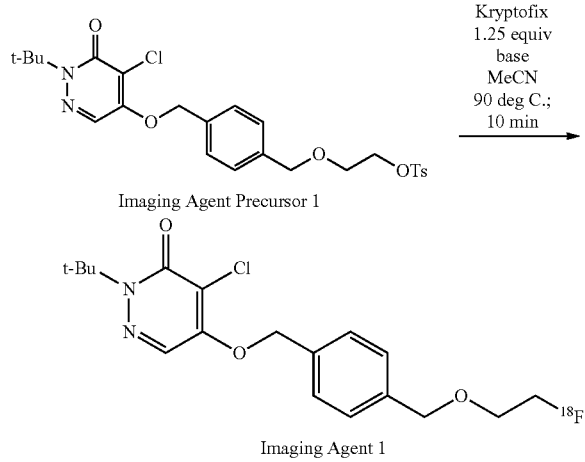

The following example describes the effect that different salt additives may have on nucleophilic fluorination. A yield of 35% is obtained in the presence of potassium carbonate, while a yield of 71% is obtained in the presence of potassium bicarbonate.

Example 17

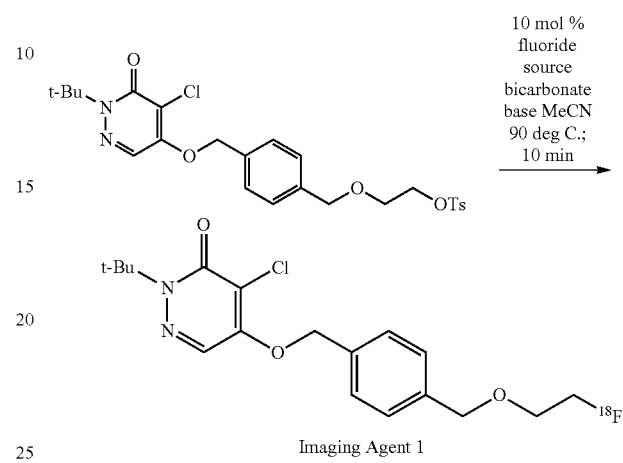

The following example describes the results obtained using different fluoride sources in a nucleophilic fluorination reaction. A yield of 71% is obtained in the presence of KF/Kryptofix® 222, while a yield of 83% is obtained in the presence of tetrabutylammonium fluoride.

Example 18

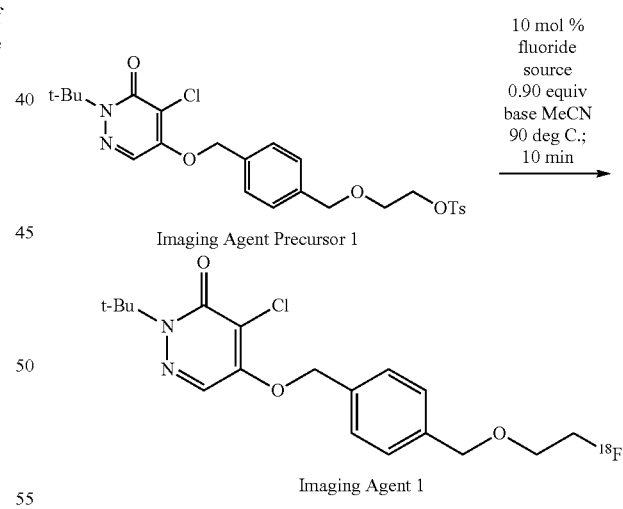

The following example describes the results obtained using different bases in a nucleophilic fluorination reaction utilizing tetrabutylammonium fluoride as the fluoride salt. A yield of 83% is obtained in the presence of the bicarbonate base, while a yield of 36% is obtained in the presence of the hydroxide base.

Example 19

The following describes a comparison of imaging agent 1 and $^{82}$Rb PET versus SPECT for detection of myocardial ischemia. In preclinical studies, myocardial uptake of imaging agent 1 exhibits a stronger relationship with myocardial blood flow across the range of achievable flow than $^{201}$Tl, $^{99m}$Tc sestamibi and $^{82}$Rb. The following experiments were conducted to determine if the improved extraction and retention of imaging agent 1 would result in a greater difference between PET and SPECT ischemia detection by imaging agent 1 versus $^{82}$Rb.

Methods:

Twenty-six patients (20 men) who underwent $^{99m}$Tc sestamibi SPECT and imaging agent 1 PET within 6 months at a single center in a phase II clinical trial were compared to 23 patients (matched by summed difference score (SDS) on SPECT) who underwent $^{99m}$Tc sestamibi SPECT and $^{82}$Rb PET (25-50 mCi) within 6 months without change in clinical state. PET was performed with imaging agent 1 at rest (2.3-3.9 mCi) followed 60 min or 24 h later with exercise or adenosine stress (7.3-8.6 mCi). Perfusion defects on SPECT and PET were assessed by computer-assisted visual interpretation, using the standard 17 segment, 5 point-scoring model (0=normal; 4=absent uptake). The extent and severity of ischemia (SDS) was derived from the difference between summed stress score (SSS) and summed rest scores (SRS).

Results:

In 14 patients with abnormal SPECT (SSS≥4), mean SDS was greater with imaging agent 1 than with SPECT (9.6±1.8 versus 5.4±0.7, p=0.02). In a matched group of 13 patients with abnormal SPECT, mean SDS was similar with $^{82}$Rb PET and SPECT (4.9±1.4 versus 4.6±1.3, p=0.8). In patients with normal SPECT (SSS<4), no differences in SDS were observed with either imaging agent 1 (n=12) or $^{82}$Rb (n=10) PET when compared to SPECT.

Imaging agent 1 PET showed an increase in the amount of ischemia detected relative to $^{99m}$Tc sestamibi SPECT that was not seen when comparing $^{82}$Rb PET to SPECT in a comparable patient group. These results suggest that imaging agent 1 show greater improvement in detection of myocardial ischemia when PET is compared to SPECT than is associated with the use of $^{82}$Rb.

Example 20

The following describes multicenter development of normal perfusion and function limits for stress and rest cardiac PET. The study included development of normal perfusion distribution limits and characterization of normal cardiac function measured by a cardiac perfusion $^{18}$F based agent (imaging agent 1).

Methods:

Normal limits were established from 15 low likelihood patients (7F/8M) average age 54.7 y, average weight 74.2 kg with treadmill exercise stress/rest datasets (30 datasets in total), recruited in a clinical trial (phase 2) for the $^{18}$F imaging agent 1 perfusion agent, acquired on a Siemens Biograph-64 PET/CT scanner in list mode. Standard reconstruction (2D Attenuation Weighted Ordered Subsets Expectation Maximization) with voxel size of 2.6×2.6×2.0 (mm) 8-bin gating was used for the gated reconstruction. 5-minute reconstructions were considered obtained approximately 5 min after isotope injection for stress and rest. The Cedars-Sinai QPET PET function and perfusion analysis software was used for all the processing and for the normal perfusion database creation. 2 out of 30 scans (6.7%) for gated studies and 1 out of 30 for ungated studies (3.3%) required manual intervention in the definition of the left ventricle (LV) all other processing was fully automatic.

Results:

Left ventricular counts were 33.33±6.44 million counts, range (22.76-44.29) for stress and 7.56±1.86 million counts, range (5.12-11.77) for rest. The stress/rest count ratio was 4.53±0.88 (2.88-6.16). Average trans-ischemic dilation (TID) was 0.974±0.124 with upper normal limit of 1.22. QPET relative perfusion normal limits were created for stress and rest scans. There was evidence of apical thinning on stress and rest with apical counts at 80/79% respectively. The variation of counts in the normal database was between 5-9% in all 17 AHA segments. The functional parameters are given in Table 2:

TABLE 2

| | Functional Parameters from Stress and Rest Scans | | | | |
|---|---|---|---|---|---|
| | EDV | ESV | EF | PFR | TTPF |
| Stress | 96.1 ± 25.2 ml | 33.5 ± 14.2 ml | 65.9 ± 6.3% (52.5-74.4%) | 2.12 ± 0.49 | 205 ± 51 ms |
| Rest | 91.2 ± 20.0 ml | 31.6 ± 12.7 ml | 66.5% ± 8.4% (50-80%) | 2.39 ± 0.50 | 162 ± 24.8 ms |

Example 21

The following describes results of absolute quantification of rest and stress myocardial blood flow with imaging agent 1 PET in normal and coronary artery disease patients. Imaging agent 1 is a new myocardial perfusion PET tracer that targets mitochondrial complex 1. In this study, the quantification of rest (R) and stress (S) myocardial blood flows (MBFs) and coronary flow reserve (CFR) was explored with this tracer in normal and coronary artery disease (CAD) patients.

Methods:

Eleven patients (8 with a low likelihood of CAD and 3 with CAD and presence of reversible defects) received IV injection of imaging agent 1 at rest and at peak adenosine pharmacological vasodilation. Dynamic PET images were obtained for 10 minutes, beginning with the administration of the tracer. On reoriented short axis images, regions of interest were placed on the normal and defect regions of the myocardium and the left ventricular blood pool, from which time activity curves (TACs) were generated. Patlak analysis was applied to myocardial TAC (~0.4-1.5 min) using the blood pool TAC as the input function to give the uptake constant (K) in the myocardium. Partial volume and spillover corrections were applied to blood pool and myocardial TACs to ensure the intercept of the regression line on the Patlak plot was close to zero. The first pass extraction fraction for imaging agent 1 in humans was assumed to be 0.94 (i.e., MBF=K/0.94), equivalent to that observed in prior studies (e.g., see Huisman et al., *J Nucl Med* 2008; 49:630-6).

Results:

S MBF was similar (p=NS) in LL patients and in the myocardial regions which were supplied by normal coronary arteries in CAD patients (NCA). R MBF, however, was higher (p<0.05) in NCA versus LL, resulting in a lower (p<0.05) CFR in NCA patients. In contrast, S MBF and CFR were significantly lower in CAD regions (see Table 3). These findings are in agreement with the published literature using N-13 ammonia PET.

TABLE 3

|  | Rest MBF | Stress MBF | CFR |
| --- | --- | --- | --- |
| LL | 0.66 ± 0.12 | 2.36 ± 0.49 | 3.73 ± 1.24 |
| NCA | 0.90 ± 0.15 | 2.38 ± 0.23 | 2.68 ± 0.32 |
| CAD | 0.76 ± 0.13 | 1.18 ± 0.25 | 1.58 ± 0.33 |

The study data showed that absolute MBF could be quantified at rest and stress in humans using imaging agent 1 myocardial perfusion PET imaging.

Example 22

The following describes an iterative technique for optimizing injected tracer dosage and acquisition time for $^{18}$F-labeled myocardial perfusion tracer imaging agent 1. Public and staff concerns about radiation exposure necessitate optimization of the dosage acquisition time product (DATP) to obtain the optimal tradeoff between dose, acquisition time, and image noise. An iterative algorithm was developed for determining optimal dosage and acquisition time based on a task-limited noise level.

Methods:

The mean and standard deviation (SD) were determined from a region of interest (ROI) of the myocardium to define a ratio: mean/SD (MSD). Using SD and a surrogate for "noise" has its limitations: 1) intrinsic count variability due to partial volume, and tracer uptake and, 2) non-Poisson nature of reconstructed and post filtered data. The iterative algorithm was used to fit a model to the limiting MSD. From this, an optimal acquisition time was determined for a target MSD to detect a 5% perfusion defect.

Data Acquisitions:

Phantom data simulating patient distributions and a 40% septal defect were acquired on a Biograph 64 slice PET/CT scanner using a 30 minute listmode acquisition. The technique was also tested in 18 subjects. Patients received a 2 mCi at rest and ~2 mCi stress on the following day. A dynamic series for 10, 20, 40, 80, 160, and 320 seconds was acquired 10 minutes post injection. The myocardial ROI was taken from a separate 600 second acquisition using >70% of the maximum myocardial voxel limit.

Data Analysis:

The phantom data converged to theoretical DATP of 9.5 mCi (simulated)*min. In patients, the iterative algorithm converged to a solution in 18 Rest, 9 Ad and 8 Ex. The results are summarized in Table 4:

TABLE 4

DATP for detection of 5% defect. 95% time is the limit in which 95% of patients would have detection of the 5% defect.

|  | MEAN | STDEV | 95% ACQ TIME (for 1 mCi) |
| --- | --- | --- | --- |
| REST | 2.48 | 1.25 | 4.98 |
| EX Stress | 1.80 | 0.57 | 2.94 |
| AD Stress | 1.22 | 0.55 | 2.32 |

The iterative technique for solving for optimal dosage acquisition time product converged for phantom and patient studies. Using this result, an optimal acquisition times for rest, adenosine and exercise stress was determined. Furthermore, it was determined that the algorithm can be used to test alternative filtering, and detection limit and used to extrapolate to the performance of lower sensitivity scanners.

Example 23

The following describes the independence of myocardial functional parameters (LVEF, EDV and ESV) across a large range of acquisition times as measured from radiotracer, imaging agent 1. The accurate measurement of functional parameters using myocardial perfusion PET requires adequate count density. The correlation of functional parameters [left ventricular ejection fraction (LVEF), end-systolic volume (ESV), and end-diastolic volume (EDV)] were examined with acquisition time.

Methods:

To analyze the robustness of functional measurements to variations in count density, a series of low count [1, 3, 5 minute adenosine (AD), 3, 5 minute rest, 5, 10 minute exercise (EX)] to high count (15 minute AD, 10 minute rest, 15 minute EX) ECG gated (16 time bin) PET data sets from "listmode" data were produced. LVEF, ESV and EDV were measured using the QPET analysis program.

Data Acquisition:

from 23 patients from two study centers. Data for this study was acquired using a same day, rest stress study. Patients received ~2 mCi at rest and also received a ~6 mCi "same day" stress (8 EX, 13 AD) dosage. Functional values from shorter rebinning times were compared with the longest acquisition time dataset. Correlations were determined using linear regression analysis.

Results:

For all acquisition times examined, regression slopes were within 10% of unity (with the exception of the 1 minute adenosine, 20%). Correlation coefficients are in Table 5.

TABLE 5

Correlation coefficient between list rebinning and longest acquisition.

|  | EDV | ESV | LVEF |
| --- | --- | --- | --- |
| 3 min-rest | 0.970 | 0.985 | 0.985 |
| 5 min-rest | 0.995 | 0.990 | 0.985 |
| 1 min-AD | 0.970 | 0.975 | 0.906 |
| 10 min-AD | 0.997 | 0.998 | 0.995 |
| 5 min-EX | 0.990 | 0.995 | 0.990 |
| 10 min-EX | 0.999 | 0.999 | 0.999 |

The high count density present in cardiac imaging agent 1 myocardial perfusion PET images showed robust functional measurements across a wide range of count densities is possible. Modest variations in parameters affecting count density, such as BMI and variations in dosage, are unlikely to alter functional measurements.

Example 24

The following describes the development of a method for the determination of minimum inter-injection interval for a one-day rest-stress protocol with imaging agent 1 PET myocardial perfusion. A one-day rest-stress protocol for myocardial perfusion imaging (MPI) needs minimization of wait time between injections (WT) as shorter times require greater stress/rest dosing ratios (DR) and minimum rest dose is dictated by image statistics. A method for determining the dependence of DR on WT and to identify a WT for acceptable total dose was developed.

Methods:

Two-day rest-stress imaging agent 1 PET image data of the heart (5 adenosine (AD) and 5 exercise (EX) stress) from 20 patients with known reversible defects on Tc-99m MPI were combined to create artificial blended images by adding 16%, 23%, 48% or 100% of rest image to the stress image. These were paired with rest images, 2-day stress images and read by 3 blinded readers. Results were recorded by segment as reader response (RR) (0 to 4) and as quantitative defect severity (QDS) in % decrease.

Results:

RR was found to be linearly related to the QDS. In general, decreases greater than 80% of maximum were read as 0, 70% to 80% as 1, 60% to 70% as "2," 50% to 60% as "3" and below 50% as "4." Analysis of RR indicated that greater than 1 unit change from the 2-day data were observed in reader response in general only for the 48% and 100% blended image sets. Therefore 23% was deemed the maximum tolerable rest-to-stress contamination. Using the relationship between rest-stress contamination and dosing, it was found that, for AD a minimum DR of 2.2 was required with a 0.5 hour WT, and for EX a minimum DR of 3.0 was needed with a 1-hour WT.

Maximum tolerated rest-to-stress contamination levels were determined from modeled images. The uptake properties of imaging agent 1 with elevated coronary flow made it possible to tolerate a relatively low DR and short WT for AD studies while a longer WT and higher DR is needed for EX studies.

Example 25

The following describes the design of a 1-day rest-stress PET MPI protocol that requires selection of doses and imaging times for both rest and stress phases as well as the interval between rest and stress doses.

These parameters were determined using three properties of imaging agent 1 in myocardial perfusion imaging: 1) the injected dose at rest that yields a diagnostic quality image for a given acquisition time, 2) the maximum acceptable contribution of the rest dose to the stress image and 3) the maximum total injected dose that may be administered based on radiation dose considerations.

The minimum rest dose for a given imaging acquisition time in which the count-related signal-to-noise did not meaningfully contribute to reader error was determined. This was done by simulating increasing doses using multiple rebinnings of patient rest study with increasingly greater amounts of data. This method uses the increasing number of coincidence events in sequential rebinnings to create images that model increasing dose and/or acquisition duration. This method is valid for relatively low concentrations of radioactivity, such as are used here.

When the relationship between the dose and acquisition time are known, the rest dose for Cohort 2 was calculated. After considering the dosing required for a range of acquisition times from two minutes up to a practical maximum of 10 minutes, five minutes was selected. This permitted an initial dose of 2.9 mCi for the rest acquisition.

To determine the stress dose for a given rest dose, the dosing ratio was determined. To do this, first, the maximum tolerable contribution of the rest dose to the-stress image was determined. This was assessed by creating simulated stress images with a range of rest dose contributions using combinations of data from the Study Day 1 rest and Study Day 2 stress studies.

The final step of the method is the need to maintain the total dose below a limit of 14 mCi, with some additional margin, to limit the radiation dose to 5 rem to the critical organ and 1 rem effective dose (ED) or lower.

Using the maximum rest contribution to the stress image from the analysis, a range of dosing intervals was considered from a minimum of 15 minutes (essentially immediately) to a maximum practical limit of 2 hours. Based on this it was possible to select a 30 minute interval for adenosine stress that yielded a corresponding ratio of the stress dose to the rest dose of 2.0.

For exercise stress, a combination of a longer dosing interval and greater dose ratio was needed due to the lower net myocardial uptake of radioactivity with exercise. Thus, a dosing interval of 60 minutes was chosen which corresponded to a dose ratio of 3.0. The rest acquisition time was increased to 7 minutes and the rest dose reduced to 1.7 mCi to allow for the greater required stress/rest dose ratio while still maintaining the total comfortably within the 14 mCi limit.

In order to allow some range of dosing and to avoid variations in dosing that might jeopardize the integrity of the study, the dose and dose ratio values above were set as the lower limits of 15% to 20% ranges for each variable and the acquisition times increased to a minimum of 15 minutes for all acquisitions to account for the possibility of lower sensitivity of the 2D PET scanners. The data acquisition was broken into sections so that images derived from shorter acquisition times may be obtained from the same data as necessary. This resulted in the final specified dosing of 2.9 mCi to 3.4 mCi rest with a stress dose of 2.0 to 2.4 times the rest dose for adenosine stress. For exercise stress, the final doses were set at 1.7 mCi to 2.0 mCi for rest with a stress dose 3.0 to 3.6 times the rest dose. These doses are intended to reflect the actual net injected radioactivity so that additional radioactivity is required in the syringe prior to injection to compensate for losses due to adsorption and the dead volume of the syringe.

Example 26

The following describes human safety, dosimetry, biodistribution, and rest-stress myocardial imaging characteristics of $^{18}$F-labeled imaging agent 1 myocardial perfusion PET tracer. $^{18}$F-labeled imaging agent 1 is a novel myocardial perfusion imaging PET tracer that targets mitochondrial complex 1. Studies of human safety, dosimetry, biodistribution, and myocardial imaging characteristics of this tracer were evaluated.

Methods:

25 normal subjects were enrolled in 2 studies: 13 received 222 MBq I.V. At rest (R) only and 12 more subjects received 94 MBq at R and, on a second day, 124 MBq at peak adenosine stress (Adeno, n=6) or at peak treadmill exercise (Ex, n=6). Physical exam, laboratory, vital signs, ECG, and EEG were monitored pre- and post-injection. Myocardial (Myo), liver, blood pool and lung Standardized Uptake Values (SUV) were determined from sequential PET images over time. Mean dose for various organs and mean effective dose (ED in mSv/MBq) were estimated.

Results:

There were no adverse events related to the tracer. The top highest-dose organs were kidneys at R and heart with Adeno and Ex. ED was 0.019 at R and with Adeno and 0.015 with Ex. Myo SUV's remained high during imaging. Ex myo SUV was lower with Ex due to higher skeletal muscle uptake. Ex myo SUV was lower with Ex due to higher skeletal muscle uptake. Myo/liver was highest with Ex, followed by Adeno and R (see Table 6). Myo/blood and Myo/lung were high and rapidly improved with time.

TABLE 6

| | 10 mins | 30 mins | 60 mins | 90 mins | 149 mins |
|---|---|---|---|---|---|
| Rest Myo SUV | 3.9 ± 0.9 | 4.2 ± 1.1 | 4.5 ± 1.2 | 4.3 ± 1.3 | 4.1 ± 1.4 |
| Rest Myo/liver | 1.0 ± 0.3 | 0.9 ± 0.2 | 1.1 ± 0.2 | 1.4 ± 0.2 | 2.1 ± 0.3 |
| Adeno Myo SUV | 10.5 ± 1.5 | 10.8 ± 2.1 | 10.3 ± 2.1 | 9.6 ± 2.1 | 8.4 ± 2.1 |
| Adeno Myo/liver | 1.9 ± 0.6 | 2.0 ± 0.5 | 2.2 ± 0.5 | 2.6 ± 0.5 | 3.8 ± 1.0 |
| Exercise Myo SUV | 6.2 ± 2.1 | 5.5 ± 1.0 | 5.1 ± 0.9 | 4.9 ± 0.9 | 4.5 ± 0.8 |
| Exercise Myo/liver | 28.0 ± 33.6 | 5.6 ± 1.0 | 5.6 ± 1.3 | 5.8 ± 1.5 | 5.5 ± 1.5 |

Example 27

Studies were performed in subjects to determine dosing protocols for imaging agent 1 under various conditions. Determining dosing protocols included assessing parameters such as mCi of imaging agent 1 injected in the body of the subject; mCi of imaging agent 1 injected from the syringe; acquisition time of images after injection; delay between rest and stress studies, etc. Parameters varied for rest and stress, for example, the injected dose (in the body) for exercise stress was at least three times the injected dose (in the body) at rest. In addition, the injected dose (in the body) for pharmacological stress was at least two times the injected does (in the body) at rest. Results are shown in Table 7.

TABLE 7

Imaging agent 1 doses, acquisition times and dosing delay for exercise and pharmacologic stress.

| Stress Test | Study | Injected Dose in the Body (mCi) | Injected Dose in the Syringe (mCi) | Acquisition Time (min) | Delay between Studies (min) |
|---|---|---|---|---|---|
| Exercise | Rest | 1.7-2.0 | 2.5-3.0 | 10 | 60 |
| | Stress | 8.6 to 9.0 | 9.0-9.5 | | |
| Pharmacologic | Rest to Stress ratio | Minimum x3 injected Rest dose | | | |
| | Rest | 2.4-2.9 | 2.5-3.0 | 10 | 30 |
| | Stress | 5.7-6.2 | 6.0-6.5 | | |
| | Rest to Stress ratio | Minimum x2 injected Rest dose | | | |

Various parameters have been determined for dosing imaging agent 1 in human subjects, including injected does, delay between studies, ration of rest to stress dosing, and the amount in the syringe compared to the amount injected from the syringe.

Example 28

The following provides results obtained from a study regarding a single-dose dosimetry, biodistribution, and safety trial of imaging agent 1 in healthy subjects. Whole body PET image data for the 12 healthy volunteers were obtained using imaging agent 1 at approximately 10 minutes, 30 minutes, 50 minutes, 2 hours, 2.5 hours, 3.83 hours, and 4.5 hours post injection. Image data were attenuation corrected at the imaging site, and were quantified based on the Medical Internal Radiation Dose (MIRD) 16 methodology by Dosimetry Analysis Laboratory, CDE Dosimetry Services (CDE) to determine kinetic data in all organs showing significant uptake of activity. Dosimetry estimates were created via kinetic modeling of the quantified image data to determine residence times, and the standard MIRD methodology. These estimates were determined using 3 assumptions regarding urinary bladder voiding intervals (2.0, 3.5, and 4.8 hr). Kinetic data, residence times, and the dosimetry estimates are reported for individuals, and as summary statistics.

Terminology.

Effective Dose (ED): Developed by the ICRP for occupational radiation protection, the ED enables the comparison of radiation detriment from a uniform external dose and a non-uniform internal dose. The risk for a 1 rem ED determined for an non-uniform internal dose is equal to the risk from a 1 rem uniform external exposure (total body dose). As defined in ICRP publication 60 [ICRP-60 1991].

Effective Dose Equivalent (EDE): Developed by the ICRP for occupational radiation protection, the EDE enables the comparison of radiation detriment from a uniform external dose and a non-uniform internal dose. The risk for a 1 rem EDE determined for an non-uniform internal dose is equal to the risk from a 1 rem uniform external exposure (total body dose). As defined in ICRP publication 30 [ICRP-30 1981].

MIRD Methodology: The methodology developed by the Medical Internal Radiation Dose Committee for the determination of radiation absorbed dose. This methodology included the use of radiation transport factors (S-values), and bio-kinetic parameters (residence times). As defined in the MIRD Primer, Society of Nuclear Medicine, 1991.

% CV is Coefficient of variation (Ratio of the standard deviation to the mean times 100).

Percent Injected Dose Vs. Time from Whole Body Images.

Percent injected activity as a function of time was determined for brain, heart wall, kidneys, liver, lungs, red marrow (lumbar region), salivary glands, spleen, stomach wall, thyroid, and urinary bladder. On average, the organ that showed the largest peak uptake was the liver with approximately 19.1% of the injected activity (data not shown). The next largest peak uptake occurred in the kidneys with approximately 9.4% of the injected activity (data not shown).

Dosimetry Estimates.

On average, for the urinary bladder voiding interval of 3.5 hours the organ receiving the largest absorbed dose was the kidneys at 0.24 rem/mCi (0.066 mSv/MBq) and the heart wall at 0.18 rem/mCi (0.048 mSv/MBq). The mean ED (effective dose) was 0.071 rem/mCi (0.019 mSv/MBq). Table 8 shows the absorbed dose estimates (rem/mCi). The mean adsorbed dose for the listed organs is found in column one of Table 8.

TABLE 8

|  | Mean | % CV | Min | Max |
|---|---|---|---|---|
| Adrenals | 5.8E−02 | 7% | 4.9E−02 | 6.4E−02 |
| Brain | 9.4E−02 | 25% | 5.7E−02 | 1.3E−01 |
| Breasts | 3.2E−02 | 8% | 2.8E−02 | 3.5E−02 |
| Gallbladder Wall | 6.4E−02 | 8% | 5.4E−02 | 7.1E−02 |
| LLI Wall | 4.3E−02 | 8% | 3.7E−02 | 4.8E−02 |
| Small Intestine | 4.7E−02 | 8% | 4.0E−02 | 5.2E−02 |
| Stomach Wall | 1.5E−01 | 26% | 9.0E−02 | 2.3E−01 |
| ULI Wall | 4.7E−02 | 7% | 4.1E−02 | 5.2E−02 |
| Heart Wall | 1.8E−01 | 17% | 1.2E−01 | 2.4E−01 |
| Kidneys | 2.4E−01 | 22% | 1.6E−01 | 3.5E−01 |
| Liver | 1.5E−01 | 19% | 1.0E−01 | 1.9E−01 |
| Lungs | 4.2E−02 | 7% | 3.6E−02 | 4.6E−02 |
| Muscle | 3.8E−02 | 8% | 3.2E−02 | 4.1E−02 |
| Ovaries | 4.5E−02 | 8% | 3.9E−02 | 5.0E−02 |
| Pancreas | 5.9E−02 | 8% | 4.8E−02 | 6.7E−02 |
| Red Marrow | 6.0E−02 | 11% | 4.7E−02 | 6.9E−02 |
| Osteogenic Cells | 6.9E−02 | 8% | 5.7E−02 | 7.8E−02 |
| Salivary | 1.3E−01 | 38% | 8.6E−02 | 2.5E−01 |
| Skin | 2.9E−02 | 8% | 2.5E−02 | 3.2E−02 |
| Spleen | 6.0E−02 | 21% | 4.0E−02 | 7.6E−02 |
| Testes | 3.4E−02 | 9% | 3.0E−02 | 3.8E−02 |
| Thymus | 4.1E−02 | 8% | 3.5E−02 | 4.5E−02 |
| Thyroid | 1.2E−01 | 30% | 7.1E−02 | 1.8E−01 |
| Urinary Bladder Wall | 8.4E−02 | 18% | 6.5E−02 | 1.1E−01 |
| Uterus | 4.6E−02 | 8% | 4.0E−02 | 5.1E−02 |
| Total Body | 4.5E−02 | 7% | 3.7E−02 | 4.9E−02 |
| EDE | 8.0E−02 | 11% | 6.3E−02 | 9.1E−02 |
| ED | 7.1E−02 | 12% | 5.5E−02 | 8.9E−02 |

Example 29

Results related to a human study of imaging agent 1, a novel $^{18}$F-labeled tracer for myocardial perfusion PET imaging; dosimetry, biodistribution, safety, and imaging characteristics after a single injection at rest are described.

Methods: Study Population.

Healthy adults (as determined by medical history, physical examination, vital signs, ECG, EEG, neurological examination, and clinical laboratory testing), ages 18-40 years, participated in the study. In order to be enrolled, subjects had to meet all protocol-specified inclusion criteria and none of the exclusion criteria.

Study Design.

This was a non-randomized, open-label, single-dose study. A total of 13 healthy adult subjects were enrolled and administered a single dose of imaging agent 1 at a single study center in the United States. Subjects were screened within 14 days prior to enrollment to confirm subject eligibility, and began baseline assessments at the study center the day before study drug administration. Subjects remained at the study center until completion of the Study Day 2 safety assessments (24±8 hours post-dose). A telephone call was made to study subjects 48±8 hours post-dose for adverse event (AE) monitoring. All subjects returned to the study center approximately one week (5-7 days) post-dose for a follow-up safety visit, and were contacted by telephone approximately 14-17 days post-dose for final serious AE monitoring.

Determination of Dose and Method of Administration.

The 8 mCi target dose was selected to provide adequate count statistics and was projected to be well below the maximum acceptable radiation exposure based on preclinical data. These data demonstrated that the maximum dose of imaging agent 1 that may be administered to a human without exceeding 50 mSv (5 rem) to the target was 742 MBq (20.0 mCi) and the injected dose that yielded an effective dose (ED) of ≤10 mSv (1 rem) was 666 MBq (18.0 mCi) (Stabin, M G, Sparks, R B, et al, OLINDA/EXM: the second-generation personal computer software for internal dose assessment in nuclear medicine." *J Nucl Med* 2005 46(6):1023-7).

On day 1, each subject received a 1-3 mL intravenous bolus injection of imaging agent 1 in a sterile solution of ≤5% ethanol containing ≤50 mg/mL sodium ascorbate in water, calculated to deliver approximately the target dose of imaging agent 1 at the time of injection. The dose was administered in less than 10 seconds, followed immediately by a 3-5 mL saline flush.

The net injected dose was calculated by subtracting the decay-corrected radioactivity in the syringe and injection tubing after injection from the assayed and decay-corrected radioactivity in the syringe prior to injection.

PET Imaging Protocol.

Whole-body PET imaging from head to mid thigh was performed at protocol-specified time-windows.

Dosimetry analyses. Estimates of radiation dosimetry for the standard organs of the adult male and female models and for the, salivary glands as well as the effective dose equivalent (EDE) (International Commission on Radiological Protection (ICRP), Recommendations of the International Commission on Radiological Protection, Publication 26. *Ann ICRP.* 1977; 1(3)) and the effective dose (ED) (International Commission on Radiological Protection (ICRP), 1990 Recommendations of the International Commission on Radiological Protection, 60. *Ann ICRP.* 1990; 21(1-3)) were determined using the OLINDA/EXM software (Stabin, M G, Sparks, R B, et al, OLINDA/EXM: the second-generation personal computer software for internal dose assessment in nuclear medicine." *J Nucl Med* 2005 46(6):1023-7) Assessment of radiation dosimetry was based on the MIRD method, with data derived from imaging studies, using methods consistent with MIRD Pamphlet no. 16 (Siegel J A, Thomas S R, Stubbs J B, et al. MIRD pamphlet no. 16: Techniques for quantitative radiopharmaceutical biodistribution data acquisition and analysis for use in human radiation dose estimates. *J Nucl Med.* 1999 February; 40(2): 37S-61S).

The attenuation corrected transverse image data slice planes were combined into a single three-dimensional image matrix for each subject and each time point using custom software. These images were then divided into 6 image sets ("anterior", "posterior", "salivary", "thyroid", "source", and "full") of combined coronal plane image data for each subject at each time point, grouping organs with similar anterior to posterior depths. This was done to optimize the ROI creation, and minimize background contribution to the organs contained in each combined coronal plane image. The "anterior" images contained stomach wall, heart wall, and urinary bladder. The "posterior" images contained kidneys, lumbar spine, and spleen (when visible). The "salivary" images contained the salivary glands (parotid and submandibular). The "thyroid" images contained the thyroid. The "full" images combined all of the coronal image planes that contained subject image data and was used for quantification of the brain and liver. The "source" images contained the calibration source.

Regions of interest were drawn around all organs that showed uptake above background using custom software developed and validated for this purpose. Absolute radioactivity was determined by normalizing ROI sums by a calibration factor derived from the calibration source. Region counts were also adjusted for activity containing underlying and overlying tissue that was not part of the organ or tissue being quantified by utilization of background regions of interest. Total body region counts were also corrected for off body background counts. Appropriate normalization of region sizes for organ and adjacent regions were made. Unobstructed regions of organs with significant overlap from other activity containing organs were also employed where necessary. In order to estimate the activity in the lower legs (which were not imaged), a region of interest on the upper thigh was utilized. Activities were also normalized where necessary to account for 100% of the injected activity, and to insure conservative (slight overestimates) determination of absorbed dose. Where urinary excretion data were available beyond the end of the imaging regimen, these data were used to determine whole body retention.

Kinetic data for brain, heart wall, kidneys, liver, red marrow (lumbar spine regions were utilized), salivary glands, spleen, stomach wall, thyroid, and urinary bladder for the subjects in the study were determined using image quantification methodology. Absolute activity was converted to fractional dose by dividing by the total activity administered. Organ and tissue data were fit using non-linear least-squares regression with sums of exponentials of the form shown in Equation 1, where f and λ are the model parameters that are determined in the fitting process, $F_{ij}(t)$ is the fraction of the total injected activity, t is the time post injection, i is the $i^{th}$ ROI, j is the $j^{th}$ subject, and k is the $k^{th}$ exponential term. Between one and four exponential terms were employed, as appropriate.

$$F_{ij}(t) = \sum_k f_{ijk} e^{-\lambda_{ijk} t_j}.$$

Equation 1

The regression was performed using custom software that determines initial parameter values based on the temporal variation of the kinetic data, and the use of pre-tabulated estimates for various time activity scenarios as selected by the user. Once these data were fit, residence times were determined by integration of these empirically determined functions (sums of exponentials) from time equal zero to infinity, taking into account physical decay. Remainder of Body residence times were determined by subtraction of appropriate organ residence times from whole body residence times. Urinary bladder residence times were determined using the parameters determined by fitting the whole body activity data with a urinary bladder model as implemented in the OLINDA/EXM software with 3.5 hour bladder voiding interval. Red marrow residence time was determined based on a region of interest drawn on a portion of the lumbar spine. The lumbar spine was assumed to contain 16.1% (International Commission on Radiological Protection (ICRP) Publication 23, Report of the Task Group on Reference Man. Pergamon Press. 1975, page 125) of the total red marrow.

Organ/Tissue Dosimetry Estimates.

Absorbed dose estimates for all target organs were determined using the OLINDA/EXM software using the adult "male" model. The resulting absorbed dose estimates were scaled based on the total body mass of the individual subjects relative to that of the radiation transport phantom. Salivary gland dosimetry was determined by using a conservative estimate of the S-value for salivary glands based on the reference man total mass of the parotid and submaxilary salivary glands (International Commission on Radiological Protection (ICRP) Publication 23, Report of the Task Group on Reference Man. Pergamon Press. 1975, page 125) and assuming a spherical shape. S-Values for spheres were produced by the OLINDA/EXM software, and were linearly scaled based on the relative total body mass of reference man to that of subject. These S-values were then multiplied by the residence times to produce final salivary gland dose estimates.

Statistical Analyses.

All statistical analyses and all summary tables and listings were prepared using SAS® release 9.1.3 (SAS Institute, Inc., Cary, N.C.). Standard descriptive summaries included the N, mean, median, standard deviation (SD) and/or coefficient of variation (% CV), minimum and maximum for continuous variables, and the number and percent for categorical variables.

Results: Patient Demography.

Of the 26 subjects who were screened, 13 subjects (12 males and one female) were administered imaging agent 1, and completed all safety evaluations. The mean age was 23.4 years (range: 19-34 years) and the mean BMI was 23.4 (range: 20-26). One patient was not included in the analyses of dosimetry, biodistribution and radiokinetics, due to the inability to confirm the dose calibrator assay data for the standards preparation.

Radiation Dosimetry.

The intravenous bolus injection was calculated to deliver no more than 8 mCi of $^{18}$F at the time of injection. The mean (SD) final decay-corrected dose was 6 (0.6) mCi of $^{18}$F, with a range of 4.6 to 6.6 mCi (170 to 244 MBq). The difference between the target dose and the final dose was due to the retention of imaging agent 1 in the syringe.

The absorbed dose summary statistics are presented in Table 9 (mSv/MBq). The organ receiving the largest mean absorbed dose was the kidneys at 0.066 mSv/MBq (0.24 rem/mCi), followed by the heart wall at 0.048 mSv/MBq (0.18 rem/mCi). The mean ED was 0.019 mSv/MBq (0.072 rem/mCi).

TABLE 9

Absorbed Dose Estimates (mSv/MBq), N = 12, Void Interval = 3.5 hours.

| | Mean | % CV | Min | Max |
| --- | --- | --- | --- | --- |
| Adrenals | 1.6E$^a$–02 | 7% | 1.3E–02 | 1.7E–02 |
| Brain | 2.5E–02 | 25% | 1.5E–02 | 3.6E–02 |

TABLE 9-continued

Absorbed Dose Estimates (mSv/MBq), N = 12, Void Interval = 3.5 hours.

|  | Mean | % CV | Min | Max |
|---|---|---|---|---|
| Breasts | 8.8E−03 | 8% | 7.5E−03 | 9.6E−03 |
| Gallbladder Wall | 1.7E−02 | 8% | 1.5E−02 | 1.9E−02 |
| LLI Wall | 1.2E−02 | 8% | 1.0E−02 | 1.3E−02 |
| Small Intestine | 1.3E−02 | 8% | 1.1E−02 | 1.4E−02 |
| Stomach Wall | 4.0E−02 | 26% | 2.4E−02 | 6.2E−02 |
| ULI Wall | 1.3E−02 | 7% | 1.1E−02 | 1.4E−02 |
| Heart Wall | 4.8E−02 | 17% | 3.4E−02 | 6.4E−02 |
| Kidneys | 6.6E−02 | 22% | 4.4.E−02 | 9.5E−02 |
| Liver | 3.9E−02 | 19% | 2.7E−02 | 5.2E−02 |
| Lungs | 1.1E−02 | 7% | 9.7E−03 | 1.2E−02 | generally exhibiting an intensity similar to that of the heart, peaking between 10 and 30 minutes after injection and clearing by approximately 2 hours. The organ that showed the largest mean peak uptake was the liver with approximately 19.1% of the injected activity. The next largest mean peak uptake occurred in the kidneys with approximately 9.4% of the injected activity, followed by the brain with approximately 8.3% of the injected activity. Data from subjects in the study were used to determine the urinary excretion rate for each subject and the residence time for radioactivity in the bladder using a standard model, with a theoretical fixed voiding interval of 3.5 hours post-dose. The largest mean residence times were for remainder tissues (1.8 hours), liver (0.28 hours), and brain (0.14 hours). Summary residence time statistics are presented in Table 11.

TABLE 10

Mean Percent (%) Administered Dose versus Time (Hours Post-dose) N = 12, $^{18}$F, Decay Corrected.

|  | 0.17 hr [a] | 0.50 hr | 0.83 hr | 2.0 hr | 2.5 hr | 3.83 hr | 4.5 hr |
|---|---|---|---|---|---|---|---|
| Whole Body | 100.0% | 99.8% | 99.7% | 98.2% | 98.1% | 96.8% | 96.9% |
| Brain | 8.3% | 7.9% | 7.3% | 4.7% | 4.1% | 3.2% | 2.9% |
| GI Stomach Wall | 2.5% | 2.4% | 2.2% | 0.7% | 0.7% | 0.6% | 0.6% |
| Heart Wall | 3.1% | 3.2% | 3.4% | 2.4% | 2.5% | 2.1% | 2.1% |
| Kidneys | 9.4% | 6.5% | 4.9% | 1.6% | 1.6% | 1.2% | 1.1% |
| Liver | 19.1% | 18.0% | 16.4% | 7.5% | 7.0% | 4.5% | 4.7% |
| Marrow (lumbar) | 0.3% | 0.3% | 0.3% | NA | NA | NA | NA |
| Salivary | 0.6% | 0.7% | 0.6% | 0.5% | 0.5% | 0.4% | 0.4% |
| Spleen | 0.9% | 0.6% | 0.4% | 0.3% | 0.3% | 0.3% | NA |
| Thyroid | 0.1% | 0.1% | 0.1% | 0.1% | 0.1% | 0.1% | 0.1% |
| Urinary Bladder | 0.3% | 0.2% | 0.3% | 0.9% | 1.1% | 1.4% | 1.7% |

[a] Nominal times in hours post-dose (beginning of time window)
NA = not available TABLE 9-continued Absorbed Dose Estimates (mSv/MBq), N = 12, Void Interval = 3.5 hours.

|  | Mean | % CV | Min | Max |
|---|---|---|---|---|
| Muscle | 1.0E−02 | 8% | 8.7E−03 | 1.3E−02 |
| Ovaries | 1.2E−02 | 8% | 1.1E−02 | 1.3E−02 |
| Pancreas | 1.6E−02 | 8% | 1.3E−02 | 1.8E−02 |
| Red Marrow | 1.6E−02 | 11% | 1.3E−02 | 1.9E−02 |
| Osteogenic Cells | 1.9E−02 | 8% | 1.6E−02 | 2.1E−02 |
| Salivary | 3.5E−02 | 38% | 2.3E−02 | 6.8E−02 |
| Skin | 7.9E−03 | 8% | 6.8E−03 | 8.7E−03 |
| Spleen | 1.6E−02 | 21% | 1.1E−02 | 2.1E−02 |
| Testes | 9.2E−03 | 9% | 8.1E−03 | 1.0E−02 |
| Thymus | 1.1E−02 | 8% | 9.6E−03 | 1.2E−02 |
| Thyroid | 3.2E−02 | 30% | 1.9E−02 | 4.9E−02 |
| Urinary Bladder Wall | 2.3E−02 | 18% | 1.7E−02 | 3.0E−02 |
| Uterus | 1.2E−02 | 8% | 1.1E−02 | 1.4E−02 |
| Total Body | 1.2E−02 | 7% | 1.0E−02 | 1.3E−02 |
| EDE | 2.2E−02 | 11% | 1.7E−02 | 2.5E−02 |
| ED | 1.9E−02 | 12% | 1.5E−02 | 2.4E−02 |

[a]E followed by a − is the exponent multiple of 3 convention for decimal presentation.

Whole-Organ Biodistribution.

Figure 11:
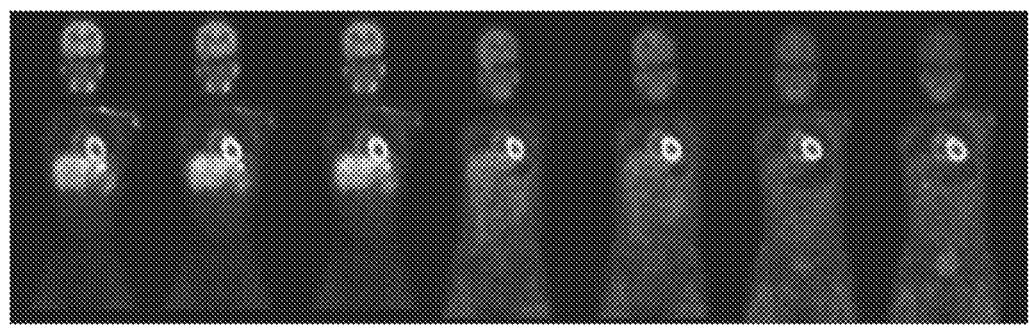
FIG. 11 shows whole body coronal sections at the level of the myocardium from a representative human subject at different time points after administration of imaging agent 1.

The biodistribution of imaging agent 1, calculated as the whole-organ percent injected radioactivity as a function of time, was determined for brain, heart wall, kidneys, liver, lungs, red marrow (lumbar region), salivary glands, spleen, stomach wall, thyroid, and urinary bladder (Table 10 and FIG. 11). FIG. 11 shows whole body coronal images through the body at the level of the myocardium from a representative subject at different time points after administration of imaging agent 1. Images have been corrected for $^{18}$F decay. It can be seen that the heart exhibits high and sustained retention of $^{18}$F from the earliest images through approximately 5 hours after injection. The liver also appears,

TABLE 11

Residence Times (Hours) Summary Statistics (N = 12, Void Interval = 3.5 Hours).

|  | Mean | % CV | Min | Max |
|---|---|---|---|---|
| Brain | 1.38E−01 | 2.69E−01 | 8.68E−02 | 2.08E−01 |
| GI Stomach Wall | 3.30E−02 | 4.46E−01 | 1.53E−02 | 6.11E−02 |
| Heart Wall | 7.28E−02 | 1.83E−01 | 4.82E−02 | 1.01E−01 |
| Kidneys | 9.52E−02 | 2.35E−01 | 6.10E−02 | 1.43E−01 |
| Liver | 2.77E−01 | 2.22E−01 | 1.83E−01 | 3.94E−01 |
| Red Marrow | 8.86E−02 | 2.10E−01 | 6.72E−02 | 1.17E−01 |
| Salivary | 1.48E−02 | 3.24E−01 | 9.68E−03 | 2.63E−02 |
| Spleen | 1.01E−02 | 1.87E−01 | 7.26E−03 | 1.25E−02 |
| Thyroid | 3.31E−03 | 3.13E−01 | 1.72E−03 | 5.06E−03 |
| Urinary Bladder | 2.65E−02 | 3.35E−01 | 1.40E−02 | 4.50E−02 |
| Remainder of Body | 1.84E+00 | 7.86E−02 | 1.65E+00 | 2.08E+00 |

[a]E followed by a − is the exponent multiple of 3 convention for decimal presentation Early Elimination of $^{18}$F in Urine.

Urine collected pre-dose (Baseline), and all voids up to 8 hours post-dose were collected and assayed for $^{18}$F. However, as in blood collection, the urine collection terminated near the 7-hour minimum specified in the protocol. Mean urinary excretion over the approximate 7-hour void interval was 4.83% ID with a % CV of 64.7 and a range of 0.64% ID to 12.41% ID. This finding is in reasonable agreement with cumulative urine excretion of 5% as measured with PET imaging.

Discussion:

The critical organ for imaging agent 1 was the kidneys, with a mean estimated dose of 0.066 mSv/MBq (0.24 rem/mCi) The maximum injected dose of the compound that may be administered without exceeding 50 mSv to the critical organ is therefore 770 MBq. This is somewhat higher than the 185 MBq to 370 mBq recommended in the widely-used guidance by the Center for Drug Evaluation and Research (CDER) that describes recommended package insert wording for facilities applying to manufacture [$^{18}$F]-FDG) (PET Drug Applications—Content and Format for NDAs and ANDAs: Fludeoxyglucose F 18 Injection, Ammonia N 13 Injection, Sodium Fluoride F 18 Injection, Attachment II, Sample Formats; Labeling for Ammonia N 13 Injection, Fludeoxyglucose F 18 Injection and Sodium Fluoride F 18 Injection, Attachment II (CDER 2000)). This behavior is a result of the very rapid urinary excretion of a large fraction of [$^{18}$F]-FDG shortly after administration, resulting in a substantially higher exposure to the urinary bladder for that compound compared with that of imaging agent 1. The ED due to imaging agent 1 (0.019 mSv/MBq), is the same as the ED of [$^{18}$F]-FDG (International Commission on Radiological Protection (ICRP), Radiation Dose to Patients from Radiopharmaceuticals, Addendum 2 to ICRP Publication 53, Publication 80, *Ann ICRP.* 1999; 28(3)). It can therefore be concluded that the radiation dose from imaging agent 1 is comparable to or less than that due to [$^{18}$F]-FDG.

Since the mean estimated effective dose (ED) for imaging agent 1 is 0.019 mSv/MBq (0.072 rem/mCi), the maximum injected dose that may be administered without exceeding 10 mSv ED is therefore 521 MBq.

The radiation dose estimates from this study are consistent with those derived from non-human primates (Lazewatsky J, Azure M, Guaraldi M et al. Dosimetry of BMS747158, a novel 18F labeled tracer for myocardial perfusion imaging, in nonhuman primates at rest. *J Nucl Med.* 2009; 49(Supplement 1):15p.) and the high and sustained retention of imaging agent 1 in the heart is consistent with data in both non-human primates and in other species (Yu M, Guaraldi M T, Mistry M, Kagan M, McDonald J L, Drew K, Radeke H, Purohit A, Azure M, Casebier D S, Robinson S P. BMS-747158-02: a Novel PET Myocardial Perfusion Imaging Agent. Journal Nuclear Cardiology 2007 November-December; 14(6):789-98). Although the critical organ in the primate-derived estimates was seen to be the heart wall, the estimated human radiation dose for the heart wall in that study was 0.067 mSv/MBq, which is very similar to the critical organ value of 0.066 mSv/MBq seen for the kidneys in this study. The doses to both organs were among the highest in both the non-human primates-derived results and in the current study and are within two standard deviations of one another.

Imaging agent 1 was well-tolerated and no clinically significant safety concerns were raised. Changes from baseline in vital signs, laboratory values (hematology, coagulation, clinical chemistry and urinalysis), ECGs, and EEGs were not clinically significant. Potential cardiotoxicity (signaled through coagulation studies and changes in Troponin-T levels) were not exhibited. Physical and neurological examinations did not reveal any pre-dose or post-dose abnormalities. The DMC did not raise safety concerns following periodic reviews of the safety data.

The results obtained in this study demonstrated that imaging agent 1 appeared to be safe and was well tolerated and exhibited a substantial and sustained retention in myocardium. The critical organ after resting injection of imaging agent 1 was determined to be the kidneys with 0.066 mSv/MBq. Based on the observed mean ED, the maximum injected dose that may be administered without exceeding 1 rem ED is 14 mCi (521 MBq). The ED from imaging agent 1 is the same as that of [$^{18}$F]-FDG, while the critical organ (kidney) dose of imaging agent 1 is significantly less than the critical organ (urinary bladder) dose of [$^{18}$F]-FDG.

Example 30

The following example describes studies relating to cardiac imaging and safety evaluation of imaging agent 1, a novel PET myocardial perfusion imaging agent, in chronic myocardial compromised rabbits.

Imaging agent 1 is an $^{18}$F labeled imaging agent for myocardial perfusion imaging (MPI) with positron emission tomography (PET) (Yu M, Guaraldi M T, Mistry M, Kagan M, McDonald J L, Drew K et al.: a novel PET myocardial perfusion imaging agent. J Nucl Cardiol 2007; 14:789-98). Cardiac imaging with this agent shows clear myocardium and identification of acute myocardial ischemia and tissue necrosis in animal models of acute coronary ligation and ischemia reperfusion injury (Yu M, Guaraldi M T, Mistry M, Kagan M, McDonald J L, Drew K et al.: a novel PET myocardial perfusion imaging agent. J Nucl Cardiol 2007; 14:789-98; Nekolla S G, Reder S, Higuchi T, Dzewas G, Poethko T, Preissl A et al. Assessment of Imaging Properties of a New F-18 Labelled Flow Tracer in a Pig Model. J Am Coll Cardiol 2008; 51:A170; and Maddahi J, Schiepers C, Czernin J, Huang H, Schelbert H, Wijatyk A et al. First human study of BMS747158, a novel F-18 labeled tracer for myocardial perfusion imaging. J Nucl Med 2008; 49:70P). In model systems imaging agent 1 has demonstrated superior characteristics over the currently available MPI agents. In comparison with single photon emission computer tomography (SPECT) based agents ($^{99m}$Tc-Sestamibi and $^{201}$Thalium), Imaging agent 1 has the advantage of PET technology with accurate attenuation correction and quantification of myocardial perfusion in absolute terms. Furthermore, imaging agent 1 heart uptake correlates better with myocardial perfusion at a large range of flow rates invitrol and at rest and stress conditions in-vivo (Nekolla S G, Reder S, Saraste A, Higuchi T, Dzewas G, Preissel A et al. Evaluation of the novel myocardial perfusion positron-emission tomography tracer 18F-BMS-747158-02: comparison to 13N-ammonia and validation with microspheres in a pig model. Circulation 2009; 119:2333-42). In comparison with current PET agents, like $^{13}$N-Ammonia and $^{82}$Rubidium, the long half-life (110 minutes) of $^{18}$F enables imaging agent 1 to be radio-synthesized and supplied centrally. It also provides the opportunity for imaging under excise stress, in addition to pharmacological stress.

Safety and radio-dosimetry studies in multiple normal species show imaging agent 1 has acceptable safety margin for clinical development (Mistry M, Onthank D, Green J, Cicio S, Casebier D, Robinson S et al. Toxicological Evaluation of BMS-747158, a PET Myocardial Perfusion Imaging Agent. The Toxicologist 2008; 102:476; and Lazewatsky J, Azure M, Guaraldi M, Kagan M, MacDonald J, Yu M et al. Dosimetry of BMS747158, a novel 18F labeled tracer for myocardial perfusion imaging, in nonhuman primates at rest. J Nucl Med 2009; 49:15p). The critical organ for radiation is the heart and the radiation doses were comparable with the commercial available agent $^{18}$F-fluorodeoxy-glucose (Lazewatsky J, Azure M, Guaraldi M, Kagan M, MacDonald J, Yu M et al. Dosimetry of BMS747158, a novel 18F labeled tracer for myocardial perfusion imaging, in nonhuman primates at rest. J Nucl Med 2009; 49:15p).

Methods: Rabbit Model of Myocardial Infarction.

Male New Zealand rabbits (body weight 2.5-3.5 kg) were purchased from Harlan (Oakwood, Mich.) and maintained in the AAALAC-accredited Animal Care Facility at Lantheus Medical Imaging. The study protocol was approved by the Institutional Animal Care and Use Committee. The procedure of developing a rabbit model of myocardial infarction (MI) was similar to the method described previously (Fujita M, Morimoto Y, Ishihara M, Shimizu M, Takase B, Maehara T et al. A new rabbit model of myocardial infarction without endotracheal intubation. J Surg Res 2004; 116:124-8). Briefly, the rabbit was anesthetized with ketamine (40 mg/Kg, im) and xylazine (9 mg/Kg, im) and placed in a supine position. The surgery was performed under aseptic conditions. A mid-sternotomy was performed carefully to avoid injury of parietal pleura. The pericardial sac was exposed and incised. The left ventricular anterior and lateral wall was revealed and a major branch of the left coronary artery was ligated. Success of the ligation was verified by the color change to pale in the affected area of the left ventricular wall. The chest was then closed and the animal allowed to recover. Four weeks after the surgery, the rabbit was used for the imaging and cardiovascular evaluation study.

Imaging and Cardiovascular Evaluation.

PET images and cardiovascular parameters were evaluated in both normal and MI rabbits. Prior to imaging, the rabbit was anesthetized with ketamine (25 mg/Kg, im) and xylazine (5 mg/Kg, im) and the marginal ear vein was catheterized for imaging agent 1 injection. The right femoral artery was isolated and canulated with a Millar catheter (SPC340, Millar Instruments, Houston, Tex.) for arterial pressure measurement. Then the animal was positioned in a microPET camera (Focus220, CTI Molecular Imaging, Inc. Knoxville, Tenn.) for cardiac imaging. The Millar catheter was connected to a computer driven data acquisition system (MP35, BIOPAC Systems, Goleta, Calif.) for recording of mean arterial pressure (MAP), and systolic and diastolic arterial pressure (SAP and DAP). In addition, electrocardiogram (ECG) was also recorded with 3 non-invasive limb leads in lead II configuration using the BIOPAC system. Heart rate (HR) and QT interval were derived from ECG recording. After a stabilization period, cardiovascular parameters: MAP, SBP, DBP and ECG, were recorded 5 minutes before imaging agent 1 intravenous injection (~1.5 mCi) and the recording continued for additional 20 minutes post-injection. The rabbit was imaged for 30 minutes.

Image Reconstruction and Analysis.

After the acquisition, images were reconstructed in a matrix of 256×256 pixels with 95 transverse slices using the OSEM2D algorithm and decay corrected (microPET Manager and ASIPro, CTI Molecular Imaging, Inc. Knoxville, Tenn.). The pixel size was 0.47 mm and the slice thickness was 0.80 mm. The images were reoriented regarding cardiac axis and serial tomographic cardiac image frames were then generated for a 10-minute period from 20 to 30 minutes. Polar map images were then generated from reconstructed cardiac short-axis image using QPS 2008 software (Cedars-Sinai Medical Center, Los Angeles, Calif.).

Radiopharmaceutical Agent.

The chemical structure and radiosynthesis of imaging agent 1 have been described previously (Yu M, Guaraldi M T, Mistry M, Kagan M, McDonald J L, Drew K et al.: a novel PET myocardial perfusion imaging agent. J Nucl Cardiol 2007; 14:789-98; and Purohit A, Radeke H, Azure M, Hanson K, Benetti R, Su F et al. Synthesis and biological evaluation of pyridazinone analogues as potential cardiac positron emission tomography tracers. J Med Chem 2008; 51:2954-70). The radiochemical purity used in this study was 99.1-99.9%, and the specific activity was 3265-7016 Ci/mmol. The agent was prepared in 5% ethanol (v/v) and 50 mg/ml ascorbic acid in water following the clinical protocol.

Data Analysis.

Data are expressed as mean±SD and unpaired student t-test (assuming unequal variances) was used for comparison of baseline values between control and MI rabbits. $p<0.05$ was considered statistically significant. At each timepoint (before and 1-, 5-, 10- and 20-minute after imaging agent 1 injection), MAP, SAP and DAP measured intraarterially averaged every 10-second, and HR and QTc interval derived from ECG recording averaged every 12 heart beats. The QT interval was manually defined by one investigator and QTc was generated from QT corrected by RR interval using Fridericia method ($QTc=QT/RR1/3$).9

Results:

The body weight of control and MI rabbits at the time of study was similar (3.35±0.19 versus 3.06±0.28 kg).

Cardiac Images

Figure 12:
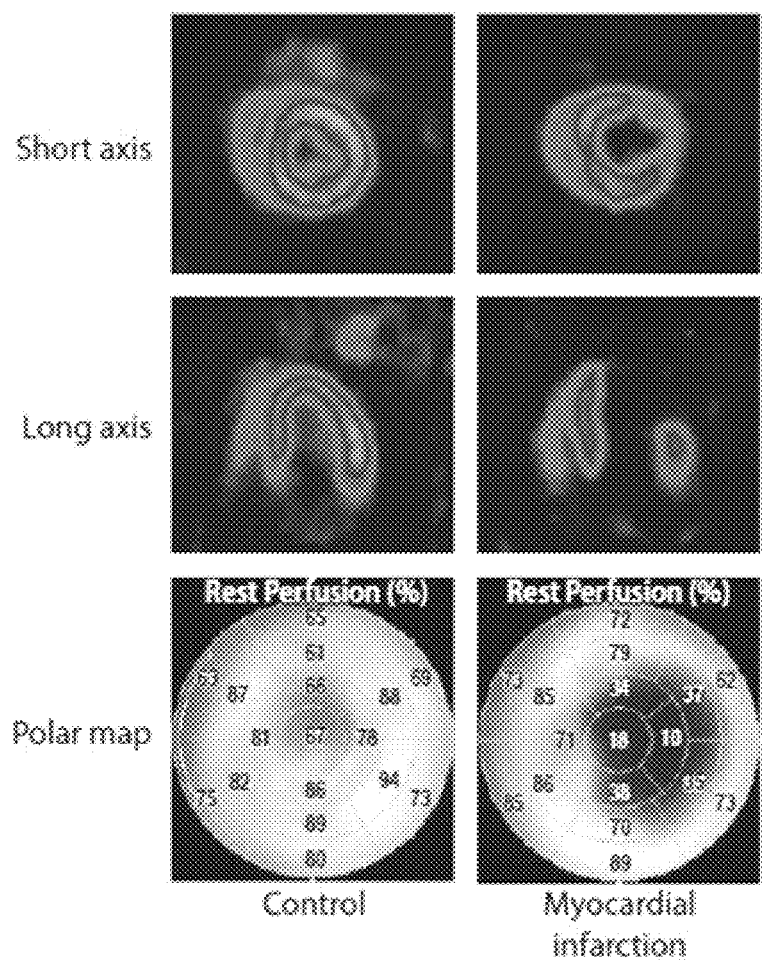
FIG. 12 shows representative cardiac images of imaging agent 1 in control and chronic myocardial infarct (MI) rabbits.

Representative cardiac short-, long-axis and polar map images of control and MI rabbits are shown in FIG. 12. FIG. 12 shows representative cardiac images of imaging agent 1 in control and chronic myocardial infarct (MI) rabbits. These images were acquired at 20-30 min after imaging agent 1 injection and presented in cardiac short- and long-axis views, and polar maps. Defect areas were clearly identified in the MI rabbit. In the control rabbit, the myocardium was clearly visible with uniform distribution of radioactivity and minimal background interference. In the MI rabbit, a perfusion defect area in the left ventricular wall was clearly detected in the cardiac short- and long-axis, and polar map views.

ECG Evaluation.

As shown in Table 12, baseline ECG tracing (before imaging agent 1 injection) recorded in lead II configuration showed a normal waveform with positive QRS complexes and T waves in the control rabbit. In contrast, the QRS complex and T wave were negative with enlarged Q wave in the MI rabbit. The study obtained ECG tracing before, 1-min and 5-min after imaging agent 1 injection in control and myocardial infarct (MI) rabbits. Table 12 shows baseline values of QTc interval (corrected by Fridericia method) and averaged changes from the baseline at 1, 5, 10 and 20 min after imaging agent 1 injection in control and MI rabbits. Similar to control, no changes in ECG wave form and QTc interval were observed after injection in MI rabbits.

TABLE 12

| QTc | | Changes from baseline after injection | | | |
|---|---|---|---|---|---|
| (msec) | Baseline | 1 min | 5 min | 10 min | 20 min |
| Control (n = 3) | 319 ± 17 | 2 ± 15 | −1 ± 11 | 6 ± 20 | 9 ± 15 |
| MI (n = 4) | 288 ± 17 | 8 ± 5 | 4 ± 6 | 4 ± 8 | 3 ± 12 |

However, the baseline values of QTc and HR (Table 12 and Table 13) were comparable in these two groups. Intravenous administration of imaging agent 1 did not alter the ECG waveform, cardiac rhythm, HR and QTc interval from the baseline values at 1-, 5-, 10- and 20-minute post injection in either control or MI rabbits. The study, in part, showed averaged heart rate (HR) tracings of control and myocardial infarct (MI) rabbits 5-min before and 20-min after imaging agent 1 administration. Table 13 shows baseline values of HR and averaged changes from the baseline at 1, 5, 10 and 20 min after the injection in control and MI rabbits. Similar to control, no changes in HR were observed after injection in MI rabbits.

TABLE 13

| Heart rate | | Changes from baseline after injection | | | |
|---|---|---|---|---|---|
| (beat/min) | Baseline | 1 min | 5 min | 10 min | 20 min |
| Control | 159 ± 8 | −4 ± 2 | −2 ± 1 | −2 ± 4 | −4 ± 4 |
| MI | 162 ± 36 | 6 ± 5 | 3 ± 8 | 1 ± 6 | −7 ± 10 |

Arterial Pressure Measurement.

In contrast to HR and QTc, the baseline values of MAP, SAP and DAP (Table 14 and Table 15) were significantly lower in MI rabbits than in control rabbits. In control rabbits, injection of imaging agent 1 did not induce changes in MAP (Table 14), SAP and DAP (Table 15). In agreement with the control animal, no alterations of these parameters were observed in the MI rabbits during and after administration of imaging agent 1. The study, in part, demonstrated averaged mean arterial pressure (AP) tracings of control and myocardial infarct (MI) rabbits 5-min before and 20-min after imaging agent 1 administration. Table 14 shows baseline values of mean AP and averaged changes from the baseline at 1, 5, 10 and 20 min after the injection in control and MI rabbits. Similar to control, no changes in mean AP were observed after injection in MI rabbits. * indicates p<0.05 vs. control. The study, in part, demonstrated averaged systolic and diastolic arterial pressure (AP) tracings of control and myocardial infarct (MI) rabbits 5-min before and 20-min after imaging agent 1 administration. Table 15 shows baseline values of systolic and diastolic AP and averaged changes from the baseline at 1, 5, 10, and 20 min after the injection in control and MI rabbits. Similar to control, no changes in mean AP were observed after injection in MI rabbits. * indicates p<0.05 vs. control.

TABLE 14

| Mean AP | | Changes from baseline after injection | | | |
|---|---|---|---|---|---|
| (mmHg) | Baseline | 1 min | 5 min | 10 min | 20 min |
| Control | 89 ± 11 | 0 ± 0 | −2 ± 0 | −2 ± 3 | −1 ± 6 |
| MI | 61 ± 6* | 2 ± 1 | 2 ± 2 | −1 ± 2 | 2 ± 3 |

TABLE 15

| AP | | Changes from baseline after injection | | | |
|---|---|---|---|---|---|
| (mmHg) | Baseline | 1 min | 5 min | 10 min | 20 min |
| Systolic AP Control | 114 ± 11 | 0 ± 1 | −2 ± 1 | −1 ± 6 | 0 ± 5 |
| MI | 79 ± 11* | 1 ± 2 | 2 ± 2 | 0 ± 1 | 1 ± 7 |
| Diastolic AP Control | 76 ± 10 | 0 ± 1 | −1 ± 2 | 0 ± 5 | 0 ± 5 |
| MI | 53 ± 4* | 1 ± 1 | 2 ± 2 | 1 ± 1 | 2 ± 2 |

Discussion:

The study was designed to study imaging agent 1 as a PET imaging agent for evaluation of myocardial perfusion in diagnosis and prognosis of coronary heart disease. It was evaluated for safety in normal animals and imaged in animal models of acute myocardial ischemia and MI induced by ischemia-reperfusion injury (Yu M, Guaraldi M T, Mistry M, Kagan M, McDonald J L, Drew K et al.: a novel PET myocardial perfusion imaging agent. J Nucl Cardiol 2007; 14:789-98; Nekolla S G, Reder S, Higuchi T, Dzewas G, Poethko T, Preissl A et al. Assessment of Imaging Properties of a New F-18 Labelled Flow Tracer in a Pig Model. J Am Coll Cardiol 2008; 51:A170; and Mistry M, Onthank D, Green J, Cicio S, Casebier D, Robinson S et al. Toxicological Evaluation of BMS-747158, a PET Myocardial Perfusion Imaging Agent. The Toxicologist 2008; 102:476). This study was designed to further assess this agent in a chronic cardiac compromised animal model. The model was created by chronic ligation of coronary artery in rabbits. This rabbit model was chosen based on several characteristics: 1) Similar to humans and compared to other species, rabbits have poor collateral circulation in the heart and develop MI readily after sudden coronary artery occlusion (Bell D R. Special Circulations. In: Rhoades R, Bell D R, editors. *Medical Physiology: Principles for Clinical Medicine.* 3rd ed. 2008. p. 290-304; and Maxwell M P, Hearse D J, Yellon D M. Species variation in the coronary collateral circulation during regional myocardial ischaemia: a critical determinant of the rate of evolution and extent of myocardial infarction. Cardiovasc Res 1987; 21:737-46). 2) Cardiac fibroblasts and regulation of collagen biosynthesis, which are critical in wound healing after myocardial injury, in rabbits are similar to that observed in humans with regard to angiotensin system (Gallagher A M, Bahnson T D, Yu H, Kim N N, Printz M P. Species variability in angiotensin receptor expression by cultured cardiac fibroblasts and the infarcted heart. Am J Physiol 1998; 274:H801-H809). 3) After coronary ligation, plasma and myocardial norepinephrine levels increase (Makino T, Hattori Y, Matsuda N, Onozuka H, Sakuma I, Kitabatake A. Effects of angiotensin-converting enzyme inhibition and angiotensin II type 1 receptor blockade on beta-adrenoceptor signaling in heart failure produced by myocardial Infarction in rabbits: reversal of altered expression of beta-adrenoceptor kinase and G i alpha. J Pharmacol Exp Ther 2003; 304:370-9; and Fujii T, Yamazaki T, Akiyama T, Sano S, Mori H. Extraneuronal enzymatic degradation of myocardial interstitial norepinephrine in the ischemic region. Cardiovasc Res 2004; 64:125-31). Norepinephrine clearance in the heart of rabbit is mainly via neuronal norepinephrine transporter (Gao D W, Stillson C A, O'Connell J W. Absence of MIBG uptake in the denervated rabbit heart. J Nucl Med 1996; 37:106p), similar to in humans (Eisenhofer G, Friberg P, Rundqvist B, Quyyumi A A, Lambert G, Kaye D M et al. Cardiac sympathetic nerve function in congestive heart failure. Circulation 1996; 93:1667-76). 5) Species size is appropriate for high quality PET imaging in a microPET camera while allowing concurrent ECG monitoring. In contrast to ECG waveform in the control rabbit, a negative QRS complex with an enlarged Q wave and inverted T wave were observed in lead II configuration in the MI rabbit, indicating an abnormal ventricular depolarization and repolarization. Following complete obstruction of a coronary artery branch (coronary ligation), oxygen carried to the region is reduced or ceased depending on collateral circulation, leading to cell death and tissue necrosis. A rapid tissue repair process is then started, including initial inflammation followed by angiogenesis, increased fibroblast proliferation and collagen production and deposition. These changes ultimately result in formation of scar tissue to 10 rebuild the necrotic region in the heart (Abbate A, Biondi-Zoccai G G, Van Tassell B W, Baldi A. Cellular preservation therapy in acute myocardial infarction. Am J Physiol Heart Circ Physiol 2009; 296: H563-H565; and Sun Y, Weber K T. Infarct scar: a dynamic tissue. Cardiovasc Res 2000; 46:250-6). Histological examination has indicated that increased fibroblast proliferation and scar formation initiate at about 2 and 18 days respectively post coronary ligation in rabbits (Morales C, Gonzalez G E, Rodriguez M, Bertolasi C A, Gelpi R J. Histopathologic time course of myocardial infarct in rabbit hearts. Cardiovasc Pathol 2002; 11:339-45). In present study, the formation of scar tissue in the left ventricle of our rabbits 4-week post coronary ligation is consistent with the findings of enlarged Q wave in ECG 20 and in other similar studies (Gonzalez G E, Palleiro J, Monroy S, Perez S, Rodriguez M, Masucci A et al. Effects of the early administration of losartan on the functional and morphological aspects of postmyocardial infarction ventricular remodeling in rabbits. Cardiovasc Pathol 2005; 14:88-95; and Connelly C M, Vogel W M, Wiegner A W, Osmers E L, Bing O H, Kloner R A et al. Effects of reperfusion after coronary artery occlusion on post-infarction scar tissue. Circ Res 1985; 57:562-77). Previously, imaging agent 1 has been demonstrated to be capable of detecting regions of acute myocardial ischemia and necrosis induced by coronary ligation and ischemia-reperfusion injury in rats, rabbits and pigs (Yu M, Guaraldi M T, Mistry M, Kagan M, McDonald J L, Drew K et al.: a novel PET myocardial perfusion imaging agent. J Nucl Cardiol 2007; 14:789-981; Nekolla S G, Reder S, Saraste A, Higuchi T, Dzewas G, Preissel A et al. Evaluation of the novel myocardial perfusion positron-emission tomography tracer 18F-BMS-747158-02: comparison to 13N-ammonia and validation with microspheres in a pig model. Circulation 2009; 119:2333-42; and Higuchi T, Nekolla S G, Huisman M M, Reder S, Poethko T, Yu M et al. A new 18F-labeled myocardial PET tracer: myocardial uptake after permanent and transient coronary occlusion in rats. J Nucl Med 2008; 49:1715-22). Imaging in this study in a rabbit model of chronic MI clearly demonstrated that imaging agent 1 imaging can detect chronic MI, possibly scar tissue suggested by ECG and other studies. imaging agent 1 has high affinity to mitochondrial complex I and, at very high concentrations (≥200 µg/kg), induces transit clinical signs, such as rapid and labored breathing, decreased activity, hunched posture, urination, in normal rats and dogs (Mistry M, Onthank D, Green J, Cicio S, Casebier D, Robinson S et al. Toxicological Evaluation of BMS-747158, a PET Myocardial Perfusion Imaging Agent. The Toxicologist 2008; 102:476). However, these signs were not observed when the dose was equal or below 100 µg/kg. In anesthetized naïve dogs, no cardiovascular changes (MAP, HR, left ventricular contractility etc) were observed during and after intravenously injection of imaging agent 1 at doses of equal or less than 10 µg/kg (unpublished data). This represents a large safety margin over the maximal clinical imaging agent 1 dose of 0.07 µg/kg.

In the present study, baseline values of MAP, SAP and DAP were lower in the MI rabbits than in control rabbits, indicating the chronic MI had compromised the cardiovascular system in these rabbits. The dose of imaging agent 1 used for rabbit imaging was in the clinical formulation and approximately 0.5 mCi/kg (~1.5 mCi in a 3-kg rabbit) which is also approximately 3-fold higher than the clinical dose (total rest and stress 11 doses: ~10 mCi in a 60 kg individual). With this dose and in a cardiac compromised condition, no change in arterial pressure, heart rates and ECG waveform were produced. These findings indicate that imaging with imaging agent 1 is safe even in a cardiac compromised condition.

The results show that cardiac PET imaging with imaging agent 1 detects chronic myocardial infarction (fibrosis and scar formation) in addition to myocardial ischemia and necrosis under an acute condition. At imaging dose levels, imaging agent 1 is safe to be used even in cardiac compromised condition, at least in rabbits.

Example 31

The following example describes brain imaging of imaging agent 1 and evaluation of the blood brain barrier permeability in rats. PET imaging in animals and humans indicate this compound crosses the normal blood brain barrier (BBB) and can image CNS disease. Studies to date have not assessed how effectively imaging agent 1 crosses the BBB. The present studies compared brain uptake in rats in the presence and absence of BBB disruption.

Methods:

Male Sprague-Dawley rats were anesthetized with sodium pentobarbital and the left external carotid artery was cannulated close to the internal and external carotid bifurcation. Using saline as control and 25% D-mannitol as hypertonic solution, each were perfused retrogradely in six animals (0.3 mL/kg/sec) for 30 seconds. Two minutes later, ~1 mCi imaging agent 1 was injected via tail vein and the brain was imaged with a microPET camera for 30 minutes. Evans blue (2%, 5 mL/kg) was also injected intravenously and only animals demonstrating clear BBB disruption by Evans blue staining were included in the study. Following completion of imaging, the brain was harvested, photographed and dissected into left and right hemispheres and cerebellum. The tissue content of imaging agent 1 radioactivity was measured by gamma counter and Evans blue levels were determined by fluorescence method for calculation of the % injected dose/gram tissue and µg Evan blue/gram tissue, respectively.

Results:

See Table 16. Infusion of 25% D-mannitol resulted in a marked increase in Evans blue uptake in the left hemisphere (633%) and some increased uptake in the right hemisphere (216%) and cerebellum (186%) compared to saline control. In normal rats and saline infused control rats a high level of imaging agent 1 accumulated in the brain shortly after administration. PET imaging showed this high uptake of imaging agent 1 in saline control rats was only minimally increased in brain region following BBB disruption.

Imaging agent 1 has a high BBB permeability that is only minimally increased following disruption and may be used for brain imaging.

TABLE 16

| Brain uptake | right hemisphere | | left hemisphere | | cerebellum | |
|---|---|---|---|---|---|---|
| | control | BBBD | control | BBBD | control | BBBD |
| Evan blue (µg/g) | 19 ± 2 | 60 ± 8 | 21 ± 2 | 154 ± 13 | 29 ± 4 | 83 ± 12 |
| imaging agent 1 (% ID/g) | 0.72 ± 0.03 | 0.81 ± 0.04 | 0.72 ± 0.03 | 0.93 ± 0.06 | 0.78 ± 0.03 | 0.95 ± 0.05 |

Example 32

The following example is related to $^{18}F$ labeled imaging agent 1 PET myocardial perfusion imaging detecting more severe and extensive stress induced myocardial ischemia than Tc-99m Sestamibi SPECT. In this study, rest-stress Tc-99m Sestamibi SPECT and imaging agent 1 PET MPI were compared for evaluation of stress induced myocardial perfusion abnormalities.

Methods:

Thirteen patients, from a single center, underwent rest-stress Tc-99m Sestamibi SPECT MPI, rest-stress imaging agent 1 PET MPI and coronary angiography. In each patient, 17 myocardial segments were visually scored for rest and stress images by independent observers who were blinded to all other results. For each patient, summed stress scores (SSS), summed rest scores (SRS), and summed difference scores (SDS) were determined from segmental scores. Percent narrowing in each coronary artery was evaluated blindly and 70% luminal diameter narrowing was considered significant.

Results:

There were 15 diseased coronary arteries; 7 left anterior descending, 5 left circumflex and 3 right coronary arteries. In myocardial segments that were supplied by diseased coronary arteries, SSS and SDS were significantly higher by PET than SPECT (Table 17).

These data showed that as compared to Sestamibi SPECT, rest-stress $^{18}F$ labeled imaging agent 1 PET MPI demonstrated more severe and extensive stress induced perfusion abnormalities in myocardial regions that are supplied by diseased coronary arteries.

TABLE 17

|  | imaging agent 1 PET | Tc-99m Sestamibi SPECT | P Value |
|---|---|---|---|
| SSS | 16.1 ± 7.8 | 8.6 ± 5.8 | <0.001 |
| SDS | 12.3 ± 7 | 5.4 ± 4.2 | <0.05 |
| SRS | 3.8 ± 6.6 | 3.1 ± 3.3 | NS |

Example 33

The following example describes a comparison of myocardial stress perfusion defect assessment using $^{99m}Tc$ sestamibi SPECT versus imaging agent 1 PET. Myocardial uptake of imaging agent 1 exhibits a stronger relationship with myocardial blood flow across the range of achievable flow than $^{99m}Tc$ sestamibi. The assessment of myocardial perfusion defects by imaging agent 1 PET and $^{99m}Tc$ sestamibi SPECT were compared.

Methods and Results:

Twenty six patients (20 men) underwent SPECT and PET within 6-months. PET was performed with imaging agent 1 at rest (2.3-3.9 mCi) followed 60 min (n=18) or 24 h (n=8) later with exercise (n=16) or adenosine (n=10) stress (7.3-8.6 mCi). Image quality of SPECT and PET was consensually assessed by 2 independent blinded readers and graded as excellent, good, or fair. Stress and rest perfusion defects on SPECT and PET were assessed by the same readers by computer-assisted visual interpretation, using the standard 17 segment, 5 point-scoring model (0=normal; 4=absent uptake). The extent and severity of ischemia (summed difference score (SDS)) was derived from the difference between summed stress (SSS) and summed rest scores (SRS). Image quality with PET was excellent in 24 and good in 2 patients. In contrast, there were 7 excellent, 18 good, and 1 fair quality study, p<0.001 by SPECT. In 14 patients with abnormal SPECT (SSS≥4), mean SDS was greater with PET than with SPECT (9.6±1.8 vs. 5.4±0.7, p=0.02). In all 12 patients with normal SPECT (SSS<4), SDS was zero by PET and SPECT.

Compared to $^{99m}Tc$ sestamibi SPECT, imaging agent 1 PET provides better image quality and results in a significant increase in the SDS in patients with abnormal SPECT. These results showed that PET imaging with imaging agent 1 provided better assessment of the magnitude of myocardial ischemia than SPECT.

Example 34

The following describes cardiac phantom simulation of dose injection parameters for one-day rest/stress myocardial perfusion (MP1) PET imaging with imaging agent 1 tracer. A 1-day rest/stress (RS) protocol for MPI with imaging agent 1 can create cross contamination (CC) in the stress image. A phantom simulation was conducted to assess the impact of CC on image characteristics for a range of conditions.

Methods:

A F18 phantom with myocardium (M)=0.21 uCi/ml and liver (L)=0.22, simulating normal rest, was scanned on a Siemens Biograph-64 PET/CT for 30 min. It was washed and refilled with L=0.42, torso=0.09 and M=0.9 with a 40% defect in septal wall, then scanned for another 30 min. SUV from 12 patients in a Phase II trial was used to assure realistic simulation. Registered RS images were blended to simulate CC for combinations of dose ratio (DR=1-5) and wait time (WT=30-120 min) between RS injections using blending coefficients determined by M-SUV, DR, rest dose decay and WT. Each blended image set was measured for defect contrast (DC) using $(SUV_n-SUV_d)/SUV_n$, defect volume (DV) using pixel values $\geq(SUV_n+SUV_d)/2$ in defect, and wall uniformity (WU) using (SD/mean) in normal wall. Degradation ≤10% for DC, DV and WU was applied to determine the minimal WT for DR.

Results:

WU (<7.6%) and DV (<2%) for any type of stress were not significantly affected by any combination. DC degradation was reduced to the acceptable range by increasing DR, WT or both.

Example 35

The following describes high definition cardiac perfusion PET using a new $^{18}F$ imaging agent, imaging agent 1. HD˙PET technology improves spatial resolution and signal-to-noise on reconstructed PET images (IEEE TMI 2006:25: 7:907-921) but the thermal path of the positron emitted by rubidium limits its benefits in $^{82}Rb$ perfusion images. To evaluate its full potential for high-resolution cardiac imaging, HD˙PET with myocardial perfusion images obtained with a new $^{18}F$ based agent (imaging agent 1) was evaluated.

Methods:

Images of 15 subjects in a study of imaging agent 1 perfusion agent were acquired on a 4-ring Siemens Biograph-64. Static and 8-bin ECG-gated images were generated using standard reconstruction (SR—2D Attenuation Weighted Ordered Subsets Expectation Maximization) and HD˙PET. The wall/cavity contrast and contrast-to-noise ratio (CNR), and maximum to defect contrast were computed. Wall thickness at three different levels of heart (basal, mid, apical), wall motion, wall thickening and ejection fraction (EF) were also estimated with automatic quantification.

Results:

HD*PET showed significant contrast change compared to SR (+32.3±17.9%, p<0.05). CNR also was improved with HD*PET (+26.7±22.3% vs. SR, p<0.05). The average contrast between the maximum in the myocardium and the 22 defects in the 15 patients was increased with HD*PET (4.0±1.7) compared to SR (3.2±1.2, p<0.05). The average wall thickness was 16:3±2.9 mm, 16.7±2.9 min and 15.6±2.2 min (basal, mid, apical) with SR compared with 14.7±2.8 mm, 14.1±3.0 min and 13.0±1.7 mm with HD*PET (p<0.05). EF, wall motion and wall thickening did not show any Significant differences with HD*PET.

Conclusion:

Perfusion studies with imaging agent 1 show significantly improved image resolution, contrast and contrast-to-noise with HD*PET reconstruction as compared with the standard reconstruction technique.

Example 36

Using tracer kinetic modeling with imaging agent 1 PET, absolute quantification of myocardial blood flow (MBF) was shown to be feasible even at high flow rates. The study examined whether retention and SUV calculations were also suitable for the assessment of coronary flow reserve (CFR) in a pig model.

Methods:

Nine pigs were subjected to dynamic PET imaging of 100-200 MBq imaging agent 1 at rest and stress. MBF was evaluated using both imaging agent 1 PET 3-compartmental modeling and the co-injected microspheres. Retention was calculated as uptake between 5-10 and 10-20 min divided by the integral under the input function. Standard SUV calculation for the same time points was also used.

Results:

MBF ranged from 0.5-2.8 mL/min/g. Both retention and SUV showed good correlation with both imaging agent 1 and microsphere MBF (5-10 min: r=0.69, p<0.05 and 0.69, p<0.05 for retention, r=0.86, p<0.001 and 0.88, p<0.001 for SUV). Linear regression analysis revealed good results only for the earlier interval (y=8.27x+1.45 and 7.11x+3.63 for retention, 1.11x+0.01 and 0.99x+0.26 for SUV), but at later interval an underestimation was found. Calculation of stress/rest ratio for retention and SUV allows assessment of CFR. The agreement between retention and SUV derived CFR and both imaging agent 1 and microspheres CFR, yielded modest mean differences in the early interval (0.1 and −0.05, for retention, 0.05 and −0.09 for SUV) and larger deviations in the late interval (−0.47 and −0.62 for retention, −0.4 and −0.54 for SUV).

Using imaging agent 1, a simplified kinetic analysis model for the assessment of MBF index and CFR was feasible. Furthermore, SUV derived values were suitable for tracer injection outside the imaging device and allowed for a physical stress test. These results provided a basis for a simplified quantitative approach in the routine clinical setting.

Example 37

The following example describes the synthesis of imaging agent precursor 1, according to the scheme shown in FIG. 3.

Example 37A

Synthesis of 2-(t-butyl)-4,5-dichloropyridazin-3 (2H)-one (Compound 11)

Solid t-butyl hydrazine hydrochloride (1 equiv) was added to a stirred solution of sodium hydroxide (0.95 equiv) dissolved in 10% water/toluene mixture (6 vol) at ambient temperature. The resulting white suspension was cooled slightly while mucochloric acid (1 equiv) was slowly added. After completion of the addition, the reaction mixture was stirred at ambient temperature for 20-30 minutes followed by dropwise addition of acetic acid (0.95 equiv). The reaction mixture was heated to 45-50° C. and stirred for 18 h, until starting material was consumed, as measured by HPLC. The reaction solution was allowed to cool to ambient temperature and then was diluted with water (~7 vol) and the organic layer separated. The organic layer was cooled to 0° C. and washed with 30% NaOH (3.6 vol), followed by 35% HCl (3.6 vol) and water (2×3.6 vol). The organic solution was concentrated under vacuum and restripped with methanol (1.5 vol) to yield compound 11 as a brown solid that was dried under vacuum at 35° C. (65-75% yield, 100% purity by HPLC).

Example 37B

Synthesis of 2-(t-butyl)-4-chloro-5-((4-(hydroxymethyl)benzyl)oxy)pyridazin-3(2H)-one (Compound 13)

A solution of compound 11 (222 g) in dry dimethylformamide (780 mL) was slowly added to a stirred mixture of 1,4-phenylenedimethanol (compound 2, 690 g) and cesium carbonate (1.3 kg) in dry dimethylformamide (2.22 L) heated to 65° C. The resultant mixture was stirred at 65° C. for an additional 4 h, when the reaction was cooled and filtered. The filtrate was diluted with 5% brine and extracted with toluene. The combined toluene extracts were washed twice with 5% brine and the organics concentrated under reduced pressure. The resulting crude was crystallized from hot methanol/water mixture, filtered, washed with methanol/water and dried under vacuum at 40-45° C. to afford compound 3 (224 g) as an off-white powder in 69% yield, contaminated with 6% of the product of dialkylation of compound 12 with compound 11.

Example 37C

Synthesis of 5-((4-(bromomethyl)benzyl)oxy)-2-(t-butyl)-4-chloropyridazin-3(2H)-one (Compound 14)

A dry vessel was charged with anhydrous dichloromethane (670 mL) and compound 13 (224 g). A 1.0M solution of phosphorous tribromide in dichloromethane (345 mL) was added to the mixture over 30 min at 25° C. and the solution stirred for another 30 min. The reaction was diluted with dichloromethane (450 mL) and water (670 mL), the layers separated, and the aqueous phase extracted with dichloromethane (670 mL). The combined organic layers were washed twice with 5% brine, concentrated under vacuum, and dried for 34 h under vacuum at 40° C. to yield compound 14 as an off-white solid (258 g, 96% yield).

Example 37D

Synthesis of 2-(t-butyl)-4-chloro-5-((4-((2-hydroxyethoxy)methyl)benzyl)oxy) pyridazin-3(2H)-one (Compound 15)

Ethylene glycol (2.9 L) was charged into a dry vessel and treated with solid potassium t-butoxide (74 g). The suspension was heated to 60° C. to form a solution and then cooled to 20-25° C. A solution of compound 14 (290 g) in dry THF (1.45 L) was added in one portion to the stirring ethylene glycoxide solution. The resultant mixture was heated to 60° C. and stirred at this temperature for 16.5 h when it was then cooled to 25° C. and diluted with water (2.9 L) and toluene (4.35 L). The organic layer was separated, washed three times with water and concentrated under vacuum. Another charge of toluene (4.35 L) was added and concentrated under vacuum again to afford crude compound 15 as a brown viscous oil (260 g, 95% yield)

Crude compound 15 (690 g) was dissolved in dichloromethane (0.5 kg/L) and purified by chromatography (silica column, 1:1 heptane/ethyl acetate, flow rate=6 L/min, 10 L fractions). The combined fractions were combined and concentrated under vacuum to afford compound 15 as a clear, viscous oil (520 g, 70% yield).

Example 37D-1

The following example describes the synthesis of compound 15, using an alternate synthetic method relative to Example 37D. Into a clean, dry reactor equipped with overhead stirrer and temperature probe was charged anhydrous ethylene glycol (2900 mL), followed by potassium t-butoxide (42.2 g) at ambient temperature. The solution was heated to 55 to 60° C. to form a clear solution of the ethylene glycoxide and then cooled to 20° C. to 30° C. under an inert atmosphere. This solution was assayed for total base content. A separate vessel was charged with anhydrous tetrahydrofuran (725 mL) and compound 14 (145 g) with stirring to form a solution at ambient temperature. This solution was added in a single portion directly to the ethylene glycoxide solution at 20 to 30° C. The mixture was heated to 60° C. and stirred at this temperature. When the reaction was complete, it was cooled to 20° C. and toluene (2200 mL) and water (2200 mL) were added with stirring to form two layers when allowed to settle. The layers were separated and the organic layer washed with 2200 mL each of sodium bicarbonate solution and water (twice). The organic layer was concentrated at ≤50° C. under vacuum to give compound 15 as a viscous oil (133.4 g, 91% when corrected for residual toluene).

Example 37E

Synthesis of Constrast Agent Precursor 1

A dry reactor was charged sequentially with dichloromethane (6.6 L), compound 15 (510 g) dissolved in dichloromethane (1.1 L), triethylamine (0.25 L), p-toluenesulfonyl chloride (305 g), and dimethylaminopyridine (7 g). The solution was stirred at ambient temperature for 28 h when it was washed with 1.0 M HCl (2×10 L), water (10 L), 5% sodium bicarbonate (2×10 L), and water (10 L). The organic solution was filtered and dichloromethane removed under reduced pressure to afford imaging agent precursor 1 as a thick oil.

Crude imaging agent precursor 1 (21.5 g) was added to cumene (125 mL) and heated to 60° C. to dissolve the solids. It was cooled to 40° C. and 1% w/w imaging agent precursor 1 crystals added to seed the crystallization. The solution was held for 3 h at 35° C. to allow crystallization, and then cooled to ambient temperature and stirred for 6 h to complete crystallization. The solids were filtered, dried briefly under vacuum, and then added to isobutyl acetate (125 mL). After heating to 70° C., the solids dissolved, and the solution was then cooled to 40-50° C. and seeded with 1% w/w imaging agent precursor 1. After holding at 40-50° C. for five hours, the slurry was cooled to ambient temperature over 2 hours and held for 12 h. The resulting solids were filtered, rinsed with cold isobutyl acetate, and dried under vacuum to afford 12.8 g of imaging agent precursor 1 (60% from compound 15).

In some cases, the triethylamine stoichiometry was increased from about 1.15 to about 1.40 equiv. In some cases, the p-toluenesulfonyl chloride stoichiometry was increased from about 1.15 to about 1.20 equiv. In some cases, the dimethylaminopyridine stoichiometry was increased from about 0.04 to about 0.10 equiv.

In some embodiments, the cumene crystallization was completed under the following conditions: Dilution: 10.0 volumes; Seeding temperature: 45° C.; Crystallization hold time at seeding temperature: 3 h; Cooling rate: 5° C./h; Granulation temperature: 20° C.; Granulation time: >3 h; Filtration temperature: 20° C.

In other embodiments, the cumene crystallization was completed under the following conditions: Dilution: 6.5 volumes; Seeding temperature: 50° C.; Crystallization hold time at seeding temperature: 6 h; Cooling rate: 10° C./h; Granulation temperature: 10° C.; Granulation time: >8 h; Filtration temperature: 10° C.

In a certain embodiment, compound 16 (20.0 g) was suspended in cumene (6.5 volumes) then warmed to 68° C. The resulting solution was cooled to 50° C. then seeded with compound 16; slow formation of a precipitate was observed. The resulting suspension was held at 50° C. for 6 h then cooled at 10° C./h to 10° C., maintained 12 h, filtered and washed. Following in vacuo drying at 60° C., 16.4 g of compound 6 was obtained (82% recovery; 96% solvent and purity adjusted).

In some embodiments, the isobutyl actetate crystallization was conducted under the following conditions: Dilution: 8 volumes; Seeding temperature: 50° C.; Crystallization hold time at seeding temperature: 3 h; Cooling rate: 5° C. per hour; Granulation temperature: 20° C.; Granulation time: >10 h; Filtration temperature: 20° C.

In other embodiments, the isobutyl actetate crystallization was conducted under the following conditions: Dilution: 5 volumes; Seeding temperature: 48° C.; Crystallization hold time at seeding temperature: 10 h; Cooling rate: 2.5° C./h; Granulation time: 0 h; Filtration temperature: 10° C.

In a certain embodiment, cumene crystallized compound 16 (15.40 g) was suspended in isobutyl actetate (5 volumes) then warmed to 68° C. The resulting solution was cooled to 48° C. then seeded with BMS-747155-01 (0.1% w/w); immediate formation of a precipitate was observed. The resulting suspension was held at 48° C. for 10 h then cooled at 2.5° C./h to 10° C., filtered and washed. Following in vacuo drying at 60° C., 13.10 g of compound 16 was obtained (85% recovery) which passed all specifications.

Example 38

The following example describes an alternate route to synthesizing 2-(t-butyl)-4-chloro-5-((4-(hydroxymethyl) benzyl)oxy) pyridazin-3(2H)-one (compound 13), as shown in FIG. 4.

Example 38A

Synthesis of 2-(t-butyl)-4-chloro-5-hydroxy-pyridazin-3(2H)-one (Compound 17)

A dry vessel was sequentially charged while stirring with compound 11 (100 g), potassium hydroxide (76.1 g), and ethylene glycol (1 L). The resulting suspension was heated to 115° C. and stirred at this temperature for 5 hrs. The brown solution was cooled to 0° C. and 1 M hydrochloric acid solution (1 L) added slowly with stirring over 60 minutes, keeping the temperature below 25° C. during the addition, resulting in precipitation of a light brown solid. The slurry was stirred for 2 hrs and filtered, washing the cake with cold water (4×500 mL) and ethanol (100 mL). The Crude compound 17 thus obtained was then recrystallized from hot ethanol (1 L), filtered, and dried under vacuum for 34 h at 45° C. to yield pure compound 17 (68.3 g, 75% yield).

Example 38B

Synthesis of methyl 4-(((1-(t-butyl)-5-chloro-6-oxo-1,6-dihydropyridazin-4-yl)oxy)methyl)benzoate (Compound 18)

A dry vessel under nitrogen atmosphere was charged sequentially with compound 17 (66 g), dimethylformamide (660 mL) and potassium carbonate (45 g). To this was added methyl 4-(bromomethyl)benzoate (78 g) and the resulting suspension stirred for 18 h at 20° C. Water (700 mL) was added over 30 minutes to precipitate the product and dissolve remaining salts. The slurry was stirred for 1.5 h and the resulting solids filtered, washed with water (4×300 mL) and cyclohexane (2×150 mL) and dried under vacuum at 45° C. to afford compound 18 (112.8 g, 99%) as a white powder.

Example 38C

Alternate synthesis of 2-(t-butyl)-4-chloro-5-((4-(hydroxymethyl)benzyl)oxy) pyridazin-3(2H)-one (Compound 13)

A dry vessel with overhead agitation under an atmosphere of dry nitrogen was charged sequentially with 2-methyltetrahydrofuran (500 mL) and compound 18 (50 g) at ambient temperature. The resulting suspension was cooled to −7° C. and a solution of diisobutylaluminum hydride in toluene (1.5M, 119 mL) added drop-wise over 1 h keeping the temperature below 3° C. After stirring for 1.5 h at −5° C. -0° C., the reaction was quenched by addition of propan-2-ol (50 mL) at a rate to keep the temperature below 4° C. The quenched reaction mixture was then added dropwise to a solution of hydrochloric acid (2M, 500 mL) over 75 min, keeping the temperature below 7° C. The biphasic solution was warmed to 22° C. and the layers separated. The organic layer was then washed with 500 mL each of 2M hydrochloric acid, saturated sodium bicarbonate solution and water and then concentrated under reduced pressure to afford crude compound 13 as an off-white solid (42.4 g). This was recrystallized from hot isopropyl acetate (200 mL), seeding the solution at 65° C. and holding at this temperature for one h, followed by cooling to 0° C. over 4 h. The resulting white solid was filtered and dried under vacuum at 45° C. to afford compound 13 (35 g, 76% yield).

In some cases, the above experiment was performed with both lithium aluminum hydride and sodium bis(2-methoxyethyoxy)aluminum hydride (Red Al) as well as diisobutylaluminum hydride (DIBAL-H). In some cases, solutions of DIBAL-H in dichloromethane, toluene, and hexane were employed. In some cases, selection of 2-MeTHF (vs. THF) as co-solvent was performed due to its reduced aqueous solubility. In some cases, stress studies revealed the DIBAL reduction performed well, in particular, at temperatures between −15 to +10° C. In some cases, the DIBAL-H was charged in two portions; 2.20 equiv followed by additional reagent if incomplete reaction was observed. In some cases, residual water was found to have hydrolyzed DIBAL-H and the impurity profile remained unchanged.

In some embodiments, the reaction was conducted under the following conditions: −15 to +10° C.; up to ~2.35 equiv DIBAL-H; up to 5% $H_2O$ (w/w) in precursor; <0.75% precursor remaining at full conversion.

Example 39

The following example described an alternate synthetic route to 2-(t-butyl)-4-chloro-5-((4-((2-hydroxyethoxy)methyl) benzyl)oxy) pyridazin-3(2H)-one (Compound 15), as shown in FIG. 5.

Example 39A

Preparation of methyl 4-(1,3-dioxolan-2-yl)benzoate (compound 19)

Methyl 4-formylbenzoate (3.28 g, 20.0 mmol) was suspended in ethylene glycol (4.46 mL, 80.0 mmol), then successively treated with triethyl orthoformate (3.66 mL, 22.0 mmol) and $Me_3NPhBr_3$ (376 mg, 1.00 mmol) at 22° C.; within 5 min, all solids dissolved. The resulting orange solution was stirred 0.5 h, then diluted with saturated aqueous $NaHCO_3$(50 mL), transferred to separatory funnel and washed with EtOAc (3×50 mL). The combined EtOAc washes were dried over $MgSO_4$, filtered and concentrated in vacuo to a colorless oil ($R_f$ 0.4 in 4:1 pentane/EtOAc, $KMnO_4$). This material was used without further purification in the subsequent reduction step.

Example 39B

Preparation of (4-(1,3-dioxolan-2-yl)phenyl)methanol (Compound 20)

The crude acetal (20.0 mmol theoretical) was dissolved in dry THF (100.0 mL), cooled to 0° C. and treated with $LiAlH_4$ (20.00 mmol; 20.00 mL of a 1.0 M solution in THF) at a rate of 1.0 mL/min using a syringe pump. Upon completion of the addition, excess $LiAlH_4$ was consumed by the careful addition of $H_2O$ (800 µL). CAUTION: vigorous gas evolution! The resulting white suspension was successively treated with 15% aqueous NaOH (800 µL) and $H_2O$ (2.40 mL), then stirred 0.5 h to a fine white slurry. The solids were removed by filtration through a pad of Celite then exhaustively washed with Et$_2$O. The combined filtrates were concentrated in vacuo to a colorless oil and purified by chromatography on silica (50×175 mm) using 1:1 pentane/ EtOAc. The main product peak eluting 470-790 mL was collected, pooled and concentrated in vacuo to a colorless oil, which solidified in the freezer (2.46 g, 13.7 mmol; 68.3% over two steps).

Example 39C

Synthesis of (4-(1,3-dioxolan-2-yl)phenyl)methanol (Compound 20)

Methyl 4-formylbenzoate (4.92 g, 30.0 mmol) was dissolved in dry toluene (50.0 mL), successively treated with ethylene glycol (1.84 mL, 33.0 mmol) and p-TsOH.H$_2$O (57.1 mg, 0.30 mmol), then heated to reflux under Dean-Stark conditions; acetal formation was complete within 1 h. The solution was then cooled to 22° C. and treated with sodium bis(2-methoxyethoxy)aluminum hydride (45.0 mmol; 12.7 mL of a 70.3 wt. % solution in toluene) at a rate of 0.5 mL/min using a syringe pump. CAUTION: vigorous gas evolution! Upon completion of the addition, the resulting solution was further cooled to 0° C., carefully treated with a saturated aqueous solution of K,Na-tartrate (100 ml), then vigorously stirred 1 h; steady formation of a clear solution was observed. The resulting biphase was then diluted with EtOAc (50 mL), with transfer to a conical funnel, and the layers separated. The aqueous layer was then washed with EtOAc (3×50 mL) and the combined EtOAc and toluene solutions dried over MgSO$_4$, filtered and concentrated in vacuo to a colorless oil. The crude product was then purified by chromatography on silica (50×135 mm) using 1:1 pentane/EtOAc. The main product peak eluting 425-725 mL was collected, pooled and concentrated in vacuo to a colorless oil, which solidified in the freezer (4.50 g, 83.2% over two steps).

Example 39D

Synthesis of 2-(t-butyl)-4-chloro-5-[(4-(1,3-dioxolan-2-yl)phenyl)methoxy]-2-hydropyridazin-3-one (Compound 21)

A solution of 2-(t-butyl)-4,5-dichloro-2-hydropyridazin-3-one (829 mg, 3.75 mmol) and the compound 10 (451 mg, 2.50 mmol) in dry DMF (12.5 mL) was treated with Cs$_2$CO$_3$ (1.63 g, 5.00 mmol) in one portion at 22° C. The resulting suspension was then immersed in a pre-heated oil bath (65° C.) and maintained 6 h with vigorous stirring. After cooling to ambient temperature, the suspension was partitioned between EtOAc and H$_2$O (50 mL each), with transfer to a conical funnel, and the layers separated. The remaining aqueous layer was washed with additional EtOAc (3×50 mL) then discarded. The combined EtOAc solutions were further washed with saturated aqueous NaCl (5×50 mL), then dried over MgSO$_4$, filtered and concentrated in vacuo to an off-white solid. In some cases, trituration with several small volumes of pentane was performed to generate the solid. The crude product was then recrystallized from hot EtOAc/hexanes to afford colorless needles that were collected on a scintered glass funnel of medium porosity, exhaustively washed with pentane and dried in vacuo (573 mg, 62.8%).

Example 39E

Synthesis of 2-(t-butyl)-4-chloro-5-[(4-(1,3-dioxolan-2-yl)phenyl)methoxy]-2-hydropyridazin-3-one (Compound 21)

To a vessel charged with (4-(1,3-dioxolan-2-yl)phenyl) methanol (20 g, 110 mmol), benzyltriethylammonium chloride (2.27 g, 10 mmol), toluene (100 mL) and sodium hydroxide (50% in water, 22 mL, 420 mmol) was added a solution of 2-(t-butyl)-4,5-dichloro-2-hydropyridazin-3-one (22.1 g, 100 mmol) in toluene (100 mL) over 5 min. A gradual and accelerating exotherm occurred with the final internal temperature reaching 39° C. After 2.5 h stirring was halted and MTBE (50 mL) and water (100 mL) added. The phases were split and the organic layer was washed with water (100 mL) and brine (100 mL). The organic extracts were dried (MgSO$_4$), filtered, and concentrated under vacuum to afford a tan solid (39 g). The solids were slurried in toluene/heptane (430 mL, 1:1) at 40° C. for 2 h, cooled to ambient temperature, filtered and dried under vacuum at 40° C. for 24 h (29.7 g, 69%).

Example 39F

Synthesis of 2-(t-butyl)-4-chloro-5-({4-[(2-hydroxyethoxy)methyl]phenyl}methoxy)-2-hydropyridazin-3-one (Compound 15)

A solution of compound 21 (365 mg, 1.00 mmol) in dry CH$_2$Cl$_2$ (10.0 mL) was cooled to −40° C. using a dry ice/MeCN bath, then treated with DIBAL-H (4.00 mmol; 4.00 mL of a 1.0 M solution in CH$_2$Cl$_2$) at a rate of 0.25 mL/min using a syringe pump. The solution was maintained 1 h with periodic addition of dry ice to the cooling bath, then carefully treated with wet MeOH (1 mL) and warmed to 22° C. The resulting solution was diluted with EtOAc (20 mL), treated with an equal volume of saturated aqueous K,Na-tartrate, then vigorously stirred 1 h; steady formation of a clear solution should be observed. The resulting biphase was further diluted with H$_2$O (50 mL), with transfer to a conical funnel, and the layers separated. The aqueous layer was then washed with EtOAc (3×50 mL) and discarded. The combined EtOAc washes were dried over MgSO$_4$, filtered and concentrated in vacuo to a colorless oil (R$_f$ 0.2 in 1:1 pentane/EtOAc, KMnO$_4$). The crude product was purified by chromatography on silica (30×190 mm) using a step gradient from 1:1 pentane/EtOAc (250 mL) to 3:2 pentane/ EtOAc (500 mL). The main product eluting between 415-580 mL was collected, pooled and concentrated in vacuo to a colorless oil (286 mg, 0.780 mmol; 78.0%).

Example 40

Synthesis of 2-((4-(((1-(t-butyl)-5-chloro-6-oxo-1,6-dihydropyridazin-4-yl)oxy)methyl)benzyl)oxy)ethyl 4-methylbenzenesulfonate (Imaging Agent Precursor 1)

A dry reactor was charged sequentially with dichloromethane (6.6 L), compound 15 (510 g) dissolved in dichloromethane (1.1 L), triethylamine (0.25 L), p-toluenesulfonyl chloride (305 g), and dimethylaminopyridine (7 g). The solution was stirred at ambient temperature for 28 h when it was washed with 1.0M HCl (2×10 L), water (10 L), 5% sodium bicarbonate (2×10 L), and water (10 L). The organic solution was filtered and dichloromethane exchanged for ethyl acetate. The product was crystallized from hot 1:1 heptane/ethyl acetate (~11 L). by slowly cooling to 0-5° C. The resulting solids were filtered, washed with cold ethyl acetate/heptane and dried under vacuum at 40° C. for 42 h to yield imaging agent precursor 1 (555 g, 77% yield).

Example 41

The following describes remote camera qualification (RCQ) of PET and PET/CT scanners for imaging agent 1 myocardial perfusion using a standardized phantom procedure.

As will be known to those of ordinary skill in the art, in a medical imaging clinical trial, camera qualification is a critical step in assessing whether individual clinical site (CS) possesses the capability to execute the protocol. In some cases, a challenge lies in how to standardize a task-specific phantom and the associated qualification procedure that can effectively determine if specific site scanners meet the study requirement to join the trial.

Methods.

Using various cameras, the RCQ procedure with an imaging manual customized for each scanner model utilized step-by-step instruction for CS to follow. A low-cost, standardized phantom using a 2 liter soda bottle with an acrylic rod (L=21 cm, D=2 cm) sealed inside the cap was provided to each CS (see Example 42 for more details). CS injected 3-4 mCi F18 solution to the water-filled phantom to acquire image data and to test existing cardiac misregistration (MR) correction software in each system. The RCQ procedure was performed by the CS with telephone support as necessary. All image data was sent to the imaging core laboratory to analyze in terms of quantitative imaging parameters. Minimum performance criteria were established to identify cameras whose performance was inconsistent with accepted norms. The results are shown in Table 18.

TABLE 18

| | Consistency of Dynamic Acq. | Consistency of Gated Acq. | Noise Variation of Gated Acq. | Image Contrast | Spatial Resolution (mm) | Image Uniformity | Accuracy of Calibration Factor |
|---|---|---|---|---|---|---|---|
| Dedicated PET (no MR) | 93.36% ± 2.72% | 98.25% ± 1.88% | 19.94% ± 6.18% | 0.91 ± 0.04 | 8.36 ± 1.40 | 2.58% ± 0.86% | 64.62% ± 20.00% |
| PET/CT (no MR) | 93.57% ± 3.96% | 98.24% ± 0.66% | 14.30% ± 5.41% | 0.97 ± 0.03 | 6.77 ± 1.20 | 2.58% ± 0.46% | 93.66% ± 3.84% |
| PET/CT (MR correction) | 93.70% ± 3.60% | 98.05% ± 0.91% | 16.02% ± 4.44% | 0.95 ± 0.03 | 7.42 ± 0.75 | 3.18% ± 0.56% | 94.37% ± 2.87% |
| Minimal requirement | >85% | >85% | <25% | >0.9 | <10 mm | <5% | >90% |

Conclusions.

Remote camera qualification when integrated with a standardized phantom, comprehensive imaging manuals, full technical support and centralized data analysis can be a cost-effective and efficient method to assess the performance of PET and PET/CT scanners in a large clinical trial.

Example 42

The following example describes a low cost refillable phantom for standardization of PET Scanners Standardization and harmonization of imaging methodology and scanner performance is critical to the success of clinical studies using PET (e.g., as described in Example 41). Generally, this may be accomplished with a test object called a phantom that is loaded with an appropriate quantity of radioactive material and imaged in the same way with each scanner. Phantoms may be constructed either of solid materials with long-lived positron-emitters embedded or they may be filled with water and short-lived radioactivity added as needed. Differences in observed imaging performance allow adjustment of methods or repair of equipment as necessary to assure uniformity of image quality among all systems used. Conventional phantoms, both solid and refillable are sufficiently expensive that the cost of simultaneous assessment at a large number of sites is prohibitive. The device described in this example is a simple task-specific phantom for cardiac PET using readily available materials that can be constructed for approximately 1% the price of a conventional refillable phantom. When combined with routine quality control, it allows the simultaneous characterization of a large number of PET and PET-CT systems for standardization in PET cardiac clinical trials.

Materials and Methods.

The phantom was constructed from a standard 2-liter soda bottle. A rod of acrylic plastic 8¼ inches long and ¾ inches in diameter was centered and fixed to the inside of the cap of the bottle using an external screw. The surface between the end of the rod and the inside of the cap and under the screw head was sealed with glue appropriate to the materials prior to final tightening of the screw and the phantom tested for leakage.

The phantom was filled in the following way:
1. The phantom was placed on an absorbent surface or, preferably, in a sink and filled the phantom with tap water to the top. Bubbles were minimized using a slow rate of water flow into the bottle.
2. The acrylic rod (attached to the cap) was inserted into the soda bottle fully and the cap screwed in place. The entire overflow was allowed to be removed from the phantom. It was important not to squeeze the phantom while doing this. The cap was unscrewed and the rod slowly removed to allow any water clinging to it to drain back into the phantom.
3. A clean syringe was used to draw 2 ml of water from the phantom. Approximately 10 drops of liquid soap was added into the phantom to prevent FDG or other F18 compounds from sticking to the inner surface of bottle or the rod. The phantom was shaken by tilting it up and down vertically for at least 30 sec to ensure uniform distribution of liquid soap.
4. $^{18}$F activity (3-4 mCi) and the volume (several ml) in a syringe was measured and then recorded, including volume and assay time.
5. $^{18}$F was injected into the phantom slowly and the syringe drawn back and forth to flush the remaining activity from the syringe vigorously three times.
6. The same syringe was used to carefully draw out a volume of liquid from the phantom equal to the volume plus 1 ml of the $^{18}$F solution injected into it. This ensured the solution will not overflow when the rod is replaced and will include a small bubble to facilitate mixing.
7. The $^{18}$F activity in the syringe was measured and the radioactivity and assay time was recorded.

8. The rod was reinserted into the phantom and the cap was hand-tightened in place and ensured that it was secure and leak-free.
9. The surface of the phantom was wiped with a paper towel which was checked for radioactive contamination prior to discarding.
10. Image data was then acquired using any PET scanner that was to be evaluated, under any conditions or acquisition settings that are to be evaluated.

The resulting image data were assessed using conventional tools. A large region of interest covering the central 60% of several slices that do not include the acrylic rod may be used to determine the degree of uniformity and correctness of calibration factors. Region-of-interest analysis with one or more slices containing the acrylic rod may also be used to determine the contrast between the radioactivity-filled volume and the area within the acrylic rod from which radioactivity is excluded. Integration of a line profile including the edge between the rod and the liquid may be used to assess resolution. A variety of other factors may also be assessed, including calibration linearity and the capacity and accuracy of PET-CT mismatch correction using appropriate data acquisition.

Example 43

The following example describes a comparison of imaging agent 1 and 18F fluorodeoxyglucose (FDG) for assessment of left ventricular viability following myocardial infarction in rats.

$^{18}$F fluorodeoxyglucose (FDG) imaging of the heart is used to assess myocardial viability. This example describes a comparision of the volume of viable tissue in the left ventricle of normal and myocardial infarcted (MI) rats determined by imaging agent 1 imaging with that detected by FDG imaging.

Methods.

MI was induced in rats by 30 minutes of\ coronary occlusion followed reperfusion. Imaging agent 1 (1 mCi) and FDG (1 mCi) cardiac imaging in 2 days apart was performed in rats of before, two days (early MI) and four weeks (late MI) post surgery. A regimen of glucose and insulin was injected before FDG imaging to ensure high cardiac uptake. Viable left ventricle was quantified in images as the volume with ≥50% of maximum activity.

Results.

In control rats, cardiac imaging with both imaging agent 1 and FDG showed well-defined left ventricular wall and the left ventricular volume was measured as 1.17±0.04 and 1.11±0.07 cm3 respectively before surgery. In early and late stage MI rats, the myocardial defect area was clearly identified by imaging with both agents. The viable left ventricular tissue volume measured with imaging agent 1 was slightly larger than the viable tissue area measured with FDG (0.94±0.01 vs. 0.75±0.04 and 1.18±0.04 vs. 0.99±0.09 cm3 at early and late stage MI). In addition, imaging agent 1 imaging showed similar detectable left ventricular areas at 20 and 80 minutes post injection (no refill-in) in both early and late stage MI. This example shows that imaging agent 1 has the potential to be used to assess myocardial viability, like FDG, however without the need for insulin pre-treatment.

Example 44

The following demonstrates that a quantitative and perceived defect severity are proportional with imaging agent 1 PET myocardial perfusion imaging.

In order to identify the minimum rest dose of imaging agent 1, a comparison was made between the count-related variation in normal myocardium and the minimum change in defect severity that would result in 50% probability of a reader's changing a segmental score by 1. In order to determine this limiting change in defect severity, a comparison was made between reader scores from a blinded read and the corresponding quantitative defect severity.

Method.

Figure 13:
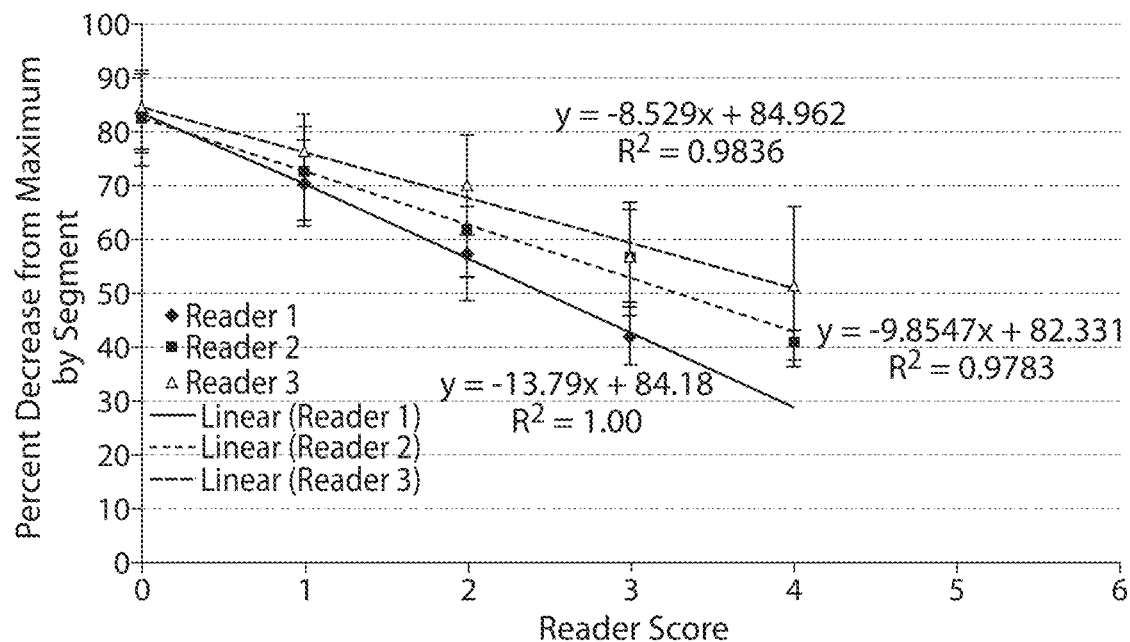
FIG. 13 shows a plot of reader's scores versus percentage decreases from the maximum value for rest image data of a study following administration of imaging agent 1 injection to subjects, according to a non-limiting embodiment.

Patients selected for one or more at least partially reversible defects on SPECT studies were evaluated as part the first cohort in the Phase 2 study of imaging agent 1. Rest and stress images were read by a panel of three blinded readers. Reader' scores using a 17-segment model from the rest image data only derived from the first 20 patients were compared with the percentage decreases from the maximum value in each image as calculated by standard cardiac MPI analysis software (Cedars QPS). The values were plotted and a linear regression calculated for the data from each reader (see FIG. 13).

Results.

Although there was significant range in quantitative severity values at each reader score value (% SD~20% of image maximum), the data was well modeled with the simple linear regression resulting in $R^2$ values of 1.00, 0.978 and 0.984 for readers 1, 2 and 3 respectively. The intercept values were 84.18%, 82.33% and 84.96% respectively while the slopes were −13.8, −9.86 and −8.53 respectively.

Discussion.

These results suggest that, at least with imaging agent 1, it may be possible to estimate reader responses using a simple linear relationship and the quantitative fraction of the maximum value without the need for a normal database. Based on a mean slope of −10.7, it was estimated that a 50% probability of a change of 1 in reader score corresponded to a change in quantitative severity by 5.4%

Example 45

The following examples describes a comparison of imaging agent 1 and Tc-99m labeled SPECT myocardial perfusion imaging for identifying severity and extent of stress induced myocardial ischemia in Phase 2 clinical trials In this multi-center Phase 2 study, imaging agent 1 and Tc-99m labeled SPECT rest-stress MPI were compared for evaluation of stress induced myocardial perfusion abnormalities in patients (Pts) with coronary artery disease (CAD).

Methods:

84 Pts from 21 centers, presenting with an intermediate to high CAD pre-test likelihood, underwent rest-stress Tc-99m labeled SPECT MPI, imaging agent 1 PET MPI and coronary angiography. Their mean age was 64.5 years (range: 36-85) and 68 were males. In each patient, 17 myocardial segments were visually scored on rest and stress images by 3 independent, blinded readers. For each pt, summed difference scores (SDS) were determined from segmental scores. Percent narrowing in each coronary artery was quantitatively and blindly determined and ≥50% luminal diameter narrowing was considered significant. Of the 84 Pts, 52 had CAD and 32 had insignificant CAD/normal coronary arteries.

Results.

There were 105 diseased coronary arteries in 52 patients; 40 left anterior descending, 30 left circumflex and 35 right coronary arteries. In patients with at least one diseased artery, the mean (SD) PET SDS score ranged among the three readers from 6.8 (5.75) to 9.4 (7.51) and the mean (SD) SPECT SDS score ranged from 4.1 (4.75) to 5.7 (6.51). The differences in SDS scores between PET and SPECT were statistically significant in all readers (p<0.01). In 52 patients with multivessel disease and multi-readers, the adjusted mean PET SDS score was significantly higher than that of SPECT SDS score (p<0.001).

Conclusions.

These data suggest that as compared to Tc-99m SPECT, rest-stress imaging agent 1 PET MPI demonstrates more severe and extensive stress induced perfusion abnormalities in myocardial regions that are supplied by diseased coronary arteries.

Example 46

The following example describes a Phase 2 clinical comparison of imaging agent 1 injection PET and Tc-99m labeled SPECT myocardial perfusion imaging for diagnosis of coronary artery disease.

In the Phase 2 study, the clinical safety of imaging agent 1 injection was evaluated and its diagnostic performance for detection of coronary artery disease (CAD) was compared to rest-stress Tc-99m labeled SPECT MPI.

Methods.

143 patients (Pts) from 21 centers, presenting with a broad spectrum of CAD pre-test likelihoods, underwent rest-stress Tc-99m labeled SPECT MPI and imaging agent 1 PET MPI. 84/143 who had an intermediate to high CAD likelihood underwent coronary angiography. Their mean age was 64.5 (range: 36-85) years and 68 were males. % narrowing in each coronary artery was quantified blindly. 52/84 Pts had significant CAD (≥50% luminal diameter narrowing) and 32/84 had insignificant CAD/normal coronary arteries. In each patient, 17 myocardial segments were visually scored on rest and stress images by 3 independent, blinded readers and majority rule interpretation was determined in each patient for both PET and SPECT studies. Diagnostic performance of PET was compared to that of SPECT using ROC analysis.

Results.

A significantly higher % of images were rated as either excellent or good on PET vs SPECT stress images (99.2% vs. 88.8%, p<0.01) and rest images (96.8% vs. 64.8%, p<0.01). Diagnostic certainty of interpretation (% of cases with definitely abnormal/normal interpretation) was significantly higher for PET vs. SPECT (92.0% vs. 76.8%, P<0.01). The area under the ROC curve for overall diagnosis of CAD was significantly higher for PET vs. SPECT (0.79±0.05 vs. 0.67±0.05, p<0.05). 61/143 patients reported 100 treatment emergent adverse events (AEs). Of these, 7 AEs reported in 2 patients were judged to be related to the study drag, but none were serious. No clinical laboratory changes from baseline were reported as TEAEs or considered as clinically significant. The ECG data at rest revealed no evidence of any clinically relevant effect on heart rate, atrio-ventricular conduction (PR interval), depolarization (QRS duration) or repolarization (QTcF duration).

Conclusions.

Within this Phase 2 clinical trial imaging agent 1 appeared to be safe and superior to Tc-99m labeled SPECT with respect to image quality, certainty of image interpretation and overall diagnosis of CAD.

Example 47

The following described a streamlined quantification of absolute myocardial blood flow at rest and stress with imaging agent 1 injection PET in normal subjects and patients with coronary artery disease.

Objectives.

The feasibility of streamlined quantification of rest (R) and stress (S) myocardial blood flows (MBFs) and coronary flow reserve (CFR) with imaging agent 1 for clinical use in normal subjects and coronary artery disease (CAD) patients (Pts) was evaluated.

Methods.

Ten Pts [6 with a low likelihood of CAD and 4 with CAD (>50% stenosis) and reversible defects] received imaging agent 1 injection at Rand at peak adenosine S followed by 10-min dynamic acquisition. The R-S imaging protocol was same-day in 5 Pts and separate-day in 5 Pts. Rand S polar maps were automatically generated from summed dynamic scans (0.5-2 min post injection) and the 3 coronary territories (LAD, RCA, LCX) and the left ventricular blood pool (LV) were defined automatically. Reversible defects were manually assigned on the polar maps, from which time activity curves (TACs) were generated. A single-compartment model that included an irreversible uptake constant (K) and a spillover from blood pool activity was used to fit the tissue TACs at early times (0-2 min). LV TAC was used as the input function. Recovery coefficient due to partial volume effect of myocardium was estimated as (1-spf), with spf denoting the blood spillover fraction determined from model fitting. The first pass extraction fraction for imaging agent 1 in humans was assumed to be 0.94 equivalent to that observed in pre-clinical studies. CFR was calculated as S/R MBF.

Results.

MBF and CFR were compared between 18 normal territories (in 6 low likelihood Pts) and 5 reversible defect territories which were supplied by CAD coronaries (Table 19, *=p<0.05). The results are in agreement with the published literature using N-13 ammonia PET.

TABLE 19

| | Normal | | | CAD Reversible |
|---|---|---|---|---|
| | LAD | RCA | LCX | defect |
| RMBF | 0.76 ± 0.15 | 0.75 ± 0.17 | 0.74 ± 0.10 | 0.69 ± 0.22 |
| SMBF | 2.48 ± 0.50 | 2.78 ± 0.43 | 2.66 ± 0.62 | 1/12 ± 0.19* |
| CFR | 3.25 ± 0.25 | 3.72 ± 0.49 | 3.60 ± 0.86 | 1.71 ± 0.41* |

Conclusions.

Quantification of MBF using imaging agent 1 injection PET myocardial perfusion imaging can be streamlined in clinical applications to give robust MBF results.

Example 48

Synthesis of 5-((4-((2-bromoethoxy)methyl)benzyl)oxy)-2-(t-butyl)-4-chloropyridazin-3(2H)-one A solution of imaging agent precursor 1 (0.521 g, 1.00 mmol) in dry acetone (10.0 mL) was treated with LiBr (0.261 g, 3.00 mmol) in one portion at 22° C. then warmed to 56° C. and maintained 2.5 h. The now heterogeneous reaction mixture was cooled to ambient temperature and all volatiles removed in vacuo. The crude product was then purified by chromatography on silica (30×190 mm) using 3:1 pentane/EtOAc. The main product peak eluting 180-360 mL was collected, pooled and concentrated in vacuo to a colorless oil. Final purification through recrystallization from warm EtOAc and pentane afforded a white crystalline solid (0.369 g, 0.859 mmol; 85.9%).

Example 48

Syringe Adsorption of Imaging Agent 1

Three two-component syringes (Henke Sass Wolf) as well as three three-component syringes (Becton and Dickinson) were each filled with a 1 mL solution of imaging agent 1 (<5 volume % EtOH in $H_2O$ containing <50 mg/mL ascorbic acid); total initial radioactivity in each syringe was comparable. The two sets of filled syringes were maintained at ambient temperature and humidity for a period of three hours, at which time the contents were injected into a clean 5 cc glass vial; a consistent volume of imaging agent 1 (0.1 mL) remained in the hub of each syringe. The total radioactivity content of both the vial and syringe were measured, decay corrected and the percent retention calculated. The values of percent radioactivity retained in each syringe are summarized in Table 20. The difference in percent retained activity is statistically significant at the 95% confidence level (i.e. Prob>|t| 0.0005).

TABLE 20

Compiled Data for imaging agent 1 Retained in Syringes

| Syringe | Retained Activity [%] |
|---|---|
| B&D | 32.4 |
| B&D | 35.2 |
| B&D | 38.9 |
| HSW | 11.3 |
| HSW | 7.0 |
| HSW | 5.1 |

B&D = Becton & Dickinson-HSW = Henke Sass Wolf

Example 49

Syringe Component Adsorption of Imaging Agent 1

To further identify the contact surface material that contributed to syringe retention of imaging agent 1, three additional B&D syringes were each filled with a 1 mL solution of imaging agent 1 then maintained at ambient temperature and humidity for a period of three hours. Following transfer of the individual doses as described in Example 1, the syringe barrel and butyl rubber tip plunger were then separated, measured for retained radioactivity and decay corrected. The values of percent retained radioactivity for each syringe component are summarized in Table 21. The difference in percent retained activity is statistically significant at the 95% confidence level (i.e. Prob>|t| 0.0017).

TABLE 21

Percent imaging agent 1 Retained in B&D Syringe Components Post-Injection

| Syringe Part | Retained Activity [%] |
|---|---|
| Plunger | 30.9 |
| Plunger | 27.7 |
| Plunger | 21.8 |
| Barrel | 6.9 |
| Barrel | 5.5 |
| Barrel | 7.0 |

B&D = Becton & Dickinson

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element or a list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A cassette for the preparation of an imaging agent comprising the formula:

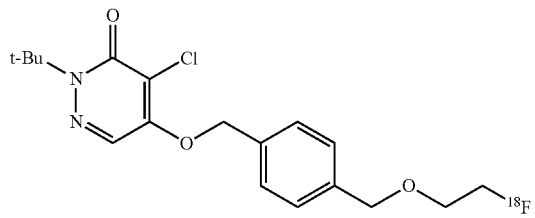 [SMILES: CC(C)(C)n1ncc(OCc2ccc(COCC[18F])cc2)c(Cl)c1=O]

comprising:
(i) a vessel containing an imaging agent precursor comprising the formula:

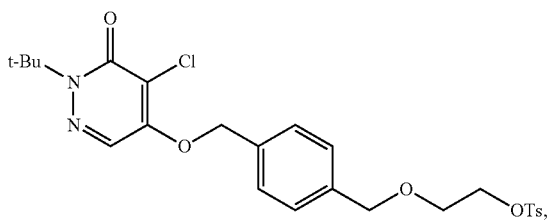 [SMILES: Cc1ccc(S(=O)(=O)OCCOCc2ccc(COc3cnn(C(C)(C)C)c(=O)c3Cl)cc2)cc1]

(ii) a conduit for adding a source of $^{18}F$; and
(iii) a vessel containing a bicarbonate salt.

2. An automated reaction system, comprising:
the cassette of claim 1, further comprising a purification module and a formulation module.

3. The automated reaction system of claim 2, wherein the formulation module comprises a source of a diluent, optionally wherein the diluent comprises ascorbic acid.

4. The automated reaction system of claim 3, wherein the diluent comprises ascorbic acid.

5. The cassette of claim 1, wherein the bicarbonate salt is a tetraalkylammonium bicarbonate salt.

6. The cassette of claim 1, wherein the molar ratio of the bicarbonate salt to the imaging agent precursor is between 1.5:1 and 0.25:1.

7. An automated reaction system, comprising:
a reaction module, wherein the reaction module comprises a source of $^{18}F$; a source of a salt additive; and a source of an imaging agent precursor of the formula:

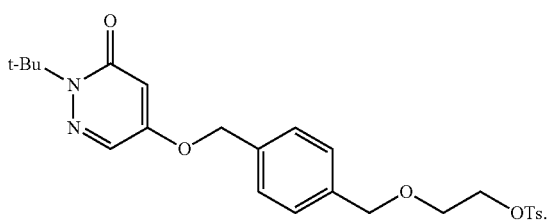 [SMILES: Cc1ccc(S(=O)(=O)OCCOCc2ccc(COc3cnn(C(C)(C)C)c(=O)c3)cc2)cc1]

8. The automated reaction system of claim 7, wherein the salt additive is a bicarbonate salt.

* * * * *

UNITED STATES PATENT AND TRADEMARK OFFICE
CERTIFICATE OF CORRECTION

PATENT NO. : 10,842,892 B2
APPLICATION NO. : 15/901286
DATED : November 24, 2020
INVENTOR(S) : James F. Castner et al.

It is certified that error appears in the above-identified patent and that said Letters Patent is hereby corrected as shown below:

In the Claims

Claim 3, at Column 138, should read:
3. The automated reaction system of claim 2, wherein the formulation module comprises a source of a diluent.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*